US005874279A

United States Patent [19]
Cochran et al.

[11] Patent Number: 5,874,279
[45] Date of Patent: Feb. 23, 1999

[54] RECOMBINANT INFECTIOUS BOVINE RHINOTRACHEITIS VIRUS

[75] Inventors: Mark D. Cochran, Carlsbad; Richard D. Macdonald, San Diego, both of Calif.

[73] Assignee: Syntro Corporation, Lenexa, Kans.

[21] Appl. No.: 185,949

[22] PCT Filed: Jul. 20, 1992

[86] PCT No.: PCT/US92/06034

§ 371 Date: Nov. 3, 1994

§ 102(e) Date: Nov. 3, 1994

[87] PCT Pub. No.: WO93/02104

PCT Pub. Date: Feb. 4, 1993

Related U.S. Application Data

[63] Continuation-in-part of Ser. No. 732,584, Jul. 18, 1991, abandoned.

[51] Int. Cl.$^6$ .................................................. C12N 7/01
[52] U.S. Cl. .................................. 435/235.1; 435/320.1
[58] Field of Search .......................... 435/320.1, 235.1, 435/172.1, 172.3; 424/93.2; 536/23.72

[56] References Cited

U.S. PATENT DOCUMENTS

| | | | |
|---|---|---|---|
| 4,703,011 | 10/1987 | Kit et al. | 435/236 |
| 4,769,331 | 9/1988 | Roizman et al. | 435/91.5 |
| 4,810,634 | 3/1989 | Post et al. | 435/235.1 |
| 4,824,667 | 4/1989 | Kit et al. | 424/205.1 |
| 4,877,737 | 10/1989 | Shih et al. | 424/205.1 |
| 5,593,873 | 1/1997 | Cochran et al. | 435/172.3 |

FOREIGN PATENT DOCUMENTS 326127  8/1989  European Pat. Off. .......... C12N 7/04

OTHER PUBLICATIONS

Lerch et al., *Virology*, v. 181, 1991, pp. 118–131.
Honess, *J. Gen. Virol.*, vol. 65, 1984, pp. 2077–2107.
Wirth et al., *J. Virol.*, vol. 63, 1989, pp. 4882–4889.
Gillam et al., in *Recombinant DNA Methodology*, Dillon et al., eds., 1985, John Wiley & Sons, New York, pp. 157–186.
Petrovskis et al., *J. Virol.*, vol. 60, 1986, pp. 1166–1169.
van Zijl et al., *J. Gen. Virol.*, vol. 71, 1990, pp. 1747–1755.
Weir et al., *Nuc. Acids Res.*, vol. 16, 1988, pp. 10267–10282.
Kit, et al. (1992) Arch. Virol. 124: 1–20 (Exhibit 1).
Kit, S. et al., (1991) Arch. Virol. 120: 1–17 (Exhibit 2).
Schwyzer M., (1993) Genome Map of BOvine Herpesvirus 1 O'Brien, S.J. (Ed.) Genetic Maps: Locus Maps of Complex Genomes, Sixth Edition, No. 1 Viruses. Cold Spring Harbor Laboratory Press: Plainview, New York, USA.,pp. 166–170 (Exhibit 3).
Van Oirshot, J.T., et al. (1990) Agricultural Biotechnology in Focus in the Netherlands, Dekkers, J.J. et al. eds, Pudoc Wageninen (Exhibit 4).
Whetstone, C.A., et al. (1992) Arch. Virol. 122: 207–214 (Exhibit 5).

E.A. Petrovskis, et al., (1986) Deletions in Vaccine Strains of Pseudo–rabies Virus and Their Effect on Synthesis of Glycoprotein gp63. J. Virol. 60: 1166–1169.
T. Ben–Porat, etal. (1986) Role of Glycoproteins of Pseudorabies Virus in Eliciting Neutralizing Antibodies. Virology 154: 325–334.
R.W.Price and A.Khan, (1981) Resistance of Peripheral Autonomic Neurons to In Vivo Productive Infection by Herpes Simplex Virus Mutants Deficient in Thymidine Kinase Activity. Infection and Immunity 34:571–580.
R.B.Tenser, etal. (1983) The Role of Pseudorabies Virus Thymidine Kinase Expression in Trigeminal Ganglion Infection. J.Gen.Virol.64: 1369–1373.
B.Lomniczi, etal. (1984) Deletions in theGenomes of Pseudorabies Virus Vaccine Strains and Existence of Four Isomers of the Genomes, J.of Virol. 49: 970–979.
B. Roizman, etal. (1983) Bioengineering of Herpes SimplexVirus Variants for Potential Use as Live Vaccines. Cold SpringHarbor conference on New Approaches to Viral Vaccines, Sep., pp. 275–281.
R.L.Thompson, et al. (1983) Physical Location of a Herpes Simplex Virus Type–1 Gene Function(s) Specifically Associated with a 10 Million–Fold Increase in HSV Neurovirulence. Virology 131: 180–192.
K.Fukuchi , et al(1985) The Structure of Marek Disease Virus DNA: The Presence of Unique Expansion in Non-pathpagenic Viral DNA. Proc.Natl.Acad. Sci, U.S.A. 82: 751–754.
J.M.Koomey, et al., (1984) Deletion of DNA Sequences in a Nononcogenic Variant of Herpesvirus saimiri. J. of Virol. 50: 662–665.
F.Zucjerman, et al., (1989) Vaccination and Control of Aujeszky's Disease "Role ofPeudorablies Virus Glycoproteins in Immune Response", J.T. van Oirshot(ed.Kluwer Academic Publishers London, pp. 107–117.
M.Kit, et al. (1990) Bovine Herpesvirus–1 (BHV–1)– Based viral Vector Which Expresses Foot and Mouth Disease Virus (FMDV) Epitopes on Surface of Virus Particles. Cold Spring Harbor conference on Modern Approaches toNew Vaccines including AIDS, Sep. p. 106.
U.V. Wirth, et al., (1989) Spatial and Temporal Distribution of Bovine Herpesvirus 1 Transcripts. J. of Virology 63: 4882–4889.

(List continued on next page.)

*Primary Examiner*—James Ketter
*Attorney, Agent, or Firm*—John P. White; Cooper & Dunham LLP

[57] ABSTRACT

The present invention provides recombinant infectious bovine rhinotracheitis (IBR) viruses useful in vaccines to protect bovines from diseases particular to them, including infectious bovine rhinotracheitis and bovine respiratory disease complex. The present invention further provides methods for distinguishing an animal vaccinated with a vaccine of the present invention from an animal infected with a naturally-occurring IBR virus. The present invention also provides isolated DNA encoding the gpE glycoprotein, the gpG glycoprotein, and US2 genes of an IBR virus. The present invention further provides homology vectors for producing recombinant IBR viruses.

7 Claims, 45 Drawing Sheets

OTHER PUBLICATIONS

B. Moss, (1991) Vaccinia Virus: A Tool for Research and Vaccine Development, Science 252: 1662–1667.

R.W.Honess, (1984) Herpes Simplex and "The Herpes Complex": Diverse Observations and A Unifying Hypothesis. J. gen. Virol. 65: 2077–2107.

R.C. Desrosiers et al., (1985) Synthesis of Bovine Growth Hormone in Primates by Using a Herpesvirus Vector, Molecular and Cellular Biology 5: 2796–2803.

D.R. Thomsen et al,. (1987) Pseudorabies Virus as a LIve Virus Vector for Expression of Foreign Genes. Gene57: 261–265.

J.P. Weir and P.R. Narayanan, (1988) The Use of §–galactosidase as a Marker Gene to Define the Regulatory Sequences of the Herpes Simplex Virus Type 1 Glycoprotein C Gene in Recombinant Herpesviruses, Nucleic Acids Research 16: 10267–10282.

R.R.Spaete and E.S. Mocarski, (1987) Insertion and Deletion Mutagenesis of the Human Cytomegalovirus Genome. Proc. Natl. Acad. Sci. USA 84: 7213–7217.

M. Shih et al., (1984) Expression of Hepatitis B Virus S Gene by Herpes Simplex Virus Type 1 Vectors Carrying the and B–regulated Gene Chimeras Proc. Natl. Acad. Sci. USA 81: 5867–5870.

S.J. Edwards et al., (1988) Plasmodium Falciparum Antigens in Recombinant HSV–1. Technological Advances in Vaccine Development pp. 223–234.

D.R. Fitzpatrick et al., (1988) Expression of Bovine Herpesvirus 1 Glycoproteins gI and gIII in Transfected Murine Cells. J. of Virol. 62: 4239–4248.

Federal Register, May 9, 1990; 55: No. 90, pp. 19245–19253.

Kit et al., (1990) Gene–deleted IBRV Marker Vaccine. Veterinary Record 127: 363–364.

M.L. Cook and J.G. Stevens (1976) Latent Herpetic Infections J. Gen. Virol. 31: 75–80.

FIGURE 3

TTAAGCGTTGCCCGTGGCCGGTGTCGCCATGGTGACTATAGTCACGTGTGCCGGATAGGCCG
                              MetValThrIle......

GCGCCTTCCAGGCAAGCCCAGACGTGCCGCCGGGTGTGGCGTTTCCTTGCCGAGCAG
AGCCGGGCGCTGACGGCAAGCGGCGGCTGGGGACGACGTCGTTGTCTTCGATCACGCCCTA
GTAAAACGGCGAAGGGCTGCACGTCGACGTCAACGTCAAGCCAGCGCGGGTGGCTT
TTGTCGACACAGCGCCCTTGCCGGGCTTAGCCGCCACCGCCAACCGGCGAG
TGGGTCAGCTGGTCGACGGCTACAAACTTGCTGAAACTCGGCCGCGAGGGCTCGGCCC
TTCCACATGTGGGTTTTGGCCCGCTACGCGCCCTATTTTTGCGCACATTGCC
GCCACGACGCGCTTGGTTTACGCGGCACTGGACTGTACGTTTGCGGAGCGGCGTGGCGG
CTCCCCGCGCGGCCCGGCCATCGCTAGCCGTGCCCTACGATACCCCGACACTC
CCTGAGCTGGTGGCCGGTGGTTCCTTTCCGGCTGTCTACGAAGTCGTAGACCGCGGG
CGGCGCGCCCAAACGCGAGCCGTGCCCCAGGGCTCGCCCCGCGCGC
CATGTGCTATCCTTAAAGGCCGCCACCCAGGCGTTTGGTCATTTGCTTTGTGACC
GCGCCGAGGACCATGTTCCGCCACGCCGTGGTGATCAGCACAGTGCC
GTTGAGCAGAGAGGCGACGCGACCCGGTCCCGATGCGAGGGGG
GCTTGGTGGCTGGCACTCTTTACAGTGCCGCCACGAGCAAGAAGACGGCCTGTATGCTA
TCGTCCCGGACTATTTTCCGGTGCCCCTCGTCCAAGCCCCTGCTGGTGAAAGTTC
                                      ......ProSerProCysTrp---

CCGCTCCCGGCGCGAGTCCCGACCGAACTGGGGGCGCAGTTCACTTTGAATGTGTTCCCG
CGCCGGCCGAGCCGCTGCAGTTCTTCGTCAGCTTTACGAGCTTCATTCGTTAAGCTT

| IBR US2   | 115 | H-MWVFGAADLYAPIFAHI |
| HSV-1 US2 | 124 | H-LWVVGAADLCVPFLEYA |
| PRV US2   | 148 | H-LWILGAADLCDQVLLAA |
| HSV-2 US2 | 123 | H-LWVVGAADLCVPFFEYA |
| MDV US2   | 132 | HSLWIVGAADICRIALECI |

FIGURE 5B

```
IBR Cooper     HindIII O    TGAGCGCGCGCCGCCGCTGCATGCTGCTGGTGCGCGAACTCACGCCGAGCGCGTGCGAGCAAGCTT
                                                                                                    HindIII
                            ||||||||||||||||||||||||||||||||||||||||||||||||||||||||||||||||
IBR Nasalgen   HindIII K    CTAGTAAAAACGGGCGAAGGGCTGGTGCGAACTCACGCCGAGCGCGTGCGAGCAAGCTT
                            |||||||||||||||||||||||||
IBR Cooper     HindIII K    CTAGTAAAAACGGGCGAAGGGCTGCACGTCGACGTCAAC

FIGURE 8

GCGATCATGCCTGCCGCCCCGGACCGGCACCTTGGCCGCCGTCGCCCTAATCCTGCTCTGC
       MetProAlaAlaArg..........

GGGGCCGCCGTTTGCGGCCCCGCCCGCCGACGACCCTCTGTTCGCCGACGTGCCGCCGCAC
TGGCATGGCGCCCCTCCCCGCCCGCCTGGGCCCCGTCCTGAACCTAGCGGCCTCGGATTGAC
CTCGCGGGTTTCGGTGCGCCGGTGGTTGCGCCGGTGGAGCTTCGCGCGCTGCGCCTCCTGACA
TGGCGGAGACGGTGGTGCCCGGCGACCGGCCSCACGTCGTCGACGTCGGCTGGGCT
TACCAAGACGGGGACTGCTGCCTCTGCGATATCGCCAGTACTTTAACTGCACGGGG
GGCGCGTGCCCCGGCCAAAACGTCTGCGCTCTACGGGACGTCGCTAGTACTGCGCCCGGTGGC
TTTGGAACCTCCGACTCCGCGCTCTACGCGTCTACGGGACGTCGCTAGTACTGCGCCCCGTAC
GACCGCGGGACCTACATCTACTTCCTTGGATACGCCCAGACGACATCTACGTGGGCAGC
GTCACGCTCATGTGGGCGCCACATCCACAATACCCCTGCGGGCTGACCGAGGGCTC
GGTGTGCCCTGCACCACAAGAGCGGACGGCCCGACCTCTGACAGAGGACGACCACC
GGCGACTGGGCCTGCCTGCCTCTTCCCCGCCTGCCGACGGTTGAGCGCGGTGTGGGGCAAC
GTAAGCGCCGACAGAGCTGGGACGGGAGCCTGGGCCGATCGACTACGCCGCAGGACCCC
GTCGAAGTGCTCGAGGACGAAGCCGGAGCCAGGGAAAACCTGCCGCAGGACGACCCC
GACCCCGACCTCGCAGATTGCCGGACCGGCTCGGGCTCTTTAGCGAAAGCGACATGTTCCGG
ACCGCCACGGGCCCGAATCGCTGCTGATCGGCGCGAAGACGTTCTGACGGTG
CCCCTCAATCTGCCGCCCGCGCTCTTACGAGGCCCTGCGAAACGCATCGCTGGAGTGC
AACTCCCCGCGGACGCGCGAGACCGGCAGCGGTGTGGTGATGTCTCTCCAGGAGCCC
GCTCGCCTCGAGCCTCGATGACCCCGATGCCCCGGCCATTCTCATGGCCTCGATCGCTCTGG
CTGCCCCGATGACCCCGTGCTGGTTCGCTGGTGATCGTCGCGCCTGCCGCCCAGCCAA
TGCTGCTGTTCGCTGGTGATCGTCGCGCCACGTTCGCCAAGAGCAACCCCGGTACGAGCCCC
GGCTGCCGCACGCCCGCCCACGTTCGCCAAGAGCAACCCCCGTACGAGCCGATG
CTCAGCGTCTGATCGCCGGCACCCCACGCGCCGACCCCGCTGTCCCCGGCGTTTACAAT
       ..SerVal---

AAACAG

| | | |
|---|---|---|
| IBR gpG | 95 | VGWAYQDGDCMVPLAYRQYFNCTGGALPGNVLCA |
| PRV gpX | 89 | VAWFFDGGHCKVPLVHREYYGCPGDAMPSVETCT |
| HSV-2 gpG | 111 | VTYYRLTRACRQPILLRQYGGCRGGEPPSPKTCG |
| | | V      C   P    R Y   C G    P     C |

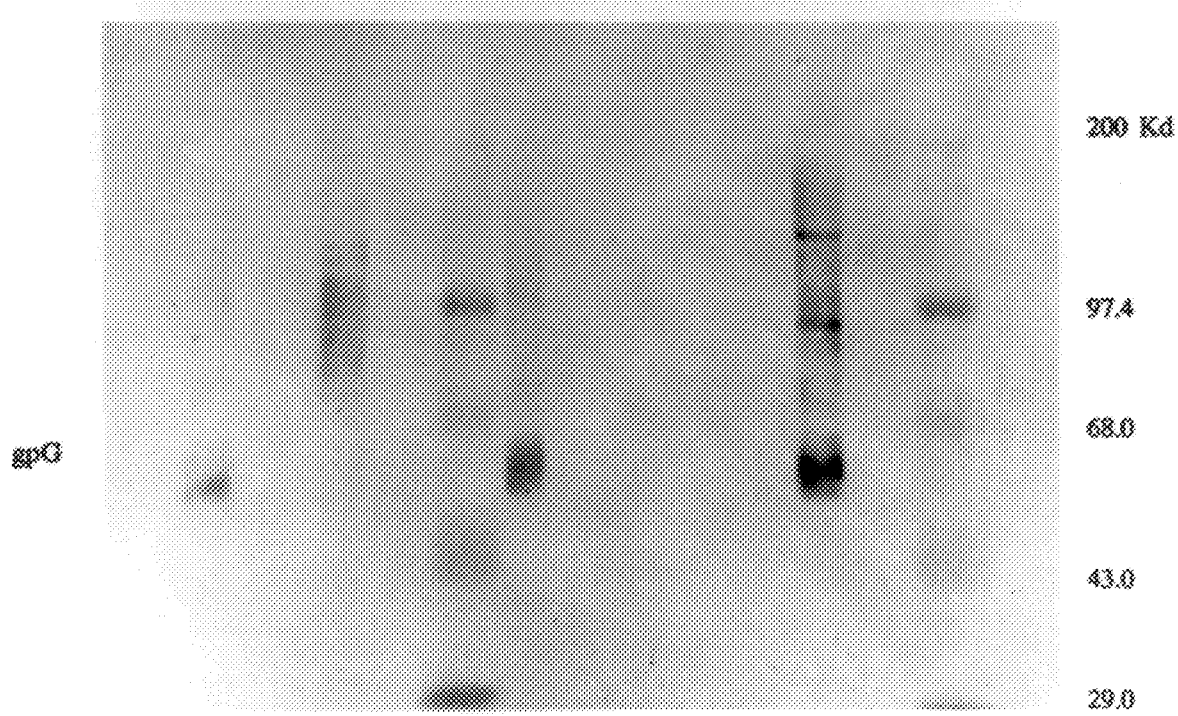

FIGURE 12A

| FIGURE 12A |
|---|
| FIGURE 12B |
| FIGURE 12C |
| FIGURE 12D |

| DNA | Origin | Sites | Size |
|---|---|---|---|
| Vector | pSP64 | HindIII - SmaI | ~2965 BP |
| Fragment 1 | IBR HindIII K | HindIII - XhoI | ~3593 BP |
| Fragment 2 | PRV BamHI #7 | SalI - NdeI* | ~753 BP |
| Fragment 3 | pJF751 | BalI - BamHI | ~3347 BP |
| Fragment 4 | HCMV XbaI B | AvaII - PstI | ~1191 BP |
| Fragment 5 | IBR HindIII K | XhoI - NdeI | ~785 BP |

* resected with ExoIII/S1

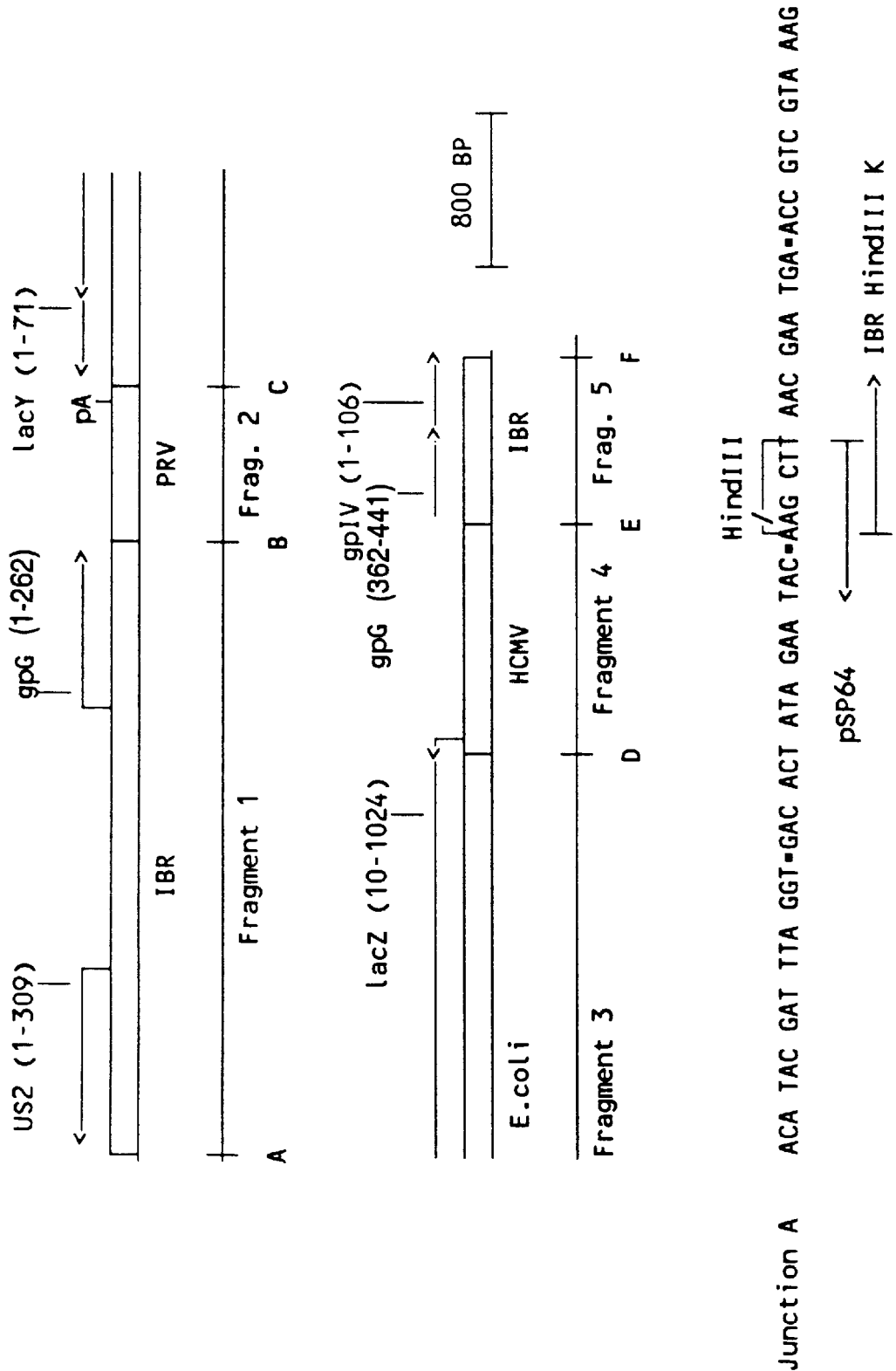

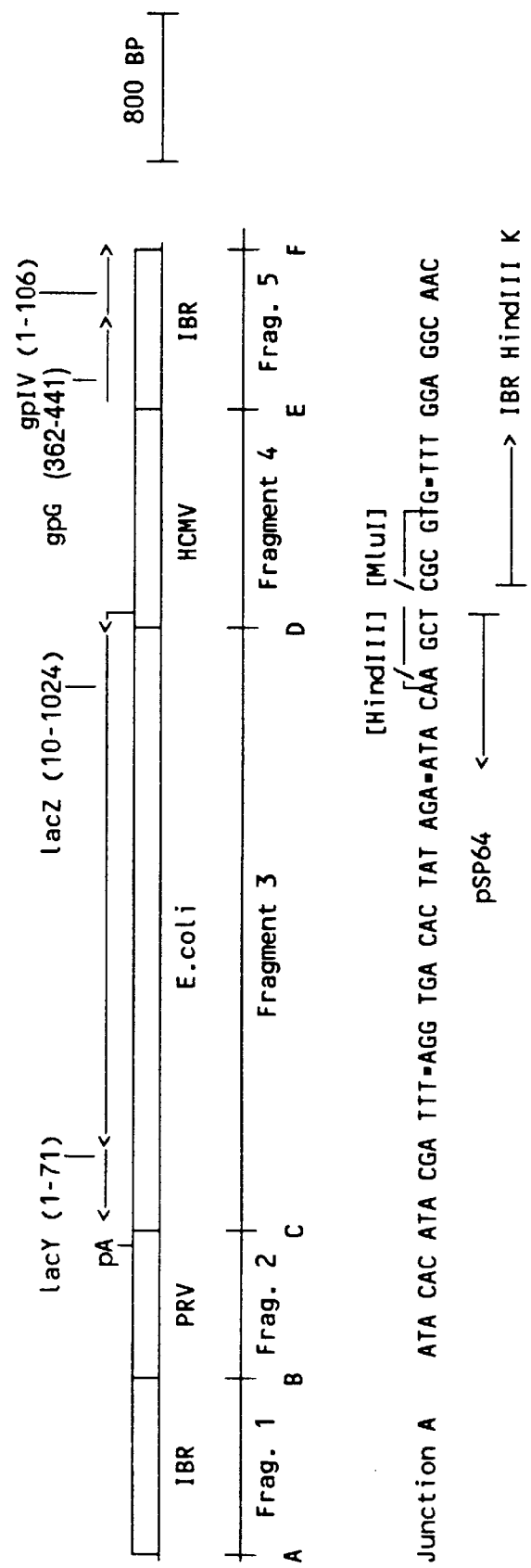

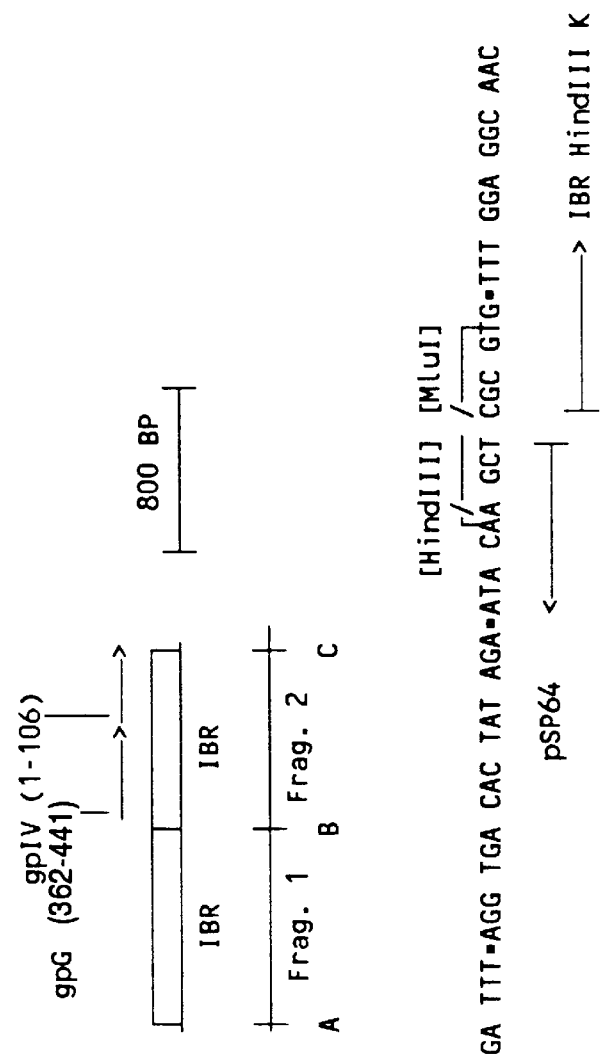

FIGURE 15A

| FIGURE 15A |
|---|
| FIGURE 15B |

GCGGGCAAGGCCGAGGAAGACCGGGGCAGGAGCTGCGTGAGGGCCGAGCCGTTGAGCG
GCCCGACCCGCCCGGTTGTTAAATGGGTCTCGCGGCGGCTCGTGGTTCCACACCGCGCC
                            MetGlyLeuAlaArg............

GGAGAACCAGCGCGCAGCTTCGCTGCGTGTCCCGCGAGCTGCGTTCCGGGAACGGCG
CGGCGAGAGGGTTCGAAAAGGGCATTTGGCAATGCAACCCACCGCCCGCCCCGGCSSG
GTTGCGCCGCTGCTGCCGCAGTTATTGCTTTTCGGCTGATGGCCGAGGCCAAGCCC
GCGACCGAAACCCCGGCTCGGCTTCGGCTCGACACGGTCTTCACGGCCGCTGGCGCG
CCCGTCTTTCTCCAGGCCCGCCCTGCTCGCCGCCCGTGCCGCCCCGTTCGCGACTGGAGC
GTCCTCGGCGCGCCCTGCTCGCCCTGACGCGGCCCGTGCCGAGCCCCGTCCGACCGCGAG
TGCTTCACCGACGTGGCCCTGCCCCGACGCGCCCGACTCAACGGCGACAAAGAGTTTGTTCTCGCC
GCCATCGCGGAGCTCGCGGCGCAGCTGGGTCGCAACGCGGACCGGGTGCTGATCGCGCCGCA
GACCCGCACGTCTCGCGGCGGCGGCGTGTACTTCCTGACGCGGCTCATCGGCGACGCCGGCGAC
GCCGAGGAGGACGCGGCCAGTTGGCGCTGACGCTGCAGTTCGCGCAGGGGCCGGCCGCG
CGGGACGAGGAGAGGAACCAGCGCGGCGCCCCCGGCGGGCTTCCGGTGCCTTGCAGTCTGAGTTTTC
ACGACGACGACACCCCCGGCGATTCCTTTCTGCTATCGGCTCTGCCAGTCTGAGTTTTTC
CACGTATACACCCCGGCGATTCCTTTCTCGCCAGCATGACTGGTACTTCCTGCGACGGCGACTGC
GACGAGGCTCCCCTTCTCGGCCAGCATGACTGGTACTTCCTGCGACGGCGACTGC
GCGCTCATCCGCATATACGAGACGTGCATCTTCCACCCGAGGCACCGGCTGCCTGCAC
CCCGCCGACGCGGCAGTGCCGCCGACCCTCGCCCGAGACCTCCGAGACCGTGTACAGCCGG
CTGTACGAGCAGTGCCGCCCCGACCCTCGCCCGTCGGCCGAGTGCCGAGTGGGCGCC
GCGTACGCGCCCCGGCACCTGCGCATAACAGCGTAGACCTGCTGTCTTT
GACGACGCCGGCTGCGCCGCTCCGGGCTTTACGTCTTTGTGCTGCAGTACAACGGCCAC

FIGURE 15B

```
GTGGAAGCTTGGGACTACTGCCTAGTCGTTACTTCGGACCCGTTTGGTGCGCGGCGGTCACC
GACCACACGCGCCGGCCCCGAGCCCAGGCCCGACGCTCCCGAGCCCAGGCCCACCGCTCACC
AGCGAGCCCGGCGGGGSGCCCACCGGGCCCCTGGCTTGTGCTTGTGGTGCGCGGTGGGCGCG
CTTGGACTCGCGGGACTGGGCATGCGAGCCTCGCCGTTCGGGTGTGCGCGGTGTGCGCGCCGC
GCAAGCCAGAAGCGCACCTACGACATCCTCAACCCCTTCGGGCCCGTATACACCAGCTTG
CCGACCCAAACGAGCCGCTCGACGTGGTGCCAGTTAGCGACGACGAATTTCCCTCGAC
GAAGACTCTTTGCGGATGACGACAGCAGACGGCCCCGCTAGCAACCCCCCTGCG
GATGCCCTACGACCTCGCCCGCTCGAGTCGCTCGGTTCAAAGTTTGCGGAGCCCCGCC
AACGGCACGCGCTCGAGTCGCTCGGTTCAAAGTTTGGTTTAGGACCCGCTTGAAGAC
GATGCCGCGCCAGCGCGGGACCCCCCGCCACCAGATTACACCGTGGTAGCAGCGGACTC
AAGTCCATCCTCCGCTAGGCGCCCCCCCGCCGTCTGACGCGGAAAGCACCC
......IleLeuArg---

GCGTGTAGGGCTGCATATAAATGGAGCGCTCACACAAAGCCTCGTGCGGCTGCTTCGAAG
```

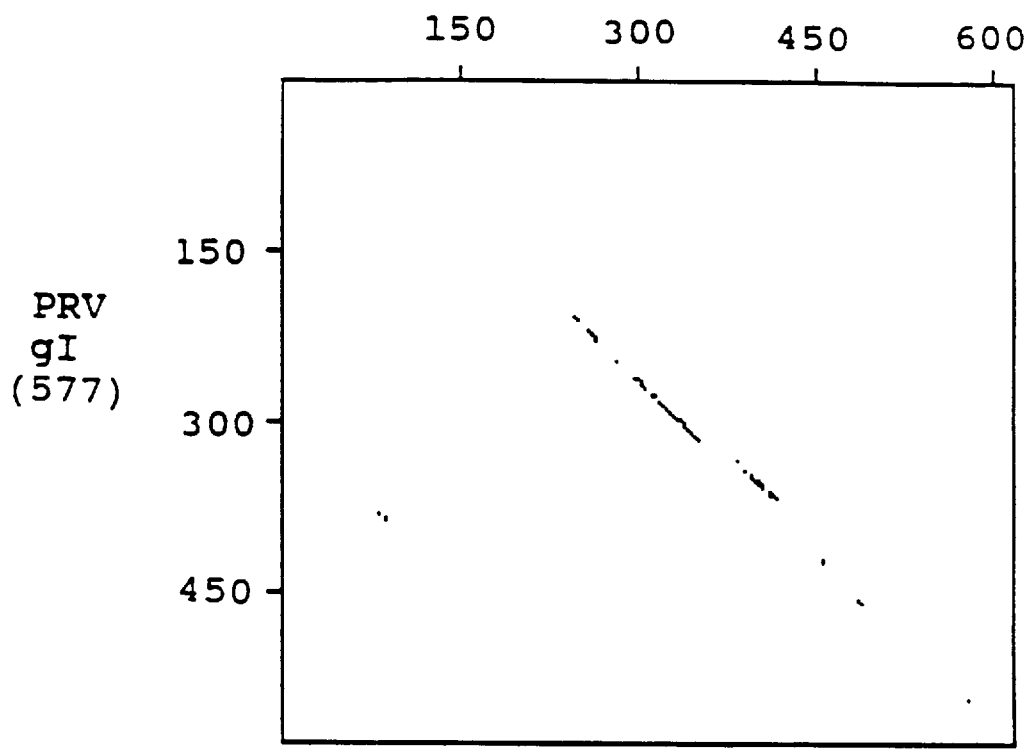

FIGURE 16B

```
HSV-1 gpE  262  WLRFDVPTSCAEMRIYESCLYHPQLPECLSPADAPC--AASTWTSRLAVRSY
PRV gI     265  WYYARAPPRCLLYYVYEPCIYHPRAPECLRPVDPACSFTSPARAALVARRAY
VZV gpI    378  WLYVPIDPTCQPMRLYSTCLYHPNAPQCLSHMNSGCTFTSPHLAQRVASTVY
IBR gpE    303  WYFLRTAGDCALIRIYETCIFHPEAPACLHPADAQCSFASPYRSETVYSRLY
                 W       C    Y  C  HP  P  CL              C          Y
```

FIGURE 18A

| FIGURE 18A |
|------------|
| FIGURE 18B |
| FIGURE 18C |
| FIGURE 18D |
| FIGURE 18E |

| DNA | Origin | Sites | Size |
|---|---|---|---|
| Vector | pSP65 | SmaI - HindIII | ~2975 BP |
| Fragment 1 | IBR HindIII K | SmaI - SmaI | ~1704 BP |
| Fragment 2 | PRV BamHI #10 | SalI - BamHI | ~413 BP |
| Fragment 3 | pJF751 | BamHI - PvuII | ~3010 BP |
| Fragment 4 | PRV BamHI #7 | NdeI - SalI | ~754 BP |
| Fragment 5 | IBR SmaI 2.5KB | NheI - BglI | ~742 BP |

FIGURE 18E

Junction E

GGC GCC TGG TGT CCG TCG ACT CTA GAG TCG ACC TGC AGC CCA

SalI  XbaI  SalI  PstI

PRV BamHI #7

[NheI]

AGC TCT AGC AAC CCC CCT GCG GAT GCC TAC GAC CTC GCC GGC GCC CCA
Ser Asn Pro Pro Ala Asp Ala Tyr Asp Leu Ala Gly Ala Pro

→ gpE (548)
→ IBR SmaI 2.5KB

```
AGGAACAAAGTTGTTCAACACAGCAGCAGCGAACAGACCCAAAGGCAGCGAGGCGACACCGAACCCA
AATGGAATATTGGAAACACACAAACAGCACACAAAAACCACCAATGAAACCGAAACAACCAGAGGCAA
          METGluTyrTrpLys..............

ACACAGTAGCAAGGTTACAAATATCATAATGTACACCTTCTGGACAATAACATCAACAATATTATTAGTC
ATTTTATAATGATATTGACAAACTTAATTCAAGAGAACAATCATATAATAATGTTGCAGGAAATAA
GAAAAGAATTCGCGGCAATAGACCTTCAGAGATTCAGAGACCTCGGATGACATTGAACCTCAATACAGTC
AGGAATAAATACAAGACTTCTCACAATTCAGAGTCATGTTCAAAACTATATCCCACTATCACTAACACAA
CAAATGTCAGATCTCAGAAAATTATCAATGATCTAACAAATAAAAGAGAACATCAAGAAGTGCCAATAC
AGAGAATGACTCATGATGAGGTATAGAGTCCTAAGATAAGGTTAATACCAGAGGGCCAGTTTATTAGCAACATCTACTACA
CCCATCTCTAACAAGTAGTCGTTAGAATATCCCATCGTTAGCAATCATTAATCTACGCTTACACCTCTAATCTTA
GTAAATGGCTGTGTATTAGAATCCCATCGTTAGCAATCATTAATCTACGCTTACACCTCTAATCTTA
TCACCCAGGCTGTCAAAATATAGGGAAATCTTACCAAGTACAAATAGGATAATTACTATAAATTC
GGACCTAGTACCTGATTAAATCCCAGAGTCACACATACATTTAATATTGATGATAATAGGAAATCTTGC
TCTCTGGCACTATTGAATACAGATGTTTATCAGTTCAGTCAACACCAAAAGTTGATGAGAGATCCGATT
ATGCATCAACAGGTATTGAGGATATTGTACTTGACATTGTCACTAATAATGGATTAATTATAACAACAAG
```

FIGURE 21B

```
GTTTACAAATAATAATATAACTTTTGATAAACCGTATGCAGCATTGTATCCATCAGTAGGACCAGGAATC
TATTATAAGGGTAAAGTTATCTTTCTCGGATATGGAGGTCTAGAGCATGAAGAAAACGGAGACGTAATAT
GTAATACAACTGGTTGTCCTGGCAAAACACAGAGAGACTGTAATCAGGCTTCTTATAGCCCATGGTTCTC
AAATAGGAGAATGGTAAACTCTATTATTGTTGATAAAGGCATAGATGCAACTTTTAGTGTTGAGGGTG
TGGACTATTCCAATGAGCCAAATTATTGGGATCAGAAGGAAGATTACTTTTATTAGGTGACAGAATAT
ACATATATACTAGATCCACAAGTTGGCACAGTAAATTACAGTTAGGGTAATTGATATATTCTGATTATAA
TAATATAAGAATAAATTGGACTTGGCATAATGTACCATCACGGCCAGAAATGATGAATGTCCATGGGGT
CATTCATGCCCAGACGGATGTATAACAGGAGTTTACACTGATGCATATCCGCTAAACCCATCGGGAGTG
TTGTATCATCAGTAATTCTTGACTCACAAAGTCTAGAGAACACTTCCAGCTGCATATACAACAATTGTATC
AATAGAATAAATGAATTAGCTATATATAACAGAAATAATAGTAGAAATAAATCACAGAAGTTTGAATACGTTTCAAC
ACACATTATGATAAAGGGTATTGTTTCATATAGTGTTCCAAAAAAACTGCAGCTAAANTGATCATCGGATGCCAGATG
CTATGTTATTCAAAACAGAAGTTCCAAAAAAACTGCAGCTAAANTGATCATCGCATATCGGATGCCAGATG
      .......ProLysAsnCysSer----

ACATTAAAAGAGACCACCAGACAACAGGAGAGATGATGCAAGATATAAAGGAATAAT
```

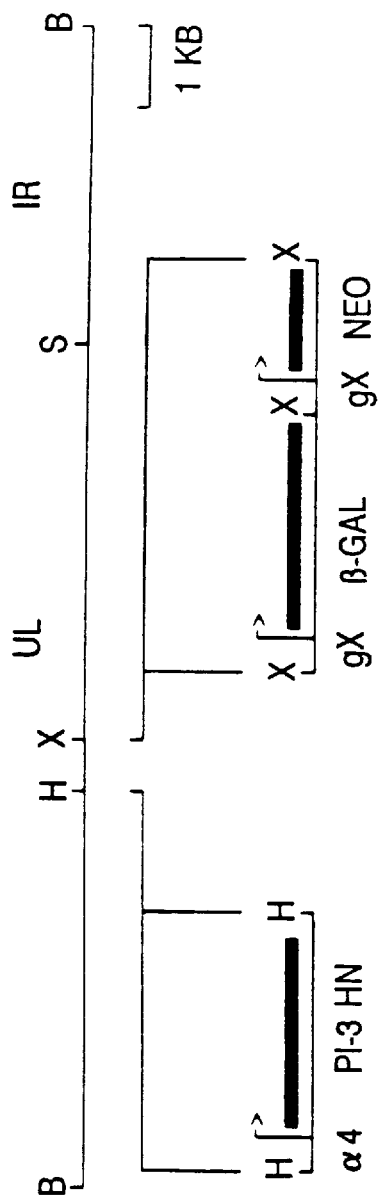
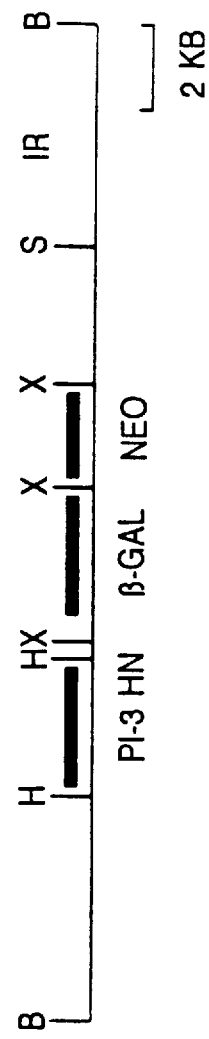
FIGURE 22A
FIGURE 22B
FIGURE 22C

RECOMBINANT INFECTIOUS BOVINE RHINOTRACHEITIS VIRUS

This application is a national stage application of PCT/US92/06034, filed 20 Jul. 1992, under 37 CFR 371, which is a continuation-in-part of U.S. application Ser. No. 07/732,584, filed 18 Jul. 1991, now abandoned.

Within this application several publications are referenced by arabic numerals within parentheses. Full citations for these publications may be found at the end of the specification immediately preceding the claims. The disclosures of these publications are hereby incorporated by reference into this application in order to more fully describe the state of the art to which this invention pertains.

FIELD OF THE INVENTION

The present invention involves recombinant infectious bovine rhinotracheitis (IBR) viruses useful in vaccines to protect bovines from naturally-occurring infectious bovine rhinotracheitis virus and other bovine diseases.

BACKGROUND OF THE INVENTION

The ability to isolate viral DNA and clone this isolated DNA into bacterial plasmids has greatly expanded the approaches available to make viral vaccines. The methods used to make the present invention involve modifying cloned viral DNA sequences by insertions, deletions and single or multiple base changes. The modified DNA is then reinserted into the viral genome to render the virus non-pathogenic. The resulting live virus may then be used in a vaccine to elicit an immune response in a host animal and to protect the animal against a disease.

One group of animal viruses, the herpes viruses or Herpetoviridae, is an example of a class of viruses amenable to this approach. These viruses contain 100,000 to 200,000 base pairs of DNA as their genetic material. Importantly, several regions of the genome have been identified that are nonessential for the replication of virus in vitro in cell culture. Modifications in these regions of the DNA may lower the pathogenicity of the virus, i.e., attenuate the virus. For example, inactivation of the thymidine kinase gene renders human herpes simplex virus non-pathogenic (28), and pseudorabies virus of swine non-pathogenic (29).

Removal of part of the repeat region renders human herpes simplex virus non-pathogenic (30,31). A repeat region has been identified in Marek's disease virus that is associated with viral oncogenicity (32). A region in herpesvirus saimiri has similarly been correlated with oncogenicity (33). Removal of part of the repeat region renders pseudorabies virus non-pathogenic (U.S. Pat. No. 4,877,737, issued Oct. 31, 1989). A region in pseudorabies virus has been shown to be deleted in naturally-occurring vaccine strains (11,3) and it has been shown that these deletions are at least partly responsible for the lack of pathogenicity of these strains.

It is generally agreed that herpes viruses contain nonessential regions of DNA in various parts of the genome, and that modifications of these regions can attenuate the virus, leading to a non-pathogenic strain from which a vaccine may be derived. The degree of attenuation of the virus is important to the utility of the virus as a vaccine. Deletions which cause too much attenuation of the virus will result in a vaccine that fails to elicit an adequate immune response. Although several examples of attenuating deletions are known, the appropriate combination of deletions is not readily apparent.

Infectious bovine rhinotracheitis (IBR) virus, an alphaherpesvirus with a class D genome, is an important pathogen of cattle. It has been associated with respiratory, ocular, reproductive, central nervous system, enteric, neonatal, and dermal diseases (34). Cattle are the normal hosts of IBR virus, however it also infects goats, swine, water buffalo, wildebeest, mink, and ferrets. Experimental infections have been established in mule deer, goats, swine, ferrets, and rabbits (35).

Conventional modified live virus vaccines have been widely used to control diseases caused by IBR virus. However, these vaccine viruses may revert to virulence. More recently, killed virus IBR vaccines have been used, but their efficacy appears to be marginal.

IBR virus has been analyzed at the molecular level as reviewed in Ludwig (36). A restriction map of the genome is available in this reference, which will aid in the genetic engineering of IBR according to the methods provided by the present invention.

As reported in the current literature, IBR virus has been engineered to contain a thymidine kinase deletion (43,44) and a deletion in the gIII gene (45,46). However, no evidence has been presented for the deletions in the US2, repeat, gpG, or gpE regions. In the subject application, we demonstrate the usefulness of such deletions for both the attenuation of IBR virus and for the development of gene deleted marker vaccines.

As with other herpes viruses, IBR virus can become latent in healthy animals which makes them potential carriers of the virus. For this reason it is clearly advantageous to be able to distinguish animals vaccinated with non-virulent virus from animals infected with disease-causing wild type virus. The development of differential vaccines and companion diagnostic tests has proven valuable in the management of pseudorabies disease (47).

A similar differential marker vaccine would be of great value in the management of IBR disease. The construction of differential diagnostics has focused on the deletion of glycoproteins. Theoretically, the glycoprotein chosen to be the diagnostic marker should have the following characteristics: (1) the glycoprotein and its gene should be non-essential for the production of infectious virus in tissue culture; (2) the glycoprotein should elicit a major serological response in the animal; and (3) the glycoprotein should not be one that makes a significant contribution to the protective immunity. Four major IBR virus glycoproteins (gI, gII, gIII, and gIV) have been described in the literature (48). Three of these genes, gI, gIII, and gIV, have been sequenced and shown to be homologous to the HSV glycoproteins gB, gC, and gD, respectively. Although it has been suggested that the gII protein is analogous to HSV gE, no sequence evidence has been presented to confirm that suggestion (48). The gB and gD homologues are essential genes and would not be appropriate as deletion marker genes. The gC gene of herpes viruses has been shown to make a significant contribution to protective immunity as a target of neutralizing antibody (49) and as a target of cell-mediated immunity (50). Therefore, the gC gene is not desirable as a deletion marker gene. As indicated above, Kit et al. (45) have described the deletion of the IBR virus gIII as a marker gene. It would be expected that such a deletion would compromise the efficacy of an IBR vaccine.

For pseudorabies virus (PRV) the criteria for a deletion marker gene are best met by the glycoprotein X (51). Wirth et al. (52) suggests the existence of a "gx homologue of HSV-1" in the IBR virus. It is not clear what is meant by this because although there is a PRV gX gene, there is no reported HSV-1 gX gene or gX homologous gene. In any case, no sequence evidence is presented to support this suggestion. We present clear evidence of homologues of PRV gX (HSV-2 gG) and PRV gI (HSV gE) in IBR virus and demonstrate their usefulness as diagnostic markers.

The present invention provides a method of producing a fetal-safe, live recombinant IBR virus which comprises treating viral DNA from a naturally-occurring live IBR virus so as to delete from the virus DNA corresponding to the US2 region of the naturally-occurring IBR virus. The present invention also provides viruses in which (1) DNA corresponding to the US2 region of naturally-occurring IBR virus has been deleted, and (2) DNA encoding gpG and/or gpE has been altered or deleted. Such viruses are useful in vaccines which need diagnostic markers and are safe for use in pregnant animals.

The ability to engineer DNA viruses with large genomes, such as vaccinia virus and the herpes viruses, has led to the finding that these recombinant viruses can be used as vectors to deliver immunogens to animals (53). The herpes viruses are attractive candidates for development as vectors because their host range is primarily limited to a single target species (54), and they have the capacity for establishing a latent infection (55) that could provide for stable in vivo expression of a desired cloned polypeptide. Herpes viruses have been engineered to express a variety of foreign gene products, such as bovine growth hormone (56), human tissue plasminogen activator (57), and E. coli β-galactosidase (58,59). In addition, possible immunogenic polypeptides have been expressed by herpesviruses. Whealy et al. (60) expressed portions of the human immunodeficiency virus type 1 envelope glycoprotein in pseudorabies virus (PRV) as fusions to the PRV glycoprotein III. The hepatitis B virus surface antigen (61) and a hybrid human malaria antigen from Plasmodium falciparum have been expressed in herpes simplex virus type 1 (HSV-1) (62). The IBR viruses described above may be used as vectors for the insertion of genes encoding antigens from microorganisms causing important cattle diseases. Such recombinant viruses would be multivalent vaccines protecting against IBR as well as other diseases. Kit et al. (63) have described the expression of a Foot and Mouth disease antigen in IBR virus. In some of the prior applications from which the subject application claims priority (which precedes the Kit publication by at least three years), we described the use of IBR virus to express several foreign genes including the E. coli β-galactosidase (lacZ) gene, the TN5 neomycin resistance gene, and antigens from bovine rota virus, and parainfluenza type 3 virus (see U.S. Ser. No. 06/933,107, filed Nov. 20, 1986 and U.S. Ser. No. 07/078,519, filed Jul. 27, 1987). These applications precede the Kit publication by at least three years. The viruses described in this application provide a combination of attenuation, differentiation and multivalency. These properties make such viruses useful as vaccines for the management of cattle diseases.

SUMMARY OF THE INVENTION

The present invention provides recombinant infectious bovine rhinotracheitis (IBR) viruses useful in vaccines to protect bovines from infectious bovine rhinotracheitis and other bovine diseases. The present invention further provides methods for distinguishing an animal vaccinated with the vaccine of the present invention from an animal infected with a naturally-occurring IBR virus. The present invention also provides isolated DNA encoding the gpE glycoprotein of IBR virus and isolated DNA encoding the gpG glyco-protein of IBR virus. The present invention also provides a method of producing a fetal-safe, live recombinant IBR virus which comprises treating viral DNA from a naturally-occurring live IBR virus so as to delete from the virus DNA corresponding to the US2 region of the naturally-occurring IBR virus.

The present invention also provides isolated DNA encoding the US2 gene of an IBR virus. The present invention further provides a homology vector for producing a recombinant IBR virus by inserting foreign DNA into the genomic DNA of an IBR virus which comprises a double-stranded DNA molecule consisting essentially of double-stranded foreign DNA encoding RNA which does not naturally occur in an animal into which the recombinant IBR is introduced and at one end of the foreign DNA, double-stranded IBR viral DNA homologous to genomic DNA located at one side of a site on the genomic DNA which is not essential for replication of the IBR virus and at the other end of the foreign DNA, double-stranded IBR viral DNA homologous to genomic DNA located at the other side of the same site on the genomic DNA.

The present invention also provides for a homology vector for producing a recombinant IBR virus by deleting DNA which encodes a detectable marker which had been inserted into the genomic DNA of an IBR virus comprising a double-stranded DNA molecule consisting essentially of double-stranded IBR viral DNA homologous to the genomic DNA which flanks on each side the DNA to be deleted. The present invention further provides a recombinant IBR virus comprising viral DNA from a naturally-occurring IBR virus from which DNA from the US2 gene, the gpE glycoprotein gene and the gpG glycoprotein gene has been deleted so that upon replication, the recombinant IBR virus produces no gpE glycoprotein and no gpG glycoprotein. The invention also provides a vaccine which comprises an effective immunizing amount of a recombinant virus protective against bovine respiratory disease complex and a suitable carrier.

BRIEF DESCRIPTION OF THE FIGURES

FIG. 3 DNA sequence of the IBR Unique Short 2 gene. The sequence of the first 1080 base pairs of the HindIII K fragment, reading from the HindIII K/HindIII O junction, are shown. The unique short 2 (US2) gene is transcribed toward the HindIII K/HindIII O junction as indicated in FIG. 1. The sequence has been reversed and complemented in order to show the translation start and termination of US2 gene.

FIGS. 5A and 5B Details of the Nasalgen deletion. Diagram of IBR genomic DNA showing the unique long, internal repeat, unique short, and terminal repeat regions. A restriction map for the enzyme HindIII is indicated. Fragments are lettered in order of decreasing size. The unique short region is expanded for inclusion of more detail. The location of the deletion in the Nasalgen HindIII K fragment is shown. Three regions of DNA sequence are also shown. The first line shows the first 60 base pairs upstream of the HindIII O/HindIII D junction in the IBR Cooper strain. The second line shows the first 60 base pairs upstream of the HindIII K/HindIII D junction in the Nasalgen strain. The third line shows 60 base pairs flanking the DNA encoding amino acid 59 of the IBR US2 gene in the IBR cooper strain.

FIG. 8 DNA sequence of the IBR glycoprotein G gene. The sequence of approximately 1400 base pairs of the HindIII K fragment, starting approximately 2800 base pairs downstream of the HindIII K/HindIII O junction, are shown. The glycoprotein G (gpG) gene is transcribed away from the HindIII K/HindIII O junction as indicated in FIG. 1. The translational start and termination of the gpG gene are indicated.

FIG. 10 Western blot of proteins released into the medium of IBR and PRV infected cells, showing the absence of gpG in S-PRV-013, S-IBR-035, S-IBR-036, S-IBR-037, and S-IBR-038 but its presence in S-PRV-160 and wild type S-IBR-000. Lanes (A) 0.5 μg purified gpG, (B) blank lane, (C) S-PRV-160, (D) S-PRV-013, (E) pre-stained molecular weight markers, (F) 0.5 μg purified gpG, (G) S-IBR-038, (H) S-IBR-037, (I) S-IBR-036, (J) S-IBR-035, (K) S-IBR-000, (L) uninfected MDBK cells, (M) pre-stained molecular weight markers. Media samples were prepared as described in the PREPARATION OF HERPESVIRUS CELL LYSATES. The concentrated media from the infection of one 6 cm dish of infected cells was loaded in each sample lane except for samples S-PRV-013 and S-PRV-160 for which the media from two 6 cm dishes were loaded.

FIGS. 12A–12D Detailed description of the DNA insertion in Homology Vector 439-01.31. Diagram showing the orientation of DNA fragments assembled in plasmid 439-01.31. The origin of each fragment is indicated in the table. The sequences located at each of the junctions between fragments is also shown. The restriction sites used to generate each fragment as well as synthetic linker sequences which were used to join the fragments are described for each junction. The synthetic linker sequences are underlined by a heavy bar. The location of several gene coding regions and regulatory elements is also given. The following two conventions are used: numbers in parentheses, ( ), refer to amino acids, and restriction sites in brackets, [ ], indicate the remnants of sites which were destroyed during construction. The following abbreviations are used: unique short 2 (US2), glycoprotein G (gpG), glycoprotein IV (gpIV), polyadenylation signal (pA), infectious bovine rhinotracheitis virus (IBR), pseudorabies virus (PRV), and human cytomegalovirus (HCMV).

FIGS. 13A–13C Detailed description of the DNA insertion in Homology Vector 439-21.69. Diagram showing the orientation of DNA fragments assembled in plasmid 439-21.69. The origin of each fragment is indicated in the table. The sequences located at each of the junctions between fragments is also shown. The restriction sites used to generate each fragment as well as synthetic linker sequences which were used to join the fragments are described for each junction. The synthetic linker sequences are underlined by a heavy bar. The location of several gene coding regions and regulatory elements is also given. The following two conventions are used: numbers in parentheses, ( ), refer to amino acids, and restriction sites in brackets, [ ], indicate the remnants of sites which were destroyed during construction. The following abbreviations are used: unique short 2 (US2), glycoprotein G (gpG), glycoprotein IV (gpIV), polyadenylation signal (pA), infectious bovine rhinotracheitis virus (IBR), pseudorabies virus (PRV), and human cytomegalovirus (HCMV).

FIGS. 14A and 14B Detailed description of the DNA insertion in Homology Vector 439-70.4. Diagram showing the orientation of DNA fragments assembled in plasmid 439-70.4. The origin of each fragment is indicated in the table. The sequences located at each of the junctions between fragments is also shown. The restriction sites used to generate each fragment as well as synthetic linker sequences which were used to join the fragments are described for each junction. The synthetic linkers sequences are underlined by a heavy bar. The location of several gene coding regions and regulatory elements is also given. The following two conventions are used: numbers in parentheses, ( ), refer to amino acids, and restriction sites in brackets, [ ], indicate the remnants of sites which were destroyed during construction. The following abbreviations are used: glycoprotein G (gpG), glycoprotein IV (gpIV), and infectious bovine rhinotracheitis virus (IBR).

FIGS. 15A and 15B DNA sequence of the IBR glycoprotein E gene. The sequence of 2038 base pairs of the IBR unique short region, starting approximately 1325 base pairs upstream in the HindIII K/HindIII F junction in the HindIII K fragment, are shown. The glycoprotein E (gpE) gene is transcribed toward the HindIII K/HindIII F junction as indicated in FIG. 1. The translation start and termination of the gpE gene are indicated. Note that IUPAC-IUB Biochemical Nomenclature Commission conventions are used.

FIGS. 16A and 16B Homology between the IBR gpE protein and the gpE protein of HSV-1, the gpI protein of VZV, and the gI protein of PRV. (a) Matrix plot of the amino acid sequence of the IBR gpE protein (617) against the amino acid sequence of the PRV gI protein (577) (64). (b) Alignment of the conserved region between IBR gpE protein, PRV gI protein, and VZV gpI protein (37).

FIGS. 18A–18E Detailed description of the DNA insertion in the homology vector 536-03.5. Diagram showing the orientation of DNA fragments to be assembled in the homology vector. The origin of each fragment is indicated in the table. The sequences located at each of the junctions between fragments is also shown. The restriction sites used to generate each fragment as well as synthetic linker sequences which were used to join the fragments are described for each junction. The synthetic linker sequences are underlined by a heavy bar. The location of several gene coding regions and regulatory elements is also given. The following two conventions are used: numbers in parentheses, ( ), refer to amino acids, and restriction sites in brackets, [ ], indicate the remnants of sites which were destroyed during construction. The following abbreviations are used: glycoprotein E (gpE), immediate early promoter (IE), infectious bovine rhinotracheitis virus (IBR), and pseudorabies virus (PRV).

DETAILED DESCRIPTION OF THE INVENTION

Figure 1:
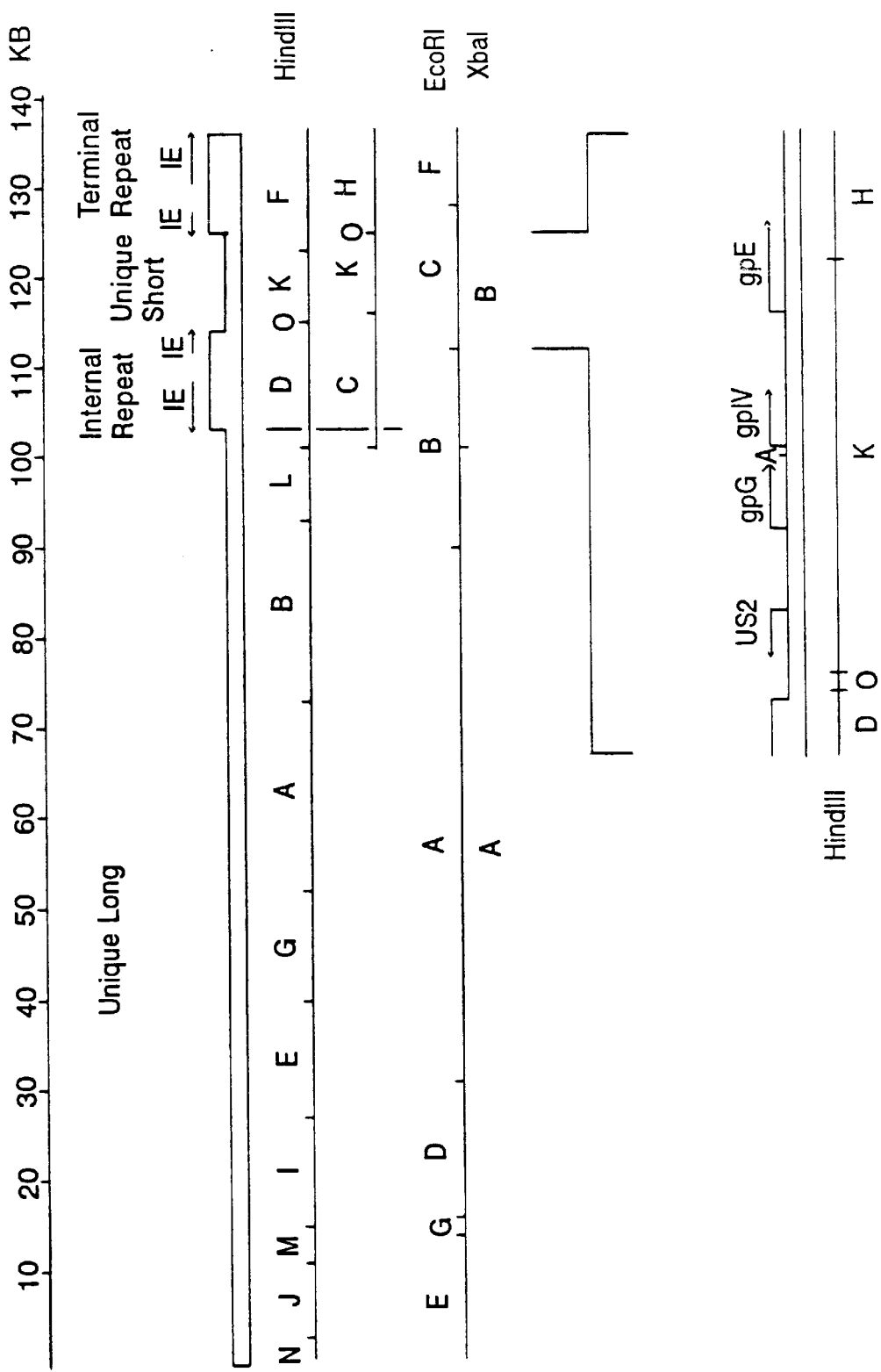
FIG. 1 Details of the IBR Cooper Strain. Diagram of IBR genomic DNA showing the unique long, internal repeat, unique short, and Terminal repeat regions. Restriction maps for the enzymes HindIII, EcoRI, and XbaI are indicated (7). Fragments are lettered in order of decreasing size. The unique short region is also expanded for inclusion of more detail. The location of several genes is also indicated, they are unique short 2 (US2), immediate early genes (IE) (20), glycoprotein G (gpG), glycoprotein IV (gpIV) (17), glycoprotein E (gpE). Note that due to the inversion of the short region, which includes the unique short, internal, and terminal repeats, four half molar HindIII fragments are present (HindIII D, C, F, and H).
Figure 2:
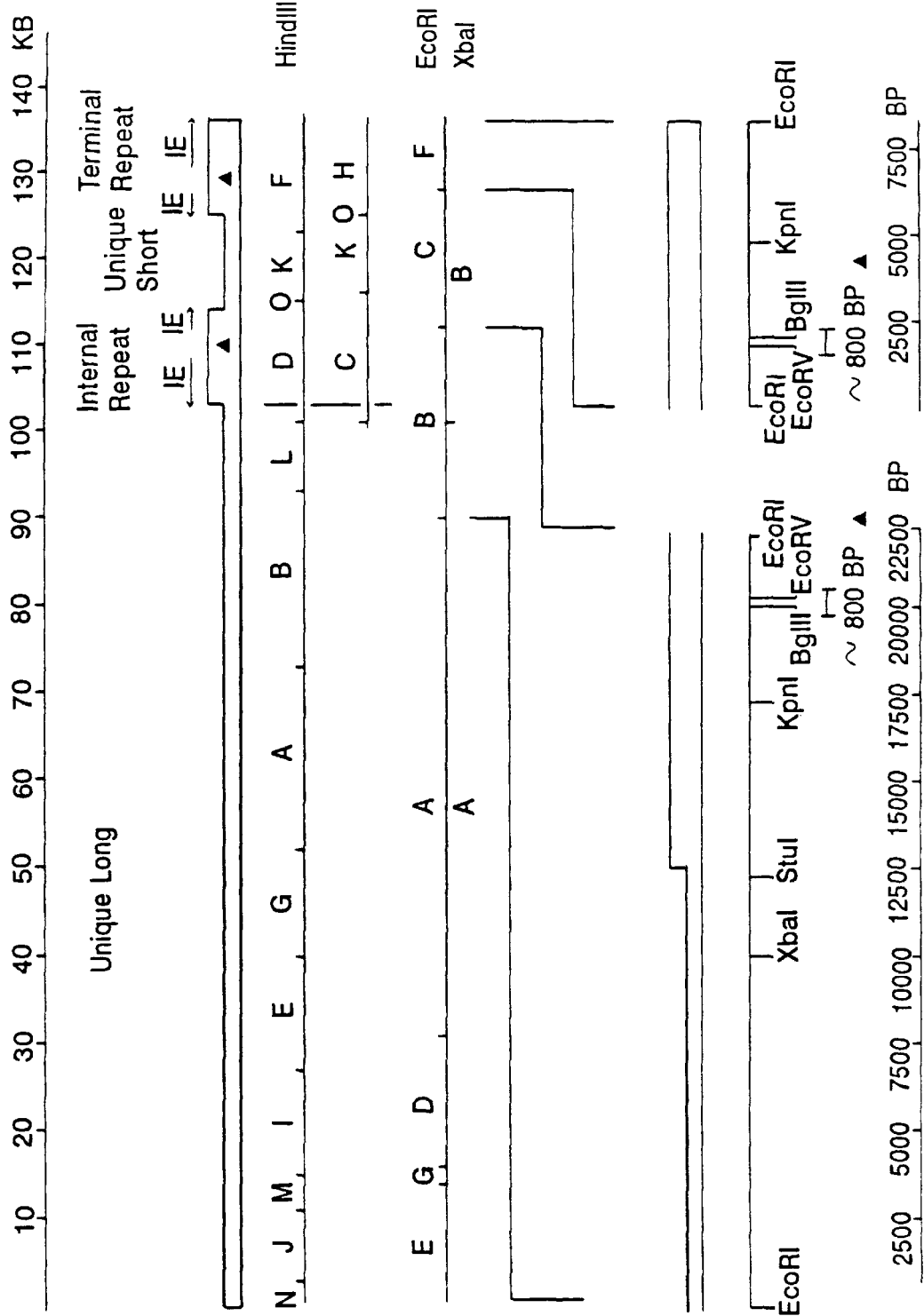
FIG. 2 Details of S-IBR-002. Diagram of S-IBR-002 genomic DNA showing the unique long, internal repeat, unique short, and Terminal repeat regions. Restriction maps for the enzymes HindIII, EcoRI, and XbaI are indicated (7). Fragments are lettered in order of decreasing size. The EcoRI B and F fragments are-expanded for inclusion of more detail. The ~800 BP repeat deletions are indicated by deltas. Note that due to the inversion of the short region, which includes the unique short, internal, and terminal repeats, four half molar HindIII fragments are present (HindIII D, C, F, and H).
Figures 4A, 4B:
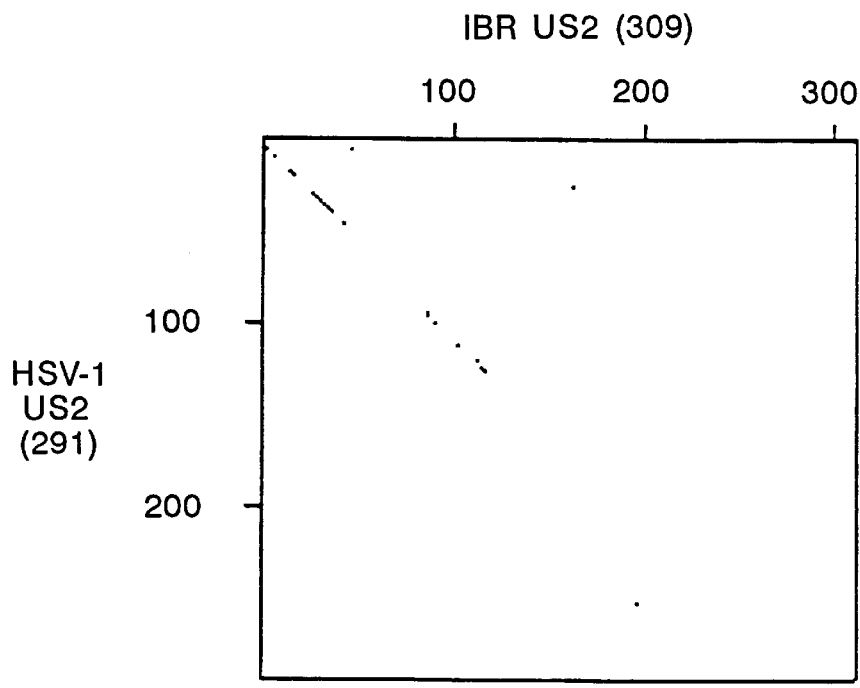
FIGS. 4A and 4B Homology between the IBR US2 protein and the US2 proteins of HSV-1, PRV, HSV-2, and MDV. (a) Matrix plot of the amino acid sequence of the IBR US2 protein (309) against the amino acid sequence of the HSV-1 US2 protein (291) (8). (b) Alignment of the conserved region between IBR US2 protein, HSV-1 US2 protein, PRV US2 protein (256 amino acids) (21), HSV-2 US2 protein (291) (9), and MDV US2 protein (270 amino acids) (1).
Figure 5A:
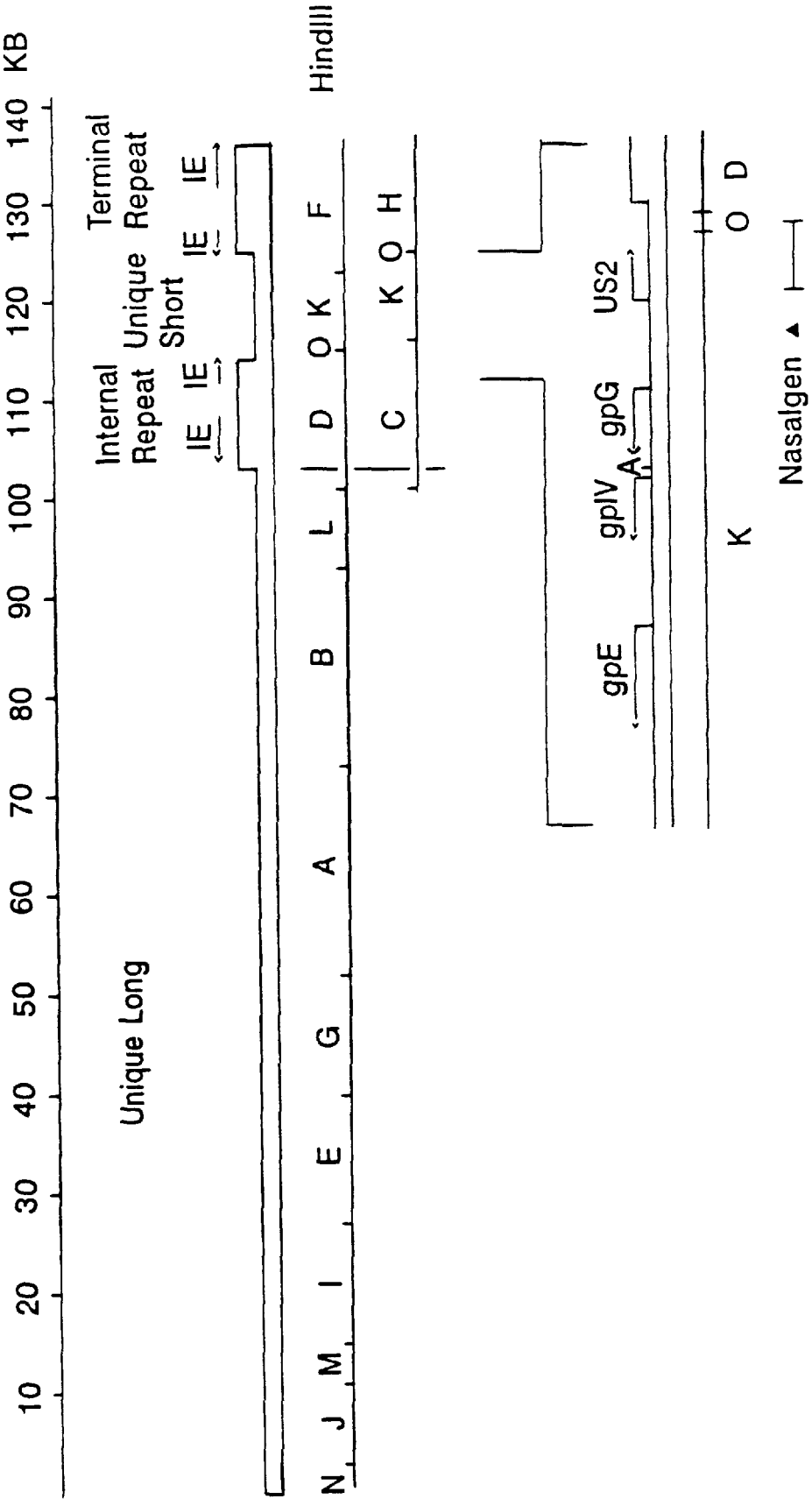
Figure 6:
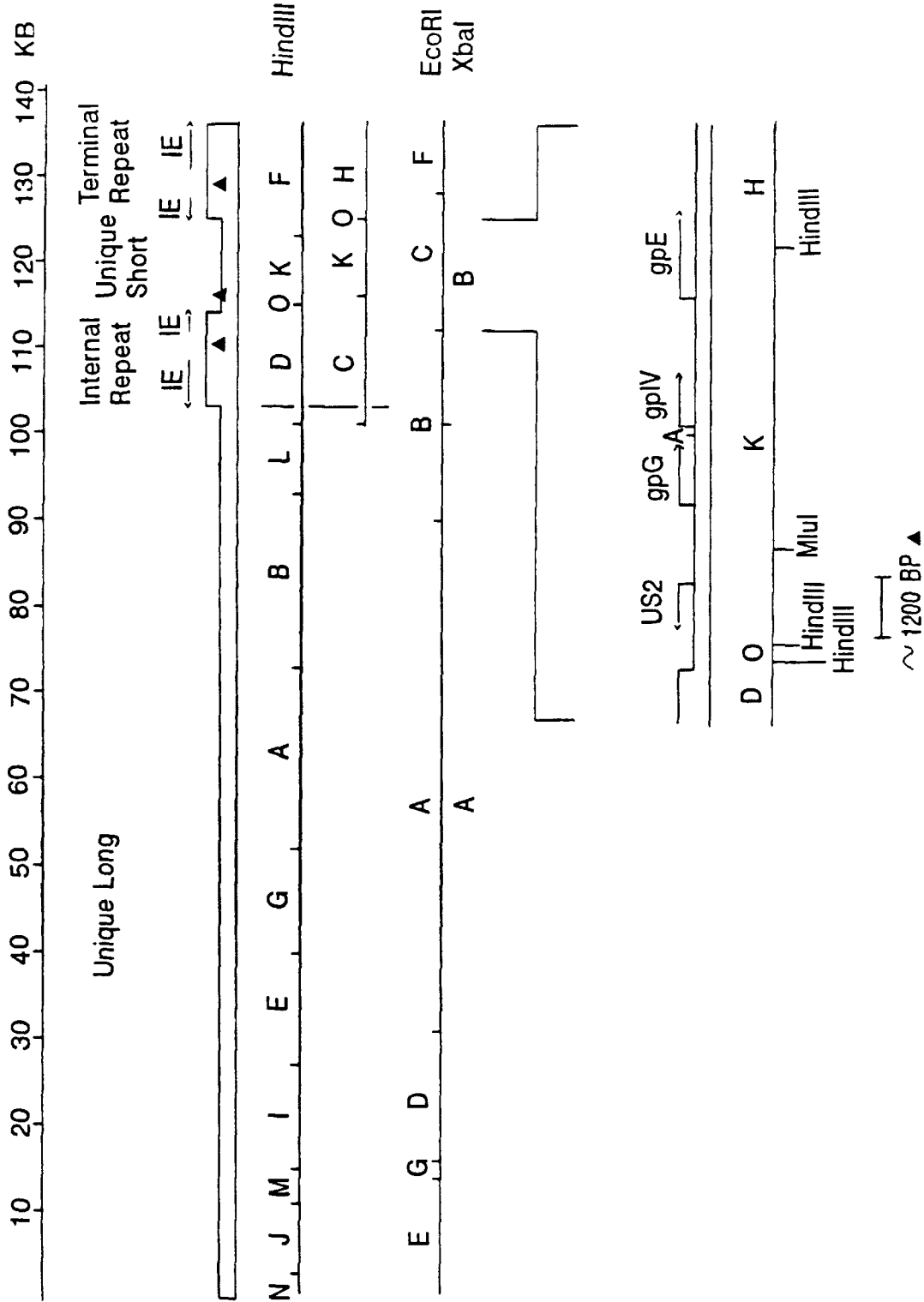
FIG. 6 Details of S-IBR-027. Diagram of S-IBR-027 genomic DNA showing the unique long, internal repeat, unique short, and terminal repeat regions. Restriction maps for the enzymes HindIII, EcoRI, and XbaI are indicated (7). Fragments are lettered in order of decreasing size. The unique short region is also expanded for inclusion of more detail. The location of several genes is also indicated, they are unique short 2 (US2), immediate early genes (IE) (20), glycoprotein G (gpG), glycoprotein IV (gpIV) (17), glycoprotein E (gpE). The unique short region and repeat region deletions are indicated by deltas. The location of the approximately 1200 BP deletion of the US2 gene is shown in the expanded region. Note that due to the inversion of the short region, which includes the unique short, internal, and terminal repeats, four half molar HindIII fragments are present (HindIII D, C, F, and H).

The present invention provides a recombinant IBR virus comprising viral DNA from a naturally-occurring IBR virus in which DNA encoding gpG glycoprotein has been altered or deleted so that upon replication the recombinant IBR virus produces no gpG glycoprotein. The DNA encoding gpG glycoprotein may be deleted or foreign DNA may be inserted into the DNA encoding gpG glycoprotein. The DNA encoding gpG glycoprotein may be deleted and foreign DNA may be inserted in place of the deleted DNA encoding gpG glycoprotein.

The present invention further provides a recombinant IBR virus comprising viral DNA from a naturally-occurring IBR virus in which DNA encoding gpG glycoprotein has been altered or deleted and DNA encoding the gpE glycoprotein has been altered or deleted so that upon replication the recombinant IBR virus produces no gpG glycoprotein and no gpE glycoprotein. The DNA encoding gpE glycoprotein may be deleted or foreign DNA may be inserted into the DNA encoding gpE glycoprotein. The DNA encoding gpE glycoprotein may be deleted and foreign DNA may be inserted in place of the deleted DNA encoding gpE glycoprotein.

The present invention further provides a recombinant IBR virus comprising viral DNA from a naturally-occurring IBR virus in which DNA encoding gpG glycoprotein has been altered or deleted so that upon replication the recombinant IBR virus produces no gpG glycoprotein, DNA corresponding to the US2 region of the naturally-occurring IBR virus has been deleted, and DNA encoding the gpE glycoprotein has been altered or deleted.

The present invention also provides a recombinant IBR virus comprising viral DNA from a naturally-occurring IBR virus in which (1) DNA corresponding to the US2 region of the naturally-occurring IBR virus has been deleted, and (2) DNA encoding gpG glycoprotein has been altered or deleted. The DNA encoding the gpG glycoprotein may be deleted or foreign DNA may be inserted in place of the deleted DNA encoding gpG glycoprotein. Foreign DNA may be inserted in place of the deleted DNA corresponding to the US2 region of the naturally-occurring IBR virus.

The present invention also provides S-IBR-037, a recombinant IBR virus comprising viral DNA from a naturally-occurring IBR virus in which (1) DNA corresponding to the US2 region of the naturally-occurring IBR virus has been deleted, and (2) DNA encoding gpG glycoprotein has been deleted. S-IBR-037 was deposited on Apr. 16, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2320.

The present invention also provides a recombinant IBR virus comprising viral DNA from a naturally-occurring IBR virus in which (1) DNA corresponding to the US2 region of the naturally-occurring IBR virus has been deleted and a foreign DNA sequence which encodes *Escherichia coli* β-galactosidase has been inserted in place of the deleted DNA encoding gpG glycoprotein, and (2) DNA encoding gpG glycoprotein has been altered or deleted. The present invention also provides two examples of such viruses, S-IBR-035 and S-IBR-036.

The present invention further provides a recombinant IBR virus comprising viral DNA from a naturally-occurring IBR virus in which DNA encoding gpE glycoprotein has been altered or deleted so that upon replication the recombinant IBR virus produces no gpE glycoprotein. The DNA encoding gpE glycoprotein may be deleted or foreign DNA may be inserted in the DNA encoding gpE glycoprotein. The DNA encoding gpE glycoprotein may be deleted and foreign DNA may be inserted in place of the deleted DNA encoding gpE glycoprotein.

The present invention further provides a recombinant IBR virus comprising viral DNA from a naturally-occurring IBR virus in which DNA encoding gpE glycoprotein has been altered or deleted so that upon replication the recombinant IBR virus produces no gpE glycoprotein and DNA corresponding to the US2 region of the naturally-occurring IBR virus has been deleted.

The present invention further provides a recombinant IBR virus comprising viral DNA from a naturally-occurring IBR virus from which DNA in the unique short region of the naturally-occurring IBR virus has been deleted. Foreign DNA may be inserted into the DNA of the recombinant IBR virus. The foreign DNA may be inserted into the XbaI site in the long unique region. The foreign DNA may be a sequence which encodes bovine rotavirus glycoprotein 38; this sequence may be inserted into the XbaI site in the long unique region.

The present invention provides S-IBR-008, a recombinant IBR virus comprising viral DNA from a naturally-occurring IBR virus from which DNA corresponding to the US2 region of the naturally-occurring IBR virus has been deleted and in which a foreign DNA sequence which encodes bovine rotavirus glycoprotein 38 has been inserted into the XbaI site in the long unique region. S-IBR-008 was deposited on Jun. 18, 1986 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2141.

The present invention further provides a recombinant IBR virus comprising viral DNA from a naturally-occurring IBR virus from which (1) DNA corresponding to the US2 region of the naturally-occurring IBR virus has been deleted and (2) at least a portion of both repeat sequences has been deleted. The present invention further provides an example of such a recombinant virus, designated S-IBR-027. S-IBR-027 was deposited on Apr. 17, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2322.

The present invention further provides a recombinant IBR virus comprising viral DNA from a naturally-occurring IBR virus from which at least a portion of both repeat sequences has been deleted.

The present invention further provides a recombinant IBR virus comprising viral DNA from a naturally occurring IBR virus from which (1) at least a portion of both repeat sequences has been deleted and (2) DNA encoding one or more EcoRV restriction sites has been deleted. The present invention further provides an example of such a recombinant virus, designated S-IBR-002. S-IBR-002 was deposited on Jun. 18, 1986 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2140.

The present invention further provides a recombinant IBR virus comprising viral DNA from a naturally-occurring IBR virus from which (1) at least a portion of both repeat sequences has been deleted and (2) wherein foreign DNA has been inserted into the DNA of the recombinant IBR virus. The foreign DNA may be a sequence which encodes the Tn5 NEO gene.

The present invention further provides S-IBR-020, a recombinant IBR virus comprising viral DNA from a naturally-occurring IBR virus from which (1) at least a portion of both repeat sequences has been deleted and (2) wherein a foreign DNA sequence which encodes the Tn5 NEO gene has been inserted into the DNA of the recombinant IBR virus.

The present invention also provides a recombinant IBR virus comprising viral DNA from a naturally-occurring IBR virus from which (1) at least a portion of both repeat sequences has been deleted, (2) wherein a foreign DNA sequence which encodes the Tn5 NEO gene has been inserted into the DNA of the recombinant IBR virus, and (3) wherein at least a portion of the thymidine kinase gene has been deleted.

The present invention also provides a recombinant IBR virus comprising viral DNA from a naturally-occurring IBR virus from which (1) at least a portion of both repeat sequences has been deleted, (2) wherein a foreign DNA sequence which encodes the Tn5 NEO gene has been inserted into the DNA of the recombinant IBR virus, and (3) wherein at least a portion of the thymidine kinase gene has been deleted. The subject invention provides an example of such a recombinant virus, designated S-IBR-028. S-IBR-028 was deposited on May 14, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2326.

The present invention further provides a recombinant IBR virus comprising viral DNA from a naturally-occurring IBR virus in which a foreign DNA sequence which encodes the Tn5 NEO gene has been inserted into the viral DNA. The Tn5 NEO gene may be under the control of an inserted, upstream, pseudorabies virus glycoprotein X promoter. The subject invention further provides an example of a recombinant virus wherein the Tn5 NEO gene is under the control of an inserted, upstream, pseudorabies virus glycoprotein X promoter, designated S-IBR-004. S-IBR-004 was deposited on May 23, 1986 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2134.

The subject invention further provides a recombinant IBR virus comprising viral DNA from a naturally-occurring IBR virus in which a foreign DNA sequence which encodes the *Escherichia coli* β-galactosidase and Tn5 NEO genes, and the parainfluenza type 3 virus hemagglutinin gene, HN, has been inserted into the viral DNA. The subject invention provides an example of such a recombinant virus, designated S-IBR-018.

The subject invention further provides a recombinant IBR virus comprising viral DNA from a naturally-occurring IBR virus in which a foreign DNA sequence which encodes the *Escherichia coli* β-galactosidase and Tn5 NEO genes, and the parainfluenza type 3 virus fusion gene, F, has been inserted into the viral DNA. The subject invention provides an example of such a recombinant virus, designated S-IBR-019.

The recombinant viruses of the subject invention were derived from the Cooper Strain. However, other IBR viruses, such as the LA strain or the 3156 strain, may also be used.

The subject invention also provides a vaccine which comprises a suitable carrier and an effective immunizing amount of any of the recombinant viruses of the present invention. The vaccine may contain either inactivated or live recombinant virus.

Suitable carriers for the recombinant virus are well known in the art and include proteins, sugars, etc. One example of such a suitable carrier is a physiologically balanced culture medium containing one or more stabilizing agents such as hydrolyzed proteins, lactose, etc. Preferably, the live vaccine is created by taking tissue culture fluids and adding stabilizing agents such as stabilized, hydrolyzed proteins. Preferably, the inactivated vaccine uses tissue culture fluids directly after inactivation of the virus.

The subject invention also provides a vaccine which comprises a suitable carrier and an effective immunizing amount of a recombinant virus comprising viral DNA from a naturally-occurring IBR virus in which DNA encoding gpG glycoprotein has been altered or deleted so that upon replication the recombinant IBR virus produces no gpG glycoprotein.

The subject invention provides a vaccine which comprises a suitable carrier and an effective immunizing amount of a recombinant IBR virus comprising viral DNA from a naturally-occurring IBR virus in which DNA encoding gpG glycoprotein has been altered or deleted and DNA encoding the gpE glycoprotein has been altered or deleted so that upon replication the recombinant IBR virus produces no gpG glycoprotein and no gpE glycoprotein.

The subject invention also provides a vaccine which comprises a suitable carrier and an effective immunizing amount of a recombinant IBR virus comprising viral DNA from a naturally-occurring IBR virus in which DNA encoding gpG glycoprotein has been altered or deleted so that upon replication the recombinant IBR virus produces no gpG glycoprotein, DNA corresponding to the US2 region of the naturally-occurring IBR virus has been deleted, and DNA encoding the gpE glycoprotein has been altered or deleted.

The subject invention further provides a vaccine which comprises a suitable carrier and an effective immunizing amount of a recombinant IBR virus comprising viral DNA from a naturally-occurring IBR virus in which (1) DNA corresponding to the US2 region of the naturally-occurring IBR virus has been deleted, and (2) DNA encoding gpG glycoprotein has been altered or deleted.

The subject invention also provides a vaccine which comprises a suitable carrier and an effective immunizing amount of a recombinant IBR virus comprising viral DNA from a naturally-occurring IBR virus in which DNA encoding gpE glycoprotein has been altered or deleted so that upon replication the recombinant IBR virus produces no gpE glycoprotein.

The subject invention provides a vaccine which comprises a suitable carrier and an effective immunizing amount of a recombinant IBR virus comprising viral DNA, from a naturally-occurring IBR virus in which DNA encoding gpE glycoprotein has been altered or deleted so that upon replication the recombinant IBR virus produces no gpE glycoprotein and DNA corresponding to the US2 region of the naturally-occurring IBR virus has been deleted.

The subject invention also provides a vaccine which comprises a suitable carrier and an effective immunizing amount of a recombinant IBR virus comprising viral DNA from a naturally-occurring IBR virus from which DNA corresponding to the US2 region of the naturally-occurring IBR virus has been deleted.

The subject invention provides a vaccine which comprises a suitable carrier and an effective immunizing amount of a recombinant IBR virus comprising viral DNA from a naturally-occurring IBR virus from which at least a portion of both repeat sequences has been deleted.

The subject invention further provides a vaccine which comprises a suitable carrier and an effective immunizing amount of a recombinant IBR virus comprising viral DNA from a naturally-occurring IBR virus in which a foreign DNA sequence which encodes the Tn5 NEO gene has been inserted into the viral DNA.

The subject invention also provides a vaccine which comprises a suitable carrier and an effective immunizing amount of a recombinant IBR virus comprising viral DNA from a naturally-occurring IBR virus in which a foreign DNA sequence which encodes the *Escherichia coli* β-galactosidase and Tn5 NEO genes, and the parainfluenza type 3 virus hemagglutinin gene,. HN, has been inserted into the viral DNA.

The subject invention also provides a vaccine which comprises a suitable carrier and an effective immunizing amount of a recombinant IBR virus comprising viral DNA from a naturally-occurring IBR virus in which a foreign DNA sequence which encodes the *Escherichia coli* β-galactosidase and Tn5 NEO genes, and the parainfluenza type 3 virus fusion gene, F, has been inserted into the viral DNA.

All of the vaccines described hereinabove and hereinbelow may contain either inactivated or live recombinant virus. The vaccines may be administered by any of the methods well known to those skilled in the art, for example, by intramuscular, subcutaneous, intraperitoneal, or intravenous injection. Alternatively, the vaccine may be administered intranasally or orally.

The present invention also provides a method of immunizing an animal against infectious bovine rhinotracheitis virus which comprises administering to the animal an effective immunizing dose of any of the vaccines of the present invention. The animal may be a bovine.

The subject invention also provides a method for distinguishing an animal vaccinated with a vaccine which comprises an effective immunizing amount of a recombinant virus of the present invention from an animal infected with a naturally-occurring IBR virus which comprises analyzing a sample of a body fluid from the animal for the presence of gpG glycoprotein of IBR virus and at least one other antigen normally expressed in an animal infected by a naturally-occurring IBR virus, identifying antigens which are present in the body fluid, and determining whether gpG glycoprotein is present in the body fluid. The presence of antigens which are normally expressed in an animal by a naturally-occurring IBR virus and the absence of gpG glycoprotein in the body fluid is indicative of an animal vaccinated with the vaccine and not infected with a naturally-occurring IBR virus. The presence of antigens and gpG glycoprotein in the body fluid may be determined by detecting in the body fluid antibodies specific for the antigens and gpG glycoprotein.

One of the vaccines that is useful in this method is a vaccine which comprises a suitable carrier and an effective immunizing amount of a recombinant virus comprising viral DNA from a naturally-occurring IBR virus in which DNA encoding gpG glycoprotein has been altered or deleted so that upon replication the recombinant IBR virus produces no gpG glycoprotein. Another vaccine that is useful in this method is a vaccine which comprises a suitable carrier and an effective immunizing amount of a recombinant IBR virus comprising viral DNA from a naturally-occurring IBR virus in which DNA encoding gpG glycoprotein has been altered or deleted and DNA encoding the gpE glycoprotein has been altered or deleted so that upon replication the recombinant IBR virus produces no gpG glycoprotein and no gpE glycoprotein. Yet another vaccine that is useful in this method is a vaccine which comprises a suitable carrier and an effective immunizing amount of a recombinant IBR virus comprising viral DNA from a naturally-occurring IBR virus in which DNA encoding gpG glycoprotein has been altered or deleted so that upon replication the recombinant IBR virus produces no gpG glycoprotein, DNA corresponding to the US2 region of the naturally-occurring IBR virus has been deleted, and DNA encoding the gpE glycoprotein has been altered or deleted. Still another vaccine that is useful in this method is a vaccine which comprises a suitable carrier and an effective immunizing amount of a recombinant IBR virus comprising viral DNA from a naturally-occurring IBR virus in which (1) DNA corresponding to the US2 region of the naturally-occurring IBR virus has been deleted, and (2) DNA encoding gpG glycoprotein has been altered or deleted.

The present invention also provides a method for distinguishing an animal vaccinated with a vaccine which comprises an effective immunizing amount of a recombinant virus of the present invention from an animal infected with a naturally-occurring IBR virus which comprises analyzing a sample of a body fluid from the animal for the presence of gpE glycoprotein of IBR virus and at least one other antigen normally expressed in an animal infected by a naturally-occurring IBR virus, identifying antigens which are present in the body fluid and determining whether gpE glycoprotein is present in the body fluid. The presence of antigens which are normally expressed in an animal by a naturally-occurring IBR virus and the absence of gpE glycoprotein in the body fluid is indicative of an animal vaccinated with the vaccine and not infected with a naturally-occurring IBR virus. The presence of antigens and gpE glycoprotein in the body fluid may be determined by detecting in the body fluid antibodies specific for the antigens and gpE glycoprotein.

One of the vaccines useful in this method is a vaccine which comprises a suitable carrier and an effective immunizing amount of a recombinant IBR virus comprising viral DNA from a naturally-occurring IBR virus in which DNA encoding gpG glycoprotein has been altered or deleted and DNA encoding the gpE glycoprotein has been altered or deleted so that upon replication the recombinant IBR virus produces no gpG glycoprotein and no gpE glycoprotein. Another vaccine that is useful in this method is a vaccine which comprises a suitable carrier and an effective immunizing amount of a recombinant IBR virus comprising viral DNA from a naturally-occurring IBR virus in which DNA encoding gpG glycoprotein has been altered or deleted so that upon replication the recombinant IBR virus produces no gpG glycoprotein, DNA corresponding to the US2 region of the naturally-occurring IBR virus has been deleted, and DNA encoding the gpE glycoprotein has been altered or deleted. Yet another vaccine that is useful in this method is a vaccine which comprises a suitable carrier and an effective immunizing amount of a recombinant IBR virus comprising viral DNA from a naturally-occurring IBR virus in which DNA encoding gpE glycoprotein has been altered or deleted so that upon replication the recombinant IBR virus produces no gpE glycoprotein. Still another vaccine that is useful in this method is a vaccine which comprises a suitable carrier and an effective immunizing amount of a recombinant IBR virus comprising viral DNA from a naturally-occurring IBR virus in which DNA encoding gpE glycoprotein has been altered or deleted so that upon replication the recombinant IBR virus produces no gpE glycoprotein and DNA corresponding to the US2 region of the naturally-occurring IBR virus has been deleted.

The present invention also provides isolated DNA encoding the gpG glycoprotein of IBR virus. The subject invention also provides purified recombinant gpG glycoprotein encoded by the DNA encoding the gpG glycoprotein of IBR virus. The subject invention further provides a recombinant cloning vector which comprises the DNA encoding the gpG glycoprotein of IBR virus. The subject invention also provides a recombinant expression vector which comprises the DNA encoding the gpG glycoprotein of IBR virus. The subject invention provides a host cell which comprises the recombinant expression vector which comprises the DNA encoding the gpG glycoprotein of IBR virus.

The subject invention also provides a method of producing a polypeptide which comprises growing the host cell which comprises the recombinant expression vector which comprises the DNA encoding the gpG glycoprotein of IBR virus under conditions such that the recombinant expression vector expresses gpG glycoprotein and recovering the gpG glycoprotein so expressed.

The subject invention also provides an antibody directed to an epitope of the purified gpG glycoprotein of IBR virus encoded by the DNA encoding the gpG glycoprotein of IBR virus. The antibody may be a monoclonal antibody.

The subject invention also provides a method of detecting the presence or absence of gpG glycoprotein of IBR virus in a sample which comprises contacting the sample with an antibody directed to an epitope of the purified gpG glycoprotein of IBR virus encoded by the DNA encoding the gpG glycoprotein of IBR virus under conditions such that the antibody forms a complex with any gpG glycoprotein present in the sample and detecting the presence or absence of such complex. The sample may be bovine-derived.

The subject invention also provides isolated DNA encoding the gpE glycoprotein of IBR virus. The subject invention also provides purified recombinant gpE glycoprotein encoded by the DNA encoding the gpE glycoprotein of IBR virus. The subject invention further provides a recombinant cloning vector which comprises the DNA encoding the gpE glycoprotein of IBR virus. The subject invention provides a recombinant expression vector which comprises the DNA encoding the gpE glycoprotein of IBR virus. The subject invention also provides a host cell which comprises the recombinant expression vector which comprises the DNA encoding the gpE glycoprotein of IBR virus.

The subject invention also provides a method of producing a polypeptide which comprises growing the host cell which comprises the recombinant expression vector which comprises the DNA encoding the gpE glycoprotein of IBR virus under conditions such that the recombinant expression vector expresses gpE glycoprotein and recovering the gpE glycoprotein so expressed.

The subject invention also provides an antibody directed to an epitope of the purified gpE glycoprotein of IBR virus encoded by the DNA encoding the gpE glycoprotein of IBR virus. The antibody may be a monoclonal antibody.

The subject invention also provides a method of detecting the presence or absence of gpE glycoprotein of IBR virus in a sample which comprises contacting the sample with an antibody directed to an epitope of the purified gpE glycoprotein of IBR virus encoded by the DNA encoding the gpE glycoprotein of IBR virus under conditions such that the antibody forms a complex with any gpE glycoprotein present in the sample and detecting the presence or absence of such complex. The sample may be bovine-derived.

The subject invention also provides a method of producing a fetal-safe, live recombinant IBR virus which comprises treating viral DNA from a naturally-occurring live IBR virus so as to delete from the virus DNA corresponding to the US2 region of the naturally-occurring IBR virus.

The subject invention also provides a recombinant pseudorabies virus designated S-PRV-160. The subject invention also provides an antibody which directed to an epitope of the recombinant pseudorabies virus designated S-PRV-160.

The subject invention also provides isolated DNA encoding the US2 gene of an IBR virus. The present invention further provides a homology vector for producing a recombinant IBR virus by inserting foreign DNA into the genomic DNA of an IBR virus which comprises a double-stranded DNA molecule consisting essentially of double-stranded foreign DNA encoding RNA which does not naturally occur in an animal into which the recombinant IBR is introduced, with at one end of the foreign DNA, double-stranded IBR viral DNA homologous to genomic DNA located at one side of a site on the genomic DNA which is not essential for replication of the IBR virus and at the other end of the foreign DNA, double-stranded IBR viral DNA homologous to genomic DNA located at the other side of the same site on the genomic DNA. The double-stranded foreign DNA may further comprise a promoter. The promoter can be from HSV-1 α 4 immediate early gene, Human cytomegalovirus immediate early gene or pseudorabies virus glycoprotein X gene. The double-stranded foreign DNA may further comprise a polyadenylation signal. The polyadenylation signal may be from HSV-1 thymidine kinase gene or pseudorabies virus glycoprotein X gene. The subject invention also provides a homology vector wherein the RNA encodes a polypeptide. The polypeptide may be a detectable marker such as *Escherichia coli* β-galactosidase or bacterial transposon neomycin resistance protein. The DNA which encodes the polypeptide may be flanked on each side by restriction sites permitting said DNA to be cut out with a restriction endonuclease which cuts at a limited number of sites on the genome. The subject invention further provides for a homology vector wherein the upstream double-stranded IBR viral DNA is homologous to genomic DNA present within the approximately 860 bp NcoI to BamHI subfragment of the HindIII A fragment of IBR virus and the downstream double-stranded IBR viral DNA is homologous to genomic DNA present within the approximately 1741 bp BglII to StuI subfragment of the HindIII A fragment of IBR virus.

The subject invention further provides a homology vector wherein upstream double-stranded foreign DNA which comprises a promoter and downstream double-stranded foreign DNA which comprises a polyadenylation signal flank on each side double-stranded foreign DNA which encodes a detectable marker. The invention further a homology vector wherein the upstream promoter is homologous to genomic DNA present within the approximately 490 bp PvuII to BamHI subfragment of the BamHI N fragment of HSV-1 and the downstream polyadenylation signal is homologous to genomic DNA present within the approximately 784 bp SmaI to SmaI subfragment of the BamHI Q fragment of HSV-1. The invention further provides a homology vector wherein the DNA which encodes a detectable marker is homologous to the approximately 1541 bp BglII to BamHI fragment of Tn5.

The subject invention also provides a homology vector wherein the upstream double-stranded IBR viral DNA is homologous to genomic DNA present within the approximately 3593 bp HindIII to XhoI subfragment of the HindIII X fragment of IBR virus and the downstream double-stranded IBR viral DNA is homologous to genomic DNA present within the approximately 785 bp XhoI to NdeI subfragment of the HindIII K fragment of IBR virus. The invention further provides a homology vector wherein upstream double-stranded foreign DNA which comprises a promoter and downstream double-stranded foreign DNA which comprises a polyadenylation signal flank on each side double-stranded foreign DNA which encodes a detectable marker. This upstream promoter is homologous to genomic DNA present within the approximately 1191 bp AvaII to PstI subfragment of the XbaI B fragment of HCMV and the downstream polyadenylation sequence is homologous to genomic DNA present within the approximately 753 bp SalI to NdeI subfragment of the BamHI #7 fragment of PRV. The DNA which encodes a detectable marker is homologous to the approximately 3347 bp BalI to BamHI fragment of pJF751.

The invention further provides a homology vector wherein the upstream double-stranded IBR viral DNA is homologous to genomic DNA present within the approximately 888 bp MluI to SmaI subfragment of the HindIII K fragment of IBR virus and the downstream double-stranded IBR viral DNA is homologous to genomic DNA present within the approximately 785 bp XhoI to NdeI subfragment of the HindIII K fragment of IBR virus. The upstream double-stranded foreign DNA may comprise a promoter and double-stranded foreign DNA which comprise a polyadenylation signal flank on each side double-stranded foreign DNA which encodes a detectable marker. The subject invention also provides a homology vector wherein the upstream promoter is homologous to genomic DNA present within the approximately 1191 bp AvaII to PstI subfragment of the XbaI B fragment of HCMV and the downstream polyadenylation signal is homologous to genomic DNA present within the approximately 753 bp SalI to NdeI subfragment of the BamHI #7 fragment of PRV. The DNA which encodes a detectable marker is homologous to the approximately 3347 bp BalI to BamHI fragment of pJF571.

The present invention further provides a homology vector wherein the upstream double-stranded IBR viral DNA is homologous to genomic DNA present within the approximately 1704 bp SmaI to SmaI subfragment of the HindIII K fragment of IBR virus and the downstream double-stranded IBR viral DNA is homologous to genomic DNA present within the approximately 742 bp NheI to BglI subfragment of the SmaI 2.5 KB fragment of IBR virus. The present invention further provides a homology vector wherein upstream double-stranded foreign DNA which comprises a promoter and downstream -double-stranded foreign DNA which comprises a polyadenylation signal flank on each side double-stranded foreign DNA which encodes a detectable marker. The upstream promoter is homologous to genomic DNA present within the approximately 413 bp SalI to BamHI subfragment of the BamHI #10 fragment of PRV and the downstream polyadenylation signal is homologous to genomic DNA present within the approximately 754 bp NdeI to SalI subfragment of the BamHI #7 fragment of PRV. The detectable marker is homologous to the approximately 3010 bp BamHI to PvuII fragment of pJF751.

The present invention provides for a homology vector for producing a recombinant IBR virus by deleting DNA which encodes a detectable marker which had been inserted into the genomic DNA of an IBR virus comprising a double-stranded DNA molecule consisting essentially of double-stranded IBR viral DNA homologous to the genomic DNA which flank on each side the DNA to be deleted. The subject invention further provides a homology vector wherein the upstream double-stranded IBR viral DNA is homologous to genomic DNA present within the approximately 888 bp MluI to SmaI subfragment of the HindIII K fragment of IBR virus and the downstream double-stranded IBR viral DNA is homologous to genomic DNA present within the approximately 785 bp XhoI to NdeI subfragment of the HindIII K fragment of IBR virus.

The present invention also provides a method of immunizing an animal against infectious bovine rhinotracheitis virus which comprises administering to the animal an effective immunizing dose of any of the vaccines of the present invention. The animal may be a bovine. The subject invention also provides a recombinant IBR virus comprising viral DNA from a naturally-occurring IBR virus from which at least a portion of both repeat sequences have been deleted, specifically, wherein DNA encoding one or more EcoRV restriction sites has been deleted, and wherein foreign DNA has been inserted into the DNA of the recombinant virus. The foreign DNA may be a DNA sequence which encodes bovine viral diarrhea virus glycoprotein gp53. The subject invention provides an example of such a recombinant IBR virus, designated S-IBR-032.

The subject invention provides a recombinant IBR virus comprising viral DNA from a naturally-occurring IBR virus from which DNA from the US2 gene, the gpE glycoprotein gene and the gpG glycoprotein gene have been deleted so that upon replication, the recombinant IBR virus produces no gpE glycoprotein and no gpG glycoprotein. A Foreign DNA sequence may be inserted in place of the deleted DNA which encodes gpE glycoprotein. The foreign DNA sequence that may be inserted can be a foreign DNA sequence which encodes *Escherichia coli* β-galactosidase. The subject invention provides an example of such a recombinant virus, designated S-IBR-039.

The subject invention further provides a recombinant IBR virus comprising viral DNA from a naturally-occurring IBR virus in which DNA from the US2, gpE glycoprotein gene, the gpG glycoprotein gene and the thymidine kinase gene has been deleted so that upon replication, the recombinant IBR virus produces no gpE glycoprotein, no gpG glycoprotein and no thymidine kinase. The subject invention provides an example of such a recombinant virus, designated S-IBR-045. A foreign DNA sequence may be inserted in place of the deleted DNA encoding gpE glycoprotein. The foreign DNA sequence may encode *Escherichia coli* β-galactosidase. The subject invention provides an example of such a recombinant virus, designated S-IBR-044. The foreign DNA sequence may encode bovine viral diarrhea virus gp53 glycoprotein. The subject invention provides an example of such a recombinant virus, designated S-IBR-046. The foreign DNA sequence may encode Parainfluenza virus type 3 fusion protein and Parainfluenza virus type 3 hemagglutinin protein. The subject application provides an example of such a virus, designated S-IBR-047. The foreign DNA sequence may encode Bovine respiratory syncytial virus fusion protein, Bovine respiratory syncytial virus attachment protein and Bovine respiratory syncytial virus nucleocapsid protein. The subject invention provides an example of such a recombinant virus, designated S-IBR-049. The foreign DNA sequence may encode *Pasteurella haemolytica* leukotoxin and *Pasteurella haemolytica* iron regulated outer membrane proteins. The subject invention provides an example of such a recombinant virus, designated S-IBR-051.

The subject invention also provides a recombinant IBR virus comprising viral DNA from a naturally-occurring IBR virus from which DNA from the US2 gene, the gpE glycoprotein gene, the gpG glycoprotein gene and the thymidine kinase gene have been deleted so that upon replication, the recombinant IBR virus produces no gpE glycoprotein, no gpG glycoprotein and no thymidine kinase. The subject invention provides for a foreign DNA sequence inserted in place of the DNA which encodes thymidine kinase. The foreign DNA sequence may encode *Escherichia coli* β-glucuronidase. The present invention further provides a recombinant virus wherein a foreign DNA sequence is inserted in place of the DNA encoding gpE glycoprotein. The foreign DNA sequence may encode *Escherichia coli* β-galactosidase. The present invention further provides an example of such a recombinant virus, designated S-IBR-043.

The subject invention also provides a vaccine which comprises an effective immunizing amount of any of the recombinant viruses of the present invention and a suitable carrier. The vaccine may contain either inactivated or live recombinant virus.

The present invention provides a vaccine which comprises an effective immunizing amount of recombinant virus protective against bovine respiratory disease complex and a suitable carrier. A recombinant virus may be a recombinant IBR virus and the recombinant virus can consist essentially of any or all of the recombinant viruses of the present invention.

The subject invention also provides for a vaccine which comprises an effective immunizing amount of a recombinant virus and non-recombinant virus protective against bovine respiratory disease complex and a suitable carrier.

The subject invention further provides a vaccine which comprises an effective immunizing amount of a recombinant IBR virus and non-recombinant virus protective against bovine respiratory disease complex and a suitable carrier. The recombinant IBR virus can consist essentially of any or all of the recombinant viruses of the subject invention.

For purposes of this invention, the infectious diseases that contribute to bovine respiratory disease complex include infectious bovine rhinotracheitis, parainfluenza type 3 virus, bovine viral diarrhea virus, bovine respiratory syncytial virus and *Pasteurella haemolytica*.

For purposes of the present invention, non-recombinant viruses can include, but are not limited to, conventionally derived viruses which include killed virus, inactivated bacterins, and modified live viruses.

The subject invention further provides for a method of immunizing an animal against infectious bovine rhinotracheitis which comprises administering to the animal an immunizing dose of any of the vaccines of the present invention. The subject invention further provides a method of immunizing an animal against Parainfluenza type 3 which comprises administering to the animal an immunizing dose of the vaccine of the present invention that contains the IBR virus encoding antigens for Parainfluenza type 3 virus. The subject invention further provides a method of immunizing an animal against bovine viral diarrhea which comprises administering to the animal an immunizing dose of the vaccine of the present invention that contains the IBR virus encoding antigens for bovine viral diarrhea virus. The subject invention further provides a method of immunizing an animal against bovine respiratory syncytial virus disease which comprises administering to the animal an immunizing dose of the vaccine of the present invention that contains the IBR virus encoding antigens for bovine respiratory syncytial virus. The subject invention further provides for a method of immunizing an animal against *Pneumonic pasteurellosis* which comprises administering to the animal an immunizing dose of the vaccine of the present invention that contains the IBR virus encoding antigens for *Pasteurella haemolytica*.

The invention further provides a method of immunizing an animal against bovine respiratory disease complex which comprises administering to an animal an immunizing dose of the vaccine containing the recombinant IBR viruses of the present invention or the recombinant viruses of the present invention and non-recombinant viruses. For purposes of this invention, the animal may be a bovine. The invention further provides a method for distinguishing an animal vaccinated with a vaccine which comprises an effective immunizing amount of a recombinant virus of the present invention from an animal infected with a naturally-occurring IBR virus which comprises analyzing a sample of a body fluid from the animal for the presence of gpE glycoprotein of IBR virus and at least one other antigen normally expressed in an animal infected by a naturally-occurring IBR virus, identifying antigens which are present in the body fluid and determining whether gpE glycoprotein is present in the body fluid, the presence of antigens which are normally expressed in an animal by a naturally-occurring IBR virus and the absence of gpE glycoprotein in the body fluid being indicative of an animal vaccinated with the vaccine and not infected with a naturally-occurring IBR virus.

Materials and Methods PREPARATION OF IBR VIRUS STOCK SAMPLES

IBR virus stock samples were prepared by infecting MDBK cells at a multiplicity of infection of 0.01 PFU/cell in Dulbecco's Modified Eagle Medium (DMEM) containing 2 mM glutamine, 100 units/ml penicillin, 100 units/ml streptomycin (these components were obtained from Irvine Scientific or an equivalent supplier, and hereafter are referred to as complete DME medium) plus 1% fetal bovine serum. After cytopathic effect was complete, the medium and cells were harvested and the cells were pelleted at 3000 rpm for 5 minutes in a clinical centrifuge. Cells were resuspended in ⅒ the original volume of medium, and an equal volume of skim milk (9% skim milk powder in $H_2O$ weight/volume) was added. The virus sample was frozen at −70° C. The titers were usually about $10^8$ PFU/ml.

PREPARATION OF HERPESVIRUS DNA

For herpesvirus DNA preparation, a confluent monolayer of cells (MDBK for IBR virus or Vero for PRV) in a 25 cm² flask or 60 mm petri dish was infected with 100 μl of virus sample. After overnight incubation, or when the cells were showing 100% cytopathic effect, the cells were scraped into the medium. The cells and medium were centrifuged at 3000 rpm for 5 minutes in a clinical centrifuge. The medium was decanted, and the cell pellet was gently resuspended in 0.5 ml of solution containing 0.5% NONIDET P-40™ (NP-40, purchased from Sigma Chemical Co., St. Louis, Mo.). The sample was incubated at room temperature for 10 minutes. Ten μl of a stock solution of RNase A (Sigma) was added (stock was 10 mg/ml, boiled for 10 minutes to inactivate DNAse). The sample was centrifuged to pellet nuclei. The DNA pellet was removed with a pasteur pipette or wooden stick and discarded. The supernatant fluid was decanted into a 1.5 ml Eppendorf tube containing 25 μl of 20% sodium dodecyl sulfate (Sigma) and 25 μl proteinase-K (10 mg/ml; Boehringer Mannheim). The sample was mixed and incubated at 37° C. for 30–60 minutes. An equal volume of water-saturated phenol was added and the sample was mixed briefly. The sample was centrifuged in an Eppendorf minifuge for 5 minutes at full speed. The upper aqueous phase was removed to a new Eppendorf tube, and two volumes of absolute ethanol were added and the tube put at −20° C. for 30 minutes to precipitate nucleic acid. The sample was centrifuged in an Eppendorf minifuge for 5 minutes. The supernatant was decanted, and the pellet was washed with ~300 μl of 80% ethanol, followed by centrifugation in an Eppendorf minifuge for 5 minutes. The supernatant was decanted, and the pellet was air dried and rehydrated in ~16 μl $H_2O$. For the preparation of larger amounts of DNA, the procedure was scaled up to start with a 850 cm² roller bottle of MDBK cells. The DNA was stored in 0.01M tris pH 7.5, 1 mM EDTA at 4° C.

PREPARATION OF HERPESVIRUS CELL LYSATES

For cell lysate preparation, serum free medium was used. A confluent monolayer of cells (MDBK for IBR virus or Vero for PRV) in a 25 cm² flask or a 60 mm petri dish was infected with 100 μl of virus sample. After cytopathic effect was complete, the medium and cells were harvested and the cells were pelleted at 3000 rpm for 5 minutes in a clinical centrifuge. For media samples medium was concentrated approximately 10-fold by filtration with a centricon-10 microconcentrator (Amicon). For cell samples the cell pellet was resuspended in 250 μl of disruption buffer (2% sodium dodecyl sulfate, 2% β-mercaptoethanol). The samples were sonicated for 30 seconds on ice and stored at −20° C.

WESTERN BLOTTING PROCEDURE

Samples of lysates, controls and protein standards were run on a polyacrylamide gel according to the procedure of Laemmli (2). After gel electrophoresis the proteins were transferred according to Sambrook (14). The primary antibody was a mouse hyper-immune serum raised against chemically-synthesized gpG peptides (amino acids 232–252 and 267–287) linked to keyhole limpet hemocyanin. The secondary antibody was a goat anti-mouse alkaline phosphatase coupled antibody.

MOLECULAR BIOLOGICAL TECHNIQUES

Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Maniatis (6). Except as noted, these were used with minor variation.

LIGATION

DNA was joined together by the action of the enzyme T4 DNA ligase (BRL). Ligation reactions contained various amounts of DNA (from 0.2 to 20 μg), 20 mM Tris pH 7.5, 10 mM $MgCl_2$, 10 mM dithiothreitol (DTT), 200 μM ATP and 20 units T4 DNA ligase in 10–20 μl final reaction volume. The ligation proceeded for 3–16 hours at 15° C.

DNA SEQUENCING

Sequencing was performed using the BRL Sequenase Kit and $^{35}$S-dATP (NEN). Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence. Sequence obtained was assembled and compared using Dnastar software. Manipulation and comparison of sequences obtained was performed with Superclone and Supersee programs from Coral Software.

SOUTHERN BLOTTING OF DNA

The general procedure for Southern blotting was taken from Maniatis (6). DNA was blotted to nitrocellulose filters and hybridized to appropriate, labeled DNA probes. Probes for southern blots were prepared using either the Nonradioactive DNA Labeling and Detection Kit of Boehringer Mannheim or the nick translation kit of Bethesda Research Laboratories (BRL). In both cases the manufacturers' recommended procedures were followed.

DNA TRANSFECTION FOR GENERATING RECOMBINANT VIRUS

The method is based upon the calcium phosphate procedure of Graham and Van der Eb (24) with the following modifications. Virus and/or plasmid DNA were diluted to 298 μl in 0.01M Tris pH 7.5, 1 mM EDTA. Forty μl 2M $CaCl_2$ was added followed by an equal volume of 2× HEPES buffered saline (10 g N-2-hydroxyethyl piperazine N'-2-ethanesulfonic acid (HEPES), 16 g NaCl, 0.74 g KCl, 0.25 g $Na_2HPO_4.2H_2O$, 2 g dextrose per liter $H_2O$ and buffered with NaOH to pH 7.4). The mixture was then incubated on ice for 10 minutes, and then added dropwise to an 80% confluent monolayer of MDBK or rabbit skin (RS) cells growing in a 60 mm petri dish under 5 ml of medium (DME plus 2% fetal bovine serum). The cells were incubated 4 hours at 37° C. in a humidified incubator containing 5% $CO_2$. The cells were then washed with three 5 ml aliquots of 1×PBS (1.15 g $Na_2HPO_4$, 0.2 g $KH_2PO_4$, 0.8 g NaCl, 0.2 g KCl per liter $H_2O$), and fed with 5 ml of medium (DME plus 2% fetal bovine serum). The cells were incubated at 37° C. as above for 3–7 days until cytopathic effect from the virus was 50–100%. Virus was harvested as described above for the preparation of virus stocks. This stock was referred to as a transfection stock and was subsequently screened for recombinant virus by the BLUOGAL™ SCREEN FOR RECOMBINANT IBR VIRUS.

HOMOLOGOUS RECOMBINATION PROCEDURE FOR GENERATING RECOMBINANT HERPESVIRUS

This method relies upon the homologous recombination between herpesvirus DNA and plasmid homology vector DNA which occurs in tissue culture cells co-transfected with these elements. From 0.1–1.0 μg of plasmid DNA containing foreign DNA flanked by appropriate herpesvirus cloned sequences (the homology vector) were mixed with approximately 0.3 μg of intact herpesvirus DNA. The DNAs were diluted to 298 μl in 0.01M Tris pH 7.5, 1 mM EDTA and transfected into MDBK cells according to the DNA TRANSFECTION FOR GENERATING RECOMBINANT VIRUS (see above).

DIRECT LIGATION PROCEDURE FOR GENERATING RECOMBINANT HERPESVIRUS

Rather than using homology vectors and relying upon homologous recombination to generate recombinant virus, we have also developed the technique of direct ligation to engineer herpesviruses. In this instance, a cloned foreign gene did not require flanking herpesvirus DNA sequences but only required that it have restriction sites available to cut out the foreign gene fragment from the plasmid vector. A compatible restriction enzyme was used to cut herpesvirus DNA. A requirement of the technique was that the restriction enzyme used to cut the herpesvirus DNA must cut at a limited number of sites. We have used XbaI, which cuts IBR virus DNA in one place. We have also used EcoRV which cuts IBR virus DNA in two places. For PRV we have used XbaI and HindIII, both of which cut in two places. Restriction sites previously introduced into herpesviruses by other methods may also be used. The herpesvirus DNA was mixed with a 30-fold molar excess of plasmid DNA (typically 5 μg of virus DNA to 10 μg of plasmid DNA), and the mixture was cut with the appropriate restriction enzyme. The DNA mixture was phenol extracted and ethanol precipitated to remove restriction enzymes, and ligated together according to the ligation procedure detailed above. The ligated DNA mixture was then resuspended in 298 μl 0.01M Tris pH 7.5, 1 mM EDTA and transfected into cells (MDBK or RS for IBR virus and Vero for PRV) according to the DNA TRANSFECTION FOR GENERATING RECOMBINANT VIRUS (see above). The direct ligation procedure may also be used to delete DNA from herpesviruses. Non-essential DNA which is flanked by appropriate restriction enzyme sites may be deleted by digesting the virus DNA with such enzymes and religation. The frequency of engineered viruses generated by the direct ligation procedure is high enough that screening can be accomplished by restriction enzyme analysis of randomly picked plaques from the transfection stock.

BLUOGAL™ SCREEN FOR RECOMBINANT HERPESVIRUS

When the E. coli β-galactosidase (lacZ) marker gene was incorporated into a recombinant virus the plaques containing recombinants were visualized by a simple assay. The chemical BLUOGAL™ (GIBCO-Bethesda Research Labs) was incorporated (200 μg/ml) into the agarose overlay during the plaque assay, and plaques that expressed active β-galactosidase turned blue. The blue plaques were then picked onto fresh cells (MDBK for IBR virus and Vero for PRV) and purified by further blue plaque isolations. In recombinant virus strategies in which the E. coli β-galactosidase marker gene is removed, the assay involves plaque purifying white plaques from a background of parental blue plaques. In both cases viruses were typically purified with three rounds of plaque purification.

SCREEN FOR RECOMBINANT HERPESVIRUS EXPRESSING ENZYMATIC MARKER GENES

When the E. coli β-galactosidase (lacZ) or β-glucuronidase (uidA) marker gene was incorporated into a recombinant virus the plaques containing recombinants were visualized by a simple assay. The enzymatic substrate was incorporated (300 μg/ml) into the agarose overlay during the plaque assay. For the lacZ marker gene the substrate BLUOGAL™ (halogenated indolyl-β-D-galactosidase, Bethesda Research Labs) was used. For the uidA marker gene the substrate X-Glucuro Chx (5-bromo-4-chloro-3-indolyl-β-D-glucuronic acid Cyclohexylammonium salt, Biosynth AG) was used. Plaques that expressed active marker enzyme turned blue. The blue plagues were then picked onto fresh cells and purified by further blue plaque isolation. In recombinant virus strategies in which the enzymatic marker gene is removed the assay involves plaque purifying white plaques from a background of parental blue plaques. In both cases viruses were typically purified with three rounds of plaque purification.

ANTIBODY SCREEN FOR RECOMBINANT HERPESVIRUS

A third method for screening the recombinant virus stock was to look directly for the expression of the foreign gene with antibodies. Herpesvirus plaques were spotted and picked by inserting a toothpick through the agarose above the plaque and scraping the plaque area on the dish. Viruses were then rinsed from the toothpick by inserting the toothpick into a well of a 96-well micro-titer dish (Falcon Plastics) containing a confluent monolayer of tissue culture cells that had been washed 3 times in DME medium without serum. It was important for the virus to grow without serum at this stage to allow the immunological procedure to work. After cytopathic effect was complete, the plates were put at −70° C. to freeze and lyse the cells. The medium was thawed, and the freeze/thaw procedure was repeated a second time. Then 50–100 microliters of medium were removed from each well and filtered under vacuum through a nitrocellulose membrane (S&S BA85) using a DotBlot~ apparatus (BRL). The filter blots were soaked in a blocking solution of 0.01M Tris pH 7.5, 0.1M NaCl, 3% bovine serum albumin at room temperature for two hours with shaking. The filter blots were then placed in a sealable bag (Sears SEAL-A-MEAL™ or equivalent), and 10 mls of the blocking solution that contained 10 microliters of antibody specific for the foreign protein were added. After overnight incubation at room temperature with shaking, the blot was washed 3 times with 100 mls 0.01M Tris, pH 7.5, 0.1M NaCl, 0.05% Tween 20 detergent (Sigma). The blot was put in another sealable bag and 10 mls blocking solution containing 106 counts per minute of $^{125}$I-protein A (New England Nuclear) were added. After allowing the protein A to bind to the antibody for 2 hours at room temperature with shaking, the blot was washed as above, dried, and overlayed with an X-ray film and an intensifying screen (Dupont) and autoradiographed for 1–3 days at −70° C. The film was developed by standard procedures. Virus from the positive wells which contained the recombinant virus was further purified.

SELECTION OF G418 RESISTANT IBR VIRUS

The antibiotic G418 (GIBCO) has a wide range of inhibitory activity on protein synthesis. However, recombinant viruses expressing the aminoglycosidase 3'-phosphotransferase, encoded by the NEO gene of the transposable element Tn5, are resistant to G418. The transfection stocks of recombinant viruses were grown on MDBK cells in the presence of 500 μg/ml G418 in complete DME medium plus 1% fetal bovine serum. After one or two days at 37° C., plaques from the dishes inoculated with the highest dilution of virus were picked for virus stocks. The selection was repeated a second or third time. The virus stocks generated from the G418 selection were tested for NEO gene insertion by the SOUTHERN BLOTTING OF DNA hybridization procedure described above.

CONSTRUCTION OF DELETION VIRUSES

The strategy used to construct deletion viruses involved the use of either homologous recombination and/or direct ligation techniques. Initially a virus was constructed via homologous recombination, in which the DNA to be deleted was replaced with a marker gene such as *E. coli* β-galactosidase (lacZ) or β-glucuronidase (uidA). A second virus was then constructed in which the marker gene was deleted either by homologous recombination or via direct ligation. The advantage of this strategy is that both viruses may be purified by the SCREEN FOR RECOMBINANT HERPESVIRUS EXPRESSING ENZYMATIC MARKER GENES. The first virus is purified by picking blue plaques from a white plaque background, the second virus is purified by picking white plaques from a blue plaque background.

Several homology vectors were constructed for the purpose of deleting the gpG, gpE and Tk gene coding regions. A detailed description of these homology vectors follows.

HOMOLOGY VECTOR 129-71.5

Figure 7A:
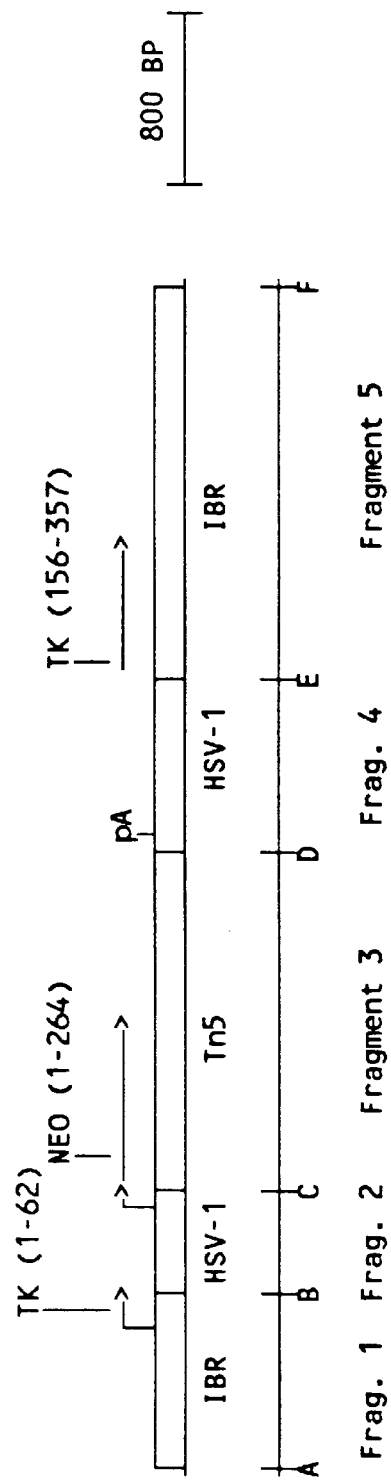
FIGS. 7A–7C Detailed description of the DNA insertion in Homology Vector 129-71.5. Diagram showing the orientation of DNA fragments assembled in plasmid 129-71.5. The origin of each fragment is indicated in the table. The sequences located at each of the junctions between fragments is also shown. The restriction sites used to generate each fragment as well as synthetic linker sequences which were used to join the fragments are described for each junction. The synthetic linker sequences are underlined by a heavy bar. The location of several gene coding regions and regulatory elements is also given. The following two conventions are used: numbers in parentheses, ( ), refer to amino acids, and restriction sites in brackets, [ ], indicate the remnants of sites which were destroyed during construction. The following abbreviations are used: polyadenylation signal (pA), infectious bovine rhinotracheitis virus (IBR), Herpes simplex virus type 1 (HSV-1), thymidine kinase (TK), neomycin resistance (NEO), bacterial transposon Tn5 (Tn5).
Figure 7B:
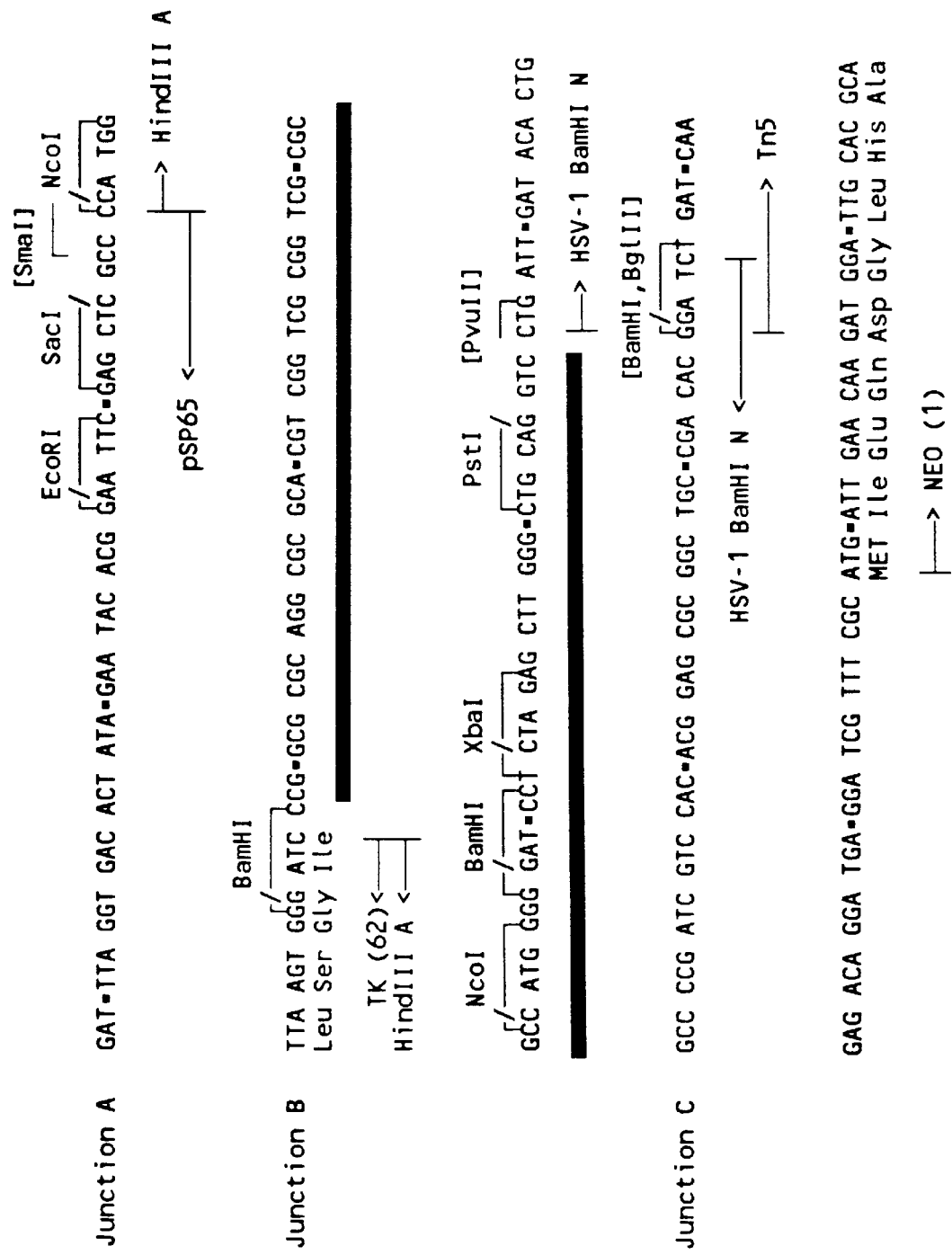
Figure 7C:
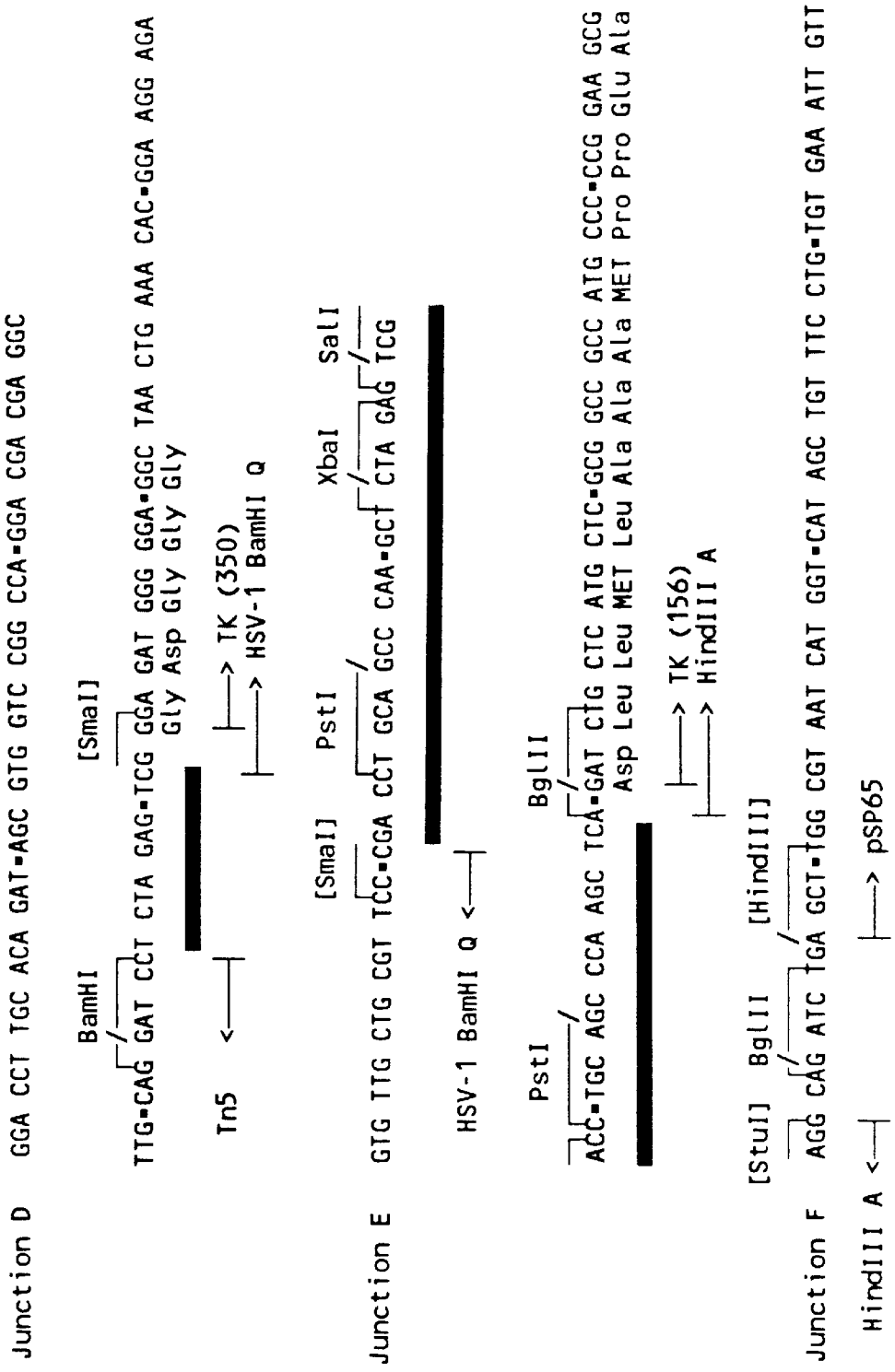

The plasmid 129-71.5 was constructed for the purpose of deleting a portion of the TK gene coding region from the IBR virus. It incorporates a selectable marker, the bacterial transposon neomycin resistance gene, flanked by IBR virus DNA. Upstream of the marker gene is an approximately 860 base pair fragment of IBR virus DNA which ends with sequences encoding amino acids 1–62 of the TK primary translation product. Downstream of the marker gene is an approximately 1741 base pair fragment of IBR virus DNA which begins with sequences encoding amino acids 156–367 of the TK primary translation product. When this plasmid is used according to the HOMOLOGOUS RECOMBINATION PROCEDURE FOR GENERATING RECOMBINANT HERPESVIRUS, it will replace the DNA coding for amino acids 63–155 of the TK primary translation product with DNA coding for the marker gene. Note that the marker gene will be under the control of the herpes simplex type 1 alpha-4 immediate early gene promoter (5). A detailed description of the plasmid is given in FIGS. 7A–7C. It was constructed from the indicated DNA sources utilizing standard recombinant DNA techniques (6). It may be constructed by joining restriction fragments from the following sources with the synthetic DNA sequences indicated in FIGS. 7A–7C. The plasmid vector is derived from an approximately 2975 base pair SmaI to HindIII restriction fragment of pSP65 (Promega). Fragment 1 is an approximately 860 base pair NcoI to BamHI restriction fragment of the IBR virus HindIII restriction fragment A (7). This fragment is located on an approximately 5500 base pair ClaI to NruI fragment contained in the IBR virus HindIII A fragment. Fragment 2 is an approximately 490 base pair PvuII to BamHI restriction sub-fragment of the HSV-1 BamHI restriction fragment N (5). Note that the HSV-1 oriS region has been removed from this fragment by deletion of the sequences between the SmaI sites located 1483 and 128 base pairs away from the PvuII end (10). Fragment 3 is an approximately 1541 base pair BglII to BamHI restriction fragment of plasmid pNEO (P. L. Biochemicals, Inc.). Fragment 4 is an approximately 784 base pair SmaI to SmaI restriction sub-fragment of the HSV-1 BamHI restriction fragment Q (10). Note that this fragment is oriented such that the polyadenylation sequence (AATAAA) is located closest to junction D. Fragment 5 is an approximately 1741 base pair BglII to StuI restriction sub-fragment from the IBR HindIII restriction fragment A (7).

PLASMID 459-12.6

Figure 11A:
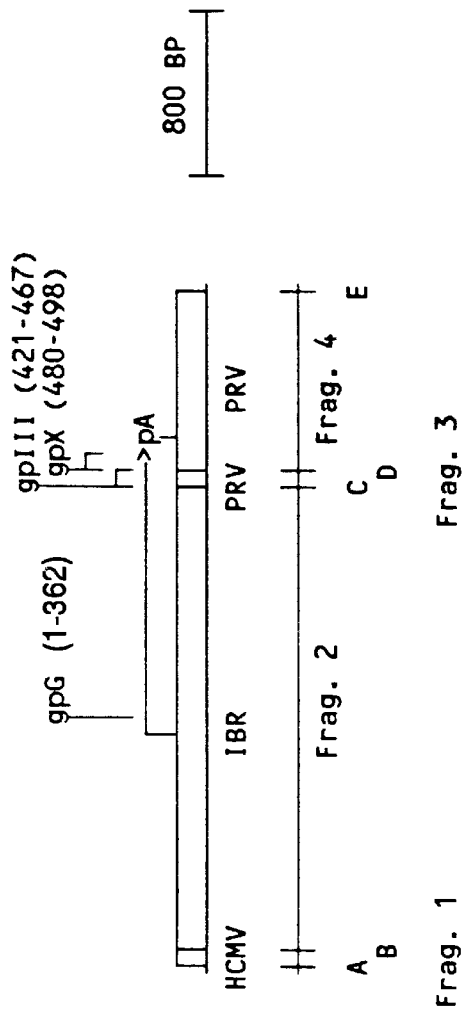
FIGS. 11A–11C Detailed description of the DNA insertion in Plasmid 459-12.6. Diagram showing the orientation of DNA fragments assembled in plasmid 459-12.6. The origin of each fragment is indicated in the table. The sequences located at each of the junctions between fragments is also shown. The restriction sites used to generate each fragment as well as synthetic linker sequences which were used to join the fragments are described for each junction. The synthetic linker sequences are underlined by a heavy bar. The location of several gene coding regions and regulatory elements is also given. The following two conventions are used: numbers in parentheses, ( ), refer to amino acids, and restriction sites in brackets, [ ], indicate the remnants of sites which were destroyed during construction. The following abbreviations are used: unique glycoprotein G (gpG), glycoprotein III (gpIII), glycoprotein X (gpX), polyadenylation signal (pA), infectious bovine rhinotracheitis virus (IBR), pseudorabies virus (PRV), and human cytomegalovirus (HCMV).
Figure 11B:
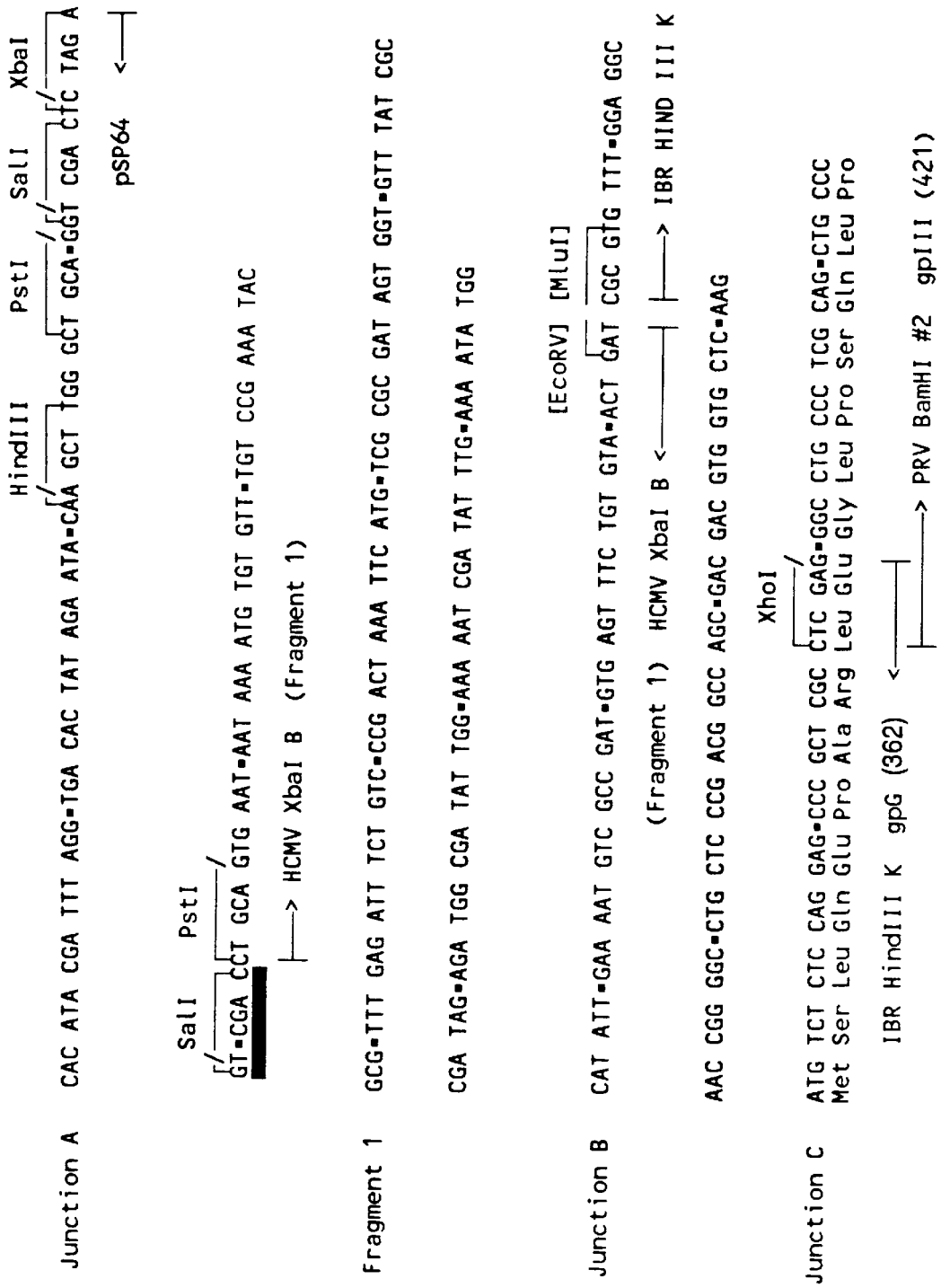
Figure 11C:
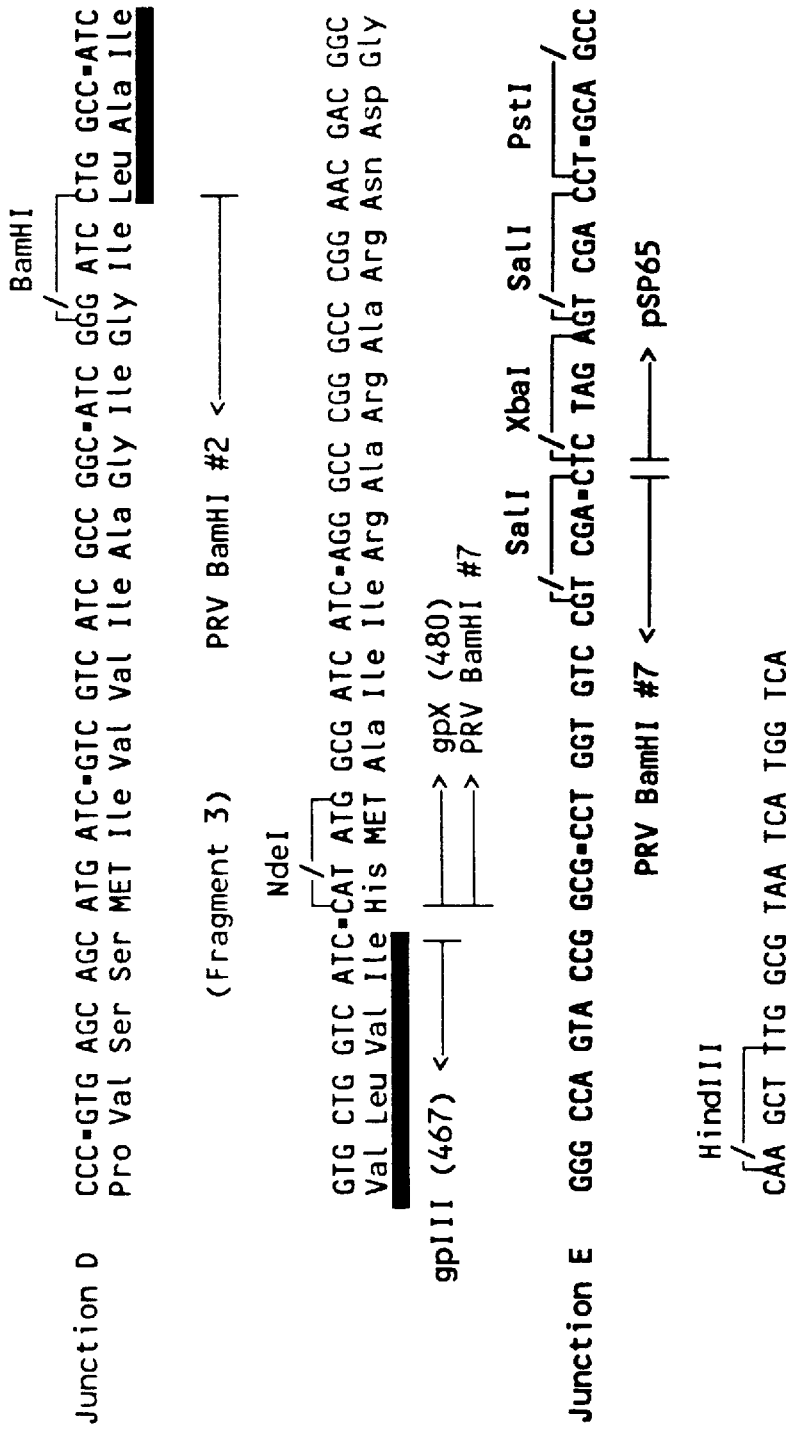
Figure 12C:
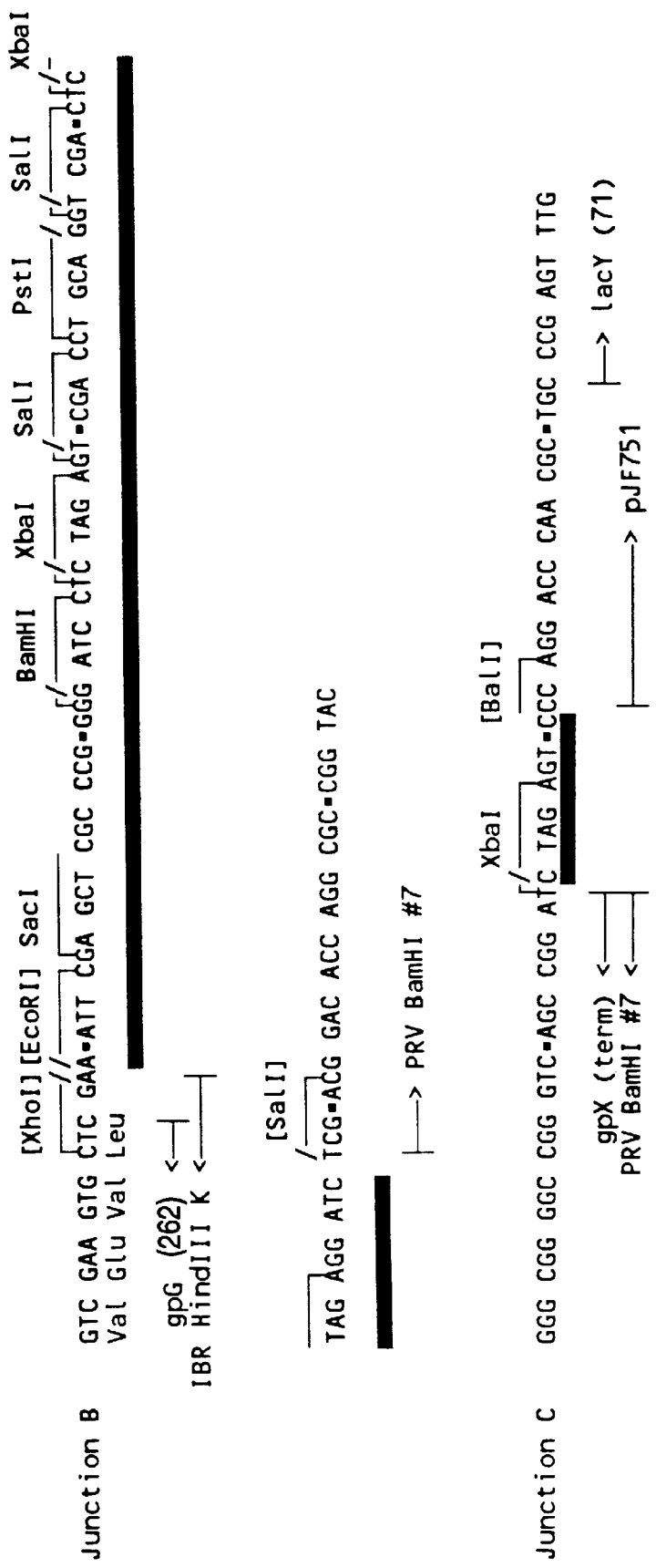
Figure 12D:
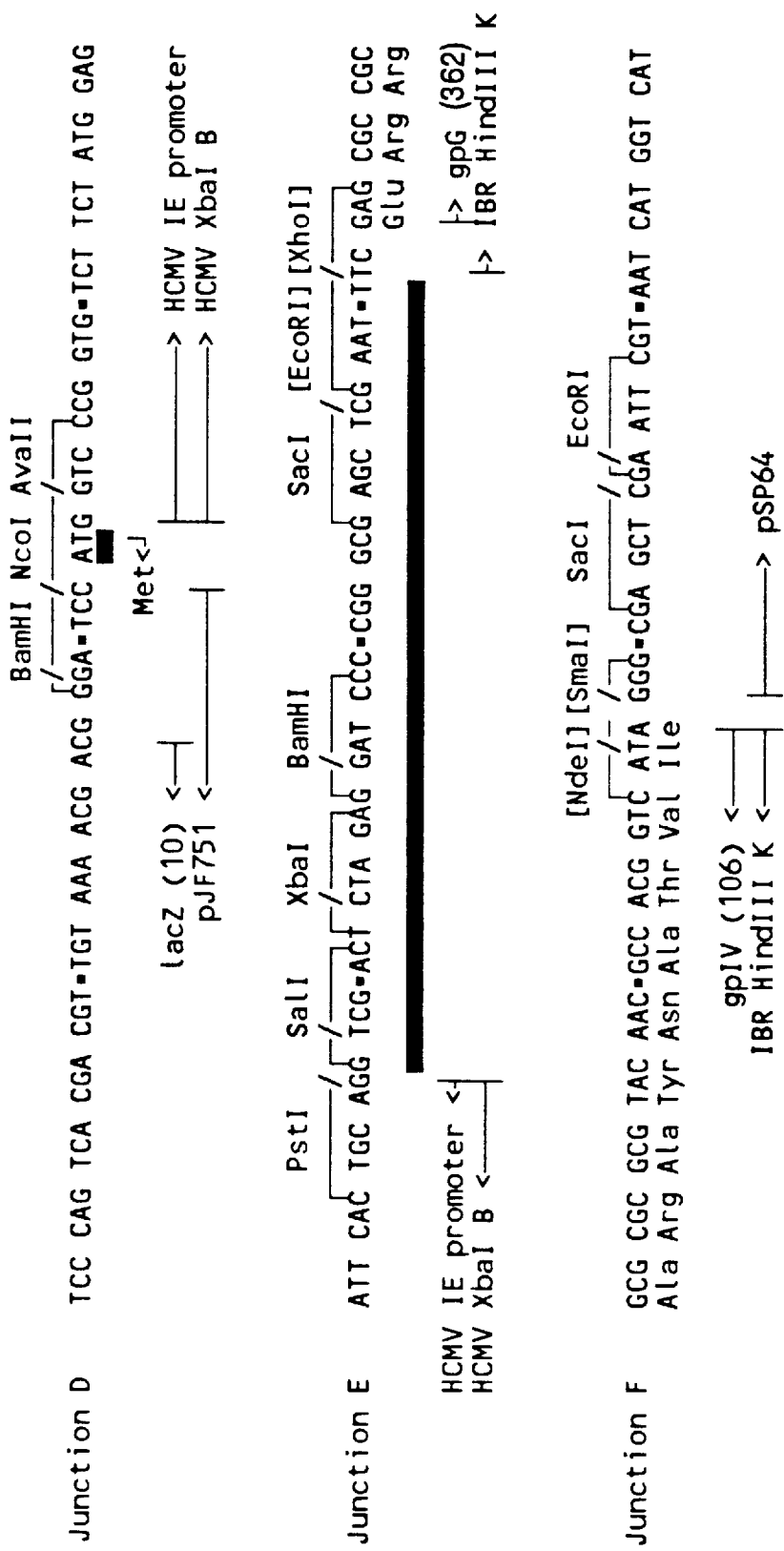
Figure 13B:
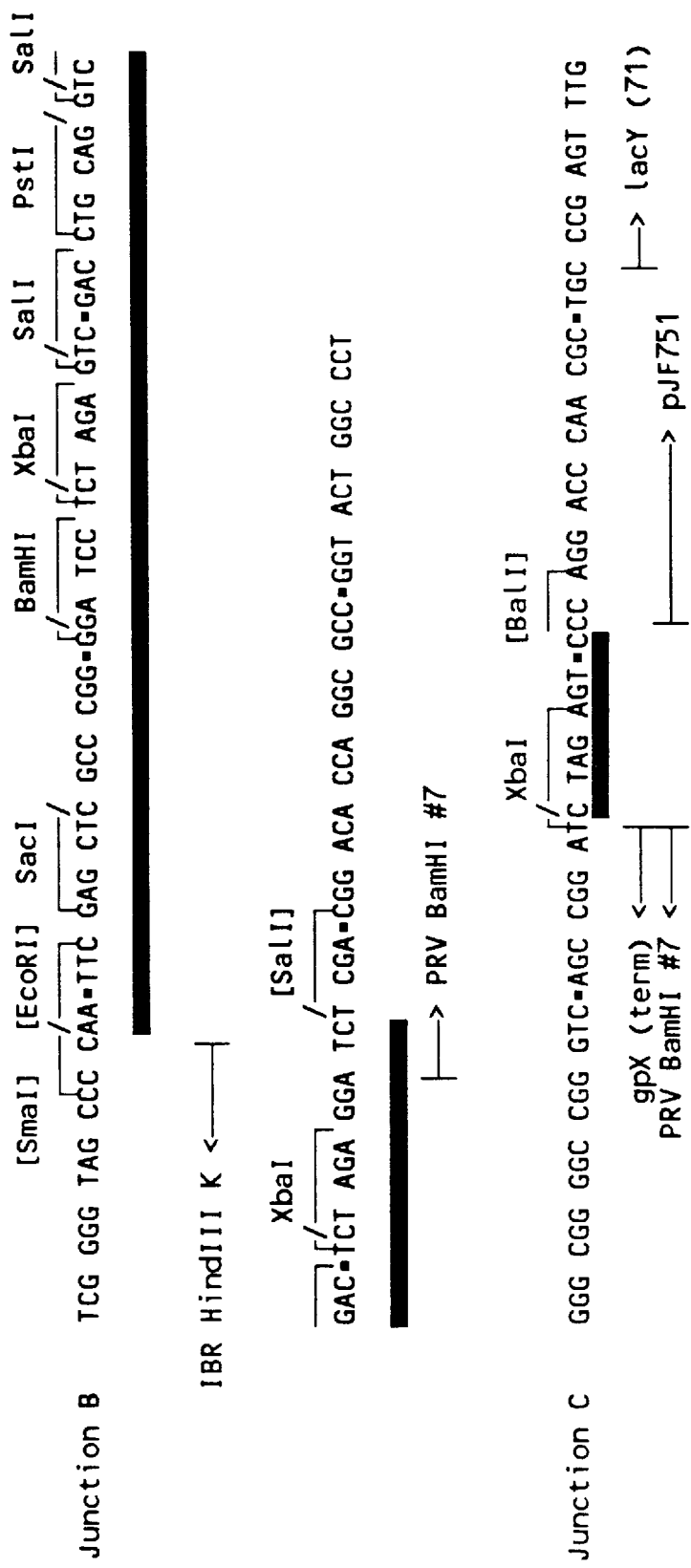
Figure 13C:
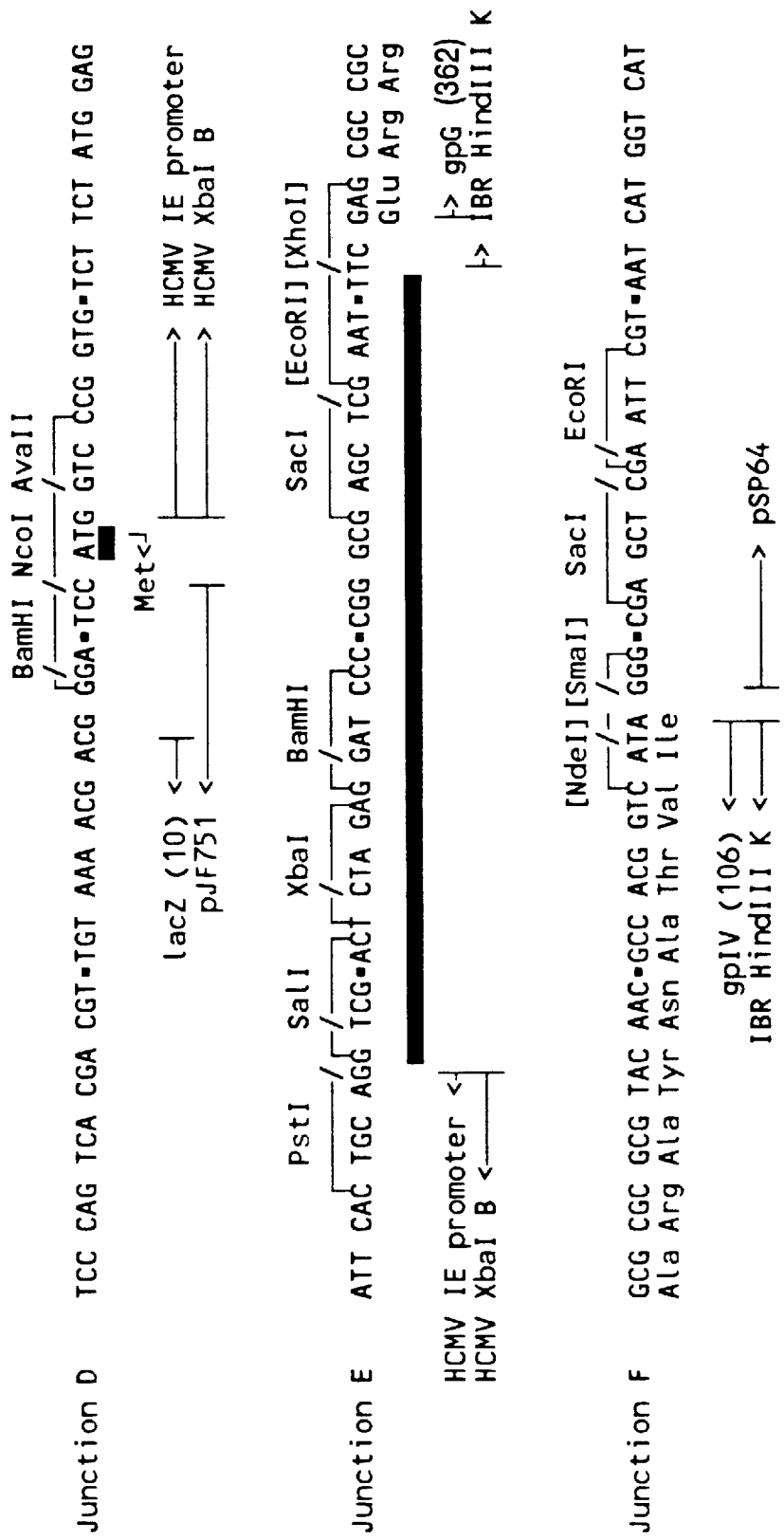
Figure 14B:
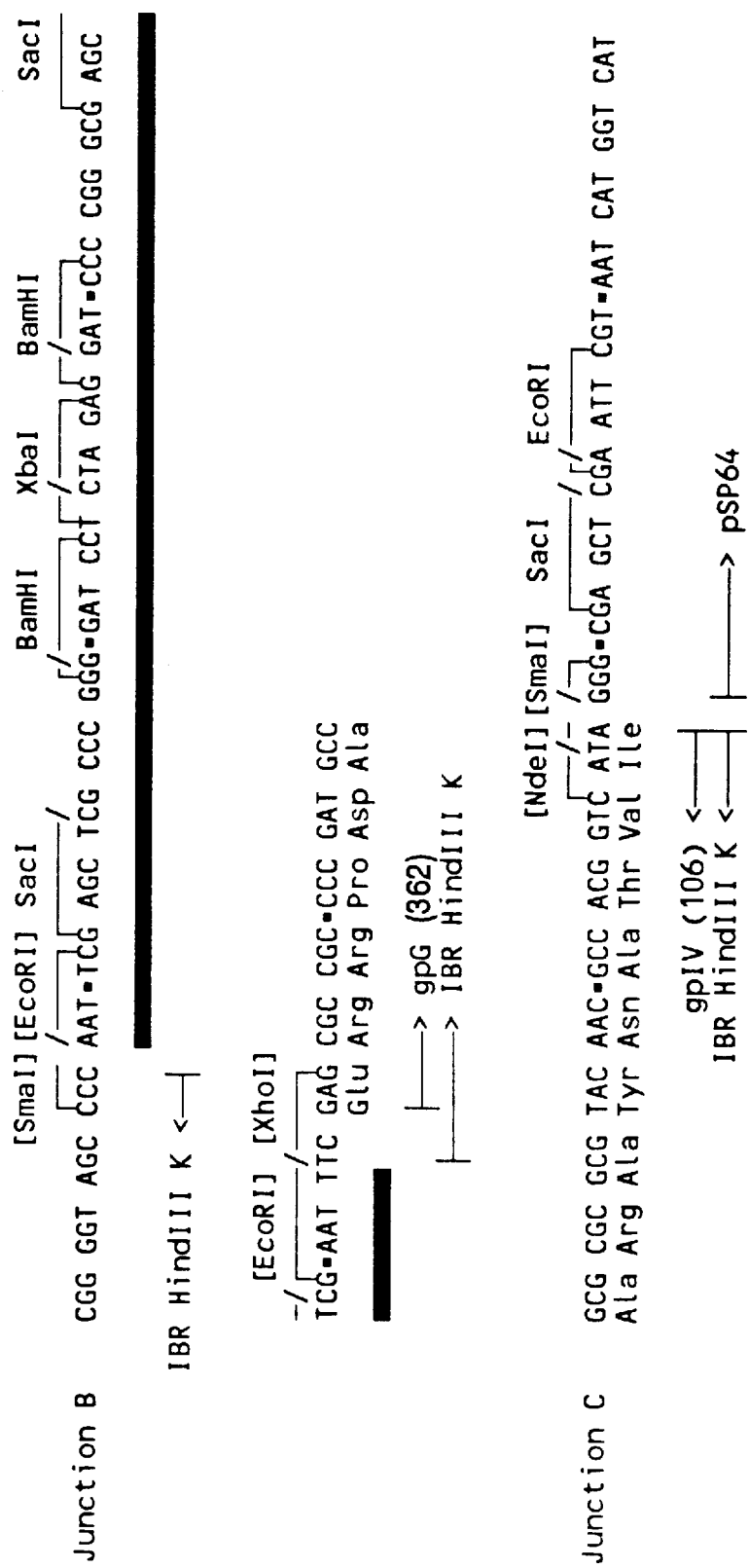
Figure 17A:
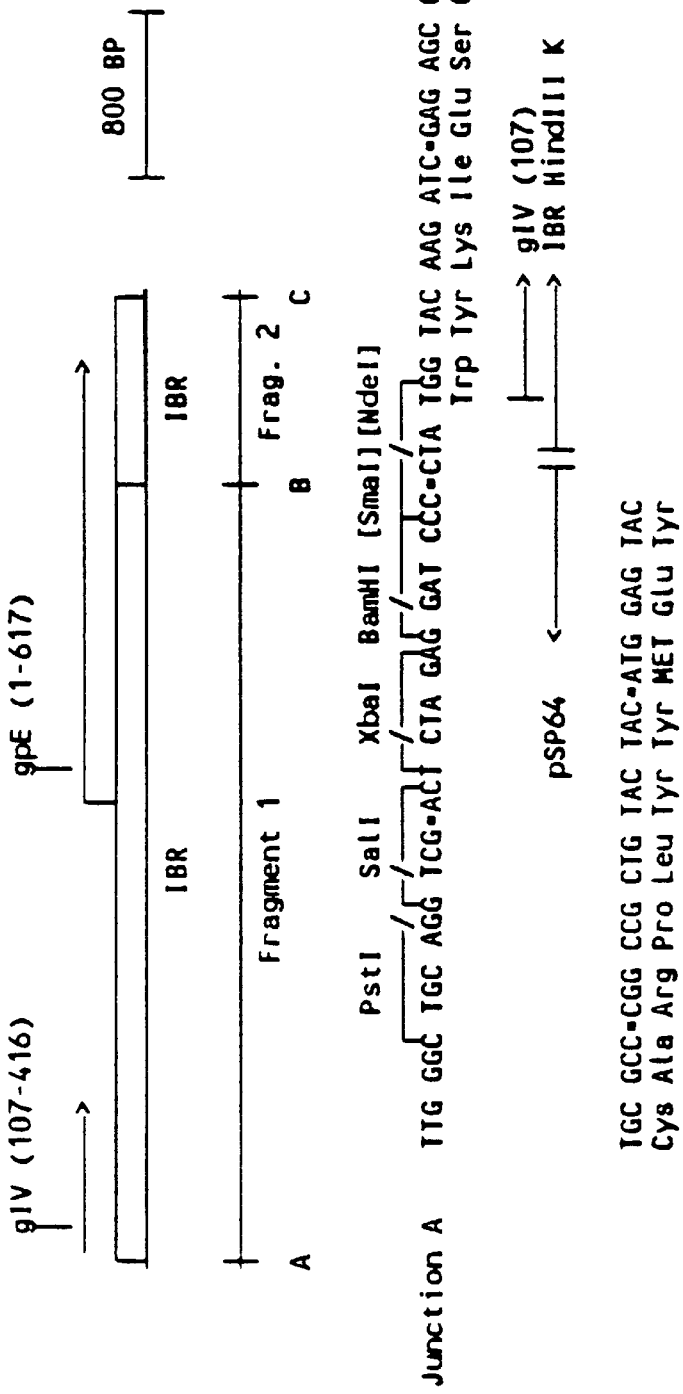
FIGS. 17A and 17B Detailed description of a plasmid containing the gpE gene. Diagram showing the orientation of DNA fragments to be assembled in the gpE-containing plasmid. The origin of each fragment is indicated in the table. The sequences located at each of the junctions between fragments are also shown. The restriction sites used to generate each fragment are described for each junction. The location of several gene coding regions and regulatory elements is also given. The following two conventions are used: numbers in parentheses, ( ), refer to amino, acids, and restriction sites in brackets, [ ], indicate the remnants of sites which were destroyed during construction. The following abbreviations are used: unique glycoprotein E (gpE), glycoprotein IV (gpIV), and infectious bovine rhinotracheitis virus (IBR).
Figure 17B:
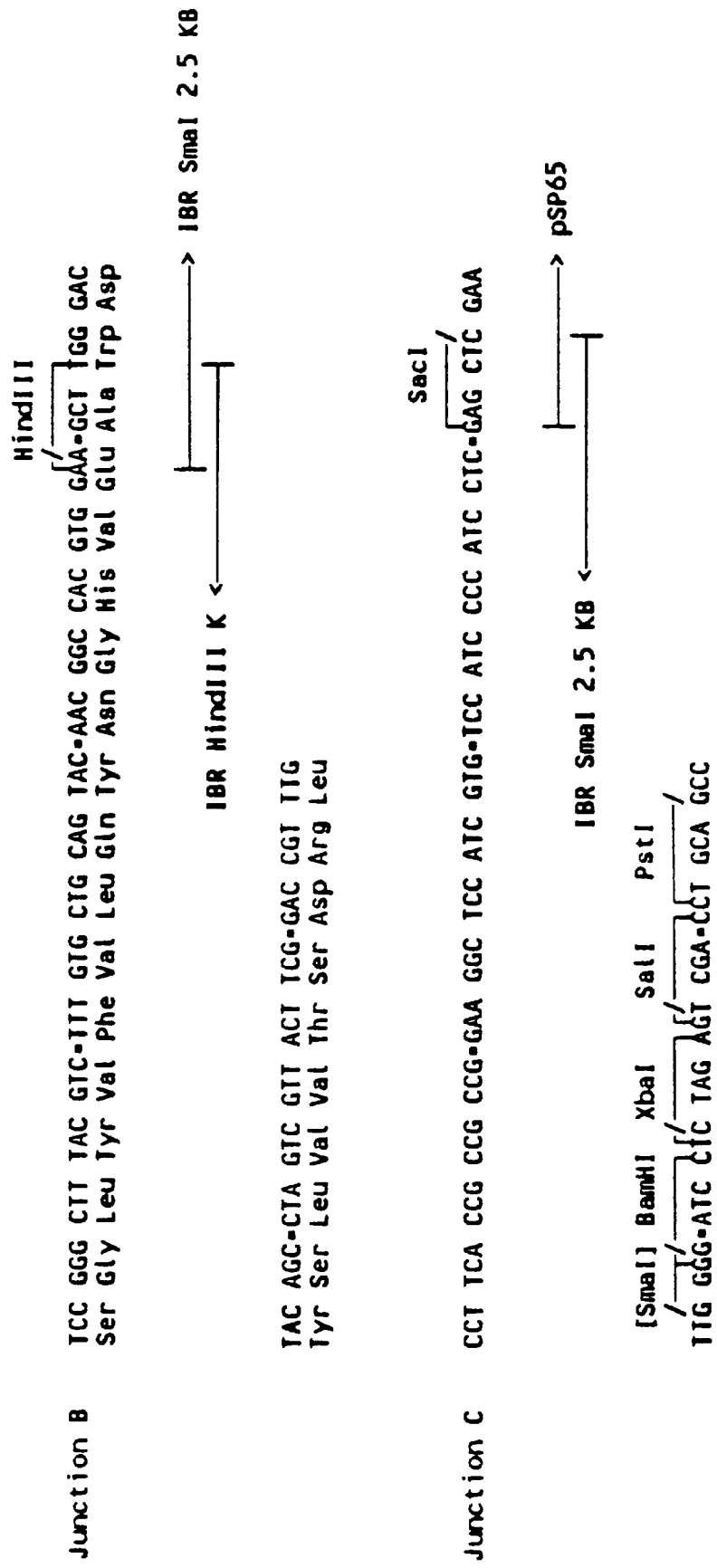
Figure 18B:
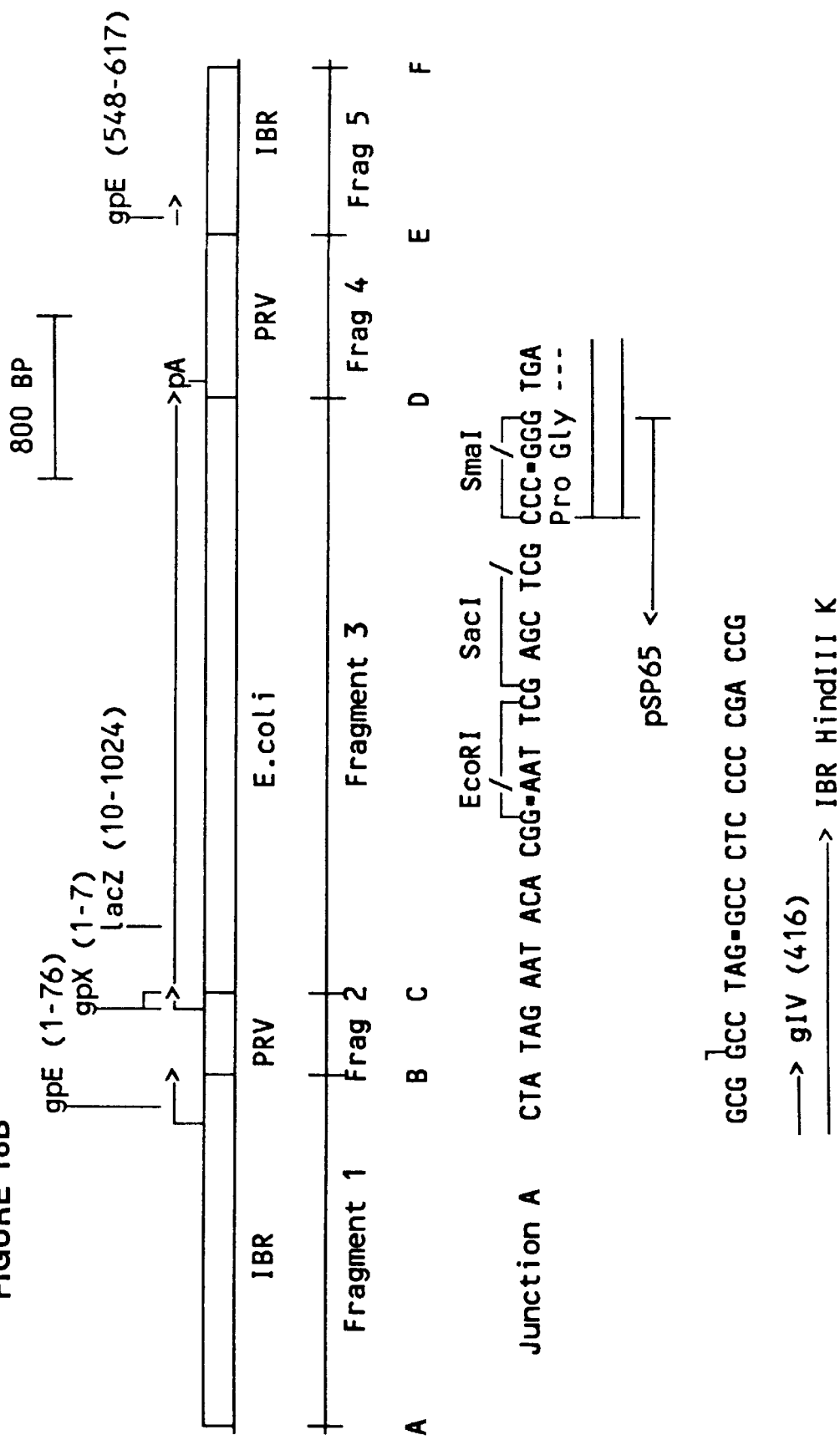
Figure 18C:
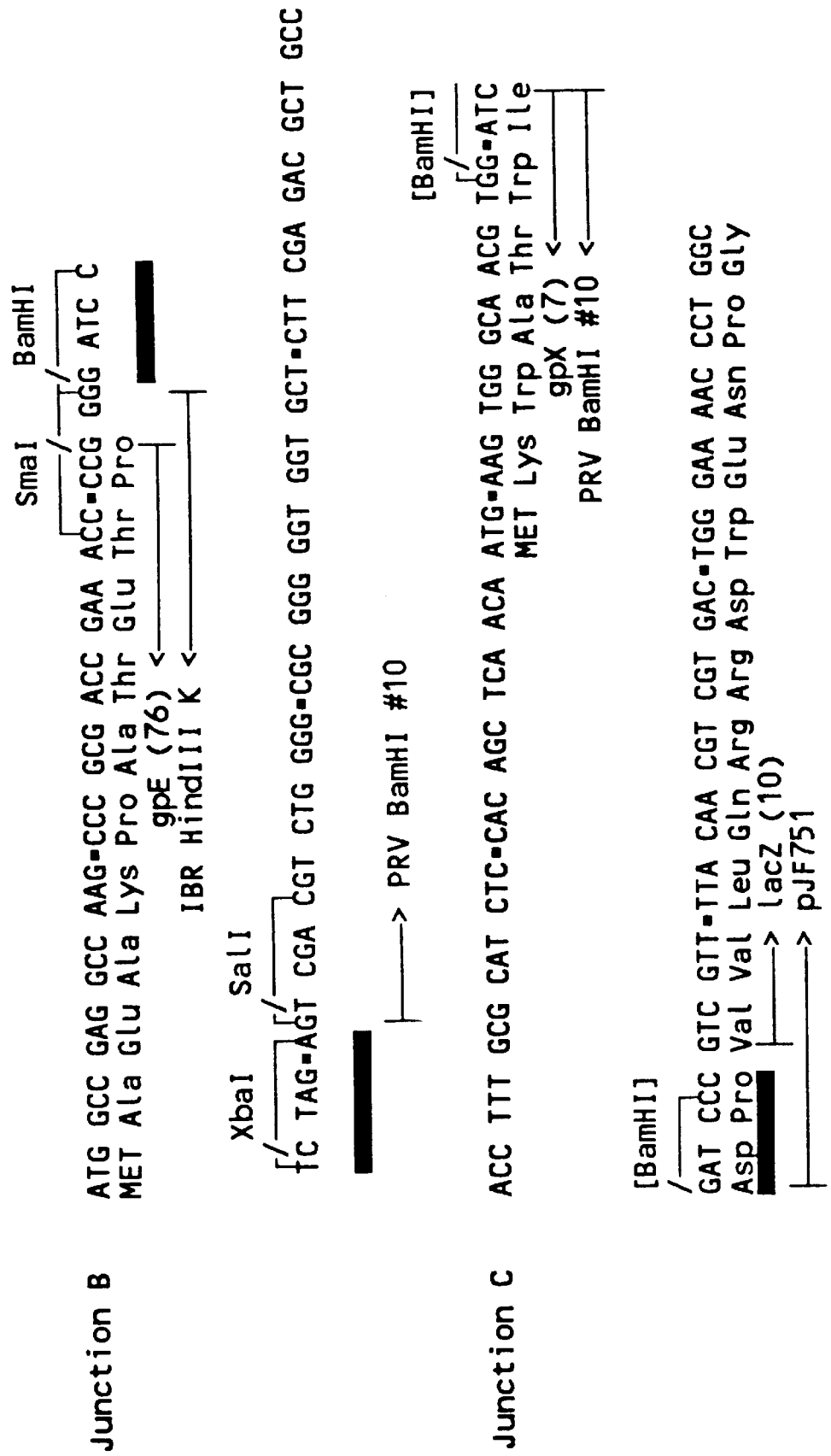
Figure 18D:
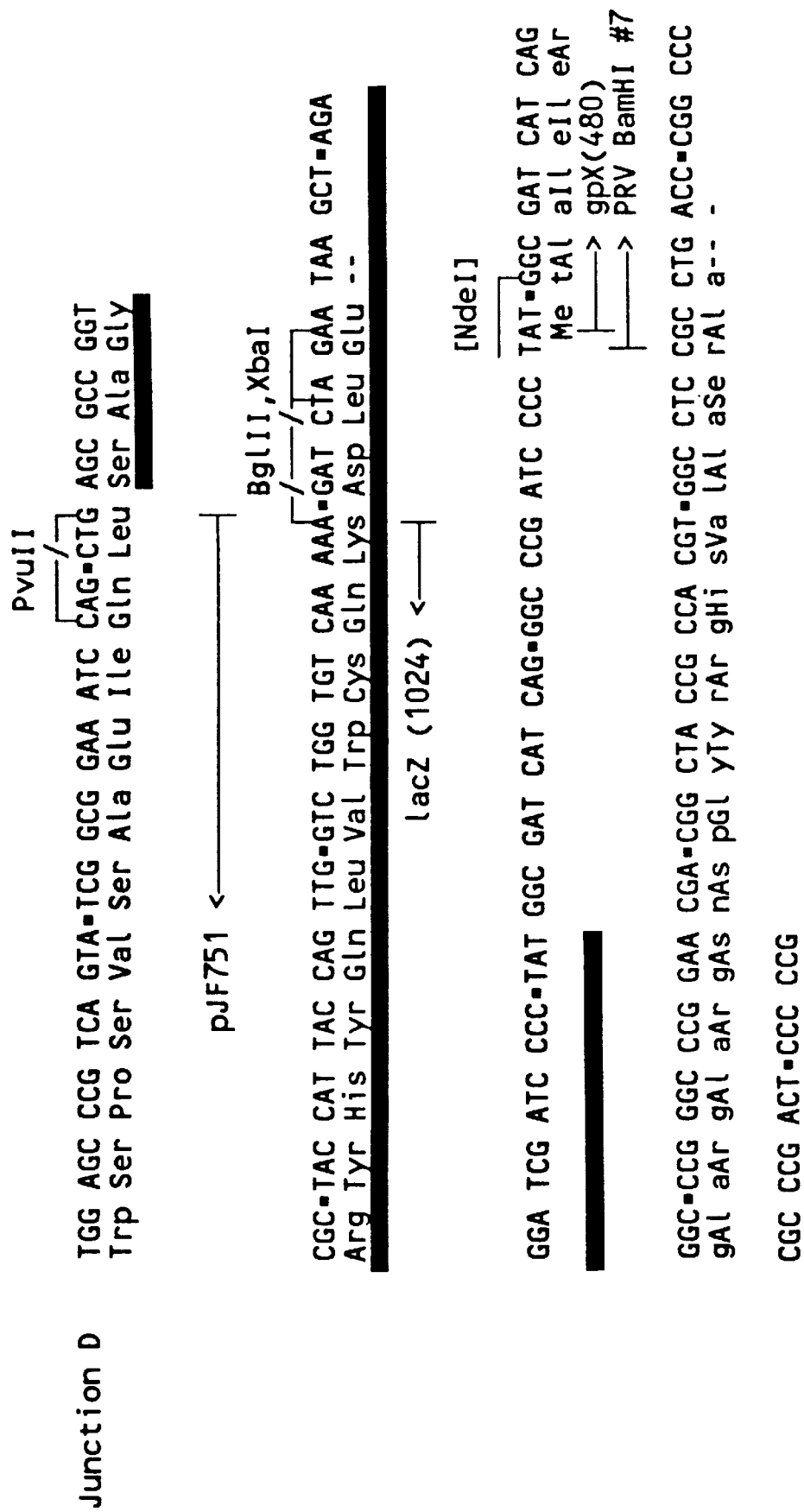

The plasmid 459-12.6 was generated for the purpose of constructing a recombinant cloning vector which expresses the IBR virus glycoprotein G. This was accomplished by inserting the IBR virus gpG gene into S-PRV-013 (U.S. Ser. No. 07/823,102 filed Jan. 27, 1986). Plasmid 459-12.6 contains a chimeric gene under the control of the IBR virus gpG promoter. The chimeric gene expresses a fusion protein consisting of the first 362 amino acids of IBR virus gpG fused to amino acids 421–467 of the PRV gpIII (13) followed by amino acids 480–498 of the PRV gpX (12). The chimeric gene is flanked by HindIII restriction sites. When this plasmid is used with S-PRV-013 and the restriction enzyme HindIII according to the DIRECT LIGATION PROCEDURE FOR GENERATING RECOMBINANT HERPESVIRUS the resulting recombinant will express the IBR virus gpG. A detailed description of the plasmid is given in FIGS. 11A–11C. It was constructed from the indicated DNA sources utilizing standard recombinant DNA techniques (6). It may be constructed by joining restriction fragments from the following sources with the synthetic DNA sequences indicated in FIGS. 11A–11C. The plasmid vector is derived from an approximately 2999 base pair XbaI to XbaI restriction fragment of a hybrid cloning vector derived from pSP64 and pSP65 (Promega). The hybrid cloning vector was constructed by joining approximately 1369 base pair PvuI to SmaI fragment from pSP64 with the approximately 1652 base pair PvuI to SmaI fragment from pSP65. Fragment 1 is an approximately 182 base pair PstI to EcoRV restriction sub-fragment of the HCMV XbaI restriction fragment B (16). Fragment 2 is an approximately 2121 base pair MluI to XhoI restriction sub-fragment of the IBR virus HindIII restriction fragment K (7). Fragment 3 is an approximately 121 base pair XhoI to BamHI restriction sub-fragment of the PRV BamHI restriction fragment #2 (3). Fragment 4 is an approximately 760 base pair NdeI to SalI restriction sub-fragment of the PRV BamHI restriction fragment #7 (3).

HOMOLOGY VECTOR 439-01.31

The plasmid 439-01.31 was constructed for the purpose of deleting a portion of the gpG gene coding region from the IBR virus. It incorporates an *E. coli* β-galactosidase marker gene flanked by IBR virus DNA. Downstream of the marker gene is an approximately 3593 base pair fragment of IBR virus DNA which ends with sequences encoding the first 262 amino acids of the gpG primary translation product. Upstream of the marker gene is an approximately 785 base pair fragment of IBR virus DNA which begins with sequences encoding the last 80 amino acids of the gpG primary translation product. When this plasmid is used according to the HOMOLOGOUS RECOMBINATION PROCEDURE FOR GENERATING RECOMBINANT HERPESVIRUS it will replace the DNA coding for amino acids 263–361 of the gpG primary translation product with DNA coding for the marker gene. Note that the β-galactosidase (lacZ) marker gene will be under the control of the human cytomegalovirus immediate early gene promoter. A detailed description of the plasmid is given in FIGS. 12A–12D. It was constructed from the indicated DNA sources utilizing standard recombinant DNA techniques (6). It may be constructed by joining restriction fragments from the following sources with the synthetic DNA sequences indicated in FIGS. 12A–12D. The plasmid vector is derived from an approximately 2965 base pair HindIII to SmaI restriction fragment of pSP64 (Promega). Fragment 1 is an approximately 3593 base pair HindIII to XhoI restriction fragment of the IBR HindIII restriction fragment K (7). Fragment 2 is an approximately 753 base pair SalI to NdeI restriction fragment of the PRV BamHI restriction fragment #7 (3). Note that this fragment was resected with Exonuclease III/S1 nuclease digestion such that approximately 57 base pairs were removed from the NdeI end. Fragment 3 is an approximately 3347 base pair BalI to BamHI restriction fragment of plasmid pJF751 (38). Fragment 4 is an approximately 1191 base pair AvaI to PstI restriction fragment from the HCMV XbaI restriction fragment E (16). Fragment 5 is an approximately 785 base pair XhoI to NdeI restriction fragment from the IBR HindIII restriction fragment K (7). Note that the lacZ marker gene is flanked by XbaI sites located at Junction B and Junction E in this plasmid permitting the marker-gene to be cut out with XbaI.

HOMOLOGY VECTOR 439-21.69

The plasmid 439-21.69 was constructed for the purpose of deleting a portion of the gpG gene coding region from the IBR virus. It incorporates an E. coli β-galactosidase (lacZ) marker gene flanked by IBR virus DNA. Downstream of the marker gene is an approximately 888 base pair fragment of IBR virus DNA which begins approximately 1042 base pairs upstream of the initiation codon of the gpG gene and ends approximately 154 base pairs upstream of the initiation codon of the gpG gene. Upstream of the marker gene is an approximately 785 base pair fragment of IBR virus DNA which begins with sequences encoding the last 80 amino acids of the gpG primary translation product. When this plasmid is used according to the HOMOLOGOUS RECOMBINATION PROCEDURE FOR GENERATING RECOMBINANT HERPESVIRUS it will replace the DNA coding for amino acids 1–361 of the gpG primary translation product with DNA coding for the marker gene. Note that the β-galactosidase (lacZ) marker gene will be under the control of the human cytomegalovirus immediate early gene promoter. A detailed description of the plasmid is given in FIGS. 13A–13C. It was constructed from the indicated DNA sources utilizing standard recombinant DNA techniques (6). It may be constructed by joining restriction fragments from the following sources with the synthetic DNA sequences indicated in FIGS. 13A—13C. The plasmid vector is derived from an approximately 2965 base pair HindIII to SmaI restriction fragment of pSP64 (Promega). Fragment 1 is an approximately 3593 base pair HindIII to XhoI restriction fragment of the IBR HindIII restriction fragment K (7). Fragment 2 is an approximately 753 base pair SalI to NdeI restriction fragment of the PRV BamHI restriction fragment #7 (3). Note that this fragment was resected with Exonuclease III/S1 nuclease digestion such that approximately 57 base pairs were removed from the NdeI end. Fragment 3 is an approximately 3347 base pair BalI to BamHI restriction fragment of plasmid pJF751 (38). Fragment 4 is an approximately 1191 base pair AvaI to PstI restriction fragment from the HCMV XbaI restriction fragment E (16). Fragment 5 is an approximately 785 base pair XhoI to NdeI restriction fragment from the IBR HindIII restriction fragment K (7). Note that the lacZ marker gene is flanked by XbaI sites located at Junction B and Junction E in this plasmid permitting the marker gene to be cut out with XbaI.

HOMOLOGY VECTOR 439-70.4

The plasmid 439-70.4 was constructed for the purpose of deleting the *E. coli* βgalactosidase (lacZ) marker gene from S-IBR-035 virus. It incorporates two regions of IBR viral DNA which flank the marker gene in S-IBR-035. The first region is an approximately 888 base pair fragment of IBR virus DNA which begins approximately 1042 base pairs upstream of the initiation codon of the gpG gene and ends approximately 154 base pairs upstream of the initiation codon of the gpG gene. The second region is an approximately 785 base pair fragment of IBR virus DNA which begins with sequences encoding the last 80 amino acids of the gpG primary translation product. When this plasmid is used in conjunction with S-IBR-035 DNA according to the HOMOLOGOUS RECOMBINATION PROCEDURE FOR GENERATING RECOMBINANT HERPESVIRUS it will delete the DNA coding for the *E. coli* β-galactosidase (lacZ) marker gene. A detailed description of the plasmid is given in FIGS. 14A and 14B. It was constructed from the indicated DNA sources utilizing standard recombinant DNA techniques (6). It may be constructed by joining restriction fragments from the following sources with the synthetic DNA sequences indicated in FIG. 14. The plasmid vector is derived from an approximately 2965 base pair HindIII to SmaI restriction fragment of psP64 (Promega). Fragment 1 is an approximately 3593 base pair HindIII to XhoI restriction fragment of the IBR HindIII restriction fragment K (7). Fragment 2 is an approximately 785 base pair XhoI to NdeI restriction fragment from the IBR HindIII restriction fragment K (7).

IBR VIRUS gpE PLASMID

A plasmid may be generated for the purpose of constructing a recombinant cloning vector which expresses the IBR virus glycoprotein E (gpE). This plasmid may be used to insert the IBR virus gpE gene into S-PRV-002 (U.S. Pat. No. 4,877,737). The plasmid will contain the gpE gene flanked by XbaI restriction sites. When this plasmid is used with S-PRV-002 and the restriction enzyme XbaI according to the DIRECT LIGATION PROCEDURE FOR GENERATING RECOMBINANT HERPESVIRUS the resulting recombinant will express the IBR virus gpE. A detailed description of the plasmid is given in FIGS. 17A and 17B. It may be constructed, utilizing standard recombinant DNA techniques (6), by joining restriction fragments from the following sources. The plasmid vector is derived from an approximately 2999 base pair XbaI to XbaI restriction fragment of a hybrid cloning vector derived from pSP64 and pSP65 (Promega). The hybrid cloning vector was constructed by joining an approximately 1369 base pair PvuI to SmaI fragment from pSP64 with the approximately 1652 base pair PvuI to SmaI fragment from pSP65. Fragment 1 is an approximately 3647 base pair NdeI to HindIII restriction sub-fragment of the IBR virus HindIII restriction fragment K (7). Fragment 2 is an approximately 832 base pair HindIII to SacI restriction sub-fragment of an IBR virus 2400 base pair SmaI restriction fragment. This SmaI fragment has been cloned into the SmaI site of the plasmid pSP64 (Promega). This plasmid is designated PSY1645. PSY1645 was deposited on Jul. 16, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 68650. Note that the lacZ marker gene is flanked by XbaI sites located at Junction B and Junction E in this plasmid permitting the marker gene to be cut out with XbaI.

HOMOLOGY VECTOR 536-03.5

The plasmid 536-03.5 was constructed for the purpose of deleting a portion of the gpE gene coding region from the IBR virus. It incorporates an *E. coli* β-galactosidase (lacZ) marker gene flanked by IBR virus DNA. Upstream of the marker gene is an approximately 1704 base pair fragment of IBR virus DNA which ends with sequences encoding amino acids 1–76 of the gpE primary translation product. Downstream of the marker gene is an approximately 742 base pair fragment of IBR virus DNA which begins with sequences encoding amino acids 548–617 of the gpE primary translation product. When this plasmid is used according to the HOMOLOGOUS RECOMBINATION PROCEDURE FOR GENERATING RECOMBINANT HERPESVIRUS, it will replace the DNA coding for amino acids 77–547 of the gpE primary translation product with DNA coding for the marker gene. Note that the β-galactosidase (lacZ) marker gene will be under the control of the PRV gpX. A detailed description of the plasmid is given in FIGS. 18A–18E. It may be constructed utilizing standard recombinant DNA techniques (6), by joining restriction fragments from the following sources with the synthetic DNA sequences indicated in FIG. 18. The plasmid vector is derived from an approximately 2975 base pair SmaI to HindIII restriction fragment of psP65 (Promega). Fragment 1 is an approximately 1704 base pair SmaI to SmaI restriction sub-fragment of the IBR HindIII restriction fragment K (7). Fragment 2 is an approximately 413 base pair SalI to BamHI restriction fragment #7 (3). Fragment 5 is an approximately 742 base pair NheI to BGlI sub-fragment of an IBR virus 2400 base pair SmaI fragment. This SmaI fragment has been cloned into the SmaI site of the plasmid pSP64 (Promega). This plasmid is designated PSY1645. PSY1645 was deposited on Jul. 16, 1991 with the American Type Culture Collection. Note that the lacZ marker gene is flanked by XbaI sites located at Junction B and Junction E in this plasmid permitting the marker gene to be cut out with XbaI.

VACCINATION STUDIES IN CALVES WITH INACTIVATED IBR VIRUS

Calves, seronegative to IBR virus, were housed in facilities secure from IBR virus exposure. Groups of four calves were vaccinated intramuscularly with vaccines containing $10^{7.3}$ or $10^{8.0}$ plaque forming units of inactivated IBR virus formulated with an oil adjuvant. A second vaccination was given 21 days later; four calves were maintained as unvaccinated controls. At 21 days after the second vaccination, animals were challenged intranasally with virulent wild-type IBR virus. After vaccination and challenge, animals were observed and the injection site was palpated weekly. Blood samples were taken on days 0, 7, 21, 28, and 42 post vaccination. After challenge, animals were observed daily for clinical signs of IBR. Blood samples were taken on days 7 and 13 post challenge. Nasal swabs were collected on days 3, 6, 9, and 12 post challenge.

PURIFICATION OF IBR VIRUS gpG gpG was purified from the tissue culture medium of infected MDBK cells. Confluent MDBK cells in serum-free medium were infected at a multiplicity of infection equal to 5, with wild-type, Cooper strain of IBR virus. The cells and media were harvested at approximately twenty-two hours after infection, when the cells showed considerable cytopathic effect and the fluids were centrifuged at 5000 rpm for 15 minutes.

The supernatant fluid was concentrated approximately 10-fold by ultrafiltration through an Amicon ym-30 membrane, and dialyzed against 10 mM $NaPO_4$ pH 7.2. The dialysate was treated for 20 minutes at 0° C. with 70% perchloric acid to a final concentration of 0.2M perchloric acid, then centrifuged at 12,000 rpm for 20 minutes. The supernatant fluid was then dialyzed against 20 mM Tris pH 9.5.

The acid-soluble proteins were separated by column chromatography on a DEAE-Sephacel anion exchange column using a liner gradient elution: 0 to 100% A to B where A=20 mM Tris pH 9.5 and B=20 mM Tris pH 9.5/800 mM NaCl. The gpG eluted at approximately 35–40% B. Peak fractions were assayed by Western blot using anti gpG peptide sera. Reactive fractions were combined and dialyzed against 5 mM Tris pH 7.0. The sample was then concentrated 10-fold by lyophilization and stored at −20° C.

ELISA ASSAY

A standard enzyme-linked immunosorbent assay (ELISA) protocol was used to determine the immune status of cattle following vaccination and challenge.

A purified gpG antigen solution (100 μl at 1 ng/μl in PBS) was allowed to absorb to the wells of microtiter dishes for 18 hours at 4° C. The coated wells were rinsed one time with PBS. Wells were blocked by adding 250 μl of PBS containing 1% BSA (Sigma) and incubating 1 hour at 37° C. The blocked wells were rinsed one time with PBS containing 0.02% Tween 20. 50 μl of test serum (previously diluted 1:2 in PBS containing 1% BSA) were added to the wells and incubated 1 hour at 37° C. The antiserum was removed and the wells were washed 3 times with PBS containing 0.02% Tween 20. 50 μl of a solution containing anti-bovine IgG coupled to horseradish peroxidase (diluted 1:500 in PBS containing 1% BSA, Kirkegaard and Perry Laboratories, Inc.) was added to visualize the wells containing antibody against the specific antigen. The solution was incubated 1 hour at 37° C., then removed and the wells were washed 3 times with PBS containing 0.02% Tween 20. 100 μl of substrate solution (ATBS, Kirkegaard and Perry Laboratories, Inc.) were added to each well and color was allowed to develop for 15 minutes. The reaction was terminated by addition of 0.1M oxalic acid. The color was read at absorbance 410 nm on an automatic plate reader.

PROCEDURE FOR GENERATING MONOCLONAL ANTIBODIES

To produce monoclonal antibodies, 8 to 10 week old BALB/c female mice were vaccinated intraperitoneally seven times at two to four week intervals with 107 PFU of S-PRV-160. Three weeks after the last vaccination, mice were injected intraperitoneally with 40 μg of purified gpG. Spleens were removed from the mice three days after the last antigen dose.

Splenocytes were fused with mouse NS1/Ag4 plasmacytoma cells by the procedure modified from Oi and Herzenberg, (39). Splenocytes and plasmacytoma cells were pelleted together by centrifugation at 300×g for 10 minutes. One ml of a 50% solution of polyethylene glycol (m.w. 1300–1600) was added to the cell pellet with stirring over one minute. Dulbecco's modified Eagles's medium (5 ml) was added to the cells over three minutes. Cells were pelleted by centrifugation at 300×g for 10 minutes and resuspended in medium with 10% fetal bovine serum and containing 100 μM hypoxanthine, 0.4 μM aminopterin and 16 μM thymidine (HAT). Cells (100 μl) were added to the wells of eight to ten 96-well tissue culture plates containing 100 μl of normal spleen feeder layer cells and incubated at 37° C. Cells were fed with fresh HAT medium every three to four days.

Hybridoma culture supernatants were tested by the ELISA ASSAY in 96-well microtiter plates coated with 100 ng of purified gpG. Supernatants from reactive hybridomas were further analyzed by black-plaque assay and by Western Blot. Selected hybridomas were cloned twice by limiting dilution. Ascetic fluid was produced by intraperitoneal injection of $5\times10^6$ hybridoma cells into pristane-treated BALB/c mice.

METHOD FOR cDNA CLONING BOVINE ROTAVIRUS gp38 GENE

The Calf Nebraska strain of bovine rotavirus (USDA) was propagated on MA-104 cells (Rhesus monkey kidney cells from MA Bioproducts). Confluent monolayers were infected at a multiplicity of infection of greater than 10 in DMEM containing 5 micrograms/ml trypsin. Cells were incubated with virus for 48 hours or until a cytopathic effect was obtained. Media and cell debris were collected and centrifuged at 10,000×g for 20 minutes at 4° C. The supernatant containing the rotavirus was then centrifuged at 10,000×g in a preparative Beckman Ti45 rotor at 4° C. Virus pellets were resuspended in SM medium (50 mM Tris-HCl pH 7.5, 100 mM KCl, 10 mM $MgCl_2$) and homogenized lightly in a Dounce-type homogenizer. The resuspended virus was centrifuged at 10,000×g for 10 minutes then loaded onto 25–50% CsCl gradients in SM buffer. Gradients were centrifuged at 100,000×g for 4 hours at 20° C. The two blue-white bands representing intact virions and cores of rotavirus were collected, diluted, and the CsCl gradient procedure was repeated a second time. Virus obtained from the second gradient was dialyzed overnight against SM buffer at 4° C.

Dialyzed bovine rotavirus was twice extracted with an equal volume of SDS/phenol, then twice more with chloroform: isoamylalcohol (24:1). The double stranded RNA was precipitated with ethanol in the presence of 0.2M sodium acetate, centrifuged and resuspended in water. The yield was typically 100 micrograms from 1,000 $cm^2$ of infected cells.

160 micrograms of double-stranded bovine rotavirus RNA obtained from the above procedure was mixed with one microgram each of two synthetic oligonucleotide primers in a volume of 160 microliter (sequences of primers were: 5'-GGGAATTCTGCAGGTCACATCATACAA TTCTAATCTAAG-3' and 5'-GGGAATTCTGCAGGC TTTAAAAGAGAGAATTTCCGTTTGGCTA-3') derived from the published sequence of bovine rotavirus (40). The RNA-primer mixture was boiled for 3 minutes in a water bath then chilled on ice. Additions of 25 microliters of 1M Tris-HCl pH 8.3, 35 microliters of 1M KCl, 10 microliters of 0.25M $MgCl_2$, 7 microliters of 0.7M 2-mercaptoethanol, 7 microliters of 20 mM dNTP's, and 6 microliters of reverse transcriptase (100 units) were made sequentially. The reaction was incubated at 42° C. for 1.5 hours then 10 microliters of 0.5M EDTA pH 8.0 was added and the solution was extracted once with chloroform:phenol (1:1). The aqueous layer was removed and to it 250 microliters of 4M ammonium acetate and 1.0 ml of 95% ethanol was added, the mixture was frozen in dry ice and centrifuged in the cold. The resulting pellet was resuspended in 100 microliters of 10 mM Tris-HCl pH 7.5 and the ammonium acetate precipitation procedure was repeated. The pellet was resuspended in 100 microliters of 0.3M KOH and incubated at room temperature overnight, then at 37° C. for 2 hours. The solution was brought to neutral pH by addition of 10 microliters of 3.0M HCl and 25 microliters of 1.0M Tris-HCl pH 7.5. The resulting single-stranded cDNA was then precipitated two times by the above-described ammonium acetate-ethanol procedure. The pellet obtained was resuspended in 50 microliters of 10 mM Tris-HCl pH 7.5, 100 mM NaCl, 1 mM EDTA, boiled in a water bath for 2 minutes, then incubated at 59° C. for 16 hours. The solution was lyophilized to a volume of 15 microliters and the resulting double-stranded cDNA was run on a 1.0% agarose gel (Sigma agarose Type II). The ethidium bromide-stained DNA migrating at 1,000–1,100 base pair length was excised from the gel and electroeluted in a CBS electroeluter device.

The solution was lyophilized, and the cDNA was resuspended in 25 microliters of water. To this solution was added 2 microliters of 1.0M Tris-HCl pH 7.5, 2 microliters of 1M KCl, 1 microliter of 0.25M $MgCl_2$, 1 microliter of 20 mM dNTP's and 5 units of *E. coli* DNA polymerase I. The reaction was incubated at room temperature for 15 minutes, then chloroform/phenol extracted and ammonium acetate-ethanol precipitated as described above. The resulting cDNA was tailed with dATP using terminal deoxynucleotide transferase (BRL buffer and enzyme used). The reaction was stopped with 2 microliters of 0.5M EDTA, chloroform/phenol extracted and precipitated with sodium acetate in the presence of micrograms of carrier TUNA. The resuspended cDNA was mixed with 200 ng of dGMP-tailed Pst I cut pBR322 (BRL catalog #5355SA) in 200 microliters of 10 mM Tris-HCl pH 7.5, 100 $\mu$M NaCl, 1 mM EDTA, heated to 65° C. for 5 minutes, then 57° C. for 2 hours. The annealed cDNA-vector pBR322 was transformed onto *E. coli* DH-1 cells prepared for high efficiency transformation. Colonies that showed sensitivity to ampicillin and tetracycline resistance were grown and DNA was prepared and cut with Pst I to determine the size of the cDNA insert. Several clones having Pst I inserts of 1,050–1,100 base pairs were analyzed and found to have identical restriction enzyme digest patterns. For one of these clones, the 1,100 base pair PstI insert was subcloned into a M13 phage sequencing vector. Part of the DNA sequence of this clone was determined and was found to be identical to the published sequence (40).

cDNA CLONING cDNA cloning refers to the methods used to convert RNA molecules into DNA molecules following state of the art procedures. Applicants' methods are described in Gubler and Hoffman (23). Bethesda Research Laboratories (Gaithersburg, Md.) have designed a cDNA Cloning Kit that is very similar to the procedures used by applicants and contains the best set of reagents and protocols to duplicate our results.

For cloning virus mRNA species, a host cell line sensitive to infection by the virus was infected at 5–10 plaque forming units per cell. When cytopathic effect was evident, but before total destruction, the medium was removed and the cells were lysed in 10 mls lysis buffer (4M guanidine thiocyanate, 0.1% antifoam A, 25 mM sodium citrate pH 7.0, 0.5% N-lauroyl sarcosine, 0.1M beta-mercaptoethanol). The cell lysate was poured into a sterilized Dounce homogenizer and homogenized on ice 8–10 times until the solution was homogenous. For RNA purification, 8 mls of cell lysate were gently layered over 3.5 mls of CsCl solution (5.7M CsCl, 25 $\mu$M sodium citrate pH 7.0) in a Beckman SW41 centrifuge tube. The samples were centrifuged for 18 hours at 20° C. at 36,000 rpm in a Beckman SW41 rotor. The tubes were put on ice and the supernatants from the tubes were carefully removed by aspiration to leave the RNA pellet undisturbed. The pellet was resuspended in 400 microliters glass distilled water, and 2.6 mls of guanidine solution (7.5M guanidine-HCl, 25 mM sodium citrate pH 7.0, 5 mM dithiothreitol) were added. Then 0.37 volumes of 1M acetic acid were added, followed by 0.75 volumes of cold ethanol and the sample was put at 20° C. for 18 hours to precipitate RNA. The precipitate was collected by centrifugation in a Sorvall centrifuge for 10 min at 4° C. at 10,000 rpm in an SS34 rotor. The pellet was dissolved in 1.0 ml distilled water, recentrifuged at 13,000 rpm, and the supernatant saved. RNA was reextracted from the pellet 2 more times as above with 0.5 ml distilled water, and the supernatants were pooled. A 0.1 volume of 2M potassium acetate solution was added to the sample followed by 2 volumes of cold ethanol and the sample was put at −20° C. for 18 hours.

The precipitated RNA was collected by centrifugation in the SS34 rotor at 4° C. for 10 minutes at 10,000 rpm. The pellet was dissolved in 1 ml distilled water and the concentration taken by absorption at A260/280. The RNA was stored at −70° C.

mRNA containing polyadenylate tails (poly-A) was selected using oligo-dT cellulose (Pharmacia #27 5543-0). Three milligrams of total RNA was boiled and chilled and applied to a 100 mg oligo-dT cellulose column in binding buffer (0.1M Tris pH 7.5, 0.5M LiCl, 5 mM EDTA pH 8.0, 0.1% lithium dodecyl sulfate). The retained poly-$A^+$ RNA was eluted from the column with elution buffer (5 mM Tris pH 7.5, 1 mM EDTA pH 8.0, 0.1% sodium dodecyl sulfate). This mRNA was reapplied to an oligo-dT column in binding buffer and eluted again in elution buffer. The sample was precipitated with 200 mM sodium acetate and 2 volumes cold ethanol at −20° C. for 18 hours. The RNA was resuspended in 50 microliters distilled water.

Ten micrograms poly-$A^+$ RNA was denatured in 20 mm methyl mercury hydroxide for 6 minutes at 22° C. Beta-mercaptoethanol was added to 75 mM and the sample was incubated for 5 min at 22° C. The reaction mixture for first strand cDNA synthesis in 0.25 ml contained 1 microgram oligo-dT primer (P-L Biochemicals) or 1 microgram synthetic primer, 28 units placental ribonuclease inhibitor (Bethesda Research Labs #5518SA), 100 mM Tris pH 8.3, 140 mM KCl, 10 $\mu$m $MgCl_2$, 0.8 mM dATP, dATP, dGTP, and dTTP (Pharmacia), 100 microcuries $^{32}$p-labelled dATP (New England Nuclear #NEG-013H), and 180 units AMV reverse transcriptase (Molecular Genetics Resources #MG 101). The reaction was incubated at 42° C. for 90 minutes, and then was terminated with 20 mM EDTA pH 8.0. The sample was extracted with an equal volume of phenol/chloroform (1:1) and precipitated with 2M ammonium acetate and 2 volumes of cold ethanol −20° C. for 3 hours. After precipitation and centrifugation, the pellet was dissolved in 100 microliters distilled water. The sample was loaded onto a 15 ml G-100 Sephadex column (Pharmacia) in buffer (100 mM Tris pH 7.5, 1 mM EDTA pH 8.90, 100 mM NaCl). The leading edge of the eluted DNA fractions were pooled, and DNA was concentrated by lyophilization until the volume was about 100 microliters, then the DNA was precipitated with ammonium acetate plus ethanol as above.

The entire first strand sample was used for second strand reaction which follow the Gubler and Hoffman (23) method except that 50 micrograms/ml dNTP's, 5.4 units DNA polymerase I (Boehringer Mannheim #642–711), and 100 units/ml E. coli DNA ligase (New England Biolabs #205) in a total volume of 50 microliters Were used. After second strand synthesis, the cDNA was phenol/chloroform extracted and precipitated. The DNA was resuspended in 10 microliters distilled water, treated with 1 microgram RNase A for 10 minutes at 22° C., and electrophoresed through a 1% agarose gel (Sigma Type II agarose) in 40 mM Tris-acetate buffer pH 6.85. The gel was stained with ethidium bromide, and DNA in the expected size range was excised from the gel and electroeluted in 8 $\mu$M Tris-acetate pH 6.85. Electroeluted DNA was lyophilized to about 100 microliters, and precipitated with Ammonium acetate and ethanol as above. The DNA was resuspended in microliters water.

Oligo-dC tails were added to the DNA to facilitate cloning. The reaction contained the DNA, 100 mm potassium cacodylate pH 7.2, 0.2 mM dithiothreitol, 2 mM $CaCl_2$, 80 micromoles dATP, and 25 units terminal deoxynucleotidyl transferase (Molecular Genetic Resources #S1001) in 50 microliters. After 30 minutes at 37° C., the reaction was terminated with 10 mM EDTA, and the sample was phenol/chloroform extracted and precipitated as above.

The dC-tailed DNA sample was annealed to 200 ng plasmid vector pBR322 that contained oligo-dG tails (Bethesda Research Labs #5355 SA/SB) in 200 microliters of 0.01M Tris pH 7.5, 0.1M NaCl, 1 mM EDTA pH 8.0 at 65° C. for 2 minutes and then 57° C. for 2 hours. Fresh competent E. coli DH-1 cells were prepared and transformed as described by Hanahan (41) using half the annealed cDNA sample in twenty 200 microliter aliquots of cells. Transformed cells were plated on L-broth agar plates plus 10 micrograms/ml tetracycline. Colonies were screened for the presence of inserts into the ampicillin gene using Ampscreen (Bethesda Research Labs #5537 UA), and the positive colonies were picked for analysis.

POLYMERASE FILL-IN REACTION

DNA was resuspended in buffer containing 50 mM Tris pH 7.4, 50 mM KCl, 5 mM $MgCl_2$, and 400 micromolar each of the four deoxynucleotides. Ten units of Klenow DNA polymerase (BRL) were added and the reaction was allowed to proceed for 15 minutes at room temperature. The DNA was then phenol extracted and ethanol precipitated as above.

HOMOLOGY VECTOR 523-78.72

The plasmid 523-78.72 was constructed for the purpose of deleting a portion of the gpE gene coding region from the IBR virus. It may also be used to insert foreign DNA into IBR. Plasmid 52378.72 may be constructed by digestion of the plasmid 53603.5 with the enzyme XbaI followed by religation to remove the lacZ marker gene.

HOMOLOGY VECTOR 591-21.20

Figure 24:
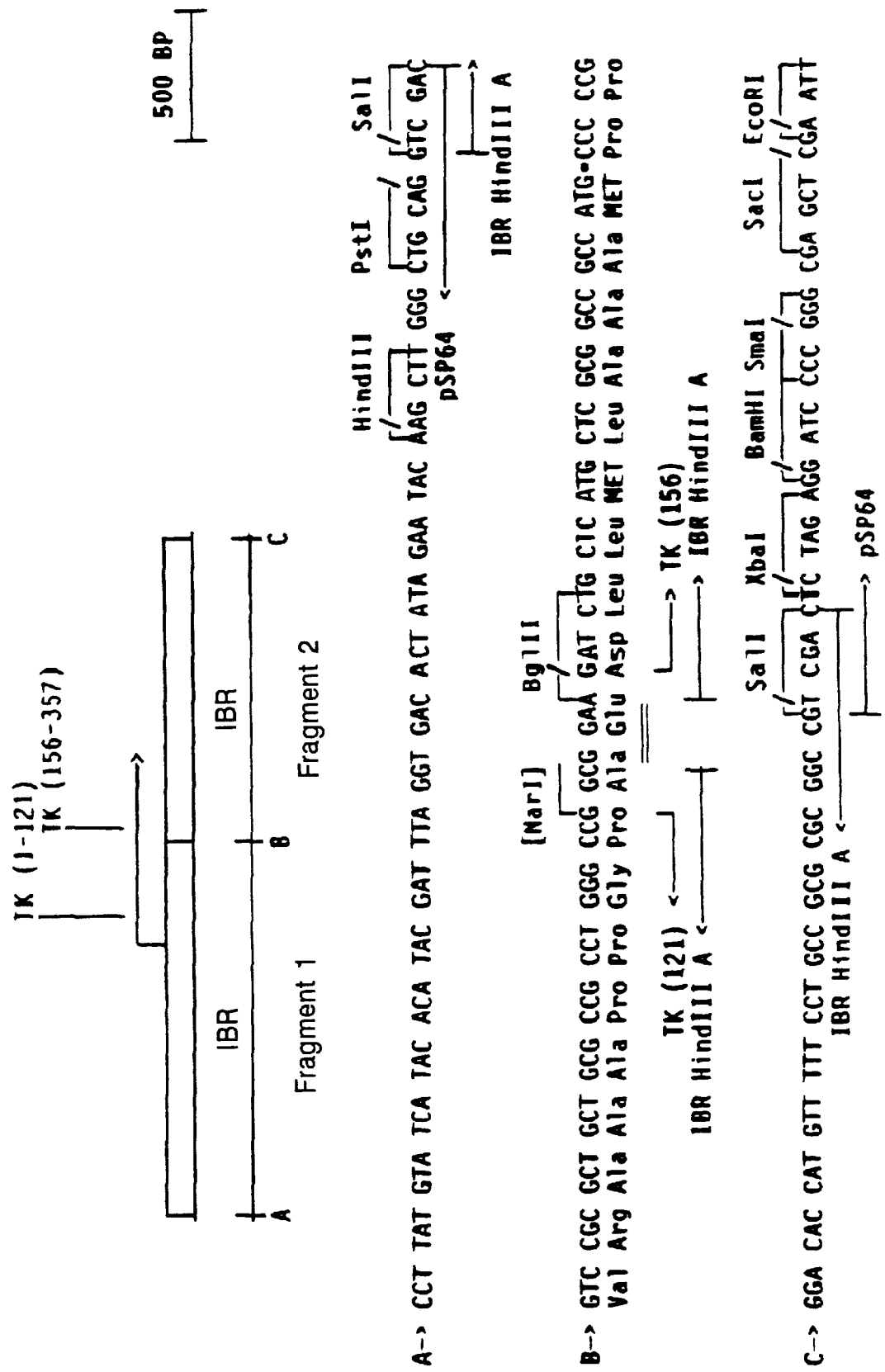

The plasmid 591-21.20 was constructed for the purpose of deleting a portion of the IBR thymidine kinase gene. It may also be used to insert foreign DNA into IBR. It contains a unique BglII restriction enzyme site into which foreign DNA may be inserted. It may be constructed utilizing standard recombinant DNA techniques (6, 14) by joining restriction fragments from the following sources with the synthetic DNA sequences indicated in FIG. 24. The plasmid vector is derived from an approximately 2999 base pair SalI to SalI restriction fragment of pSP64 (Promega). Fragment 1 is an approximately 1400 base pair SalI to NarI restriction subfragment contained on the approximately 2700 base pair SalI-SalI restriction subfragment of the IBR HindIII restriction fragment A (72). Fragment 2 is an approximately 1215 base pair BglIII to SalI restriction subfragment contained on the approximately 2700 base pair SalI-SalI restriction subfragment of the IBR HindIII restriction fragment A (72).

HOMOLOGY VECTOR 552-46.12

Figure 25A:
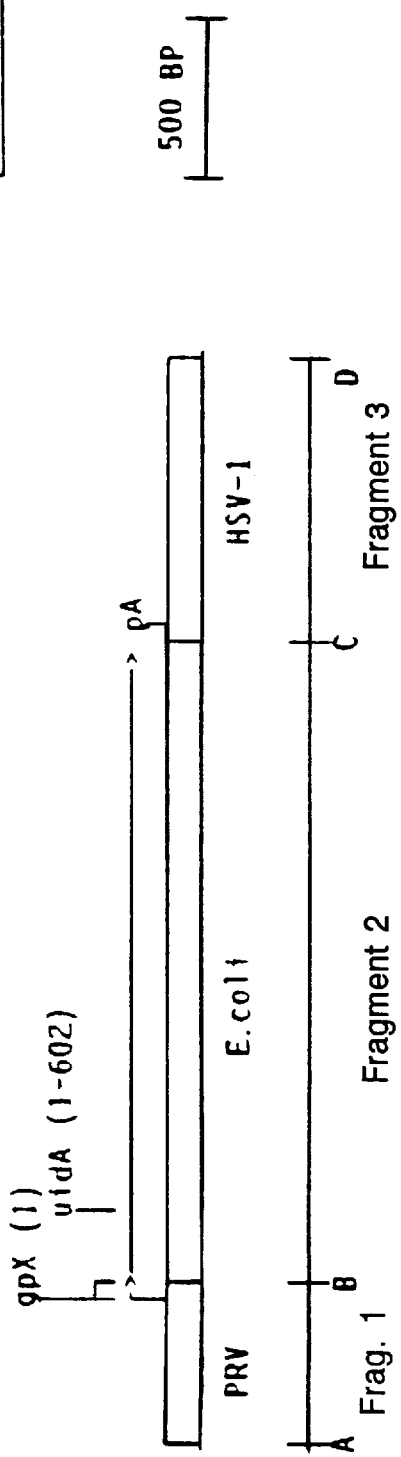
FIGS. 25A and 25B Detailed description of the marker gene insertion in Homology Vector 591-46.12. The diagram shows the orientation of DNA fragments assembled in the marker gene. The origin of each fragment is described in the MATERIALS AND METHODS section. The sequences located at the junctions between each fragment and at the ends of the marker gene are shown. The restriction sites used to generate each fragment are indicated at the appropriate junction. The location of the uidA gene coding region is also given. The following two conventions are used: numbers in parenthesis ( ) refer to amino acids, and restriction sites in brackets [ ] indicate the remnants of sites which were destroyed during construction. The following abbreviations are used, pseudorabies virus (PRV), uronidase A gene (uidA), *Escherichia coli* (*E. coli*), herpes simplex virus type 1 (HSV-1), poly adenylation signal (pA), and glycoprotein X (gpX).
Legend: B=BamHI; H=HindIII; X=XbaI; S=StuI; UL=unique long region; US=unique short region; IR=internal repeat region; TR=terminal repeat region.
Figure 25B:
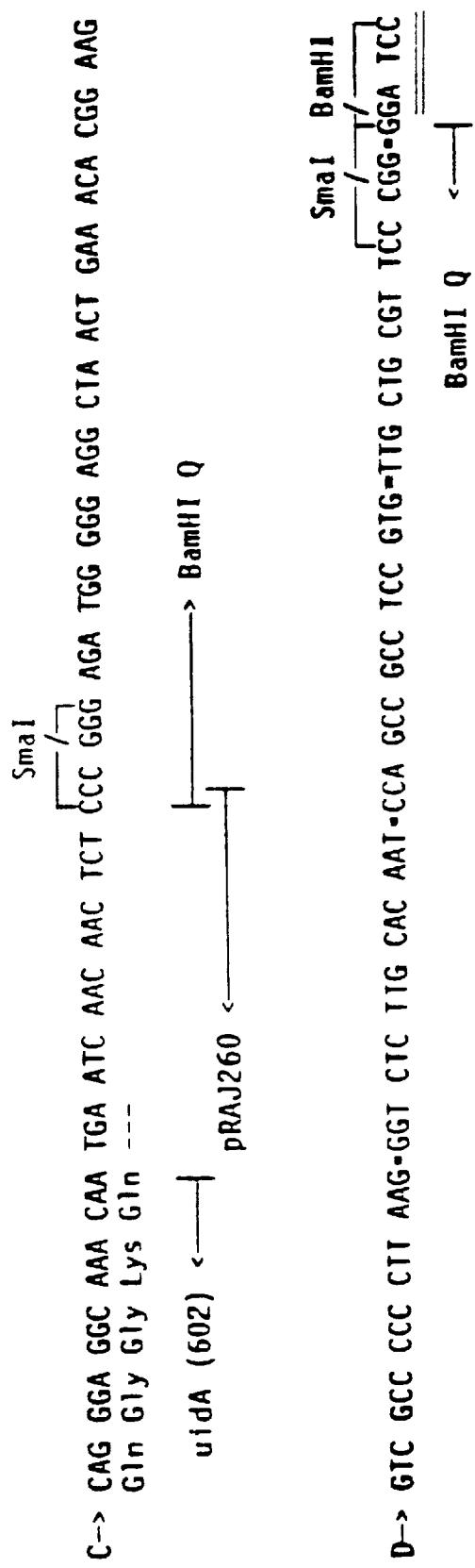

The plasmid 591-46.12 was constructed for the purpose of deleting a portion o the Tk gene coding region from the IBR virus. It incorporates an E. coli β-glucuronidase (uidA) marker gene flanked by IBR virus DNA. The uidA marker gene was inserted into the homology vector 591-21.20 at the unique BglII site. The marker gene is oriented in the same direction as the Tk gene in the homology vector. A detailed description of the marker gene is given in FIGS. 25A and 25B. It may be constructed utilizing standard recombinant DNA techniques (6, 14) by joining restriction fragments from the following sources with the synthetic DNA sequences indicated in FIG. 25. Fragment 1 is an approximately 404 base pair SalI to EcoRI restriction subfragment of the PRV BamHI restriction fragment #10 (3). Note that the EcoRI site was introduced at the location indicated in FIG. 12 by PCR cloning. Fragment 2 is an approximately 1823 base pair EcoRI to SmaI fragment of the plasmid pRAJ260 (Clonetech). Note that the EcoRI and SmaI sites were introduced at the locations indicated in FIGS. 25A and 25B by PCR cloning. Fragment 3 is an approximately 784 base pair SmaI to SmaI restriction subfragment of the HSV-1 BamHI restriction fragment Q (10). Note that this fragment is oriented such that the polyadenylation sequence (AATAAA) is located closest to junction C.

CLONING OF BOVINE VIRAL DIARRHEA VIRUS gp53 GENE

The bovine viral diarrhea (BVDV) gp53 gene was cloned essentially as described earlier (see cDNA CLONING) using the random priming method (6). Viral RNA prepared from BVDV Singer strain grown in MADIN-DARBY bovine kidney (MDBK) cells was converted to cDNA using the random priming method. The cDNA was used for second strand reaction (23) and the resulting double stranded DNA was used cloned as described in the cDNA CLONING procedure. From this procedure a series of clones were obtained that comprised parts of the genome of BVDV. The location of the gene for gp53 gene has been published (66) and this sequence information was used to locate and isolate the gp53 encoding region from the 449 kilodalton primary translation product open reading frame contained in the complete cDNA clone.

The gp53 encoding gene of BVDV was also cloned essentially as described by Katz et al. for the HA gene of human influenza virus. Viral RNA prepared from the Singer strain of BVDV virus grown in MDBK cells was first converted to cDNA utilizing an oligo nucleotide primer specific for the target gene. The cDNA was then used as a template or polymerase chain reaction (PCR) cloning (67) of the gp53 gene. The PCR primers were designed to incorporate restriction endonuclease enzyme sites that permit the cloning of the amplified coding region into vectors that contain the appropriate signals for gene expression in IBR. The gp53 gene of the Singer strain of BVDV was cloned using the following oligo nucleotide primers: 5'-CATAGATCTTGTGGTGCTGTCCGACTTCGCA-3' for cDNA priming and was combined with 5'-CGTGGATCCTCAATTACAAGAGGTATCGTCTAC-3' for PCR amplification. Note that this general strategy may be used to clone the gp53 coding region from BVDV strains other than Singer.

CLONING OF BOVINE RESPIRATORY SYNCYTIAL VIRUS FUSION PROTEIN AND NUCLEOCAPSID PROTEIN GENES

The bovine respiratory virus (BRSV) fusion (F), attachment (G), an nucleocapsid protein (N) genes may be cloned essentially as described by Katz et al. for the HA gene of human influenza. Viral RNA prepared from virus grown in bovine nasal turbinate (BT) cells is first converted to cDNA utilizing an oligo nucleotide primer specific for the target gene. The cDNA is then used as a template for polymerase chain reaction (PCR) cloning (67) of the targeted region. The PCR primers are designed to incorporate restriction sites which permit the cloning of the amplified coding regions into vectors containing the appropriate signals for expression in IBR. One pair of oligo nucleotides will be required for each coding region. The N gene coding region from the BRSV strain A51908 (or 391-2??) would be cloned utilizing the following primers: 5'-AAAAGATCTTAGCAAGGT CAAACTAAATGACACTTTCAAC-3' for cDNA priming and combined with 5'-CGTGGATCCAACTCACAATTC CACATCATTATCTTTGGGATT-3' for PCR. The G gene coding region from the BRSV strain A51908 (or 391-2??) would be cloned utilizing the following primers: 5'-TATAGATCTTCATACCCA TCATCTTAAATTCAAGACATTA-3' for cDNA priming and combined with 5'-CGTGGATCCATAATTAGATG TTATATGGAGGTGTGTTG-3' for PCR. The F gene from strain A51908 (or 391-2??) of BRSV would be cloned utilizing the following primers: 5'-TATAGA TCTAACAGCCATGAGGATGATCATCAGCATTATC-3' for cDNA priming and combined with 5'-CGTGGATCC TTCTGAGGTTTAGATTGTAAACATTATGCA-3' for PCR. Note that this general strategy may be used to clone the coding region of F and N genes from other strains of BRSV.

CLONING OF *Pasteurella haemolytica* LEUKOTOXIN AND IRON REGULATED OUTER MEMBRANE PROTEIN(S)

The *Pasteurella haemolytica* strain A1 leukotoxin gene may be cloned from a genomic DNA sample. Genomic DNA is prepared from *P. haemolytica* A1 cells grown in culture (68) by the methods described in Maniatis et al. (1982). The purified *P. haemolytica* DNA is then used as a template for polymerase chain reaction (PCR) cloning (67) of the targeted leukotoxin gene. The PCR primers are designed so that restriction endonuclease sites are incorporated that allow the cloning of the 102 kilodalton toxin portion of the gene into vectors containing the appropriate signals for expression in IBR. The *P. haemolytica* A1 (ATTC 43279 biotype A, serotype 1) leukotoxin gene would be cloned utilizing the following primers: 5'-TATAGATCTTAGACTTACAACCCTAAAAAAC-3' and 5'-CGTGGATCCAACTCTATAATGTGTGAA ACAATATAG-3' for PCR. Note that this general strategy may be used to clone the coding regions for the leukotoxin gene of all *P. haemolytica* serotypes.

The *P. haemolytica* A1 iron regulated outer membrane proteins (IRP) of 3 major polypeptides with molecular weights of 35, 70 and 100 kilodaltons. The DNA coding for the array of *P. haemolytica* genes can be cloned in *Escherichia coli* using plasmid vectors essentially as described in Maniatis et al. (1982). The clone library is constructed by partial digestion of the genomic DNA. The IRP genes can be isolated from this library of *P. haemolytica* clones by screening for the production of iron regulated outer membrane antigens by a colony enzyme-linked immunosorbent assay blot method with antiserum that is specific to the IRPs. This antiserum may be obtained by eluting antibodies derived from polyclonal antiserum raised against whole *P. haemolytica* or membrane enriched fractions but selectively bound to the IRPs on Western blots (69). The specificity of the antibodies can be verified by immunoblot screening of *P. haemolytica* polypeptides from iron restricted and iron induced cultures.

EXAMPLES

Example 1

S-IBR-002

S-IBR-002 is an IBR virus that has a deletion of approximately 800 bp in the repeat region of the genome. This deletion removes the only two EcoRV restriction sites on the virus genome and an adjacent BglII site (FIG. 2).

To construct this virus, the DIRECT LIGATION PROCEDURE FOR GENERATING RECOMBINANT HERPESVIRUS was performed. Purified IBR virus DNA (Cooper strain) digested with EcoRV restriction enzyme was mixed with DraI-restriction enzyme-digested plasmid DNA containing the *E. coli* β-galactosidase (lacZ) gene under the control of the HSV-1 TK promoter. After ligation the mixture was used to transfect animal cell s and the transfection stock was screened for recombinant IBR virus by the SOUTHERN BLOTTING OF DNA procedure. The final result of the purification was the recombinant IBR virus designated S-IBR-002. It was shown by Southern hybridization that this virus does not carry any foreign genes. Restriction enzyme analysis also showed that the insertion sites (EcoRV) in both repeats were deleted. FIG. 2 shows the restriction map of the EcoRI B fragment which contains the EcoRV restriction sites and the map of S-IBR-002 which lacks the EcoRV sites. S-IBR-002 was deposited on Jun. 18, 1986 pursuant to the Budapest Treaty on the International Deposit of Microorganisms for the Purposes of Patent Procedure with the Patent Culture Repository of the American Type Culture Collection, 12301 Parklawn Drive, Rockville, Md. 20852 U.S.A. under ATCC Accession No. VR 2140.

A study was conducted to determine the safety and serological response of young calves following intramuscular administration of S-IBR-002. These results are presented in Table 1. Three calves were inoculated intramuscularly with $10^7$ PFU of S-IBR-002. Clinical signs of IBR and febrile response were absent in these calves, as well as in the contact control calf. All three calves developed significant neutralizing antibody to IBR virus but the contact control remained seronegative. These results suggest that S-IBR-002 is useful as a vaccine against IBR disease.

TABLE 1

Serologic and Clinical Response of Young Calves Following Vaccination with S-IBR-002

| Virus Construct | Calf # | Clinical and Febrile response | Virus Isolation[a] | Antibody Titer Days Post Inoculation 0 | 7 | 14 | 21 | 28 |
|---|---|---|---|---|---|---|---|---|
| S-IBR-002 | 28 | NONE | (–) | <2 | <4 | 6 | 5 | 3 |
| | 30 | NONE | (–) | <2 | <4 | 6 | <2 | 6 |
| | 94 | NONE | (–) | <2 | <4 | 6 | 3 | 8 |
| Control | 32 | NONE | (–) | <4 | <4 | <4 | <2 | <4 |

[a]From nasal swabs and peripheral blood leukocytes.

Example 2

Unique Short 2 gene

The unique short region of IBR virus contains a gene homologous to the US2 gene of several other herpesviruses. In the studies described below we show that deletion of the IBR unique short 2 gene (US2) may render the virus safe for use in pregnant cows, as determined by direct fetal inoculation.

Observing that the Nasalgen IBR vaccine strain will not cause abortion when used in IBR-susceptible pregnant cows at various stages of gestation (18,65), we attempted to determine the genomic lesion responsible for this property. We characterized the genome of this virus by restriction mapping and DNA sequence analysis. It was determined that a major portion of the IBR virus US2 gene was deleted from the Nasalgen virus. Restriction mapping of the Nasalgen virus indicated that the HindIII K fragment contained an approximately 800 base pair deletion. The deletion was localized to the end of the HindIII K Fragment located next to the HindIII O fragment (see FIG. 1). Therefore, the HindIII K fragment from the Cooper strain was subcloned and this region was sequenced. The first 1080 base pairs of the fragment were found to contain an open reading frame (ORF) coding for 309 amino acids (see FIG. 3). The ORF is 68% G+C and encodes a protein with a predicted molecular weight of 46,094. Comparison of the sequence of the predicted protein with sequences of gene products of HSV-1, PRV, HSV-2, and MDV in the unique short region indicated that this ORF is homologous to the herpesvirus US2 gene (see FIGS. 4A and 4B). Although the function of the herpesvirus US2 gene is not known, the gene has been shown to be nonessential for growth of HSV in cell culture (4,19). The US2 gene has also been shown to be deleted in the PRV vaccine strains Norden and Bartha (11).

The HindIII K fragment from the Nasalgen virus was subcloned and the deletion region was sequenced. When the sequence obtained from the Nasalgen strain was compared to the sequence obtained from the Cooper strain (see FIGS. 5A and 5B), it was possible to determine that amino acids 59 to 309 of the US2 gene had been deleted. It was also determined that most of the HindIII O fragment had also been deleted.

Cattle studies have shown that the Nasalgen virus will not cause abortion when used in IBR-susceptible pregnant cows at various stages of gestation (18). Since the only major difference between the wild-type IBR strain and the Nasalgen strain resides in the deletion of the US2 gene, this gene may be involved in the fetal virulence observed for the wild type virus.

Example 3

S-IBR-027

S-IBR-027 is an IBR virus that has a deletion of approximately 800 bp in the repeat regions and approximately 1200 bp in the short unique region of the genome. The deletion in the short unique region removes the US2 gene (FIG. 6). The repeat deletion was derived from the parental virus S-IBR-002 and is described in Example 2.

To construct this virus, the HOMOLOGOUS RECOMBINATION PROCEDURE FOR GENERATING RECOMBINANT HERPESVIRUS was performed. A homology vector containing the bacterial transposon Tn5 NEO (aminoglycosidase 3'-phosphotransferase) gene under the control of the HSV $\alpha4$ promoter flanked by sequences from the IBR virus TK gene was constructed. The IBR virus homology regions were derived from the TK gene. The upstream homology included the first amino acid of the TK gene (15) and extended approximately 800 base pairs upstream of the TK coding region. The downstream homology included amino acids 156 to 357 and extended downstream of the TK coding region approximately 60 base pairs. S-IBR-002 DNA was mixed with the homology vector and transfected into rabbit skin cells as indicated in the methods. The transfection stock was selected according to the SELECTION OF G418 RESISTANT IBR VIRUS. Individual clones were picked after one round of selection and analyzed by the SOUTHERN BLOTTING OF DNA procedure. When a probe derived from the NEO gene was used in this analysis, one clone was found which did not hybridize to the NEO probe but had a HindIII restriction digestion pattern clearly distinct from the parental S-IBR-002. Further analysis indicated that the NEO had not been inserted into the TK region, however an approximately 1200 base pair deletion had occurred in the HindIII K fragment.

In order to characterize the HindIII K deletion, that fragment was subcloned and subjected to restriction mapping. Utilizing a series of oligonucleotide probes derived from the wild type sequence it was determined that approximately 1200 base pairs were deleted from the end of the HindIII K fragment adjacent to the HindIII K/HindIII O junction (see FIG. 6). This deletion removes the entire coding region of the US2 gene. S-IBR-027 was deposited on Apr. 17, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2322.

Direct fetal inoculation is the most sensitive test for determining the safety of live, IBR vaccines as regards their use in pregnant cows or in calves nursing pregnant cows. Three virus constructs were tested for fetal safety by inoculating directly into the vine fetus, following laparotomy to expose the uterus. Abortion occurring within seven days after inoculation was considered to be surgically-induced. If fetuses aborted after this time, tissue samples were removed and cultured for the presence of the IBR construct. Caesarean sections were performed on cows with fetuses surviving for greater than 30 days post-inoculation. Fetal tissue was removed for virus culturing and blood samples were taken for evaluation of serum antibody to IBR virus.

The S-IBR-027 construct described above was tested, as well as two other constructs, S-IBR-020 and S-IBR-028. The S-IBR-020 construct was derived from the Cooper strain of IBR virus by making deletions in the repeat regions of the DNA and by inserting the Tn5 NEO gene. The S-IBR-028 construct was derived from the Cooper strain of IBR virus by making deletions in the repeat region of the DNA and in the TK gene. The Tn5 NEO gene was also inserted into the TK deletion.

The following results were obtained from studies with the three virus constructs. In the studies with S-IBR-020, two fetuses were inoculated, one at approximately 130–140 days gestation and the other at approximately 170–180 days gestation. The younger fetus aborted twenty days after inoculation, but virus could not be recovered from tissue samples of this fetus (Table 2). The other fetus was live and appeared normal when it was surgically removed 60 days post-inoculation. In studies with S-IBR-027, four fetuses, ranging in age from 125 days to >250 days, were inoculated (Table 2). All fetuses survived and appeared normal. In studies with S-IBR-028, three fetuses, ranging in age from 140 days to >250 days, were inoculated. The youngest and eldest fetuses survived and appeared normal, however the fetus inoculated at 160–170 days gestation aborted nine days after inoculation.

Direct fetal inoculation is the most sensitive test for measuring the safety of live, IBR viruses used in pregnant cows. To date, the gene(s) involved in fetal virulence has not been reported. We have engineered IBR viruses with deletions in three different regions of IBR virus DNA and then determined the effect of the gene deletion. All three virus constructs tested have a deletion in the repeat region of the DNA and two constructs do not have TK activity. One fetus inoculated with each of the TK-constructs has aborted. In contrast, the construct with deletions in the repeat regions and the US2 gene (S-IBR-027) has been inoculated into four fetuses with no adverse reactions.

TABLE 2

Safety of IBR Viruses for Bovine Fetuses

| Construct | Fetal Age[a] | Results |
|---|---|---|
| S-IBR-020 | 130–140 Days | Fetus aborted Day 20 post-inoculation; no virus isolated |
|  | 170–180 Days | Normal, live fetus 60 days post-inoculation |
| S-IBR-027 | 125–135 Days | Normal, live fetus 60 days post-inoculation |
|  | 150–160 Days | Normal, live calf born 56 Days post-inoculation |
|  | 220–240 Days | Normal, live calf born 30 days post-inoculation |
|  | >250 Days | Normal, live calf born 30 days post-inoculation |
| S-IBR-028 | 140–150 Days | Normal, live fetus 60 days post-inoculation |
|  | 160–170 Days | Fetus aborted Day 9 post-inoculation; no virus isolated |
|  | >250 Days | Normal, live calf born 12 days post-inoculation |

[a]Approximate age at time of virus inoculation

We have shown that S-IBR-027 is safe for fetal inoculation in contrast to S-IBR-020 and S-IBR-028 which are not. Although all three viruses were engineered by similar approaches, the distinguishing difference of S-IBR-027 is the deletion of the US2 gene. We have also shown that the Nasalgen virus, which was generated by independent methods and is also safe for use in IBR-susceptible pregnant cows, has been deleted in the US2 gene.

Although the S-IBR-027 and Nasalgen have the similar property of fetal safety, S-IBR-027 offers additional advantages. The major portion of the US2 gene (251 out of 309 amino acids) has been deleted in the Nasalgen virus. This deletion would clearly inactivate the gene, however the remaining portion of the gene may make it more likely to revert to virulence via recombination with other viruses. The complete coding region of the US2 has been deleted from S-IBR-027 making it less likely that this gene could be restored and revert the virus to virulence. The S-IBR-027 construct also carries an important deletion in the repeat region, which is not present in the Nasalgen virus. A deletion in the analogous region of the pseudorabies virus (PRV) has been shown to be valuable in attenuating PRV for swine (see U.S. Pat. No. 4,877,737). This deletion has also been shown to attenuate IBR for cattle as seen in the testing of S-IBR-002 (see Example 1).

Example 4

S-IBR-028

S-IBR-028 is an IBR virus that has a deletion of approximately 800 bp in the repeat regions and approximately 250 bp in the TK region of the genome. The deletion in the TK region inactivates the TK gene. The repeat deletion was derived from the parental virus S-IBR-002 and is described in Example 2.

To construct this virus, the HOMOLOGOUS RECOMBINATION PROCEDURE FOR GENERATING RECOMBINANT HERPESVIRUS was performed. A homology vector containing the bacterial transposon Tn5 NEO (aminoglycosidase 3'-phosphotransferase) gene under the control of the HSV-1 α4 gene promoter flanked by sequences from the IBR virus TK gene was constructed. The IBR virus homology regions were derived from the TK gene. The upstream homology included amino acids 1 to 62 of the TK gene (15) and extended approximately 674 base pairs upstream of the TK coding region. The downstream homology included amino acids 156 to 357 and extended downstream of the TK coding region approximately 1138 base pairs. S-IBR-002 DNA was mixed with the homology vector 129-71.5 and transfected into rabbit-skin cells as indicated in the methods. The transfection stock was selected according to the SELECTION OF G418 RESISTANT IBR VIRUS.

Individual clones were picked after two rounds of selection and analyzed by the SOUTHERN BLOTTING OF DNA procedure. Several clones were assayed for TK activity by a $^{14}$C-thymidine incorporation assay (29). One clone which was negative for TK activity was chosen and characterized by digestion with HindIII and XbaI. The restriction endonuclease analysis confirmed that the NEO gene had been inserted into the TK gene. This clone, designated S-IBR-028, was deposited on May 14, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2326.

Example 5

Glycoprotein G gene

Deletion of the PRV gpX gene has been shown to be valuable both as an attenuating lesion and as a negative serological marker (see U.S. Ser. No. 192,866, filed May 11, 1988 now U.S. Pat. No. 5,047,237 issued Sep. 10, 1991). In the studies described below we show that the unique short region of IBR virus contains a gene homologous to the gpX gene of PRV.

Figures 9A, 9B:
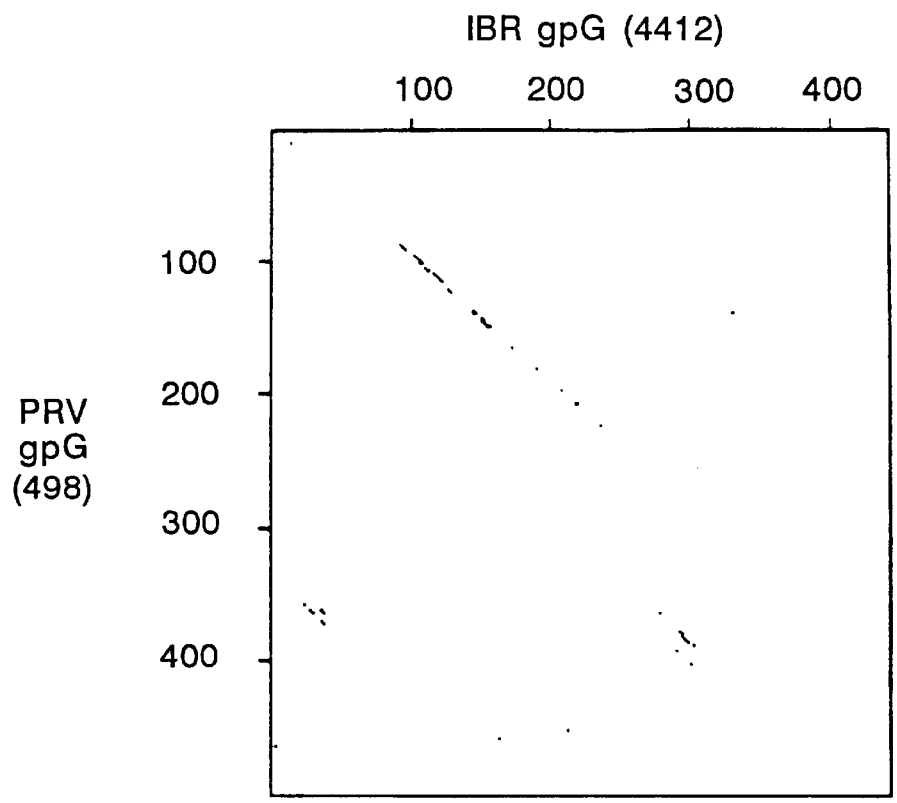
FIGS. 9A and 9B Homology between the IBR gpG protein, the gpX protein of PRV and the gpG protein of HSV-2. (a) Matrix plot of the amino acid sequence of the IBR gpG protein (441) against the amino acid sequence of the PRV gpX protein (498) (12). (b) Alignment of the conserved region between IBR gpG protein, PRV gpX protein, and HSV-2 gpG protein (699) (9). Note that IUPAC-IUB Biochemical Nomenclature Commission conventions are used.

The sequence of an approximately 1400 base pair region of the IBR HindIII K fragment (see FIG. 8), located approximately 2800 base pairs downstream of the HindIII K/HindIII O junction was determined. This region was found to contain an ORF coding for 441 amino acids translated in the direction away from the HindIII K/HindIII O junction (see FIG. 1). The ORF is 69% G+C and encodes a protein with a predicted molecular weight of 58,683. Comparison of the sequence of the predicted protein with sequences of gene products of HSV-2 and PRV in the unique short region indicated that this ORF is homologous to the herpesvirus gpG gene (see FIGS. 9A and 9B). The complete gpG gene resides on an approximately 2800 base pair MluI to NdeI sub-fragment of the IBR virus HindIII K fragment. This subfragment has been cloned as a blunt ended fragment into the plasmid pSP64. This plasmid is designated PSY1643. PSY1643 was deposited on Jul. 16, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 68652. This plasmid may be used to confirm the sequence of the gpG gene. The sequence of the gpG gene may also be confirmed by comparing the appropriate DNA sequence of the wild type virus S-IBR-000 (Cooper strain with the sequence of the gpG deleted virus S-IBR-037 (ATCC Accession No. 2320).

To confirm the expression of the IBR virus gpG gene product, cells were infected with IBR virus and samples of media from infected cultures were subjected to SDS-polyacrylamide gel electrophoresis. The gel was blotted and analyzed using the WESTERN BLOTTING PROCEDURE. The anti-serum used was a mouse hyper-immune serum raised against chemically-synthesized gpG peptides (amino acids 242–254 and 269–289) linked to keyhole limpet hemocyanin. As shown in FIG. 10, gpG is prominent in the media of cells infected with wild type virus (S-IBR-000), but is not detected in media of mock infected cells.

Example 6

S-PRV-160

S-PRV-160 is a pseudorabies virus that has a deletion in the TK gene in the long unique region, a deletion in the repeat region, and an approximately 1414 base pair deletion in the gpX coding region. The gene for *E. coli* β-galactosidase (lacZ gene) was inserted in the place of the gpX gene and is under the control of the gpX promoter. A chimeric gene coding for an IBR virus gpG, PRV gpIII and PRV gpX fusion protein was inserted at the HindIII sites located in each repeat.

S-PRV-160 was constructed utilizing plasmid 459-12.6, pseudorabies virus S-PRV-013 (see U.S. Ser. No. 823,102, filed Jan. 27, 1986 now U.S. Pat. No. 5,068,192 issued Nov. 26, 1991 and U.S. Ser. No. 07/192,866, filed May 11, 1988 now U.S. Pat. No. 5,047,237 issued Sep. 10, 1991) and the restriction enzyme HindIII in the DIRECT LIGATION PROCEDURE FOR GENERATING RECOMBINANT HERPESVIRUS. Several clones were screened by digestion with HindIII for the presence of the HindIII band containing the chimeric gene insert from plasmid 459-12.6. One clone exhibiting the correct HindIII insert band was chosen and designated S-PRV-160.

S-PRV-160 was constructed so that it would express precisely the gpG specific amino acids that were deleted in S-IBR-037. This allows the gpG fusion protein expressed in S-PRv-160 to be used as an antigen to identify antibodies directed against the wild type virus as opposed to antibodies directed against S-IBR-037. Note that gpX, the PRV homologue of IBR virus gpG, has been deleted from S-PRV-160 to prevent any confusion resulting from cross reactivity that might exist between the two proteins. To confirm that S-PRV-160 does express IBR virus gpG, a Western blot analysis was performed. As can be seen in FIG. 10, gpG specific antibody does react with an appropriately sized media protein from S-PRV-160.

S-PRV-160 may also be utilized as an antigen for the production of gpG specific monoclonal antibodies. Such antibodies are useful in the development of diagnostic tests specific for the gpG protein. Monoclonal antibodies were generated in mice utilizing S-PRV-160 according to the PROCEDURE FOR GENERATING MONOCLONAL ANTIBODIES. One of these antibodies' clone 3-1G7 was shown to react specifically with purified gpG in the gpG ELISA assay.

Example 7

S-IBR-035

S-IBR-035 is an IBR virus that has two deletions in the short unique region of the genome. The first deletion is approximately 2500 base pairs and begins in the HindIII K fragment approximately 1750 base pairs downstream of the HindIII O/HindIII K junction and extends back through that junction. This deletion removes the US2 gene. The second deletion is approximately 294 base pairs and begins in the HindIII K fragment approximately 3900 base pairs downstream of the HindIII K/HindIII O junction and extends back toward that junction. This deletion removes amino acids 263 to 361 of the gpG gene. The gene for *E. coli* β-galactosidase (lacZ gene) was inserted into the deletion in the gpG gene and is under the control of the HCMV immediate early promoter.

S-IBR-035 was derived from S-IBR-000 (Cooper strain). This was accomplished utilizing the homology vector 43901.31 (see Materials and Methods) and virus S-IBR-000 in the HOMOLOGOUS RECOMBINATION PROCEDURE FOR GENERATING RECOMBINANT HERPESVIRUS. The transfection stock was screened by the BLUOGAL™ SCREEN FOR RECOMBINANT HERPESVIRUS. The final result of blue plaque purification was the recombinant virus designated S-IBR-035. This virus was characterized by restriction mapping and the SOUTHERN BLOTTING DNA procedure. This analysis confirmed the insertion of the β-galactosidase (lacZ) marker gene and the deletion of approximately 294 base pairs of the gpG gene. It was also confirmed that an approximately 2500 base pair deletion had occurred in the region of the US2 gene.

Example 8

S-IBR-036

S-IBR-036 is an IBR virus that has two deletions in the short unique region of the genome. The first deletion is approximately 2500 base pairs and is similar to the deletion in S-IBR-035 (see Example 7) which removes the US2 gene. The second deletion is approximately 1230 base pairs and begins in the HindIII K fragment approximately 3900 base pairs downstream of the HindIII O/HindIII K junction and extends back toward that junction. This deletion removes amino acids 1 to 361 of the gpG gene. The gene for *E. coli* β-galactosidase (lacZ gene) was inserted into the deletion in the gpG gene and is under the control of the HCMV immediate early promoter.

S-IBR-036 was derived from S-IBR-000 (Cooper strain). This was accomplished utilizing the homology vector 43921.69 (see Materials and Methods) and virus S-IBR-000 in the HOMOLOGOUS RECOMBINATION PROCEDURE FOR GENERATING RECOMBINANT HERPESVIRUS. The transfection stock was screened by the BLUOGAL SCREEN FOR RECOMBINANT HERPESVIRUS. The final result of blue plaque purification was the recombinant virus designated S-IBR-036. This virus was characterized by restriction mapping and the SOUTHERN BLOTTING DNA procedure. This analysis confirmed the insertion of the β-galactosidase (lacZ) marker gene and the deletion of approximately 1230 base pairs of the gpG gene. It was also confirmed that an approximately 2500 base pair deletion had occurred in the region of the US2 gene (see above).

Example 9

S-IBR-037

S-IBR-037 is an IBR virus that has two deletions in the short unique region of the genome. The first deletion is approximately 2500 base pairs and begins in the HindIII K fragment approximately 1750 base pairs downstream of the HindIII O/HindIII K junction and extends back through that junction. This deletion removes the US2 gene. The second deletion is approximately 1230 base pairs and begins in the HindIII K fragment approximately 3900 base pairs downstream of the HindIII O/HindIII K junction and extends back toward that junction. This deletion removes amino acids 1 to 361 of the gpG gene.

S-IBR-037 was derived from S-IBR-035. This was accomplished utilizing the homology vector 439-70.4 (see Materials and Methods) and virus S-IBR-035 in the HOMOLOGOUS RECOMBINATION PROCEDURE FOR GENERATING RECOMBINANT HERPESVIRUS. The transfection stock was screened by the BLUOGAL™ SCREEN FOR RECOMBINANT HERPESVIRUS. The result of white plaque purification was the recombinant virus designated S-IBR-037. This virus was characterized by restriction mapping and the SOUTHERN BLOTTING DNA procedure. This analysis confirmed the deletion of the β-galactosidase (lacZ) marker gene and the deletion of approximately 1230 base pairs of the gpG gene. It was also confirmed that an approximately 2500 base pair deletion had occurred in the region of the US2 gene (see above). S-IBR-037 was deposited on Apr. 16, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2320.

To test the efficacy of S-IBR-037 as an inactivated IBR virus vaccine in protecting susceptible calves against virulent IBR virus challenge, a study was performed according to the VACCINATION STUDIES IN CALVES WITH INACTIVATED IBR VIRUS. The following results were observed.

Virus neutralization antibody titers were elicited in animals after the first vaccination (see Table 3). Antibody titers were not significantly different between animals that received a vaccine dose of $10^{7.3}$ virus and animals vaccinated with $10^{8.0}$ virus. After the second vaccination, mean antibody titers increased to 1:19 and 1:32, respectively, for the $10^{7.3}$ and $10^{8.0}$ vaccine groups. Control animals remained seronegative to IBR virus throughout the vaccination period. Antibody titers in both vaccinate groups showed an increase typical of an anamnestic response after challenge with virulent IBR virus. By 13 days post challenge, mean antibody titers were 1:152 and 1:215 for the $10^{7.3}$ and $10^{8.0}$ vaccinate groups respectively. In contrast, mean antibody titers in challenged control animals were 1:4 at 7 days and 1:8 at 13 days post challenge.

Nasal swabs were collected from challenged animals to determine whether vaccination decreased the time of virus shedding (Table 4). The most dramatic difference between vaccinates and control animals was observed at 12 days post challenge. At this time, seventy-five percent of control animals continue to shed, whereas, only twenty-five percent of both vaccinate groups shed virus. Virus was not isolated from control or vaccinated groups at 15 days post challenge.

TABLE 3

Generation of virus neutralizing antibody in animals vaccinated with inactivated S-IBR-037 vaccine.

| | Antibody titer[a] on days: | | | | | |
|---|---|---|---|---|---|---|
| | Post Vaccination | | | | Post Challenge | |
| Animal No. | 7 | 21 | 28 | 42 | 7 | 13 |
| Controls | | | | | | |
| 9 | ≤2 | ≤2 | ≤2 | ≤2 | 4 | 4 |
| 22 | ≤2 | ≤2 | ≤2 | ≤2 | 4 | 8 |
| 32 | ≤2 | ≤2 | ≤2 | ≤2 | 4 | 16 |
| 64 | ≤2 | ≤2 | ≤2 | ≤2 | 4 | 8 |
| GMT | ≤2 | ≤2 | ≤2 | ≤2 | 4 | 8 |
| Vaccinates dose $10^{7.3}$ | | | | | | |
| 1 | ≤2 | 8 | 32 | 64 | 64 | 128 |
| 20 | ≤2 | 8 | 32 | 64 | 64 | 256 |
| 25 | ≤2 | 8 | 16 | 8 | 64 | 512 |
| 36 | ≤2 | 4 | 16 | 4 | 16 | ≥32 |
| GMT | ≤2 | 6.7 | 22.6* | 19.0* | 45.34* | 152.2* |
| Vaccinates dose $10^{8.0}$ | | | | | | |
| 7 | ≤2 | 4 | 32 | 8 | 64 | 256 |
| 30 | ≤2 | ≥8 | 64 | 128 | 128 | ≥128 |
| 33 | ≤2 | 16 | 32 | 128 | 128 | 256 |
| 69 | ≤2 | 4 | 16 | 8 | 128 | 256 |
| GMT | ≤2 | 6.7 | 32* | 32* | 107.6* | 215.3* |

*Statistically greater than controls ($p \leq 0.05$)
[a]Expressed as reciprocal of dilution.

TABLE 4

Isolation of IBR virus from vaccinated and unvaccinated control animals after challenge with virulent IBR virus.

| | IBR virus isolated (+/−) from animals on days post challenge | | | | |
|---|---|---|---|---|---|
| Animal No. | 3 | 6 | 9 | 12 | 15 |
| Controls | | | | | |
| 9 | − | + | + | + | − |
| 22 | − | + | + | − | − |

TABLE 4-continued

Isolation of IBR virus from vaccinated and unvaccinated control animals after challenge with virulent IBR virus.

| Animal No. | IBR virus isolated (+/−) from animals on days post challenge | | | | |
|---|---|---|---|---|---|
| | 3 | 6 | 9 | 12 | 15 |
| 32 | − | + | + | + | − |
| 64 | − | + | + | + | − |
| Vaccinates dose $10^{7.3}$ | | | | | |
| 1 | − | + | + | − | − |
| 20 | − | + | + | − | − |
| 25 | − | + | + | − | − |
| 36 | − | + | + | + | − |
| Vaccinates dose $10^{8.0}$ | | | | | |
| 7 | − | + | + | − | − |
| 30 | − | − | − | − | − |
| 33 | − | + | + | + | − |
| 69 | − | + | + | − | − |

TABLE 5

Vaccinated animals demonstrate reduced clinical signs of IBR.

| Animal No. | Clinical scores post challenge | | | | |
|---|---|---|---|---|---|
| | Attitude[a] | Ulcers[b] | Serious Discharge[c] | Mucopurulent Discharge[d] | Temperature[e] |
| Controls | | | | | |
| 9 | 5 | 3 | 11 | 5 | 3 |
| 22 | 2 | 2 | 12 | 3 | 1 |
| 32 | 5 | 3 | 11 | 0 | 4 |
| 64 | 6 | 3 | 11 | 1 | 1 |
| GMS | 4.5 | 2.8 | 11.3 | 2.3 | 2.3 |
| Vaccinates dose $10^{7.3}$ | | | | | |
| 1 | 0 | 2 | 1 | 0 | 0 |
| 20 | 0 | 1 | 3 | 0 | 0 |
| 25 | 0 | 2 | 6 | 2 | 0 |
| 36[f] | 6 | 2 | 1 | 13 | 0 |
| GMS | 1.5 | 1.8 | 2.8* | 2.3 | 0 |
| Vaccinates dose $10^{8.0}$ | | | | | |
| 7 | 1 | 2 | 1 | 0 | 0 |
| 30 | 1 | 2 | 2 | 2 | 0 |
| 33 | 1 | 2 | 0 | 0 | 0 |
| 69 | 1 | 2 | 0 | 0 | 0 |
| GMS | 1 | 2 | 0.8* | 0.5 | 0 |

[a]Days with depressed attitude.
[b]Number of ulcers.
[c]Days with serous discharge.
[d]Days with mucopurulent discharge.
[e]Days with $\geq 2°$ F. above baseline temperature.
[f]Animal exhibited mucopurulent discharge on the day of challenge and for 13 days post challenge.
[g]Statistically greater than controls (p $\leq$ 0.05)

Animals were observed daily for 13 days post challenge for clinical signs of IBR infection. Clinical disease was evaluated with respect to attitude, the number of ulcers, extent of serious and mucopurulent discharge and the number of days with elevated temperature. The results presented in Table 5 show that vaccinated animals exhibited less severe disease than did unvaccinated control animals. Control animals showed clinical depression ("Attitude" in Table 5) for 4.5 days compared with 1 to 1.5 days for vaccinated animals. The amount and extent of serous discharge was substantially reduced in both vaccinate groups compared with controls. The extent of mucopurulent discharge was also reduced in vaccinated animals, although to a lesser degree. However, vaccinate animal #36 did have mucopurulent discharge on the day of challenge and is not consistent with the results for other vaccinates. None of the vaccinates exhibited temperatures of $\geq 2°$ F. above baseline. In contrast, all control animals exhibited elevated temperatures of $\geq 2°$ F. over baseline and 2 of 4 control animals had temperatures of 104° F. and above.

Vaccination of calves with inactivated S-IBR-037 vaccine protected the animals against virulent wild-type IBR virus challenge. Virus neutralization titers were statistically greater in vaccinated than in control animals. An anamnestic response in antibody titer was observed 7 days post challenge, indicating the 30 development of humoral memory response. Except for 7 days post challenge, neutralization titers between the $10^{7.3}$ and $10^{8.0}$ vaccinate groups were not statistically different. Fewer vaccinated animals shed virulent challenge virus than control animals. These results suggest that virulent IBR virus is cleared more rapidly in vaccinated than in unvaccinated animals. Clinical symptoms of IBR virus infection were also reduced in vaccinated animals. After challenge, both vaccinate groups exhibited fewer days of depressed attitude, reduced serous discharge, and no elevated temperature compared with controls.

In order to show that gpG antibody is produced in vaccinated calves following exposure to wild-type virus, serum samples taken pre- and post-exposure to wild-type viruses were subjected to the ELISA assay. Samples taken at the day of challenge and at 13 days post-challenge were analyzed. As seen in Table 6, the post-challenge absorbance readings for gpG increase for each animal (ratio of >1.0), indicating that within 13 days of infection a detectable immune response to gpG is present.

TABLE 6

Detection of antibody to gpG in serum of animals vaccinated with S-IBR-037 and challenged with wild type.

| Animal No. | Ratio of pre- vs. post challenge[a] |
|---|---|
| Controls | |
| 9 | 1.22 |
| 22 | 1.96 |
| 32 | 1.87 |
| 64 | 2.19 |
| Vaccinates dose $10^{7.3}$ | |
| 1 | 1.39 |
| 20 | 1.40 |
| 25 | 1.84 |
| 36 | 1.18 |
| Vaccinates dose $10^{8.0}$ | |
| 7 | 1.19 |
| 30 | 1.29 |
| 33 | 1.52 |
| 69 | 2.66 |

[a]Animals were challenged with $10^{7.6}$ PFU of wild type IBR virus. Pre-challenge serum from day of challenge, post-challenge serum from 13 days post challenge. Data reflects the average of the ratio of absorbance readings for three independent ELISA determinations.

Example 10

S-IBR-038

S-IBR-038 is an IBR virus that has two deletions in the short unique region of the genome. The first deletion is approximately 2500 base pairs and begins in the HindIII K fragment approximately 1750 base pairs downstream of the HindIII O/HindIII K junction and extends back through that junction. This deletion removes the US2 gene. The second deletion is approximately 294 base pairs and begins in the HindIII K fragment approximately 3900 base pairs downstream of the HindIII K/HindIII O junction and extends back toward that junction. This deletion removes amino acids 261 to 359 of the gpG gene.

S-IBR-038 resulted from the removal of the marker gene from S-IBR-035 (see above). This was accomplished by digestion of S-IBR-035 with XbaI as described in the DIRECT LIGATION PROCEDURE FOR GENERATING RECOMBINANT HERPESVIRUS. The structure of S-IBR-035 was confirmed by restriction enzyme analysis with HindIII, BamHI and XbaI.

Example 11

Glycoprotein E gene

Deletion of the PRV gI gene has been shown to be valuable both as an attenuating lesion and a negative serological marker (3,42). In the studies described below we show that the unique short region of IBV virus contains a gene homologous to the gI gene of PRV.

The sequence of 2038 base pairs of the IBR unique short region, starting approximately 1325 base pairs upstream of the HindIII K/HindIII F junction in the HindIII K fragment was determined. This region was found to contain an ORF coding for 617 amino acids translated in the direction away from the HindIII K/HindIII O junction (see FIG. 1). The ORF is 70.5% G+C and encodes a protein with a predicted molecular weight of approximately 88,980. Comparison of the sequence of the predicted protein with sequences of gene products of HSV-1, VZV, and PRV in the unique short region indicated that this ORF is homologous to the herpesvirus gpE gene (see FIGS. 16A and 16B).

The DNA encoding the gpE gene has been cloned in two plasmids, PSY1644 and PSY1645. The amino-terminal half of the gene (encoding amino acids 1–276) was cloned as an approximately 2300 base pair fragment resulting from a partial SmaI digest of wild type S-IBR-000 (Cooper Strain) DNA. This fragment was inserted into the plasmid pSP64 to yield PSY1644. This plasmid, designated PSY1644, was deposited on Jul. 16, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 68651.

The carboxyl-terminal half of the gene (encoding amino acids 277–617) was cloned as an approximately 2400 base pair SmaI fragment. The fragment was inserted into the plasmid pSP64 to yield PSY1645. This plasmid, designated PSY1645, was deposited on Jul. 16, 1991 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 68650. These plasmids may be used to confirm the sequence of the gpE gene.

Example 12

Pseudorabies virus expressing IBR virus gpE

A pseudorabies virus analogous to S-PRV-160 may be constructed for the purpose of expressing the IBR virus gpE. This may be accomplished by inserting the gene coding for IBR virus gpE into S-PRV-002 (U.S. Pat. No. 4,877,737).

Such an expression vector may be constructed utilizing the IBR virus gpE plasmid described in the methods section, pseudorabies virus S-PRV-002 and the restriction enzyme XbaI in the DIRECT LIGATION PROCEDURE FOR GENERATING RECOMBINANT HERPESVIRUS. Viruses resulting from this procedure may be screened by digestion with XbaI for the presence of the XbaI band containing the IBR virus gpE gene.

The gpE protein expressed from this vector may be used as an antigen to identify antibodies directed against the wild type virus as opposed to antibodies directed against gpE deleted viruses. This virus may also be utilized as an antigen for the production of gpE specific monoclonal antibodies. Such antibodies are useful in the development of diagnostic tests specific for the gpE protein. Monoclonal antibodies may be generated in mice utilizing this virus according to the PROCEDURE FOR GENERATING MONOCLONAL ANTIBODIES.

Example 13

Glycoprotein E deleted IBR viruses

The HOMOLOGY VECTOR 536-03.5 was used to generate various gpE-deleted IBR viruses. Utilizing the general strategy described in CONSTRUCTION OF DELETION VIRUSES, a gpE deletion of approximately 1410 base pairs (amino acids 77–547) was introduced into two different IBR virus backbones, S-IBR-000 (Cooper Strain) and S-IBR-037. The virus resulting from the S-IBR-000 parent contains the gpE deletion alone. The virus resulting from the S-IBR-037 parent contains the gpE deletion in conjunction with the US2 and gpG deletions. The lacZ marker gene may be removed from these viruses utilizing the procedures outlined in the methods section.

These gpE-deleted viruses are of great value as IBR vaccines. Their combination of different deletions will provide the varying degrees of attenuation which are required for a superior vaccine. These viruses will also provide a negative serological marker which may be used to distinguish vaccinated from infected animals. The virus containing both gpG and gpE deletions should be of even greater value by having two negative markers. The availability of two negative markers permits one marker to be used as a confirmatory test, greatly increasing the reliability of such a diagnostic determination.

Example 14

S-IBR-004

S-IBR-004 is an IBR recombinant virus carrying an inserted foreign gene, Tn5 NEO (aminoglycoside 3'-phosphotransferase) gene, under the control of the pseudorabies virus (PRV) glycoprotein X promoter.

Figure 19:
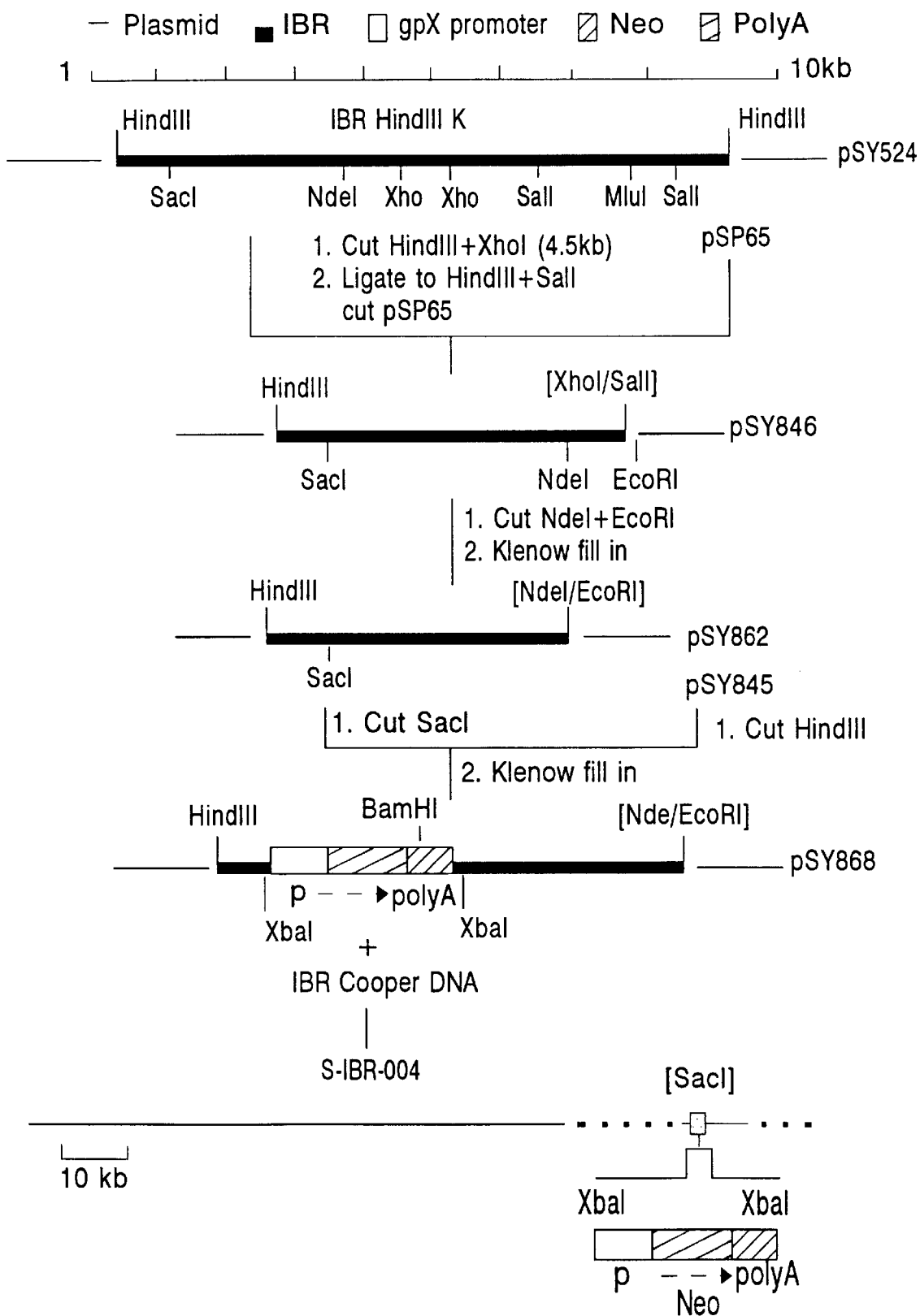
FIG. 19 Construction of Recombinant S-IBR-004 Virus. S-IBR-004 is an IBR recombinant virus carrying an inserted foreign gene (NEO) under the control of the P sites used to generate each fragment as well as synthetic linker sequences which were used to join the fragments are described for each junction. The synthetic linker sequences are underlined by a double bar. The location of the Tk gene coding region is also given. The following two conventions are used: numbers in parenthesis ( ) refer to amino acids, and restriction sites in brackets [ ] indicate the remnants of sites which were destroyed during construction. The following abbreviation is used, infectious bovine rhinotracheitis virus (IBR).
Figure 20:
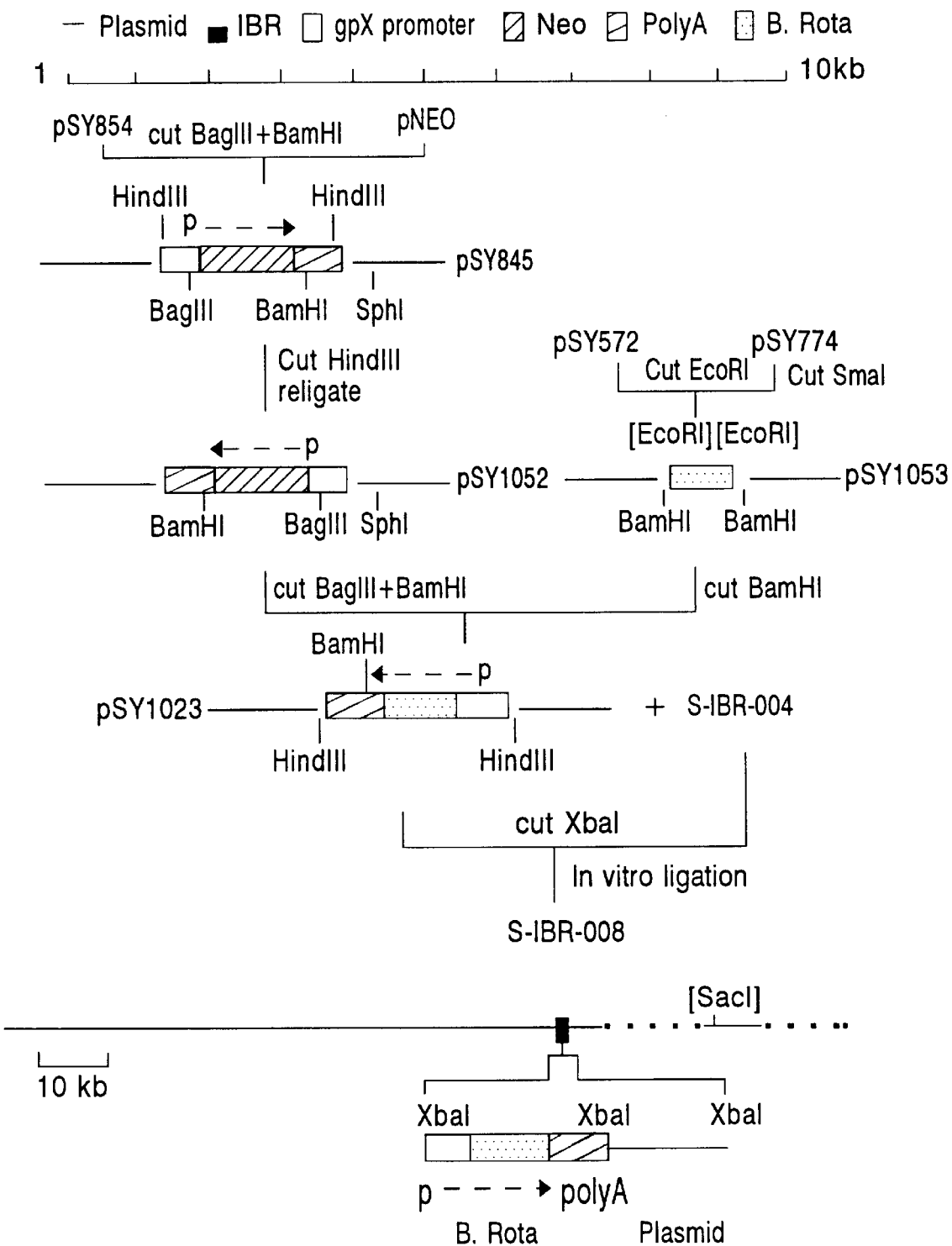

To construct this virus, the HindIII K DNA fragment from wild type IBR virus was cloned into the plasmid pSP64 at the HindIII site. This plasmid was designated pSY524. A map of the HindIII K fragment is shown in FIG. 19. The DNA from the XhoI site to the HindIII site and containing the NdeI site from pSY524 was cloned into plasmid pSP65 and called pSY846. The NdeI to EcoRI fragment was removed from pSY846 by digestion with NdeI and EcoRI restriction enzymes, followed by POLYMERASE FILL-IN REACTION and LIGATION. The resulting plasmid was called pSY862. The plasmid pNEO (P. L. Biochemicals, Inc.) contains the aminoglycoside 3'-phosphotransferase (NEO) gene and confers resistance to ampicillin and neomycin on *E. coli* hosts. The coding region of this gene (BglII-BamHI fragment) was isolated and cloned between the PRV gpX promoter and the HSV-TK poly A sequence in a plasmid called pSY845.

The NEO gene construct in pSY845 was excised with HindIII, made blunt ended by the POLYMERASE FILL-IN REACTION, and cloned into the SacI site of plasmid pSY862. The final product was called pSY868.

Wild type IBR DNA was mixed with pSY868 DNA and the mixture was transfected into rabbit skin cells to generate recombinant IBR. The recombinant IBR virus carrying a functional NEO gene was then isolated and purified according to the SELECTION OF G418 RESISTANT IBR VIRUS method.

S-IBR-004 recombinant IBR was shown to express the NEO gene by the fact that cells infected with this virus were resistant to the toxicity of G418. A detailed map of the plasmid construction is shown in FIG. 19. The structure of S-IBR-004 is also shown in FIG. 19. S-IBR-004 was deposited on May 23, 1986 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2134.

Example 15

S-IBR-008

S-IBR-008 is an IBR virus that has a deletion in the short unique region, and an insertion of the bovine rotavirus glycoprotein 38 (gp38) gene in the XbaI site in the long unique region.

The bovine rotavirus gp38 gene was cloned utilizing the METHOD FOR cDNA CLONING BOVINE ROTAVIRUS gp38 GENE. The bovine rotavirus gp38 gene was then engineered to contain herpesvirus regulatory signals as shown in FIG. 20. This was accomplished by cloning the gp38 gene BamHI fragment contained in pSY1053 between the BamHI and BglII sites in pSY1052. The resulting plasmid, pSY1023, contained the PRV gpX promoter in front of the gp38 gene, and the HSV-1 TK polyadenylation signal behind the gp38 gene. The entire construct was flanked by XbaI sites to allow for the insertion of the XbaI fragment into IBR by direct ligation.

S-IBR-004 was the starting virus for the generation of S-IBR-008. S-IBR-004 DNA and pSY1023 DNA were mixed together, cut with XbaI, and transfected into rabbit skin cells according to the DIRECT LIGATION PROCEDURE FOR GENERATING RECOMBINANT HERPESVIRUS. The transfection stock was screened for recombinant virus by the ANTIBODY SCREEN FOR RECOMBINANT HERPESVIRUS procedure using antibodies prepared against the rotavirus gp38 protein.

One of the viruses purified by this screen was S-IBR-008, which has the following characteristics. It contains the rotavirus gp38 gene plus the plasmid DNA inserted into the XbaI site in the long unique region of the virus genome, but no longer contains the NEO gene of parent S-IBR-004 in the unique short region. In fact, a small deletion was created in the unique short region at the location of the NEO gene, as evidenced by the absence of an XbaI site at this location in S-IBR-008.

S-IBR-008 was shown to be expressing the rotavirus gp38 gene by analysis of RNA transcription in infected cells, and by the ANTIBODY SCREEN FOR RECOMBINANT HERPESVIRUS procedure using antibodies specific for the gp38 gene. S-IBR-008 was deposited on Jun. 18, 1986 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2141. The structure of S-IBR-008 is shown in FIG. 20.

Example 16

S-IBR-018

S-IBR-018 is an IBR virus that has three foreign genes inserted: the *E. coli* beta-galactosidase gene and the neomycin resistance gene in the XbaI site in the unique long region, and the parainfluenza type 3 (PI-3) virus hemagglutinin gene (HN) in the HindIII site in the unique long region immediately adjacent to the XbaI site.

For cloning the PI-3 HN gene, the SF-4 strain of PI-3 was grown in MADIN-DARBY bovine kidney (MDBK) cells in culture and RNA was extracted from infected cells. The RNA was used in a reverse transcription protocol as outlined in the cDNA CLONING procedure using poly-dT as primer for reverse transcriptase. From this procedure, a series of clones was obtained that comprised parts of the genome of the PI-3 virus. The location of the gene for the human PI-3 HN gene has been published (25,26) and this information was used to locate the gene in applicants' bovine PI-3 clones. The entire open reading frame of the bovine PI-3 HN gene was sequenced by applicants and is given in FIGS. 21A and 21B.

The HSV ICP4 promoter was used to express the PI-3 HN gene and the HSV TK poly-A signal was used to terminate transcription. The engineering of this construct was done as shown in FIG. 22A and B. The construct contained (5' to 3') the HSV ICP4 promoter, the ICP4 TATA box, the ICP4 cap site, a fusion within the ICP4 5' untranslated region to the PI-3 HN gene at the HhaI site, the HN gene start codon, the HN structural gene, the HN stop codon, a fusion within the HN 3' untranslated region to the HSV TK untranslated 3' region, and the HSV TK poly-A signal sequence.

This plasmid also contained the beta-galactosidase (lacZ) gene under the control of the PRV gpX promoter with the gpX poly-A termination signal, as well as the neomycin resistance gene under the control of the gpX promoter with the TK poly-A termination signal. These latter two genes were cloned in tandem at the XbaI site in BamHI-C fragment (FIGS. 22A and B). This BamHI-C fragment contained the homology regions for use in the DNA TRANSFECTION FOR GENERATING RECOMBINANT VIRUS procedure. After the transfection step in the procedure, the resulting recombinant virus from the transfection stock was selected for by the SELECTION OF G418 RESISTANT IBR VIRUS procedure, followed by the BLUOGAL™ SCREEN FOR RECOMBINANT HERPESVIRUS procedure, and subsequently analyzed for the insertion of the PI-3 HN gene by the SOUTHERN BLOTTING OF DNA procedure. The virus that resulted from this screening was designated S-IBR-018.

S-IBR-018 was deposited on Jul. 21, 1987 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. VR 2180. The structure of S-IBR-018 is shown in FIG. 22C.

Example 17

S-IBR-019

S-IBR-019 is an IBR virus that has three foreign genes inserted: the *E. coli* beta-galactosidase (lacZ) gene and the neomycin resistance gene in the XbaI site in the inserted: the *E. coli* beta-galactosidase (lacZ) gene and virus fusion gene (F) in the HindIII site in the long unique long region, and the parainfluenza type 3 (PI-3)

For cloning the PI-3 F gene, the SF-4 strain of PI-3 was grown in MDBK cells in culture and RNA was extracted from infected cells. The RNA was used in a reverse transcription protocol as outlined in the cDNA CLONING procedure using poly-dT as primer for reverse transcriptase. From this procedure, a series of clones was obtained that comprised parts of the genome of the PI-3 virus. The location of the gene for the Sendai virus F gene has been published (27) and this comparative sequence information was used to locate the homologous gene in applicants' bovine PI-3 clones.

The HSV alpha-4 promoter was used to express the PI-3 F gene and the HSV TK poly-A signal was used to terminate transcription. The construct contained (5' to 3') the HSV alpha-4 promoter, the alpha-4 TATA box, the alpha-4 cap site, a fusion in the alpha-4 5' untranslated region to the PI-3 F gene, the F start codon, the F structural gene, the F stop codon, a fusion in the F 3' untranslated region to the HSV TK 3' untranslated region, and the TK poly-A signal sequence.

Figure 23A:
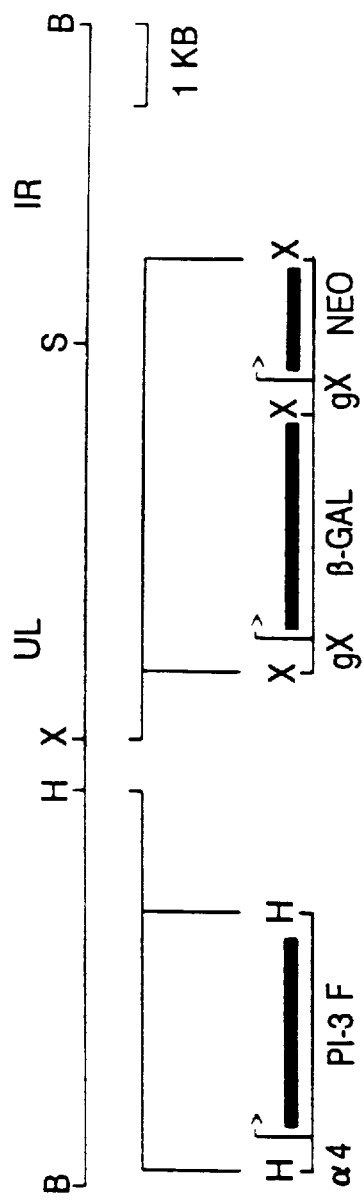
Figure 23B:
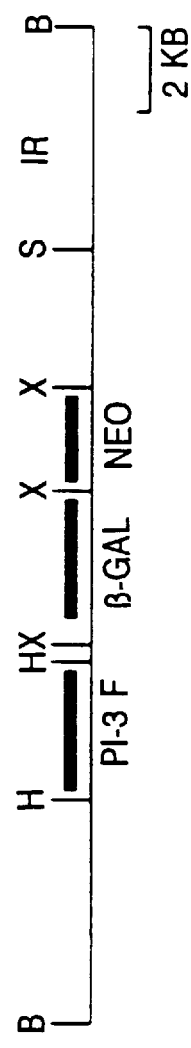

This plasmid also contained the beta-galactosidase (lacZ) gene under the control of the PRV gpX promoter with the gpX poly-A termination signal, as well as the neomycin resistance gene under the control of the gpX promoter with the TK poly-A termination signal. These latter two genes were cloned in tandem at the XbaI site in BamHI-C fragment (FIGS. 23A and B). This BamHI-C fragment contained the homology regions for use in the DNA TRANSFECTION FOR GENERATING RECOMBINANT VIRUS procedure. After the transfection step in the procedure, the resulting recombinant virus from the transfection stock was selected for by the SELECTION OF G418 RESISTANT HERPESVIRUS procedure, followed by the BLUOGAL™ SCREEN FOR RECOMBINANT HERPESVIRUS procedure, and subsequently analyzed for the insertion of the PI-3 F gene by SOUTHERN BLOTTING OF DNA procedure. The virus that resulted from this screening was designateed S-IBR-019.

Figure 23C:
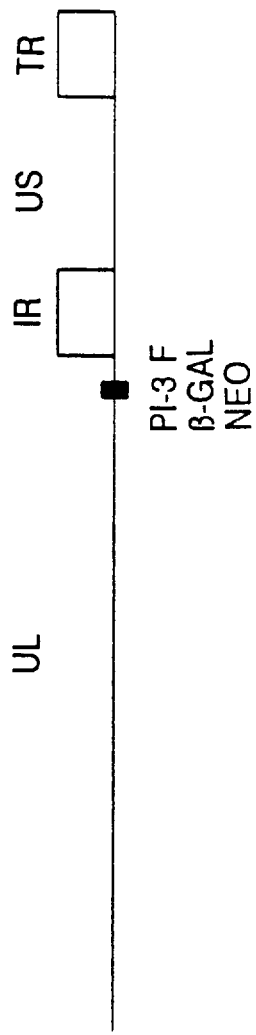

The structure of S-IBR-019 is shown in FIG. 23C.

Example 18

S-IBR-032

S-IBR-032 is an IBR virus that has two foreign genes inserted: the *Escherichia coli* beta-galasctosidease (lacZ) gene with the bovine viral diarrhea virus (BVDV) gp53 gene fused to the lacZ C-terminus and inserted in the long unique region at the XbaI restriction endonuclease site.

For cloning the BVDV gp53 gene, the Singer strain of BVDV was grown in MADIN-DARBY bovine kidney (MDBK) cells in culture and the RNA was extracted from infected cells. The RNA was used in a reverse transcriptase procedure as outlined in the cDNA CLONING procedure using random primers for reverse transcriptase. From this procedure, a series of clones was obtained that comprised parts of the genome of BVDV. The location of the gene for BVDV gp53 has been published (66) and this comparative sequence information was used to locate the homologous gene in the applicant's BVDV clones.

The PRV gpX promoter was used to express lacZ with a region of BVDV gp53 fused to the C-terminus, and the PRV poly-A signal was used to terminate transcription. A plasmid construct was engineered that contained (5' to 3') the PRV gpX promoter and then the coding region consisting of amino acid codons 1–7 of the PRV gpX gene, 10–1024 of the *Escherichia coli* lacZ gene, and 684–758 of the BVDV major open reading frame, and the PRV poly-A sequence. This lacZ fusion gene cassette was then excised from the plasmid vector at the flanking XbaI sites and cloned into the unique XbaI site in IBR-002 using the in vitro ligation method described in CONSTRUCTION OF DELETION VIRUSES. After the transfection step in DNA TRANSFECTION FOR GENERATING RECOMBINANT VIRUS procedure, the resulting recombinant virus was screened and isolated from the transfection stock using the BLUOGAL™ SCREEN FOR RECOMBINANT HERPESVIRUS procedure, and subsequently analyzed for the insertion of the BVDV gp53 region by SOUTHERN BLOTTING OF DNA procedure. The virus that resulted from this screening was designated S-IBR-032.

Example 19

S-IBR-039

S-IBR-039 is an IBR virus that has three deletions in the short unique region of the genome. The first deletion is approximately 2500 base pairs and begins in the HindIII K fragment approximately 1750 base pairs downstream of the HindIII O/HindIII K junction and extends back through that junction. This deletion removes the US2 gene. The second deletion is approximately 1230 base pairs and begins in the HindIII K fragment approximately 3900 base pairs downstream of the HindIII O/Hind K junction and extends back toward that junction. This deletion removes amino acids 1 to 361 of the gpG gene. The third deletion is approximately 1410 base pairs and removes amino acids 77–547 of the gpE gene.

S-IBR-039 was derived from S-IBR-037. This was accomplished utilizing the homology vector 536-03.5 (see MATERIALS AND METHODS) and virus S-IBR-037 in the HOMOLOGOUS RECOMBINATION PROCEDURE FOR GENERATING RECOMBINANT HERPESVIRUS. The transfection stock was screened by the SCREEN FOR RECOMBINANT HERPESVIRUS EXPRESSING ENZYMATIC MARKER GENES. The result of blue plaque purification was the recombinant virus designated S-IBR-039. This virus was characterized by restriction mapping and the SOUTHERN BLOTTING DNA procedure. This analysis confirmed the insertion of the β-galactosidase (lacZ) marker gene and the deletion of approximately 1230 base pairs of the gpG gene. It was also confirmed that an approximately 1410 base pair deletion has occurred in the region of the gpE gene (see above). This virus will be useful as a vaccine to protect cattle from infection with IBR virus. The deletions of the glycoproteins G and E genes from this virus also provides two negative serological markers for differentiating it from wild type IBR.

Example 20

S-IBR-045

S-IBR-045, a recombinant IBR virus with deletions in the Tk, US2, gpG and gpE genes may be constructed in the following manner. S-IBR-045 would be derived from S-IBR-039 (see example 19) through the construction of two intermediate viruses. The first intermediate virus, S-IBR-043, would be constructed utilizing the homology vector 591-46.12 (see MATERIALS AND METHODS) and virus S-IBR-039 in the HOMOLOGOUS RECOMBINATION PROCEDURE FOR GENERATING RECOMBINANT HERPESVIRUS. The transfection stock would be screened by the SCREEN FOR RECOMBINANT HERPESVIRUS EXPRESSING ENZYMATIC MARKER GENES for a white plaque recombinant virus (uidA substrate). The resulting virus would have deletions of the Tk, US2, gpG and gpE genes and insertion of lacZ gene in the gE gene deletion. Finally, S-IBR-045 would be constructed, utilizing the homology vector 523-78.72 (see MATERIALS AND METHODS) and virus S-IBR-044 in the HOMOLOGOUS RECOMBINATION PROCEDURE FOR GENERATING RECOMBINANT HERPESVIRUS. The transfection stock would be screened by the SCREEN FOR RECOMBINANT HERPESVIRUS EXPRESSING ENZYMATIC MARKER GENES for a white plaque recombinant virus (lacZ substrate). This virus will be useful as a vaccine to protect cattle from infection with IBR. The combination of deletions will provide the appropriate attenuation which is required for a superior vaccine. This virus will also provides two negative serological markers which may be used to distinguish vaccinated from infected animals. The availability of two negative markers permits one marker to be used as a confirmatory test, greatly increasing the reliability of such a diagnostic determination.

Example 21
S-IBR-046

S-IBR-046, a recombinant IBR virus with deletions in the Tk, US2, gpG and gpE genes and the bovine viral diarrhea virus gp53 gene inserted in place of the gpE gene, may be constructed in the following manner. S-IBR-046 would be derived from S-IBR-044 (see example 20). It would be constructed utilizing the homology vector 523-78.72, into which the bovine viral diarrhea virus gp53 gene has been inserted, and virus S-IBR-044 in the HOMOLOGOUS RECOMBINATION PROCEDURE FOR GENERATING RECOMBINANT HERPESVIRUS. Note that the bovine diarrhea virus gene would be cloned using techniques described in the methods section. The gp53 gene would be placed under the control of the HCMV immediate early promoter. The transfection stock would be screened by the SCREEN FOR RECOMBINANT HERPESVIRUS EXPRESSING ENZYMATIC MARKER GENES for a white plaque recombinant virus (lacZ substrate). This virus will be useful as a vaccine to protect cattle from infection with IBR virus and bovine viral diarrhea virus.

Example 22
S-IBR-047

S-IBR-047, a recombinant IBR virus with deletions in the Tk, US2, gpG and gpE genes and the parainfluenza type 3 genes for hemagglutinin and fusion protein inserted in place of the gpE gene may be constructed in the following manner. S-IBR-047 would be derived from S-IBR-044 (see example 20). It would be constructed utilizing the homology vector 523-78.72, into which the parainfluenza type 3 virus hemagglutinin and fusion genes has been inserted, and virus S-IBR-044 in the HOMOLOGOUS RECOMBINATION PROCEDURE FOR GENERATING RECOMBINANT HERPESVIRUS. Note that the parainfluenza type 3 virus genes would be cloned using techniques described in the methods section. The transfection stock would be screened by the SCREEN FOR RECOMBINANT HERPESVIRUS EXPRESSING ENZYMATIC MARKER GENES for a white plaque recombinant virus (lacZ substrate). This virus will be useful as a vaccine to protect cattle from infection with IBR virus and parainfluenza type 3 virus.

Example 23
S-IBR-049

S-IBR-049, a recombinant IBR virus with deletions in the Tk, US2, gpG and gpE genes and the bovine respiratory syncytial virus genes for the attachment, nucleocapsid and fusion proteins inserted in place of the gpE gene may be constructed in the following manner. S-IBR-049 would be derived from S-IBR-044 (see example 20). It would be constructed utilizing the homology vector 523-78.72, into which the bovine respiratory syncytial virus attachment nucleocapsid and fusion genes had been inserted and virus S-IBR-044 in the HOMOLOGOUS RECOMBINATION PROCEDURE FOR GENERATING RECOMBINANT HERPESVIRUS. Note that the bovine respiratory syncytial virus genes would be cloned using techniques described in the methods section. The attachment protein gene would be placed under the control of the HCMV immediate early promoter and the fusion and nucleocapsid protein genes would be placed under the PRV gpX promoter. The transfection stock would be screened by the SCREEN FOR RECOMBINANT HERPESVIRUS EXPRESSING ENZYMATIC MARKER GENES for a white plaque recombinant virus (lacZ substrate). This virus will be useful as a vaccine to protect cattle from infection with IBR virus and bovine respiratory syncytial.

Example 24
S-IBR-051

S-IBR-051, a recombinant IBR virus with deletions in the Tk, US2, gpG and gpE genes and the Pasteurella haemolytica genes for the leukotoxin and iron regulated outer membrane proteins inserted in place of the gpE gene, may be constructed in the following manner. S-IBR-051 would be derived from S-IBR-044 (see example 20). It would be constructed utilizing the homology vector 523-78.72, into which the *Pasteurella haemolytica* leukotoxin and iron regulated outer membrane protein genes had been inserted, and virus S-IBR-044 in the HOMOLOGOUS RECOMBINATION PROCEDURE FOR GENERATING RECOMBINANT HERPESVIRUS. Note that the *Pasteurella haemolytica* genes would be cloned using the techniques described in the methods section. The leukotoxin gene would be placed under the control of the HCMV immediate early promoter and the iron regulated outer membrane protein genes would be placed under the PRV gpX promoter. The transfection stock would be screened by the SCREEN FOR RECOMBINANT HERPESVIRUS EXPRESSING ENZYMATIC MARKER GENES for a white plaque recombinant virus (lacZ substrate). This virus will be useful as a vaccine to protect cattle from infection with IBR virus and *Pasteurella haemolytica*.

Example 25
Shipping Fever Vaccine

Shipping fever or bovine respiratory disease (BRD) complex is manifested as a result of a combination of infectious diseases of cattle and additional stress related factors (70). Respiratory virus infections, augmented by pathophysiological effects of stress, alter the susceptibility of cattle to Pasteurella organisms that are normally present in the upper respiratory tract by a number of mechanisms. Control of the viral infections that initiate BRD as well as control of the terminal bacterial pneumonia is essential to preventing the disease syndrome (71).

The major infectious diseases that contribute to BRD are: infectious bovine rhinotracheitis virus, parainfluenza type 3 virus, bovine viral diarrhea virus, bovine respiratory syncytial virus, and *Pasteurella haemolytica* (71). The applicants' examples 1 through 24 describe vaccine inventions that individually immunize against the various components of BRD. An extension of the applicants' approach is to combine vaccines in a manner so as to control the array of disease pathogens with a single immunization. To this end, at least two approaches can be taken: first, mixing of the various IBR vectored antigens (BRSV, PI-3, BVDV and *P. haemolytica*) in a single vaccine dose, and secondly, the individual antigens (BRSV, BVDV, PI-3 and *P. haemolytica*) can be simultaneously cloned into the same IBR backbone virus. Note that a combination of antigens could be included in one or more IBR backbone viruses so as to limit the number of IBR viruses required for BRD protection. Also, conventionally derived vaccines (killed virus, inactivated bacterins and modified live viruses) could be included as part of the BRD vaccine formulation should such vaccine components prove to be more effective.

REFERENCES

1. J. L. Cantello et al., Journal of Virology 65, 1584–1588 (1991).
2. U. K. Laemnli, Nature 227, 680–685 (1970).
3. B. Lomniczi et al., Journal of Virology 49, 970–979 (1984).
4. R. Longnecker and B. Roizman, Science 236, 573–576 (1987).
5. S. Mackem and B. Roizman, Proc. Natl. Acad. Sci. U.S.A. 79, 4917–4921 (1982).
6. T. Maniatis et al., *Molecular Cloning: A Laboratory Manual*, Cold Spring Harbor Press (1982).
7. J. E. Mayfield et al., Journal of Virology 47, 259–264 (1983).
8. D. J. McGeoch et al., Journal of Molecular Biology 181, 1–13 (1985).
9. D. J. McGeoch et al., Journal of General Virology 68, 19–38 (1987).
10. D. J. McGeoch et al., Journal of General Virology 69, 19–38 (1987).
11. E. A. Petrovskis et al., Journal of Virology 60, 116–169 (1986).
12. T. J. Rea et al., Journal of Virology 54, 21–29 (1985).
13. A. K. Robbins et al., Journal of Virology 58, 339–347 (1986).
14. J. Sambrook et al., *Molecular Cloning: A Laboratory Manual*, Second Edition, Cold Spring Harbor Press (1989).
15. G. A. Smith et al., Journal of General Virology 71, 2417–2424 (1990).
16. D. R. Thomsen et al., Gene 16, 207–217, (1981).
17. S. K. Tikoo et al., Journal of Virology 64, 5132–5142 (1990).
18. C. E. Aronson, ed., *Veterinary Pharmaceuticals and Biologicals*, Veterinary Medicine Publ. Co., Lenexa, Kans., pp. 138–139 (1982–1983).
19. P. C. Weber et al., Science 236, 576–579 (1987).
20. U. S. Wirth et al., Journal of Virology 65, 195–205 (1991).
21. M. Zijl et al., Journal of Virology 71, 1747–1755 (1990).
22. L. Villarreal and P. Berg, Science 196, 183–185 (1977).
23. U. Gubler and B. J. Hoffman, Gene 25, 263–269 (1983).
24. F. L. Graham and A. Van der Eb, Virology 52, 556–567 (1973).
25. N. Elango et al., Journal of Virology 57, 481–489 (1986).
26. M. K. Spriggs and P. L. Collins, Journal of Virology 59, 646–654 (1986).
27. B. M. Blumberg et al., Journal of General Virology 66, 317–331 (1985).
28. R. W. Price and A. Kahn, Infection and Immunity 34, 571–580 (1981).
29. P. B. Tenser et al., J. of General Virology 64, 1369–1373 (1983).
30. B. Roizman et al., Cold Spring Harbor Conference on New Approaches to Viral Vaccines (September, 1983).
31. R. L. Thompson et al., Virology 131, 180–192 (1983).
32. K. Fukuchi et al., Proc. Natl. Acad. Sci. U.S.A. 82, 751–754, 1985.
33. J. M. Koomey et al., J. of Virology 50, 662–665, 1984.
34. S. B. Mohanty and S. K. Dutta, *Veterinary Virology*, Lea and Febiger, Philadelphia (1981).
35. R. Crandell in *Current Veterinary Therapy*, pages 543–546, W. B. Saunders, Philadelphia (1981).
36. H. Ludwig in *The Herpesviruses*, Vol. 2, B. Roizman, ed., Plenum Press (1983).
37. A. J. Davison, EMBO Journal, 2, 2203–2209 (1983).
38. F. A. Ferrari et al., J. of Bacteriology 161, 556–562 1985.
39. V. T. Oi and L. A. Herzenberg, *Selected Methods in Cellular Immunology*, Freeman Publ. Co., San Francisco (1980). pp. 351–372.
40. S. Ihara et al., Virology 122, 268–278 (1982).
41. D. Hanahan, Molecular Biology 166, 557–580 (1983).
42. M. W. Mellencamp et al., J. of Clinical Microbiology 27, 2208–2213 (1989).
43. Kit et al., U.S. Pat. No. 4,824,667, issued Apr. 25, 1989.
44. Kit et al., U.S. Pat. No. 4,703,011, issued Oct. 27, 1987.
45. Kit et al., The Veterinary Record 127, 363–364 (1990).
46. European Patent Publication EP 0 326 127 A2, published Aug. 2, 1989.
47. Federal Register, Vol. 55, No. 90, pp. 19245–19253 (May 9, 1990).
48. Fitzpatrick et al., J. of Virol. 62, 4239–4288 (1988).
49. T. Ben-Porat et al., Virol. 154, 325–334 (1986).
50. F. Zuckerman et al., in *Vaccination and Control of Aujeszky's Diesase*, Ed. J. van Oirschot, Kluwer, London (1989). pp. 107–117.
51. L. E. Post et al., J. Reprod. Fert. Suppl. 41, 97–104 (1990).
52. Wirth et al., J. of Virol. 63, 4882–4889 (1989).
53. B. Moss, Science 252, 1662–1667 (1991).
54. R. W. Honess, J. of General Virology 65, 2077–2107 (1984).
55. Cook & Stevens, J. of General Virology 31, 75–80 (1976).
56. Desrosiers et al., Molecular and Cellular Biology 5, 2796–2803 (1985).
57. Thomsen et al., Gene 57, 261–265 (1987).
58. Weir and Narayanan, Nucleic Acids Research 16, 10267–10282 (1988).
59. Spaete and Mocarski, Proceedings of the National Academy of Sciences U.S.A. 84, 7213–7217 (1987).
60. Whealy et al., Journal of Virology 62, 4185–4194 (1988).
61. Shih et al., Proceedings of the National Academy of Sciences U.S.A. 81, 5867–5870 (1984).
62. Edwards et al., in *Technological Advances in Vaccine Development*, pp. 223–234, Alan Riss Inc. (1988).
63. Proceeding of the 94th Annual Meeting of the United States Animal Health Association, pp. 66–75 (1990).
64. E. A. Petrovskis et al., Journal of Virology 60, 185–193 (1986).
65. Todd et al., U.S. Pat. No. 4,132,775, issued Jan. 2, 1979.
66. M. S. Collett et al., Journal of Virology 65, 200–208, (1988).
67. M. A. Innis et al., PCR Protocols: A Guide to Methods and Applications, 84–91, Academic Press, Inc. San Diego (1990).
68. R. D. Walker, et al., Am. J. Vet Res. 65, 1230–1234 (1984).
69. E. Harlow, and D. Lane, Antibodies: A Laboratory Manual, Cold Spring Harbor Press, New York (1988).
70. C. A. Hjerpe, The Bovine Respiratory Disease Complex. In: Current Veterinary Therapy 2: Food Animal Practice. Ed. by J. L. Howard, Philadelphia, W. B. Saunders Co., 1986, pp 670–680.
71. F. Fenner, et al., "Mechanisms of Disease Production: Acute Infections", *Veterinary Virology*. Academic Press, Inc., Orlando, Fla., 1987, pp 183–202.
72. T. Inque, et al., Journal of General Virology 70, 919–934 (1989).

SEQUENCE LISTING ( 1 ) GENERAL INFORMATION:

( i i i ) NUMBER OF SEQUENCES: 104

( 2 ) INFORMATION FOR SEQ ID NO:1:

( i ) SEQUENCE CHARACTERISTICS:
( A ) LENGTH: 1079 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Bovine Herpesvirus-1 (IBR Virus)
( B ) STRAIN: Cooper
( C ) INDIVIDUAL ISOLATE: S-IBR- 000

( v i i i ) POSITION IN GENOME:
( B ) MAP POSITION: ~86.8 to ~87.8
( C ) UNITS: %G ( i x ) FEATURE:
( A ) NAME/KEY: CDS
( B ) LOCATION: 25..951

( x i ) SEQUENCE DESCRIPTION: SEQ ID NO:1:

TTAAGCGTTG CCGTGGCGGT CGCC ATG GTG ACT ATA GTC ACG TGT GGC CGG 51
Met Val Thr Ile Val Thr Cys Gly Arg
1 5

ATA GGC GCG GCG CCT TCC AGG CAA GCC CAG ACG TGC GCC GCG CGG GTG 99
Ile Gly Ala Ala Pro Ser Arg Gln Ala Gln Thr Cys Ala Ala Arg Val
10 15 20 25

TGG CGT TTC CTT GCC GAG CAG AGC CGG GCG CTG ACG GCA AGC CGG CTG 147
Trp Arg Phe Leu Ala Glu Gln Ser Arg Ala Leu Thr Ala Ser Arg Leu
30 35 40

GGG ACG ACG GTC GTT GTC TTC GAT CAC GCC CTA GTA AAA ACG GCG AAG 195
Gly Thr Thr Val Val Val Phe Asp His Ala Leu Val Lys Thr Ala Lys
45 50 55

GGC TGC ACG TCG ACG TCA ACG TCA AGC CAG CGG CGC GGG TGG CTT TTG 243
Gly Cys Thr Ser Thr Ser Thr Ser Ser Gln Arg Arg Gly Trp Leu Leu
60 65 70

TCG ACA CAG CGC CCT TGG CCC GGG CGC CGG CTT AGC CCG CCA CCG CCA 291
Ser Thr Gln Arg Pro Trp Pro Gly Arg Arg Leu Ser Pro Pro Pro Pro
75 80 85

ACC GGC GAG TGG GTC AGC TGG TCG ACG GCT ACA AAC TTG CTG AAA CTC 339
Thr Gly Glu Trp Val Ser Trp Ser Thr Ala Thr Asn Leu Leu Lys Leu
90 95 100 105

GGC CGC GCG AGG GCT CGG CCC TTC CAC ATG TGG GTT TTT GGC GCC GCC 387
Gly Arg Ala Arg Ala Arg Pro Phe His Met Trp Val Phe Gly Ala Ala
110 115 120

GAT TTG TAC GCG CCT ATT TTT GCG CAC ATT GCC GCC ACG ACG CGC TTG 435
Asp Leu Tyr Ala Pro Ile Phe Ala His Ile Ala Ala Thr Thr Arg Leu
125 130 135

GTT TAC GCG CAG CTG GAC TGT ACG TTT GCG GGA GCG GCG TGG CGG CTC 483
Val Tyr Ala Gln Leu Asp Cys Thr Phe Ala Gly Ala Ala Trp Arg Leu
140 145 150

CCG CGG CGC GGC CCG GCC ATC GCT AGC CCG TGG CCG CCC TAC GAT ACC 531
Pro Arg Arg Gly Pro Ala Ile Ala Ser Pro Trp Pro Pro Tyr Asp Thr
155 160 165

```
CCG ACA CTC CCT GAG CTG GTG GCC GGT GGT GTC CTT TTC CGG CTG GTC      579
Pro Thr Leu Pro Glu Leu Val Ala Gly Gly Val Leu Phe Arg Leu Val
170             175             180                 185

TAC GAA GTC GTA GAC CGC GGG CGG CGC CCC GCC CCG CCA AAC GCG AGC      627
Tyr Glu Val Val Asp Arg Gly Arg Arg Pro Ala Pro Pro Asn Ala Ser
                190             195                 200

CCC CGT GCC CCA GGG GCT CGC CCC CGC GCG CGC CAT GTG CTA TCC TTT      675
Pro Arg Ala Pro Gly Ala Arg Pro Arg Ala Arg His Val Leu Ser Phe
            205             210                 215

AAA GGC CGC ACC CAG CGC CGG CGT TTG GTC ATT TGC TTT GTG ACC GCG      723
Lys Gly Arg Thr Gln Arg Arg Arg Leu Val Ile Cys Phe Val Thr Ala
        220             225             230

CCG AGG GAC CAT GTT CCG CCA GGG CAC CCC CAA CCG CGT GGT GAT CAG      771
Pro Arg Asp His Val Pro Pro Gly His Pro Gln Pro Arg Gly Asp Gln
235             240             245

CAC AGT GCC GTT GAG CAG AGA GGC GAC CGC GAC CGC GAC CGC CGG CAC      819
His Ser Ala Val Glu Gln Arg Gly Asp Arg Asp Arg Asp Arg Arg His
250             255             260             265

CGG TCC CGG ATG CGA GGG GGG GCT TGG TGG CTG GCG ACT CTT TAC AGT      867
Arg Ser Arg Met Arg Gly Gly Ala Trp Trp Leu Ala Thr Leu Tyr Ser
                270             275             280

GCC GCC ACG AGC AAG AAG ACG GCC TGT ATG CTA TCG TCC CGC GGG ACT      915
Ala Ala Thr Ser Lys Lys Thr Ala Cys Met Leu Ser Ser Arg Arg Thr
            285             290             295

ATT TTC CGG TGG TGC CCT CGT CCA AGC CCC TGC TGG TGAAAGTTCC           961
Ile Phe Arg Trp Cys Pro Arg Pro Ser Pro Cys Trp
        300             305

CGCTCCCGGC GCGAGTCCCG ACCGAACTGG GGGCGCAGTT CACTTTGAAT GTGTTCCCGC   1021

GCCGCGCCGA CCGCTGCAGT TCTTTCGTCA GCTTTACGAC GGTTCATTCG TTAAGCTT     1079
```

(2) INFORMATION FOR SEQ ID NO:2:

(i) SEQUENCE CHARACTERISTICS:
        (A) LENGTH: 309 amino acids
        (B) TYPE: amino acid
        (D) TOPOLOGY: linear (ii) MOLECULE TYPE: protein (xi) SEQUENCE DESCRIPTION: SEQ ID NO:2:

```
Met Val Thr Ile Val Thr Cys Gly Arg Ile Gly Ala Ala Pro Ser Arg
1               5                   10                  15

Gln Ala Gln Thr Cys Ala Ala Arg Val Trp Arg Phe Leu Ala Glu Gln
            20                  25                  30

Ser Arg Ala Leu Thr Ala Ser Arg Leu Gly Thr Thr Val Val Val Phe
        35                  40                  45

Asp His Ala Leu Val Lys Thr Ala Lys Gly Cys Thr Ser Thr Ser Thr
    50                  55                  60

Ser Ser Gln Arg Arg Gly Trp Leu Leu Ser Thr Gln Arg Pro Trp Pro
65                  70                  75                  80

Gly Arg Arg Leu Ser Pro Pro Pro Thr Gly Glu Trp Val Ser Trp
                85                  90                  95

Ser Thr Ala Thr Asn Leu Leu Lys Leu Gly Arg Ala Arg Ala Arg Pro
                100                 105                 110

Phe His Met Trp Val Phe Gly Ala Ala Asp Leu Tyr Ala Pro Ile Phe
            115                 120                 125

Ala His Ile Ala Ala Thr Thr Arg Leu Val Tyr Ala Gln Leu Asp Cys
        130                 135                 140
```

| | | | | | | | | | | | | | | |
|---|---|---|---|---|---|---|---|---|---|---|---|---|---|---|
| Thr | Phe | Ala | Gly | Ala | Ala | Trp | Arg | Leu | Pro | Arg | Arg | Gly | Pro | Ala | Ile |
| 145 | | | | | 150 | | | | | 155 | | | | | 160 |
| Ala | Ser | Pro | Trp | Pro | Pro | Tyr | Asp | Thr | Pro | Thr | Leu | Pro | Glu | Leu | Val |
| | | | | 165 | | | | | 170 | | | | | 175 | |
| Ala | Gly | Gly | Val | Leu | Phe | Arg | Leu | Val | Tyr | Glu | Val | Val | Asp | Arg | Gly |
| | | | 180 | | | | | 185 | | | | | 190 | | |
| Arg | Arg | Pro | Ala | Pro | Pro | Asn | Ala | Ser | Pro | Arg | Ala | Pro | Gly | Ala | Arg |
| | | 195 | | | | | 200 | | | | | 205 | | | |
| Pro | Arg | Ala | Arg | His | Val | Leu | Ser | Phe | Lys | Gly | Arg | Thr | Gln | Arg | Arg |
| | 210 | | | | | 215 | | | | | 220 | | | | |
| Arg | Leu | Val | Ile | Cys | Phe | Val | Thr | Ala | Pro | Arg | Asp | His | Val | Pro | Pro |
| 225 | | | | | 230 | | | | | 235 | | | | | 240 |
| Gly | His | Pro | Gln | Pro | Arg | Gly | Asp | Gln | His | Ser | Ala | Val | Glu | Gln | Arg |
| | | | | 245 | | | | | 250 | | | | | 255 | |
| Gly | Asp | Arg | Asp | Arg | Asp | Arg | Arg | His | Arg | Ser | Arg | Met | Arg | Gly | Gly |
| | | | 260 | | | | | 265 | | | | | 270 | | |
| Ala | Trp | Trp | Leu | Ala | Thr | Leu | Tyr | Ser | Ala | Ala | Thr | Ser | Lys | Lys | Thr |
| | | 275 | | | | | 280 | | | | | 285 | | | |
| Ala | Cys | Met | Leu | Ser | Ser | Arg | Arg | Thr | Ile | Phe | Arg | Trp | Cys | Pro | Arg |
| | 290 | | | | | 295 | | | | | 300 | | | | |
| Pro | Ser | Pro | Cys | Trp | | | | | | | | | | | |
| 305 | | | | | | | | | | | | | | | |

( 2 ) INFORMATION FOR SEQ ID NO:3:

( i ) SEQUENCE CHARACTERISTICS:
        ( A ) LENGTH: 18 amino acids
        ( B ) TYPE: amino acid
        ( C ) STRANDEDNESS: double
        ( D ) TOPOLOGY: linear ( i i ) MOLECULE TYPE: Protein ( x i ) SEQUENCE DESCRIPTION: SEQ ID NO:3:

| | | | | | | | | | | | | | | |
|---|---|---|---|---|---|---|---|---|---|---|---|---|---|---|
| His | Met | Trp | Val | Phe | Gly | Ala | Ala | Asp | Leu | Tyr | Ala | Pro | Ile | Phe | Ala |
| 1 | | | | 5 | | | | | 10 | | | | | 15 | |
| His | Ile | | | | | | | | | | | | | | |

( 2 ) INFORMATION FOR SEQ ID NO:4:

( i ) SEQUENCE CHARACTERISTICS:
        ( A ) LENGTH: 18 amino acids
        ( B ) TYPE: amino acid
        ( C ) STRANDEDNESS: double
        ( D ) TOPOLOGY: linear ( i i ) MOLECULE TYPE: Protein ( i i i ) HYPOTHETICAL: NO ( i v ) ANTI-SENSE: NO ( v i ) ORIGINAL SOURCE:
        ( A ) ORGANISM: Herpes Simplex Virus Type 1

( x i ) SEQUENCE DESCRIPTION: SEQ ID NO:4:

| | | | | | | | | | | | | | | |
|---|---|---|---|---|---|---|---|---|---|---|---|---|---|---|
| His | Leu | Trp | Val | Val | Gly | Ala | Ala | Asp | Leu | Cys | Val | Pro | Phe | Leu | Glu |
| 1 | | | | 5 | | | | | 10 | | | | | 15 | |
| Tyr | Ala | | | | | | | | | | | | | | |

( 2 ) INFORMATION FOR SEQ ID NO:5:

( i ) SEQUENCE CHARACTERISTICS:

(A) LENGTH: 18 amino acids
(B) TYPE: amino acid
(C) STRANDEDNESS: double
(D) TOPOLOGY: linear (i i) MOLECULE TYPE: Protein (i i i) HYPOTHETICAL: NO (i v) ANTI-SENSE: NO (v i) ORIGINAL SOURCE:
(A) ORGANISM: Pseudorabies Virus (x i) SEQUENCE DESCRIPTION: SEQ ID NO:5:

```
His Leu Trp Ile Leu Gly Ala Ala Asp Leu Cys Asp Gln Val Leu Leu
1               5                   10                  15

Ala Ala
```

( 2 ) INFORMATION FOR SEQ ID NO:6:

( i ) SEQUENCE CHARACTERISTICS:
( A ) LENGTH: 18 amino acids
( B ) TYPE: amino acid
( C ) STRANDEDNESS: double
( D ) TOPOLOGY: linear ( i i ) MOLECULE TYPE: Protein ( i i i ) HYPOTHETICAL: NO ( i v ) ANTI-SENSE: NO ( v i ) ORIGINAL SOURCE:
( A ) ORGANISM: Herpes Simplex Virus Type 2

( x i ) SEQUENCE DESCRIPTION: SEQ ID NO:6:

```
His Leu Trp Ile Val Gly Ala Ala Asp Ile Cys Arg Ile Ala Leu Glu
1               5                   10                  15

Cys Ile
```

( 2 ) INFORMATION FOR SEQ ID NO:7:

( i ) SEQUENCE CHARACTERISTICS:
( A ) LENGTH: 19 amino acids
( B ) TYPE: amino acid
( C ) STRANDEDNESS: double
( D ) TOPOLOGY: linear ( i i ) MOLECULE TYPE: Protein ( i i i ) HYPOTHETICAL: NO ( i v ) ANTI-SENSE: NO ( v i ) ORIGINAL SOURCE:
( A ) ORGANISM: Marek's Disease Virus ( x i ) SEQUENCE DESCRIPTION: SEQ ID NO:7:

```
His Ser Leu Trp Ile Val Gly Ala Ala Asp Ile Cys Arg Ile Ala Leu
1               5                   10                  15

Glu Cys Ile
```

( 2 ) INFORMATION FOR SEQ ID NO:8:

( i ) SEQUENCE CHARACTERISTICS:
( A ) LENGTH: 60 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:8:

TGAGCGCGCG CCGCTGCATG CTGGTGCGAA CTCACGCCGA GCGCGCGTGC GAGCAAGCTT    60

( 2 ) INFORMATION FOR SEQ ID NO:9:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

CTAGTAAAAA CGGCGAAGGG CTGGTGCGAA CTCACGCCGA GCGCGCGTGC GAGCAAGCTT    60

( 2 ) INFORMATION FOR SEQ ID NO:10:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

CTAGTAAAAA CGGCGAAGGG CTGCACGTCG ACGTCAACGT CAAGCCAGCG GCGCGGGTGG    60

( 2 ) INFORMATION FOR SEQ ID NO:11:

( i ) SEQUENCE CHARACTERISTICS:
        ( A ) LENGTH: 48 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

GATTTAGGTG ACACTATAGA ATACACGGAA TTCGAGCTCG CCCCATGG    48

( 2 ) INFORMATION FOR SEQ ID NO:12:

( i ) SEQUENCE CHARACTERISTICS:
        ( A ) LENGTH: 99 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: CDS
    ( B ) LOCATION: 1..12

( x i ) SEQUENCE DESCRIPTION: SEQ ID NO:12:

```
TTA AGT GGG ATC CCGGCGCGCA GGCGCGCACG TCGGTCGCGG TCGCGCGCCA       52
Leu Ser Gly Ile
 1

TGGGGGATCC TCTAGAGCTT GGGCTGCAGG TCCTGATTGA TACACTG               99
```

( 2 ) INFORMATION FOR SEQ ID NO:13:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

```
Leu Ser Gly Ile
 1
```

( 2 ) INFORMATION FOR SEQ ID NO:14:

( i ) SEQUENCE CHARACTERISTICS:
        ( A ) LENGTH: 99 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

```
GCCCCGATCG TCCACACGGA GCGCGGCTGC CGACACGGAT CTGATCAAGA GACAGGATGA   60
GGATCGTTTC GCATGATTGA ACAAGATGGA TTGCACGCA                          99
```

( 2 ) INFORMATION FOR SEQ ID NO:15:

( i ) SEQUENCE CHARACTERISTICS:
        ( A ) LENGTH: 99 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 64..78

( x i ) SEQUENCE DESCRIPTION: SEQ ID NO:15:

```
GGACCTTGCA CAGATAGCGT GGTCCGGCCA GGACGACGAG GCTTGCAGGA TCCTCTAGAG   60
TCG GGA GAT GGG GGA GGC TAACTGAAAC ACGGAAGGAG A                     99
    Gly Asp Gly Gly Gly
     1               5
```

( 2 ) INFORMATION FOR SEQ ID NO:16:

( i ) SEQUENCE CHARACTERISTICS:
    ( A ) LENGTH: 5 amino acids
    ( B ) TYPE: amino acid
    ( D ) TOPOLOGY: linear ( i i ) MOLECULE TYPE: protein ( x i ) SEQUENCE DESCRIPTION: SEQ ID NO:16:

Gly Asp Gly Gly Gly
1              5

( 2 ) INFORMATION FOR SEQ ID NO:17:

( i ) SEQUENCE CHARACTERISTICS:
        ( A ) LENGTH: 99 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 61..99

( x i ) SEQUENCE DESCRIPTION: SEQ ID NO:17:

GTGTTGCTGC GTTCCCGACC TGCAGCCCAA GCTCTAGAGT CGACCTGCAG CCCAAGCTCA    60

GAT CTG CTC ATG CTC GCG GCC GCC ATG CCC CCG GAA GCG    99
Asp Leu Leu Met Leu Ala Ala Ala Met Pro Pro Glu Ala
1            5                        10

( 2 ) INFORMATION FOR SEQ ID NO:18:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

Asp Leu Leu Met Leu Ala Ala Ala Met Pro Pro Glu Ala
1            5                        10

( 2 ) INFORMATION FOR SEQ ID NO:19:

( i ) SEQUENCE CHARACTERISTICS:
        ( A ) LENGTH: 60 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:19:

AGGCAGATCT GAGCTTGGCG TAATCATGGT CATAGCTGTT TCCTGTGTGA AATTGTTATC    60

( 2 ) INFORMATION FOR SEQ ID NO:20:

( i ) SEQUENCE CHARACTERISTICS:
        ( A ) LENGTH: 1386 base pairs
        ( B ) TYPE: nucleic acid
        ( C ) STRANDEDNESS: double ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
                ( A ) ORGANISM: Bovine herpesvirus-1 (IBR virus)
                ( B ) STRAIN: Cooper
                ( C

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     |     |     | 210 |     |     |     |     | 215 |     |     |     | 220 |      |
| TGC | GGC | TGC | TTC | CCC | GCC | CTT | GTT | GAG | GTT | GAC | GCG | GTG | TGG | GGC | AAC | 720  |
| Cys | Gly | Cys | Phe | Pro | Ala | Leu | Val | Glu | Val | Asp | Ala | Val | Trp | Gly | Asn |      |
|     |     | 225 |     |     |     |     | 230 |     |     |     |     | 235 |     |     |     |      |
| GTA | AGC | GCC | GCA | GAG | CTG | GGC | CTG | GCC | GAC | CCG | ATC | GAC | TAC | GCC | GAC | 768  |
| Val | Ser | Ala | Ala | Glu | Leu | Gly | Leu | Ala | Asp | Pro | Ile | Asp | Tyr | Ala | Asp |      |
|     | 240 |     |     |     |     | 245 |     |     |     |     | 250 |     |     |     |     |      |
| GAA | GGG | GGT | GAG | GTC | GAA | GTG | CTC | GAG | GAC | GAA | GCC | GGG | AGC | GCC | AGC | 816  |
| Glu | Gly | Gly | Glu | Val | Glu | Val | Leu | Glu | Asp | Glu | Ala | Gly | Ser | Ala | Ser |      |
| 255 |     |     |     |     | 260 |     |     |     |     | 265 |     |     |     |     | 270 |      |
| GGA | AAC | CTG | CCG | CAG | GAC | GAC | CCC | GAC | CCC | GAC | CTC | GCA | GAT | TGC | CGG | 864  |
| Gly | Asn | Leu | Pro | Gln | Asp | Asp | Pro | Asp | Pro | Asp | Leu | Ala | Asp | Cys | Arg |      |
|     |     |     |     | 275 |     |     |     |     | 280 |     |     |     |     | 285 |     |      |
| ACC | GTC | GGG | CTC | TTT | AGC | GAA | AGC | GAC | ATG | TTC | CGG | ACC | GCC | AGC | GGG | 912  |
| Thr | Val | Gly | Leu | Phe | Ser | Glu | Ser | Asp | Met | Phe | Arg | Thr | Ala | Ser | Gly |      |
|     |     |     | 290 |     |     |     |     | 295 |     |     |     |     | 300 |     |     |      |
| CCC | GAA | TCG | CTG | CTG | ATC | GGC | GCC | GTT | GCC | AAG | GAC | GTC | CTG | ACG | GTG | 960  |
| Pro | Glu | Ser | Leu | Leu | Ile | Gly | Ala | Val | Ala | Lys | Asp | Val | Leu | Thr | Val |      |
|     |     | 305 |     |     |     |     | 310 |     |     |     |     | 315 |     |     |     |      |
| CCC | CTC | AAT | CTG | CCG | CCC | GGC | CGC | TCT | TAC | GAG | GCC | CTG | CGA | AAC | GCA | 1008 |
| Pro | Leu | Asn | Leu | Pro | Pro | Gly | Arg | Ser | Tyr | Glu | Ala | Leu | Arg | Asn | Ala |      |
|     | 320 |     |     |     | 325 |     |     |     |     | 330 |     |     |     |     |     |      |
| TCG | CTG | GAG | TGC | AAC | TCC | CGC | CCG | CGC | GAG | ACC | GGC | GAC | GCA | GCG | GTG | 1056 |
| Ser | Leu | Glu | Cys | Asn | Ser | Arg | Pro | Arg | Glu | Thr | Gly | Asp | Ala | Ala | Val |      |
| 335 |     |     |     |     | 340 |     |     |     |     | 345 |     |     |     |     | 350 |      |
| GTG | GTG | ATG | TCT | CTC | CAG | GAG | CCC | GCT | CGC | CTC | GAG | CGC | CGC | CCC | GAT | 1104 |
| Val | Val | Met | Ser | Leu | Gln | Glu | Pro | Ala | Arg | Leu | Glu | Arg | Arg | Pro | Asp |      |
|     |     |     |     | 355 |     |     |     |     | 360 |     |     |     |     | 365 |     |      |
| GCC | CGC | GCC | ACC | GAT | CCG | GAG | TTT | GGG | CTC | TTT | GGC | CTG | CCC | GAT | GAC | 1152 |
| Ala | Arg | Ala | Thr | Asp | Pro | Glu | Phe | Gly | Leu | Phe | Gly | Leu | Pro | Asp | Asp |      |
|     |     |     | 370 |     |     |     |     | 375 |     |     |     |     | 380 |     |     |      |
| CCC | GCC | GTG | CGC | GCG | GCA | TTC | TCA | TCG | GCC | TCG | CGA | TCG | CTC | TGC | TGG | 1200 |
| Pro | Ala | Val | Arg | Ala | Ala | Phe | Ser | Ser | Ala | Ser | Arg | Ser | Leu | Cys | Trp |      |
|     |     | 385 |     |     |     |     | 390 |     |     |     |     | 395 |     |     |     |      |
| TGC | TGC | TGT | TTC | GCT | GGT | GAT | CGT | GCT | CGT | CTG | CGC | CTG | CCG | GCT | CGC | 1248 |
| Cys | Cys | Cys | Phe | Ala | Gly | Asp | Arg | Ala | Arg | Leu | Arg | Leu | Pro | Ala | Arg |      |
|     |     | 400 |     |     |     |     | 405 |     |     |     |     | 410 |     |     |     |      |
| CCG | CCC | AGC | CAA | GGC | TGC | GCG | ACG | CCC | CGC | GCC | GCC | ACG | TTC | GCC | AAG | 1296 |
| Pro | Pro | Ser | Gln | Gly | Cys | Ala | Thr | Pro | Arg | Ala | Ala | Thr | Phe | Ala | Lys |      |
| 415 |     |     |     | 420 |     |     |     |     | 425 |     |     |     |     |     | 430 |      |
| AGC | AAC | CCC | GCG | TAC | GAG | CCG | ATG | CTC | AGC | GTC | TGATCGCCGG | CACCCCACGC | | | | 1349 |
| Ser | Asn | Pro | Ala | Tyr | Glu | Pro | Met | Leu | Ser | Val |  |  |  |  |  |      |
|     |     |     |     | 435 |     |     |     |     |     | 440 |     |     |     |     |     |      |
| CGCCCCGACC | CCGCTGTCCC | GCGTTTACAA | TAAACAG | | | | | | | | | | | | | 1386 |

( 2 ) INFORMATION FOR SEQ ID NO:21:

( i ) SEQUENCE CHARACTERISTICS:
        ( A ) LENGTH: 441 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

| Met | Pro | Ala | Ala | Arg | Thr | Gly | Thr | Leu | Ala | Ala | Val | Ala | Leu | Ile | Leu |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |

| Leu | Cys | Gly | Ala | Ala | Val | Leu | Arg | Pro | Arg | Ala | Arg | Arg | Pro | Leu | Phe |
| --- | --- | --- | --- | --- | --- | --- | --- | --- | --- | --- | --- | --- | --- | --- | --- |
|     |     |     |     | 20  |     |     |     |     | 25  |     |     |     |     | 30  |     |

| Arg | Arg | Arg | Ala | Pro | His | Trp | His | Gly | Ala | Leu | Pro | Pro | Ala | Gly | Ala |
| --- | --- | --- | --- | --- | --- | --- | --- | --- | --- | --- | --- | --- | --- | --- | --- |
|     |     |     | 35  |     |     |     |     | 40  |     |     |     |     | 45  |     |     |

```
Arg  Pro  Glu  Pro  Ser  Gly  Leu  Gly  Phe  Asp  Leu  Ala  Gly  Phe  Gly  Ala
     50                       55                 60

Arg  Gly  Gly  Ala  Ser  Arg  Ala  Ala  Pro  Trp  Pro  Ser  Trp  Thr  Trp  Arg
65                       70                 75                            80

Arg  Arg  Trp  Cys  Pro  Ala  Asp  Arg  Glu  Pro  His  Val  Val  Asp  Val  Gly
               85                       90                            95

Trp  Ala  Tyr  Gln  Asp  Gly  Asp  Cys  Met  Val  Pro  Leu  Ala  Tyr  Arg  Gln
               100                      105                      110

Tyr  Phe  Asn  Cys  Thr  Gly  Gly  Ala  Leu  Pro  Gly  Gln  Asn  Val  Cys  Ala
          115                      120                 125

Gly  Leu  Ser  Glu  Thr  Arg  Ile  Arg  Gly  Gly  Phe  Gly  Thr  Ser  Asp  Tyr
     130                      135                 140

Ala  Leu  Tyr  Gly  Thr  Ser  Leu  Val  Leu  Arg  Pro  Gly  Leu  Tyr  Asp  Arg
145                      150                 155                           160

Gly  Thr  Tyr  Ile  Tyr  Phe  Leu  Gly  Tyr  Gly  Pro  Asp  Asp  Ile  Tyr  Val
               165                      170                      175

Gly  Ser  Val  Thr  Leu  Met  Val  Gly  Ala  Asp  Ile  His  Lys  Tyr  Pro  Cys
               180                      185                      190

Gly  Leu  Asp  Arg  Gly  Leu  Gly  Val  Ala  Leu  His  His  Lys  Ser  Gly  Pro
          195                      200                 205

Ala  Arg  Pro  Leu  Thr  Glu  Asp  Ala  Thr  Gly  Asp  Trp  Ala  Cys  Gly
     210                      215                 220

Cys  Phe  Pro  Ala  Leu  Val  Glu  Val  Asp  Ala  Val  Trp  Gly  Asn  Val  Ser
225                      230                 235                           240

Ala  Ala  Glu  Leu  Gly  Leu  Ala  Asp  Pro  Ile  Asp  Tyr  Ala  Asp  Glu  Gly
               245                      250                      255

Gly  Glu  Val  Glu  Val  Leu  Glu  Asp  Glu  Ala  Gly  Ser  Ala  Ser  Gly  Asn
               260                      265                      270

Leu  Pro  Gln  Asp  Asp  Pro  Asp  Pro  Asp  Leu  Ala  Asp  Cys  Arg  Thr  Val
          275                      280                 285

Gly  Leu  Phe  Ser  Glu  Ser  Asp  Met  Phe  Arg  Thr  Ala  Ser  Gly  Pro  Glu
     290                      295                 300

Ser  Leu  Leu  Ile  Gly  Ala  Val  Ala  Lys  Asp  Val  Leu  Thr  Val  Pro  Leu
305                      310                 315                           320

Asn  Leu  Pro  Pro  Gly  Arg  Ser  Tyr  Glu  Ala  Leu  Arg  Asn  Ala  Ser  Leu
                    325                      330                      335

Glu  Cys  Asn  Ser  Arg  Pro  Arg  Glu  Thr  Gly  Asp  Ala  Ala  Val  Val  Val
               340                      345                      350

Met  Ser  Leu  Gln  Glu  Pro  Ala  Arg  Leu  Glu  Arg  Arg  Pro  Asp  Ala  Arg
          355                      360                 365

Ala  Thr  Asp  Pro  Glu  Phe  Gly  Leu  Phe  Gly  Leu  Pro  Asp  Asp  Pro  Ala
     370                      375                 380

Val  Arg  Ala  Ala  Phe  Ser  Ser  Ala  Ser  Arg  Ser  Leu  Cys  Trp  Cys  Cys
385                      390                 395                           400

Cys  Phe  Ala  Gly  Asp  Arg  Ala  Arg  Leu  Arg  Leu  Pro  Ala  Arg  Pro  Pro
               405                      410                      415

Ser  Gln  Gly  Cys  Ala  Thr  Pro  Arg  Ala  Ala  Thr  Phe  Ala  Lys  Ser  Asn
               420                      425                 430

Pro  Ala  Tyr  Glu  Pro  Met  Leu  Ser  Val
          435                      440
```

( 2 ) INFORMATION FOR SEQ ID NO:22:

( i ) SEQUENCE CHARACTERISTICS:

(A) LENGTH: 34 amino acids
(B) TYPE: amino acid
(C) STRANDEDNESS: double
(D) TOPOLOGY: linear (ii) MOLECULE TYPE: Protein (iii) HYPOTHETICAL: NO (iv) ANTI-SENSE: NO (vi) ORIGINAL SOURCE:
(A) ORGANISM: Bovine Herpesvirus-1 (IBR Virus)

(xi) SEQUENCE DESCRIPTION: SEQ ID NO:22:

```
Val Gly Trp Ala Tyr Gln Asp Gly Asp Cys Met Val Pro Leu Ala Tyr
 1               5                  10                  15
Arg Gln Tyr Phe Asn Cys Thr Gly Gly Ala Leu Pro Gly Asn Val Leu
            20                  25                  30
Cys Ala
```

(2) INFORMATION FOR SEQ ID NO:23:

(i) SEQUENCE CHARACTERISTICS:
(A) LENGTH: 34 amino acids
(B) TYPE: amino acid
(C) STRANDEDNESS: double
(D) TOPOLOGY: linear (ii) MOLECULE TYPE: Protein (iii) HYPOTHETICAL: NO (iv) ANTI-SENSE: NO (vi) ORIGINAL SOURCE:
(A) ORGANISM: Pseudorabies Virus (xi) SEQUENCE DESCRIPTION: SEQ ID NO:23:

```
Val Ala Trp Phe Phe Asp Gly Gly His Cys Lys Val Pro Leu Val His
 1               5                  10                  15
Arg Glu Tyr Tyr Gly Cys Pro Gly Asp Ala Met Pro Ser Val Glu Thr
            20                  25                  30
Cys Thr
```

(2) INFORMATION FOR SEQ ID NO:24:

(i) SEQUENCE CHARACTERISTICS:
(A) LENGTH: 34 amino acids
(B) TYPE: amino acid
(C) STRANDEDNESS: double
(D) TOPOLOGY: linear (ii) MOLECULE TYPE: Protein (iii) HYPOTHETICAL: NO (iv) ANTI-SENSE: NO (vi) ORIGINAL SOURCE:
(A) ORGANISM: Herpes Simplex Virus Type 2

(xi) SEQUENCE DESCRIPTION: SEQ ID NO:24:

```
Val Thr Tyr Tyr Arg Leu Thr Arg Ala Cys Arg Gln Pro Ile Leu Leu
 1               5                  10                  15
Arg Gln Tyr Gly Gly Cys Arg Gly Gly Glu Pro Pro Ser Pro Lys Thr
            20                  25                  30
Cys Gly
```

( 2 ) INFORMATION FOR SEQ ID NO:25:

( i ) SEQUENCE CHARACTERISTICS:
    ( A ) LENGTH: 102 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:25:

```
CACATACGAT   TTAGGTGACA   CTATAGAATA   CAAGCTTGGG   CTGCAGGTCG   ACTCTAGAGT        60

CGACCTGCAG   TGAATAATAA   AATGTGTGTT   TGTCCGAAAT   AC                            102
```

( 2 ) INFORMATION FOR SEQ ID NO:26:

( i ) SEQUENCE CHARACTERISTICS:
    ( A ) LENGTH: 102 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:26:

```
GCGTTTGAGA   TTTCTGTCCC   GACTAAATTC   ATGTCGCGCG   ATAGTGGTGT   TTATCGCCGA        60

TAGAGATGGC   GATATTGGAA   AAATCGATAT   TTGAAAATAT   GG                            102
```

( 2 ) INFORMATION FOR SEQ ID NO:27:

( i ) SEQUENCE CHARACTERISTICS:
    ( A ) LENGTH: 102 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:27:

```
CATATTGAAA   ATGTCGCCGA   TGTGAGTTTC   TGTGTAACTG   ATCGCGTGTT   TGGAGGCAAC        60

CGGGGCCTGC   TCCCGACGGC   CAGCGACGAC   GTGGTGCTCA   AG                            102
```

( 2 ) INFORMATION FOR SEQ ID NO:28:

( i ) SEQUENCE CHARACTERISTICS:
    ( A ) LENGTH: 102 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: CDS

-continued ( B ) LOCATION: 1..102

( x i ) SEQUENCE DESCRIPTION: SEQ ID NO:28:

| ATG | TCT | CTC | CAG | GAG | CCC | GCT | CGC | CTC | GAG | GGC | CTG | CCC | TCG | CAG | CTG | 48 |
| Met | Ser | Leu | Gln | Glu | Pro | Ala | Arg | Leu | Glu | Gly | Leu | Pro | Ser | Gln | Leu | |
| 1 | | | | 5 | | | | | 10 | | | | | 15 | | |

| CCC | GTC | TTC | GAG | GAC | ACG | CAG | CGC | TAC | GAC | GCC | TCC | CCC | GCG | TCC | GTG | 96 |
| Pro | Val | Phe | Glu | Asp | Thr | Gln | Arg | Tyr | Asp | Ala | Ser | Pro | Ala | Ser | Val | |
| | | | 20 | | | | | 25 | | | | | 30 | | | |

| AGC | TGG | | | | | | | | | | | | | | | 102 |
| Ser | Trp | | | | | | | | | | | | | | | |

( 2 ) INFORMATION FOR SEQ ID NO:29:

( i ) SEQUENCE CHARACTERISTICS:
    ( A ) LENGTH: 34 amino acids
    ( B ) TYPE: amino acid
    ( D ) TOPOLOGY: linear ( i i ) MOLECULE TYPE: protein ( x i ) SEQUENCE DESCRIPTION: SEQ ID NO:29:

| Met | Ser | Leu | Gln | Glu | Pro | Ala | Arg | Leu | Glu | Gly | Leu | Pro | Ser | Gln | Leu |
| 1 | | | | 5 | | | | | 10 | | | | | 15 | |

| Pro | Val | Phe | Glu | Asp | Thr | Gln | Arg | Tyr | Asp | Ala | Ser | Pro | Ala | Ser | Val |
| | | | 20 | | | | | 25 | | | | | 30 | | |

| Ser | Trp |

( 2 ) INFORMATION FOR SEQ ID NO:30:

( i ) SEQUENCE CHARACTERISTICS:
    ( A ) LENGTH: 102 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: CDS
    ( B ) LOCATION: 1..42

( i x ) FEATURE:
    ( A ) NAME/KEY: CDS
    ( B ) LOCATION: 43..63

( i x ) FEATURE:
    ( A ) NAME/KEY: CDS
    ( B ) LOCATION: 64..102

( x i ) SEQUENCE DESCRIPTION: SEQ ID NO:30:

| CCC | GTG | AGC | AGC | ATG | ATC | GTC | GTC | ATC | GCC | GGC | ATC | GGG | ATC | CTG | GCC | 48 |
| Pro | Val | Ser | Ser | Met | Ile | Val | Val | Ile | Ala | Gly | Ile | Gly | Ile | Leu | Ala | |
| 1 | | | | 5 | | | | | 10 | | | | | 1 | | |

| ATC | GTG | CTG | GTC | ATC | CAT | ATG | GCG | ATC | ATC | AGG | GCC | CGG | GCC | CGG | AAC | 96 |
| Ile | Val | Leu | Val | Ile | His | Met | Ala | Ile | Ile | Arg | Ala | Arg | Ala | Arg | Asn | |
| | | 5 | | | 1 | | | | 5 | | | | | 10 | | |

| GAC | GGC | | | | | | | | | | | | | | | 102 |
| Asp | Gly | | | | | | | | | | | | | | | |

( 2 ) INFORMATION FOR SEQ ID NO:31:

( i ) SEQUENCE CHARACTERISTICS:
    ( A ) LENGTH: 14 amino acids (B) TYPE: amino acid
                (D) TOPOLOGY: linear (i i) MOLECULE TYPE: protein (x i) SEQUENCE DESCRIPTION: SEQ ID NO:31:

Pro  Val  Ser  Ser  Met  Ile  Val  Val  Ile  Ala  Gly  Ile  Gly  Ile
 1                  5                        10

(2) INFORMATION FOR SEQ ID NO:32:

(i) SEQUENCE CHARACTERISTICS:
                (A) LENGTH: 7 amino acids
                (B) TYPE: amino acid
                (D) TOPOLOGY: linear (i i) MOLECULE TYPE: protein (x i) SEQUENCE DESCRIPTION: SEQ ID NO:32:

Leu  Ala  Ile  Val  Leu  Val  Ile
 1                  5

(2) INFORMATION FOR SEQ ID NO:33:

(i) SEQUENCE CHARACTERISTICS:
                (A) LENGTH: 13 amino acids
                (B) TYPE: amino acid
                (D) TOPOLOGY: linear (i i) MOLECULE TYPE: protein (x i) SEQUENCE DESCRIPTION: SEQ ID NO:33:

His  Met  Ala  Ile  Ile  Arg  Ala  Arg  Ala  Arg  Asn  Asp  Gly
 1                  5                        10

(2) INFORMATION FOR SEQ ID NO:34:

(i) SEQUENCE CHARACTERISTICS:
                (A) LENGTH: 75 base pairs
                (B) TYPE: nucleic acid
                (C) STRANDEDNESS: double
                (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:34:

GGGCCAGTAC  CGGCGCCTGG  TGTCCGTCGA  CTCTAGAGTC  GACCTGCAGC  CCAAGCTTTG      60

GCGTAATCAT  GGTCA                                                          75

(2) INFORMATION FOR SEQ ID NO:35:

(i) SEQUENCE CHARACTERISTICS:
                (A) LENGTH: 57 base pairs
                (B) TYPE: nucleic acid
                (C) STRANDEDNESS: double
                (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:35:

ACATACGATT  TAGGTGACAC  TATAGAATAC  AAGCTTAACG  AATGAACCGT  CGTAAAG        57

( 2 ) INFORMATION FOR SEQ ID NO:36:

( i ) SEQUENCE CHARACTERISTICS:
        ( A ) LENGTH: 96 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..12

( x i ) SEQUENCE DESCRIPTION: SEQ ID NO:36:

```
GTC GAA GTG CTC GAAATTCGAG CTCGCCCGGG GATCCTCTAG AGTCGACCTG        52
Val Glu Val Leu
 1

CAGGTCGACT CTAGAGGATC TCGACGGACA CCAGGCGCCG GTAC                   96
```

( 2 ) INFORMATION FOR SEQ ID NO:37:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( x i ) SEQUENCE DESCRIPTION: SEQ ID NO:37:

```
Val Glu Val Leu
 1
```

( 2 ) INFORMATION FOR SEQ ID NO:38:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:38:

```
GGGCGGGGCC GGGTCAGCCG GATCTAGAGT CCCAGGACCC AACGCTGCCC GAGTTTG     57
```

( 2 ) INFORMATION FOR SEQ ID NO:39:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:39:

```
TCCCAGTCAC GACGTTGTAA AACGACGGGA TCCATGGTCC CGGTGTCTTC TATGGAG     57
```

( 2 ) INFORMATION FOR SEQ ID NO:40:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 49..57

( x i ) SEQUENCE DESCRIPTION: SEQ ID NO:40:

```
ATTCACTGCA  GGTCGACTCT  AGAGGATCCC  CGGGCGAGCT  CGAATTTC GAG CGC CGC          57
                                                         Glu Arg Arg
                                                          1
```

( 2 ) INFORMATION FOR SEQ ID NO:41:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: protein ( x i ) SEQUENCE DESCRIPTION: SEQ ID NO:41:

```
Glu Arg Arg
 1
```

( 2 ) INFORMATION FOR SEQ ID NO:42:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..27

( x i ) SEQUENCE DESCRIPTION: SEQ ID NO:42:

```
GCG CGC GCG TAC AAC GCC ACG GTC ATA GGGCGAGCTC GAATTCGTAA                     47
Ala Arg Ala Tyr Asn Ala Thr Val Ile
 1                   5

TCATGGTCAT                                                                     57
```

( 2 ) INFORMATION FOR SEQ ID NO:43:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:43:

```
Ala Arg Ala Tyr Asn Ala Thr Val Ile
```

( 2 ) INFORMATION FOR SEQ ID NO:44:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:44:

ATACACATAC GATTTAGGTG ACACTATAGA ATACAAGCTC GCGTGTTTGG AGGCAAC  57

( 2 ) INFORMATION FOR SEQ ID NO:45:

( i ) SEQUENCE CHARACTERISTICS:
        ( A ) LENGTH: 102 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:45:

TCGGGGTAGC CCCAATTCGA GCTCGCCCGG GGATCCTCTA GAGTCGACCT GCAGGTCGAC  60

TCTAGAGGAT CTCGACGGAC ACCAGGCGCC GGTACTGGCC CT  102

( 2 ) INFORMATION FOR SEQ ID NO:46:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:46:

GGGCGGGGCC GGGTCAGCCG GATCTAGAGT CCCAGGACCC AACGCTGCCC GAGTTTG  57

( 2 ) INFORMATION FOR SEQ ID NO:47:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:47:

TCCCAGTCAC GACGTTGTAA AACGACGGGA TCCATGGTCC CGGTGTCTTC TATGGAG  57

( 2 ) INFORMATION FOR SEQ ID NO:48:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 49..57

( x i ) SEQUENCE DESCRIPTION: SEQ ID NO:48:

```
ATTCACTGCA GGTCGACTCT AGAGGATCCC CGGGCGAGCT CGAATTTC GAG CGC CGC     57
                                                    Glu Arg Arg
                                                     1
```

( 2 ) INFORMATION FOR SEQ ID NO:49:

( i ) SEQUENCE CHARACTERISTICS:
        ( A ) LENGTH: 3 amino acids
        ( B ) TYPE: amino acid
        ( D ) TOPOLOGY: linear ( i i ) MOLECULE TYPE: protein ( x i ) SEQUENCE DESCRIPTION: SEQ ID NO:49:

```
Glu Arg Arg
 1
```

( 2 ) INFORMATION FOR SEQ ID NO:50:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..27

( x i ) SEQUENCE DESCRIPTION: SEQ ID NO:50:

```
GCG CGC GCG TAC AAC GCC ACG GTC ATA GGGCGAGCTC GAATTCGTAA           47
Ala Arg Ala Tyr Asn Ala Thr Val Ile
 1               5

TCATGGTCAT                                                           57
```

( 2 ) INFORMATION FOR SEQ ID NO:51:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:51:

```
Ala Arg Ala Tyr Asn Ala Thr Val Ile
```

( 2 ) INFORMATION FOR SEQ ID NO:52:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:52:

ATACACATAC GATTTAGGTG ACACTATAGA ATACAAGCTC GCGTGTTTGG AGGCAAC 57

( 2 ) INFORMATION FOR SEQ ID NO:53:

( i ) SEQUENCE CHARACTERISTICS:
        ( A ) LENGTH: 84 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 67..84

( x i ) SEQUENCE DESCRIPTION: SEQ ID NO:53:

CGGGGTAGCC CCAATTCGAG CTCGCCCGGG GATCCTCTAG AGGATCCCCG GGCGAGCTCG 60

AATTTC GAG CGC CGC CCC GAT GCC 84
       Glu Arg Arg Pro Asp Ala
        1            5

( 2 ) INFORMATION FOR SEQ ID NO:54:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:54:

Glu Arg Arg Pro Asp Ala
1            5

( 2 ) INFORMATION FOR SEQ ID NO:55:

( i ) SEQUENCE CHARACTERISTICS:
        ( A ) LENGTH: 57 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS ( B ) LOCATION: 1..27

( x i ) SEQUENCE DESCRIPTION: SEQ ID NO:55:

| GCG | CGC | GCG | TAC | AAC | GCC | ACG | GTC | ATA | GGGCGAGCTC | GAATTCGTAA | 47 |
|---|---|---|---|---|---|---|---|---|---|---|---|
| Ala | Arg | Ala | Tyr | Asn | Ala | Thr | Val | Ile | | | |
| 1 | | | | 5 | | | | | | | |

TCATGGTCAT                                                                                              57

( 2 ) INFORMATION FOR SEQ ID NO:56:

( i ) SEQUENCE CHARACTERISTICS:
          ( A ) LENGTH: 9 amino acids
          ( B ) TYPE: amino acid
          ( D ) TOPOLOGY: linear ( i i ) MOLECULE TYPE: protein ( x i ) SEQUENCE DESCRIPTION: SEQ ID NO:56:

| Ala | Arg | Ala | Tyr | Asn | Ala | Thr | Val | Ile |
|---|---|---|---|---|---|---|---|---|
| 1 | | | | 5 | | | | |

( 2 ) INFORMATION FOR SEQ ID NO:57:

( i ) SEQUENCE CHARACTERISTICS:
          ( A ) LENGTH: 2040 base pairs
          ( B ) TYPE: nucleic acid
          ( C ) STRANDEDNESS: double
          ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
          ( A ) ORGANISM: Bovine herpesvirus-1 (IBR virus)
          ( B ) STRAIN: Cooper
          ( C ) INDIVIDUAL ISOLATE: S-IBR- 000

( v i i ) IMMEDIATE SOURCE:
          ( B ) CLONE:PSY 1644, PSY 1645

( v i i i ) POSITION IN GENOME:
          ( B ) MAP POSITION: ⁻86.8 to 87.8
          ( C ) UNITS: %G ( i x ) FEATURE:
          ( A ) NAME/KEY: CDS
          ( B ) LOCATION: 85..1935

( x i ) SEQUENCE DESCRIPTION: SEQ ID NO:57:

| GCGGGCAAGG | CGGAGGAAGA | CCGGGGGCAG | GAGCTGCGTG | GAGGGCGGAG | CCGTTGAGCG | 60 |
|---|---|---|---|---|---|---|

| GCCCGACCGC | CGCCGGGTTG | TTAA | ATG | GGT | CTC | GCG | CGG | CTC | GTG | GTT | CCA | 111 |
|---|---|---|---|---|---|---|---|---|---|---|---|---|
| | | | Met | Gly | Leu | Ala | Arg | Leu | Val | Val | Pro | |
| | | | 1 | | | | | 5 | | | | |

| CAC | CGC | GCC | GGA | GAA | CCA | GCG | CGC | AGC | TTC | GCT | GCG | TGT | GTC | CCG | CGA | 159 |
|---|---|---|---|---|---|---|---|---|---|---|---|---|---|---|---|---|
| His | Arg | Ala | Gly | Glu | Pro | Ala | Arg | Ser | Phe | Ala | Ala | Cys | Val | Pro | Arg | |
| 10 | | | | 15 | | | | 20 | | | | | 25 | | | |

| GCT | GCG | TTC | CGG | GGA | ACG | GCG | CGC | GCG | AGA | GGG | TTC | GAA | AAG | GGC | ATT | 207 |
|---|---|---|---|---|---|---|---|---|---|---|---|---|---|---|---|---|
| Ala | Ala | Phe | Arg | Gly | Thr | Ala | Arg | Ala | Arg | Gly | Phe | Glu | Lys | Gly | Ile | |
| | | | 30 | | | | 35 | | | | | 40 | | | | |

| TGG | CAA | TGC | AAC | CCA | CCG | CGC | CGC | CCC | GGC | SSG | GTT | GCG | CCG | CTG | CTG | 255 |
|---|---|---|---|---|---|---|---|---|---|---|---|---|---|---|---|---|
| Trp | Gln | Cys | Asn | Pro | Pro | Arg | Arg | Pro | Gly | Xaa | Val | Ala | Pro | Leu | Leu | |
| | | | 45 | | | | 50 | | | | | 55 | | | | |

| CTG | CCG | CAG | TTA | TTG | CTT | TTC | GGG | CTG | ATG | GCC | GAG | GCC | AAG | CCC | GCG | 303 |
|---|---|---|---|---|---|---|---|---|---|---|---|---|---|---|---|---|
| Leu | Pro | Gln | Leu | Leu | Leu | Phe | Gly | Leu | Met | Ala | Glu | Ala | Lys | Pro | Ala | |
| | | | 60 | | | | 65 | | | | | 70 | | | | |

-continued

| | | | | | | | | | | | | | | | | |
|---|---|---|---|---|---|---|---|---|---|---|---|---|---|---|---|---|
| ACC | GAA | ACC | CCG | GGC | TCG | GCT | TCG | GTC | GAC | ACG | GTC | TTC | ACG | GCG | CGC | 351 |
| Thr | Glu | Thr | Pro | Gly | Ser | Ala | Ser | Val | Asp | Thr | Val | Phe | Thr | Ala | Arg | |
| | 75 | | | | 80 | | | | | 85 | | | | | | |
| GCT | GGC | GCG | CCC | GTC | TTT | CTC | CCA | GGG | CCC | GCG | GCG | CGC | CCG | GAC | GTG | 399 |
| Ala | Gly | Ala | Pro | Val | Phe | Leu | Pro | Gly | Pro | Ala | Ala | Arg | Pro | Asp | Val | |
| 90 | | | | | 95 | | | | 100 | | | | | | 105 | |
| CGC | GCC | GTT | CGC | GGC | TGG | AGC | GTC | CTC | GCG | GCC | GCC | TGC | TCG | CCG | CCC | 447 |
| Arg | Ala | Val | Arg | Gly | Trp | Ser | Val | Leu | Ala | Ala | Ala | Cys | Ser | Pro | Pro | |
| | | | | 110 | | | | | 115 | | | | | 120 | | |
| GTG | CCG | GAG | CCC | GTC | TGC | CTC | GAC | GAC | CGC | GAG | TGC | TTC | ACC | GAC | GTG | 495 |
| Val | Pro | Glu | Pro | Val | Cys | Leu | Asp | Asp | Arg | Glu | Cys | Phe | Thr | Asp | Val | |
| | | | 125 | | | | | 130 | | | | | 135 | | | |
| GCC | CTG | GAC | GCG | GCC | TGC | CTG | CGA | ACC | GCC | CGC | GTG | GCC | CCG | CTG | GCC | 543 |
| Ala | Leu | Asp | Ala | Ala | Cys | Leu | Arg | Thr | Ala | Arg | Val | Ala | Pro | Leu | Ala | |
| | | 140 | | | | | 145 | | | | | 150 | | | | |
| ATC | GCG | GAG | CTC | GCC | GAG | CGG | CCC | GAC | TCA | ACG | GGC | GAC | AAA | GAG | TTT | 591 |
| Ile | Ala | Glu | Leu | Ala | Glu | Arg | Pro | Asp | Ser | Thr | Gly | Asp | Lys | Glu | Phe | |
| | 155 | | | | | 160 | | | | | 165 | | | | | |
| GTT | CTC | GCC | GAC | CCG | CAC | GTC | TCG | GCG | CAG | CTG | GGT | CGC | AAC | GCG | ACC | 639 |
| Val | Leu | Ala | Asp | Pro | His | Val | Ser | Ala | Gln | Leu | Gly | Arg | Asn | Ala | Thr | |
| 170 | | | | | 175 | | | | 180 | | | | | | 185 | |
| GGG | GTG | CTG | ATC | GCG | GCC | GCA | GCC | GAG | GAG | GAC | GGC | GGC | GTG | TAC | TTC | 687 |
| Gly | Val | Leu | Ile | Ala | Ala | Ala | Ala | Glu | Glu | Asp | Gly | Gly | Val | Tyr | Phe | |
| | | | | 190 | | | | | 195 | | | | | | 200 | |
| CTG | TAC | GAC | CGG | CTC | ATC | GGC | GAC | GCC | GGC | GAC | GAG | GAG | ACG | CAG | TTG | 735 |
| Leu | Tyr | Asp | Arg | Leu | Ile | Gly | Asp | Ala | Gly | Asp | Glu | Glu | Thr | Gln | Leu | |
| | | | 205 | | | | | 210 | | | | | 215 | | | |
| GCG | CTG | ACG | CTG | CAG | GTC | GCG | ACG | GCC | GGC | GCG | CAG | GGC | GCC | GCG | CGG | 783 |
| Ala | Leu | Thr | Leu | Gln | Val | Ala | Thr | Ala | Gly | Ala | Gln | Gly | Ala | Ala | Arg | |
| | | 220 | | | | | 225 | | | | | 230 | | | | |
| GAC | GAG | GAG | AGG | GAA | CCA | GCG | ACC | GGG | CCC | ACC | CCC | GGC | CCG | CCG | CCC | 831 |
| Asp | Glu | Glu | Arg | Glu | Pro | Ala | Thr | Gly | Pro | Thr | Pro | Gly | Pro | Pro | Pro | |
| | 235 | | | | | 240 | | | | | 245 | | | | | |
| CAC | CGC | ACG | ACG | ACA | CGC | GCG | CCC | CCG | CGG | CGG | CAC | GGC | GCG | CGC | TTC | 879 |
| His | Arg | Thr | Thr | Thr | Arg | Ala | Pro | Pro | Arg | Arg | His | Gly | Ala | Arg | Phe | |
| 250 | | | | | 255 | | | | 260 | | | | | | 265 | |
| CGC | GTG | CTG | CCG | TAC | CAC | TCC | CAC | GTA | TAC | ACC | CCG | GGC | GAT | TCC | TTT | 927 |
| Arg | Val | Leu | Pro | Tyr | His | Ser | His | Val | Tyr | Thr | Pro | Gly | Asp | Ser | Phe | |
| | | | | 270 | | | | | 275 | | | | | 280 | | |
| CTG | CTA | TCG | GTG | CGT | CTG | CAG | TCT | GAG | TTT | TTC | GAC | GAG | GCT | CCC | TTC | 975 |
| Leu | Leu | Ser | Val | Arg | Leu | Gln | Ser | Glu | Phe | Phe | Asp | Glu | Ala | Pro | Phe | |
| | | | 285 | | | | | 290 | | | | | 295 | | | |
| TCG | GCC | AGC | ATC | GAC | TGG | TAC | TTC | CTG | CGG | ACG | GCC | GGC | GAC | TGC | GCG | 1023 |
| Ser | Ala | Ser | Ile | Asp | Trp | Tyr | Phe | Leu | Arg | Thr | Ala | Gly | Asp | Cys | Ala | |
| | | 300 | | | | | 305 | | | | | 310 | | | | |
| CTC | ATC | CGC | ATA | TAC | GAG | ACG | TGC | ATC | TTC | CAC | CCC | GAG | GCA | CCG | GCC | 1071 |
| Leu | Ile | Arg | Ile | Tyr | Glu | Thr | Cys | Ile | Phe | His | Pro | Glu | Ala | Pro | Ala | |
| | 315 | | | | | 320 | | | | | 325 | | | | | |
| TGC | CTG | CAC | CCC | GCC | GAC | GCG | CAG | TGC | AGC | TTC | GCG | TCG | CCG | TAC | CGC | 1119 |
| Cys | Leu | His | Pro | Ala | Asp | Ala | Gln | Cys | Ser | Phe | Ala | Ser | Pro | Tyr | Arg | |
| 330 | | | | | 335 | | | | 340 | | | | | | 345 | |
| TCC | GAG | ACC | GTG | TAC | AGC | CGG | CTG | TAC | GAG | CAG | TGC | CGC | CCG | GAC | CCT | 1167 |
| Ser | Glu | Thr | Val | Tyr | Ser | Arg | Leu | Tyr | Glu | Gln | Cys | Arg | Pro | Asp | Pro | |
| | | | | 350 | | | | | 355 | | | | | 360 | | |
| GCC | GGT | CGC | TGG | CCG | CAC | GAG | TGC | GAG | GGC | GCC | GCG | TAC | GCG | GCG | CCC | 1215 |
| Ala | Gly | Arg | Trp | Pro | His | Glu | Cys | Glu | Gly | Ala | Ala | Tyr | Ala | Ala | Pro | |
| | | | 365 | | | | | 370 | | | | | 375 | | | |
| GTT | GCG | CAC | CTG | CGT | CCC | GCC | AAT | AAC | AGC | GTA | GAC | CTG | GTC | TTT | GAC | 1263 |
| Val | Ala | His | Leu | Arg | Pro | Ala | Asn | Asn | Ser | Val | Asp | Leu | Val | Phe | Asp | |
| | | 380 | | | | | 385 | | | | | 390 | | | | |

| | | | | | | | | | | | | | | | | |
|---|---|---|---|---|---|---|---|---|---|---|---|---|---|---|---|---|
| GAC | GCG | CCG | GCT | GCG | GCC | TCC | GGG | CTT | TAC | GTC | TTT | GTG | CTG | CAG | TAC | 1311 |
| Asp | Ala | Pro | Ala | Ala | Ala | Ser | Gly | Leu | Tyr | Val | Phe | Val | Leu | Gln | Tyr | |
| 395 | | | | | 400 | | | | | 405 | | | | | | |
| AAC | GGC | CAC | GTG | GAA | GCT | TGG | GAC | TAC | TGC | CTA | GTC | GTT | ACT | TCG | GAC | 1359 |
| Asn | Gly | His | Val | Glu | Ala | Trp | Asp | Tyr | Cys | Leu | Val | Val | Thr | Ser | Asp | |
| 410 | | | | 415 | | | | | 420 | | | | | | 425 | |
| CGT | TTG | GTG | CGC | GCG | GTC | ACC | GAC | CAC | ACG | CGC | CCC | GAG | GCC | GCA | GCC | 1407 |
| Arg | Leu | Val | Arg | Ala | Val | Thr | Asp | His | Thr | Arg | Pro | Glu | Ala | Ala | Ala | |
| | | | | 430 | | | | | 435 | | | | | 440 | | |
| GCC | GAC | GCT | CCC | GAG | CCA | GGC | CCA | CCG | CTC | ACC | AGC | GAG | CCG | GCG | GGG | 1455 |
| Ala | Asp | Ala | Pro | Glu | Pro | Gly | Pro | Pro | Leu | Thr | Ser | Glu | Pro | Ala | Gly | |
| | | | 445 | | | | 450 | | | | | | 455 | | | |
| GSG | CCC | ACC | GGG | CCC | GCG | CCC | TGG | CTT | GTG | GTG | CTG | GTG | GGC | GCG | CTT | 1503 |
| Xaa | Pro | Thr | Gly | Pro | Ala | Pro | Trp | Leu | Val | Val | Leu | Val | Gly | Ala | Leu | |
| | | 460 | | | | | 465 | | | | | 470 | | | | |
| GGA | CTC | GCG | GGA | CTG | GTG | GGC | ATC | GCA | GCC | CTC | GCC | GTT | CGG | GTG | TGC | 1551 |
| Gly | Leu | Ala | Gly | Leu | Val | Gly | Ile | Ala | Ala | Leu | Ala | Val | Arg | Val | Cys | |
| | | 475 | | | | | 480 | | | | | 485 | | | | |
| GCG | CGC | CGC | GCA | AGC | CAG | AAG | CGC | ACC | TAC | GAC | ATC | CTC | AAC | CCC | TTC | 1599 |
| Ala | Arg | Arg | Ala | Ser | Gln | Lys | Arg | Thr | Tyr | Asp | Ile | Leu | Asn | Pro | Phe | |
| 490 | | | | | 495 | | | | | 500 | | | | | 505 | |
| GGG | CCC | GTA | TAC | ACC | AGC | TTG | CCG | ACC | AAC | GAG | CCG | CTC | GAC | GTG | GTG | 1647 |
| Gly | Pro | Val | Tyr | Thr | Ser | Leu | Pro | Thr | Asn | Glu | Pro | Leu | Asp | Val | Val | |
| | | | | 510 | | | | | 515 | | | | | 520 | | |
| GTG | CCA | GTT | AGC | GAC | GAC | GAA | TTT | TCC | CTC | GAC | GAA | GAC | TCT | TTT | GCG | 1695 |
| Val | Pro | Val | Ser | Asp | Asp | Glu | Phe | Ser | Leu | Asp | Glu | Asp | Ser | Phe | Ala | |
| | | | 525 | | | | | 530 | | | | | 535 | | | |
| GAT | GAC | GAC | AGC | GAC | GAT | GAC | GGG | CCC | GCT | AGC | AAC | CCC | CCT | GCG | GAT | 1743 |
| Asp | Asp | Asp | Ser | Asp | Asp | Asp | Gly | Pro | Ala | Ser | Asn | Pro | Pro | Ala | Asp | |
| | | 540 | | | | | 545 | | | | | 550 | | | | |
| GCC | TAC | GAC | CTC | GCC | GGC | GCC | CCA | GAG | CCA | ACT | AGC | GGG | TTT | GCG | CGA | 1791 |
| Ala | Tyr | Asp | Leu | Ala | Gly | Ala | Pro | Glu | Pro | Thr | Ser | Gly | Phe | Ala | Arg | |
| | 555 | | | | | 560 | | | | | 565 | | | | | |
| GCC | CCC | GCC | AAC | GGC | ACG | CGC | TCG | AGT | CGC | TCT | GGG | TTC | AAA | GTT | TGG | 1839 |
| Ala | Pro | Ala | Asn | Gly | Thr | Arg | Ser | Ser | Arg | Ser | Gly | Phe | Lys | Val | Trp | |
| 570 | | | | | 575 | | | | | 580 | | | | | 585 | |
| TTT | AGG | GAC | CCG | CTT | GAA | GAC | GAT | GCC | GCG | CCA | GCG | CGG | ACC | CCG | GCC | 1887 |
| Phe | Arg | Asp | Pro | Leu | Glu | Asp | Asp | Ala | Ala | Pro | Ala | Arg | Thr | Pro | Ala | |
| | | | | 590 | | | | 595 | | | | | 600 | | | |
| GCA | CCA | GAT | TAC | ACC | GTG | GTA | GCA | GCG | CGA | CTC | AAG | TCC | ATC | CTC | CGC | 1935 |
| Ala | Pro | Asp | Tyr | Thr | Val | Val | Ala | Ala | Arg | Leu | Lys | Ser | Ile | Leu | Arg | |
| | | | 605 | | | | | 610 | | | | | 615 | | | |
| TAGGCGCCCC | CCCCCGCGCG | CTGTGCCGTC | TGACGGAAAG | CACCCGCGTG | TAGGGCTGCA | | | | | | | | | | | 1995 |
| TATAAATGGA | GCGCTCACAC | AAAGCCTCGT | GCGGCTGCTT | CGAAG | | | | | | | | | | | | 2040 |

( 2 ) INFORMATION FOR SEQ ID NO:58:

( i ) SEQUENCE CHARACTERISTICS:
        ( A ) LENGTH: 617 amino acids
        ( B ) TYPE: amino acid
        ( D ) TOPOLOGY: linear ( i i ) MOLECULE TYPE: protein ( x i ) SEQUENCE DESCRIPTION: SEQ ID NO:58:

| | | | | | | | | | | | | | | |
|---|---|---|---|---|---|---|---|---|---|---|---|---|---|---|
| Met | Gly | Leu | Ala | Arg | Leu | Val | Val | Pro | His | Arg | Ala | Gly | Glu | Pro | Ala |
| 1 | | | | 5 | | | | | 10 | | | | | 15 | |
| Arg | Ser | Phe | Ala | Ala | Cys | Val | Pro | Arg | Ala | Ala | Phe | Arg | Gly | Thr | Ala |
| | | | 20 | | | | 25 | | | | | 30 | | | |
| Arg | Ala | Arg | Gly | Phe | Glu | Lys | Gly | Ile | Trp | Gln | Cys | Asn | Pro | Pro | Arg |
| | | 35 | | | | 40 | | | | | 45 | | | | |

-continued

```
Arg  Pro  Gly  Xaa  Val  Ala  Pro  Leu  Leu  Leu  Pro  Gln  Leu  Leu  Leu  Phe
     50                  55                      60

Gly  Leu  Met  Ala  Glu  Ala  Lys  Pro  Ala  Thr  Glu  Thr  Pro  Gly  Ser  Ala
65                       70                  75                           80

Ser  Val  Asp  Thr  Val  Phe  Thr  Ala  Arg  Ala  Gly  Ala  Pro  Val  Phe  Leu
               85                       90                           95

Pro  Gly  Pro  Ala  Ala  Arg  Pro  Asp  Val  Arg  Ala  Val  Arg  Gly  Trp  Ser
               100                 105                      110

Val  Leu  Ala  Ala  Ala  Cys  Ser  Pro  Pro  Val  Pro  Glu  Pro  Val  Cys  Leu
          115                      120                      125

Asp  Asp  Arg  Glu  Cys  Phe  Thr  Asp  Val  Ala  Leu  Asp  Ala  Ala  Cys  Leu
     130                      135                      140

Arg  Thr  Ala  Arg  Val  Ala  Pro  Leu  Ala  Ile  Ala  Glu  Leu  Ala  Glu  Arg
145                      150                      155                         160

Pro  Asp  Ser  Thr  Gly  Asp  Lys  Glu  Phe  Val  Leu  Ala  Asp  Pro  His  Val
               165                      170                      175

Ser  Ala  Gln  Leu  Gly  Arg  Asn  Ala  Thr  Gly  Val  Leu  Ile  Ala  Ala  Ala
               180                      185                      190

Ala  Glu  Glu  Asp  Gly  Gly  Val  Tyr  Phe  Leu  Tyr  Asp  Arg  Leu  Ile  Gly
          195                      200                 205

Asp  Ala  Gly  Asp  Glu  Glu  Thr  Gln  Leu  Ala  Leu  Thr  Leu  Gln  Val  Ala
     210                      215                      220

Thr  Ala  Gly  Ala  Gln  Gly  Ala  Ala  Arg  Asp  Glu  Glu  Arg  Glu  Pro  Ala
225                           230                 235                         240

Thr  Gly  Pro  Thr  Pro  Gly  Pro  Pro  Pro  His  Arg  Thr  Thr  Thr  Arg  Ala
               245                      250                      255

Pro  Pro  Arg  Arg  His  Gly  Ala  Arg  Phe  Arg  Val  Leu  Pro  Tyr  His  Ser
               260                      265                 270

His  Val  Tyr  Thr  Pro  Gly  Asp  Ser  Phe  Leu  Leu  Ser  Val  Arg  Leu  Gln
          275                      280                 285

Ser  Glu  Phe  Phe  Asp  Glu  Ala  Pro  Phe  Ser  Ala  Ser  Ile  Asp  Trp  Tyr
     290                      295                 300

Phe  Leu  Arg  Thr  Ala  Gly  Asp  Cys  Ala  Leu  Ile  Arg  Ile  Tyr  Glu  Thr
305                      310                      315                         320

Cys  Ile  Phe  His  Pro  Glu  Ala  Pro  Ala  Cys  Leu  His  Pro  Ala  Asp  Ala
               325                      330                      335

Gln  Cys  Ser  Phe  Ala  Ser  Pro  Tyr  Arg  Ser  Glu  Thr  Val  Tyr  Ser  Arg
               340                      345                 350

Leu  Tyr  Glu  Gln  Cys  Arg  Pro  Asp  Pro  Ala  Gly  Arg  Trp  Pro  His  Glu
          355                      360                 365

Cys  Glu  Gly  Ala  Ala  Tyr  Ala  Ala  Pro  Val  Ala  His  Leu  Arg  Pro  Ala
     370                      375                 380

Asn  Asn  Ser  Val  Asp  Leu  Val  Phe  Asp  Asp  Ala  Pro  Ala  Ala  Ala  Ser
385                      390                      395                         400

Gly  Leu  Tyr  Val  Phe  Val  Leu  Gln  Tyr  Asn  Gly  His  Val  Glu  Ala  Trp
               405                      410                      415

Asp  Tyr  Cys  Leu  Val  Val  Thr  Ser  Asp  Arg  Leu  Val  Arg  Ala  Val  Thr
               420                      425                      430

Asp  His  Thr  Arg  Pro  Glu  Ala  Ala  Ala  Ala  Asp  Ala  Pro  Glu  Pro  Gly
          435                      440                      445

Pro  Pro  Leu  Thr  Ser  Glu  Pro  Ala  Gly  Xaa  Pro  Thr  Gly  Pro  Ala  Pro
450                           455                      460

Trp  Leu  Val  Val  Leu  Val  Gly  Ala  Leu  Gly  Leu  Ala  Gly  Leu  Val  Gly
```

```
 465                      470                      475                      480
Ile  Ala  Ala  Leu  Ala  Val  Arg  Val  Cys  Ala  Arg  Arg  Ala  Ser  Gln  Lys
                    485                      490                      495
Arg  Thr  Tyr  Asp  Ile  Leu  Asn  Pro  Phe  Gly  Pro  Val  Tyr  Thr  Ser  Leu
               500                      505                      510
Pro  Thr  Asn  Glu  Pro  Leu  Asp  Val  Val  Val  Pro  Val  Ser  Asp  Asp  Glu
               515                      520                      525
Phe  Ser  Leu  Asp  Glu  Asp  Ser  Phe  Ala  Asp  Asp  Asp  Ser  Asp  Asp  Asp
     530                      535                      540
Gly  Pro  Ala  Ser  Asn  Pro  Pro  Ala  Asp  Ala  Tyr  Asp  Leu  Ala  Gly  Ala
545                      550                      555                      560
Pro  Glu  Pro  Thr  Ser  Gly  Phe  Ala  Arg  Ala  Pro  Ala  Asn  Gly  Thr  Arg
                    565                      570                      575
Ser  Ser  Arg  Ser  Gly  Phe  Lys  Val  Trp  Phe  Arg  Asp  Pro  Leu  Glu  Asp
               580                      585                      590
Asp  Ala  Ala  Pro  Ala  Arg  Thr  Pro  Ala  Ala  Pro  Asp  Tyr  Thr  Val  Val
          595                      600                      605
Ala  Ala  Arg  Leu  Lys  Ser  Ile  Leu  Arg
     610                      615
```

( 2 ) INFORMATION FOR SEQ ID NO:59:

( i ) SEQUENCE CHARACTERISTICS:
        ( A ) LENGTH: 50 amino acids
        ( B ) TYPE: amino acid
        ( C ) STRANDEDNESS: double
        ( D ) TOPOLOGY: linear ( i i ) MOLECULE TYPE: Protein ( i i i ) HYPOTHETICAL: NO ( i v ) ANTI-SENSE: NO ( v i ) ORIGINAL SOURCE:
        ( A ) ORGANISM: Herpes Simplex Virus Type 1

( x i ) SEQUENCE DESCRIPTION: SEQ ID NO:59:

```
Trp  Leu  Arg  Phe  Asp  Val  Pro  Thr  Ser  Cys  Ala  Glu  Met  Arg  Ile  Tyr
1                   5                        10                       15
Glu  Ser  Cys  Leu  Tyr  His  Pro  Gln  Leu  Pro  Glu  Cys  Leu  Ser  Pro  Ala
               20                       25                       30
Asp  Ala  Pro  Cys  Ala  Ala  Ser  Thr  Trp  Thr  Ser  Arg  Leu  Ala  Val  Arg
          35                       40                       45
Ser  Tyr
     50
```

( 2 ) INFORMATION FOR SEQ ID NO:60:

( i ) SEQUENCE CHARACTERISTICS:
        ( A ) LENGTH: 52 amino acids
        ( B ) TYPE: amino acid
        ( C ) STRANDEDNESS: double
        ( D ) TOPOLOGY: linear ( i i ) MOLECULE TYPE: Protein ( i i i ) HYPOTHETICAL: NO ( i v ) ANTI-SENSE: NO ( v i ) ORIGINAL SOURCE:
        ( A ) ORGANISM: Pseudorabies Virus ( x i ) SEQUENCE DESCRIPTION: SEQ ID NO:60:

| Trp<br>1 | Tyr | Tyr | Ala | Arg<br>5 | Ala | Pro | Pro | Arg | Cys<br>10 | Leu | Leu | Tyr | Tyr | Val<br>15 | Tyr |
|---|---|---|---|---|---|---|---|---|---|---|---|---|---|---|---|
| Glu | Pro | Cys | Ile<br>20 | Tyr | His | Pro | Arg | Ala<br>25 | Pro | Glu | Cys | Leu | Arg<br>30 | Pro | Val |
| Asp | Pro | Ala<br>35 | Cys | Ser | Phe | Thr | Ser<br>40 | Pro | Ala | Arg | Ala | Ala<br>45 | Leu | Val | Ala |
| Arg | Arg | Ala<br>50 | Tyr | | | | | | | | | | | | |

( 2 ) INFORMATION FOR SEQ ID NO:61:

( i ) SEQUENCE CHARACTERISTICS:
        ( A ) LENGTH: 52 amino acids
        ( B ) TYPE: amino acid
        ( C ) STRANDEDNESS: double
        ( D ) TOPOLOGY: linear ( i i ) MOLECULE TYPE: Protein ( i i i ) HYPOTHETICAL: NO ( i v ) ANTI-SENSE: NO ( v i ) ORIGINAL SOURCE:
        ( A ) ORGANISM: Varicella-Zoster Virus ( x i ) SEQUENCE DESCRIPTION: SEQ ID NO:61:

| Trp<br>1 | Leu | Tyr | Val | Pro<br>5 | Ile | Asp | Pro | Thr | Cys<br>10 | Gln | Pro | Met | Arg | Leu<br>15 | Tyr |
|---|---|---|---|---|---|---|---|---|---|---|---|---|---|---|---|
| Ser | Thr | Cys | Leu<br>20 | Tyr | His | Pro | Asn | Ala<br>25 | Pro | Gln | Cys | Leu | Ser<br>30 | His | Met |
| Asn | Ser | Gly<br>35 | Cys | Thr | Phe | Thr | Ser<br>40 | Pro | His | Leu | Ala | Gln<br>45 | Arg | Val | Ala |
| Ser | Thr | Val<br>50 | Tyr | | | | | | | | | | | | |

( 2 ) INFORMATION FOR SEQ ID NO:62:

( i ) SEQUENCE CHARACTERISTICS:
        ( A ) LENGTH: 52 amino acids
        ( B ) TYPE: amino acid
        ( C ) STRANDEDNESS: double
        ( D ) TOPOLOGY: linear ( i i ) MOLECULE TYPE: Protein ( i i i ) HYPOTHETICAL: NO ( i v ) ANTI-SENSE: NO ( v i ) ORIGINAL SOURCE:
        ( A ) ORGANISM: Bovine Herpesvirus-1 (IBR Virus)

( x i ) SEQUENCE DESCRIPTION: SEQ ID NO:62:

| Trp<br>1 | Tyr | Phe | Leu | Arg<br>5 | Thr | Ala | Gly | Asp | Cys<br>10 | Ala | Leu | Ile | Arg | Ile<br>15 | Tyr |
|---|---|---|---|---|---|---|---|---|---|---|---|---|---|---|---|
| Glu | Thr | Cys | Ile<br>20 | Phe | His | Pro | Glu | Ala<br>25 | Pro | Ala | Cys | Leu | His<br>30 | Pro | Ala |
| Asp | Ala | Gln<br>35 | Cys | Ser | Phe | Ala | Ser<br>40 | Pro | Tyr | Arg | Ser | Glu<br>45 | Thr | Val | Tyr |
| Ser | Arg | Leu<br>50 | Tyr | | | | | | | | | | | | |

( 2 ) INFORMATION FOR SEQ ID NO:63:

( i ) SEQUENCE CHARACTERISTICS:
  ( A ) LENGTH: 84 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
  ( A ) NAME/KEY: CDS
  ( B ) LOCATION: 34..84

( x i ) SEQUENCE DESCRIPTION: SEQ ID NO:63:

```
TTGGGCTGCA GGTCGACTCT AGAGGATCCC CTA TGG TAC AAG ATC GAG AGC GGG          54
                                    Trp Tyr Lys Ile Glu Ser Gly
                                     1               5

TGC GCC CGG CCG CTG TAC TAC ATG GAG TAC                                   84
Cys Ala Arg Pro Leu Tyr Tyr Met Glu Tyr
         10                  15
```

( 2 ) INFORMATION FOR SEQ ID NO:64:

( i ) SEQUENCE CHARACTERISTICS:
    ( A ) LENGTH: 17 amino acids
    ( B ) TYPE: amino acid
    ( D ) TOPOLOGY: linear ( i i ) MOLECULE TYPE: protein ( x i ) SEQUENCE DESCRIPTION: SEQ ID NO:64:

```
Trp Tyr Lys Ile Glu Ser Gly Cys Ala Arg Pro Leu Tyr Tyr Met Glu
 1               5                  10                  15

Tyr
```

( 2 ) INFORMATION FOR SEQ ID NO:65:

( i ) SEQUENCE CHARACTERISTICS:
    ( A ) LENGTH: 84 base pairs
    ( B ) TYPE: nucleic acid
    ( C ) STRANDEDNESS: double
    ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: CDS
    ( B ) LOCATION: 1..84

( x i ) SEQUENCE DESCRIPTION: SEQ ID NO:65:

```
TCC GGG CTT TAC GTC TTT GTG CTG CAG TAC AAC GGC CAC GTG GAA GCT           48
Ser Gly Leu Tyr Val Phe Val Leu Gln Tyr Asn Gly His Val Glu Ala
 1               5                  10                  15

TGG GAC TAC AGC CTA GTC GTT ACT TCG GAC CGT TTG                           84
Trp Asp Tyr Ser Leu Val Val Thr Ser Asp Arg Leu
         20                  25
```

( 2 ) INFORMATION FOR SEQ ID NO:66:

( i ) SEQUENCE CHARACTERISTICS:
    ( A ) LENGTH: 28 amino acids
    ( B ) TYPE: amino acid
    ( D ) TOPOLOGY: linear (i i) MOLECULE TYPE: protein (x i) SEQUENCE DESCRIPTION: SEQ ID NO:66:

```
Ser Gly Leu Tyr Val Phe Val Leu Gln Tyr Asn Gly His Val Glu Ala
 1               5                  10                  15
Trp Asp Tyr Ser Leu Val Val Thr Ser Asp Arg Leu
            20                  25
```

(2) INFORMATION FOR SEQ ID NO:67:

(i) SEQUENCE CHARACTERISTICS:
        (A) LENGTH: 84 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (x i) SEQUENCE DESCRIPTION: SEQ ID NO:67:

```
CCTTCACCGC CGCCGGAAGG CTCCATCGTG TCCATCCCCA TCCTCGAGCT CGAATTGGGG        60
ATCCTCTAGA GTCGACCTGC AGCC                                              84
```

(2) INFORMATION FOR SEQ ID NO:68:

(i) SEQUENCE CHARACTERISTICS:
        (A) LENGTH: 60 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (i x) FEATURE:
        (A) NAME/KEY: CDS
        (B) LOCATION: 28..33

(x i) SEQUENCE DESCRIPTION: SEQ ID NO:68:

```
CTATAGAATA CACGGAATTC GAGCTCG CCC GGG TGAGCGGCCT AGGCCCTCCC            53
                              Pro Gly
                               1
CCGACCG                                                                60
```

(2) INFORMATION FOR SEQ ID NO:69:

(i) SEQUENCE CHARACTERISTICS:
        (A) LENGTH: 2 amino acids
        (B) TYPE: amino acid
        (D) TOPOLOGY: linear (i i) MOLECULE TYPE: protein (x i) SEQUENCE DESCRIPTION: SEQ ID NO:69:

```
Pro Gly
 1
```

(2) INFORMATION FOR SEQ ID NO:70:

(i) SEQUENCE CHARACTERISTICS:
        (A) LENGTH: 90 base pairs
        (B) TYPE: nucleic acid
        (C) STRANDEDNESS: double (D) TOPOLOGY: linear (ii) MOLECULE TYPE: DNA (genomic)

(iii) HYPOTHETICAL: NO (iv) ANTI-SENSE: NO (ix) FEATURE:
    (A) NAME/KEY: CDS
    (B) LOCATION: 1..33

(xi) SEQUENCE DESCRIPTION: SEQ ID NO:70:

```
ATG GCC GAG GCC AAG CCC GCG ACC GAA ACC CCG GGATCCTCT AGAGTCGACG      53
Met Ala Glu Ala Lys Pro Ala Thr Glu Thr Pro
 1               5                  10

TCTGGGGCGC GGGGGTGGTG CTCTTCGAGA CGCTGCC                              90
```

(2) INFORMATION FOR SEQ ID NO:71:

(i) SEQUENCE CHARACTERISTICS:
    (A) LENGTH: 11 amino acids
    (B) TYPE: amino acid
    (D) TOPOLOGY: linear (ii) MOLECULE TYPE: protein (xi) SEQUENCE DESCRIPTION: SEQ ID NO:71:

```
Met Ala Glu Ala Lys Pro Ala Thr Glu Thr Pro
 1               5                  10
```

(2) INFORMATION FOR SEQ ID NO:72:

(i) SEQUENCE CHARACTERISTICS:
    (A) LENGTH: 90 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (ix) FEATURE:
    (A) NAME/KEY: CDS
    (B) LOCATION: 28..48

(ix) FEATURE:
    (A) NAME/KEY: CDS
    (B) LOCATION: 49..90

(xi) SEQUENCE DESCRIPTION: SEQ ID NO:72:

```
ACCTTTGCGC ATCTCCACAG CTCAACA ATG AAG TGG GCA ACG TGG ATC GAT        51
                              Met Lys Trp Ala Thr Trp Ile Asp
                               1               5               1

CCC GTC GTT TTA CAA CGT CGT GAC TGG GAA AAC CCT GGC                  90
Pro Val Val Leu Gln Arg Arg Asp Trp Glu Asn Pro Gly
         5                       10
```

(2) INFORMATION FOR SEQ ID NO:73:

(i) SEQUENCE CHARACTERISTICS:
    (A) LENGTH: 7 amino acids
    (B) TYPE: amino acid
    (D) TOPOLOGY: linear (ii) MOLECULE TYPE: protein (xi) SEQUENCE DESCRIPTION: SEQ ID NO:73:

```
Met Lys Trp Ala Thr Trp Ile
 1               5
```

( 2 ) INFORMATION FOR SEQ ID NO:74:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( x i ) SEQUENCE DESCRIPTION: SEQ ID NO:74:

```
Asp Pro Val Val Leu Gln Arg Arg Asp Trp Glu Asn Pro Gly
 1               5                  10
```

( 2 ) INFORMATION FOR SEQ ID NO:75:

( i ) SEQUENCE CHARACTERISTICS:
        ( A ) LENGTH: 216 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..84

( i x ) FEATURE:
        ( A ) NAME/KEY: CDS
        ( B ) LOCATION: 134..190

( x i ) SEQUENCE DESCRIPTION: SEQ ID NO:75:

```
TGG AGC CCG TCA GTA TCG GCG GAA ATC CAG CTG AGC GCC GGT CGC TAC        48
Trp Ser Pro Ser Val Ser Ala Glu Ile Gln Leu Ser Ala Gly Arg Tyr
 1               5                  10                  15

CAT TAC CAG TTG GTC TGG TGT CAA AAA GAT CTA GAA TAAGCTAGAG             94
His Tyr Gln Leu Val Trp Cys Gln Lys Asp Leu Glu
            20                  25

GATCGATCCC CTATGGCGAT CATCAGGGCC CGATCCCCT ATG GCG ATC ATC AGG        148
                                            Met Ala Ile Ile Arg
                                             1               5

GCC CGG GCC CGG AAC GAC GGC TAC CGC CAC GTG GCC TCC GCC                190
Ala Arg Ala Arg Asn Asp Gly Tyr Arg His Val Ala Ser Ala
                10                  15

TGACCCGGCC CCGCCCGACT CCCCCG                                           216
```

( 2 ) INFORMATION FOR SEQ ID NO:76:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: protein ( x i ) SEQUENCE DESCRIPTION: SEQ ID NO:76:

```
Trp Ser Pro Ser Val Ser Ala Glu Ile Gln Leu Ser Ala Gly Arg Tyr
 1               5                  10                  15

His Tyr Gln Leu Val Trp Cys Gln Lys Asp Leu Glu
            20                  25
```

( 2 ) INFORMATION FOR SEQ ID NO:77:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: protein ( x i ) SEQUENCE DESCRIPTION: SEQ ID NO:77:

```
Met Ala Ile Ile Arg Ala Arg Ala Arg Asn Asp Gly Tyr Arg His Val
 1               5                  10                 15
Ala Ser Ala
```

( 2 ) INFORMATION FOR SEQ ID NO:78:

( i ) SEQUENCE CHARACTERISTICS:
        ( A ) LENGTH: 90 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 49..90

( x i ) SEQUENCE DESCRIPTION: SEQ ID NO:78:

```
GGCGCCTGGT GTCCGTCGAC TCTAGAGTCG ACCTGCAGCC CAAGCTCT AGC AAC CCC    57
                                                     Ser Asn Pro
                                                      1
CCT GCG GAT GCC TAC GAC CTC GCC GGC GCC CCA                        90
Pro Ala Asp Ala Tyr Asp Leu Ala Gly Ala Pro
     5                   10
```

( 2 ) INFORMATION FOR SEQ ID NO:79:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( x i ) SEQUENCE DESCRIPTION: SEQ ID NO:79:

```
Ser Asn Pro Pro Ala Asp Ala Tyr Asp Leu Ala Gly Ala Pro
 1               5                  10
```

( 2 ) INFORMATION FOR SEQ ID NO:80:

( i ) SEQUENCE CHARACTERISTICS:
        ( A ) LENGTH: 1880 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Parainfluenza-3 virus ( i x ) FEATURE:
        ( A ) NAME/KEY: CDS ( B ) LOCATION: 73..1788

( x i ) SEQUENCE DESCRIPTION: SEQ ID NO:80:

```
AGGAACAAAG TTGTTCAACA CAGCAGCAGC GAACAGACCC AAAGGCAGCG CAGAGGCGAC         60

ACCGAACCCA AA ATG GAA TAT TGG AAA CAC ACA AAC AGC ACA AAA AAC           108
              Met Glu Tyr Trp Lys His Thr Asn Ser Thr Lys Asn
                1               5                  10

ACC AAC AAT GAA ACC GAA ACA ACC AGA GGC AAA CAC AGT AGC AAG GTT         156
Thr Asn Asn Glu Thr Glu Thr Thr Arg Gly Lys His Ser Ser Lys Val
            15                  20                  25

ACA AAT ATC ATA ATG TAC ACC TTC TGG ACA ATA ACA TCA ACA ATA TTA         204
Thr Asn Ile Ile Met Tyr Thr Phe Trp Thr Ile Thr Ser Thr Ile Leu
        30                  35                  40

TTA GTC ATT TTT ATA ATG ATA TTG ACA AAC TTA ATT CAA GAG AAC AAT         252
Leu Val Ile Phe Ile Met Ile Leu Thr Asn Leu Ile Gln Glu Asn Asn
45                  50                  55                  60

CAT AAT AAA TTA ATG TTG CAG GAA ATA AGA AAA GAA TTC GCG GCA ATA         300
His Asn Lys Leu Met Leu Gln Glu Ile Arg Lys Glu Phe Ala Ala Ile
                65                  70                  75

GAC ACC AAG ATT CAG AGG ACC TCG GAT GAC ATT GGA ACC TCA ATA CAG         348
Asp Thr Lys Ile Gln Arg Thr Ser Asp Asp Ile Gly Thr Ser Ile Gln
            80                  85                  90

TCA GGA ATA AAT ACA AGA CTT CTC ACA ATT CAG AGT CAT GTT CAA AAC         396
Ser Gly Ile Asn Thr Arg Leu Leu Thr Ile Gln Ser His Val Gln Asn
        95                  100                 105

TAT ATC CCA CTA TCA CTA ACA CAA CAA ATG TCA GAT CTC AGA AAA TTT         444
Tyr Ile Pro Leu Ser Leu Thr Gln Gln Met Ser Asp Leu Arg Lys Phe
    110                 115                 120

ATC AAT GAT CTA ACA AAT AAA AGA GAA CAT CAA GAA GTG CCA ATA CAG         492
Ile Asn Asp Leu Thr Asn Lys Arg Glu His Gln Glu Val Pro Ile Gln
125                 130                 135                 140

AGA ATG ACT CAT GAT AGA GGT ATA GAA CCC CTA AAT CCA GAC AAG TTC         540
Arg Met Thr His Asp Arg Gly Ile Glu Pro Leu Asn Pro Asp Lys Phe
                145                 150                 155

TGG AGG TGT ACA TCT GGT AAC CCA TCT CTA ACA AGT AGT CCT AAG ATA         588
Trp Arg Cys Thr Ser Gly Asn Pro Ser Leu Thr Ser Ser Pro Lys Ile
            160                 165                 170

AGG TTA ATA CCA GGG CCA GGT TTA TTA GCA ACA TCT ACT ACA GTA AAT         636
Arg Leu Ile Pro Gly Pro Gly Leu Leu Ala Thr Ser Thr Thr Val Asn
        175                 180                 185

GGC TGT ATT AGA ATC CCA TCG TTA GCA ATC AAT CAT TTA ATC TAC GCT         684
Gly Cys Ile Arg Ile Pro Ser Leu Ala Ile Asn His Leu Ile Tyr Ala
    190                 195                 200

TAC ACC TCT AAT CTT ATC ACC CAG GGC TGT CAA AAT ATA GGG AAA TCT         732
Tyr Thr Ser Asn Leu Ile Thr Gln Gly Cys Gln Asn Ile Gly Lys Ser
205                 210                 215                 220

TAC CAA GTA CTA CAA ATA GGG ATA ATT ACT ATA AAT TCG GAC CTA GTA         780
Tyr Gln Val Leu Gln Ile Gly Ile Ile Thr Ile Asn Ser Asp Leu Val
                225                 230                 235

CCT GAT TTA AAT CCC AGA GTC ACA CAT ACA TTT AAT ATT GAT GAT AAT         828
Pro Asp Leu Asn Pro Arg Val Thr His Thr Phe Asn Ile Asp Asp Asn
            240                 245                 250

AGG AAA TCT TGC TCT CTG GCA CTA TTG AAT ACA GAT GTT TAT CAG TTA         876
Arg Lys Ser Cys Ser Leu Ala Leu Leu Asn Thr Asp Val Tyr Gln Leu
        255                 260                 265

TGC TCA ACA CCA AAA GTT GAT GAG AGA TCC GAT TAT GCA TCA ACA GGT         924
Cys Ser Thr Pro Lys Val Asp Glu Arg Ser Asp Tyr Ala Ser Thr Gly
    270                 275                 280

ATT GAG GAT ATT GTA CTT GAC ATT GTC ACT AAT AAT GGA TTA ATT ATA         972
Ile Glu Asp Ile Val Leu Asp Ile Val Thr Asn Asn Gly Leu Ile Ile
```

```
                          285                            290                            295                          300
ACA  ACA  AGG  TTT  ACA  AAT  AAT  AAT  ATA  ACT  TTT  GAT  AAA  CCG  TAT  GCA       1020
Thr  Thr  Arg  Phe  Thr  Asn  Asn  Asn  Ile  Thr  Phe  Asp  Lys  Pro  Tyr  Ala
                         305                            310                          315

GCA  TTG  TAT  CCA  TCA  GTA  GGA  CCA  GGA  ATC  TAT  TAT  AAG  GGT  AAA  GTT       1068
Ala  Leu  Tyr  Pro  Ser  Val  Gly  Pro  Gly  Ile  Tyr  Tyr  Lys  Gly  Lys  Val
               320                            325                       330

ATC  TTT  CTC  GGA  TAT  GGA  GGT  CTA  GAG  CAT  GAA  GAA  AAC  GGA  GAC  GTA       1116
Ile  Phe  Leu  Gly  Tyr  Gly  Gly  Leu  Glu  His  Glu  Glu  Asn  Gly  Asp  Val
               335                            340                       345

ATA  TGT  AAT  ACA  ACT  GGT  TGT  CCT  GGC  AAA  ACA  CAG  AGA  GAC  TGT  AAT       1164
Ile  Cys  Asn  Thr  Thr  Gly  Cys  Pro  Gly  Lys  Thr  Gln  Arg  Asp  Cys  Asn
         350                            355                       360

CAG  GCT  TCT  TAT  AGC  CCA  TGG  TTC  TCA  AAT  AGG  AGA  ATG  GTA  AAC  TCT       1212
Gln  Ala  Ser  Tyr  Ser  Pro  Trp  Phe  Ser  Asn  Arg  Arg  Met  Val  Asn  Ser
365                       370                            375                       380

ATT  ATT  GTT  GTT  GAT  AAA  GGC  ATA  GAT  GCA  ACT  TTT  AGC  TTG  AGG  GTG       1260
Ile  Ile  Val  Val  Asp  Lys  Gly  Ile  Asp  Ala  Thr  Phe  Ser  Leu  Arg  Val
                         385                            390                       395

TGG  ACT  ATT  CCA  ATG  AGC  CAA  AAT  TAT  TGG  GGA  TCA  GAA  GGA  AGA  TTA       1308
Trp  Thr  Ile  Pro  Met  Ser  Gln  Asn  Tyr  Trp  Gly  Ser  Glu  Gly  Arg  Leu
               400                            405                       410

CTT  TTA  TTA  GGT  GAC  AGA  ATA  TAC  ATA  TAT  ACT  AGA  TCC  ACA  AGT  TGG       1356
Leu  Leu  Leu  Gly  Asp  Arg  Ile  Tyr  Ile  Tyr  Thr  Arg  Ser  Thr  Ser  Trp
               415                            420                       425

CAC  AGT  AAA  TTA  CAG  TTA  GGG  GTA  ATT  GAT  ATT  TCT  GAT  TAT  AAT  AAT       1404
His  Ser  Lys  Leu  Gln  Leu  Gly  Val  Ile  Asp  Ile  Ser  Asp  Tyr  Asn  Asn
          430                           435                       440

ATA  AGA  ATA  AAT  TGG  ACT  TGG  CAT  AAT  GTA  CCA  TCA  CGG  CCA  GGA  AAT       1452
Ile  Arg  Ile  Asn  Trp  Thr  Trp  His  Asn  Val  Pro  Ser  Arg  Pro  Gly  Asn
445                       450                            455                       460

GAT  GAA  TGT  CCA  TGG  GGT  CAT  TCA  TGC  CCA  GAC  GGA  TGT  ATA  ACA  GGA       1500
Asp  Glu  Cys  Pro  Trp  Gly  His  Ser  Cys  Pro  Asp  Gly  Cys  Ile  Thr  Gly
                         465                            470                       475

GTT  TAC  ACT  GAT  GCA  TAT  CCG  CTA  AAC  CCA  TCG  GGG  AGT  GTT  GTA  TCA       1548
Val  Tyr  Thr  Asp  Ala  Tyr  Pro  Leu  Asn  Pro  Ser  Gly  Ser  Val  Val  Ser
               480                            485                       490

TCA  GTA  ATT  CTT  GAC  TCA  CAA  AAG  TCT  AGA  GAA  AAC  CCA  ATC  ATT  ACC       1596
Ser  Val  Ile  Leu  Asp  Ser  Gln  Lys  Ser  Arg  Glu  Asn  Pro  Ile  Ile  Thr
               495                            500                       505

TAC  TCA  ACA  GCT  ACA  AAT  AGA  ATA  AAT  GAA  TTA  GCT  ATA  TAT  AAC  AGA       1644
Tyr  Ser  Thr  Ala  Thr  Asn  Arg  Ile  Asn  Glu  Leu  Ala  Ile  Tyr  Asn  Arg
          510                           515                       520

ACA  CTT  CCA  GCT  GCA  TAT  ACA  ACA  ACA  AAT  TGT  ATC  ACA  CAT  TAT  GAT       1692
Thr  Leu  Pro  Ala  Ala  Tyr  Thr  Thr  Thr  Asn  Cys  Ile  Thr  His  Tyr  Asp
525                       530                            535                       540

AAA  GGG  TAT  TGT  TTT  CAT  ATA  GTA  GAA  ATA  AAT  CAC  AGA  AGT  TTG  AAT       1740
Lys  Gly  Tyr  Cys  Phe  His  Ile  Val  Glu  Ile  Asn  His  Arg  Ser  Leu  Asn
               545                            550                       555

ACG  TTT  CAA  CCT  ATG  TTA  TTC  AAA  ACA  GAA  GTT  CCA  AAA  AAC  TGC  AGC       1788
Thr  Phe  Gln  Pro  Met  Leu  Phe  Lys  Thr  Glu  Val  Pro  Lys  Asn  Cys  Ser
               560                            565                       570

TAAATGATCA  TCGCATATCG  GATGCCAGAT  GACATTAAAA  GAGACCACCA  GACAGACAAC              1848

ACAGGAGATG  ATGCAAGATA  TAAAGGAATA  AT                                              1880
```

( 2 ) INFORMATION FOR SEQ ID NO:81:

( i ) SEQUENCE CHARACTERISTICS:
        ( A ) LENGTH: 572 amino acids
        ( B ) TYPE: amino acid ( D ) TOPOLOGY: linear ( i i ) MOLECULE TYPE: protein ( x i ) SEQUENCE DESCRIPTION: SEQ ID NO:81:

| Met | Glu | Tyr | Trp | Lys | His | Thr | Asn | Ser | Thr | Lys | Asn | Thr | Asn | Asn | Glu |
|---|---|---|---|---|---|---|---|---|---|---|---|---|---|---|---|
| 1 | | | | 5 | | | | | 10 | | | | | 15 | |

| Thr | Glu | Thr | Thr | Arg | Gly | Lys | His | Ser | Ser | Lys | Val | Thr | Asn | Ile | Ile |
|---|---|---|---|---|---|---|---|---|---|---|---|---|---|---|---|
| | | | 20 | | | | | 25 | | | | | 30 | | |

| Met | Tyr | Thr | Phe | Trp | Thr | Ile | Thr | Ser | Thr | Ile | Leu | Leu | Val | Ile | Phe |
|---|---|---|---|---|---|---|---|---|---|---|---|---|---|---|---|
| | | | 35 | | | | | 40 | | | | | 45 | | |

| Ile | Met | Ile | Leu | Thr | Asn | Leu | Ile | Gln | Glu | Asn | Asn | His | Asn | Lys | Leu |
|---|---|---|---|---|---|---|---|---|---|---|---|---|---|---|---|
| | 50 | | | | | 55 | | | | | 60 | | | | |

| Met | Leu | Gln | Glu | Ile | Arg | Lys | Glu | Phe | Ala | Ala | Ile | Asp | Thr | Lys | Ile |
|---|---|---|---|---|---|---|---|---|---|---|---|---|---|---|---|
| 65 | | | | | 70 | | | | | 75 | | | | | 80 |

| Gln | Arg | Thr | Ser | Asp | Asp | Ile | Gly | Thr | Ser | Ile | Gln | Ser | Gly | Ile | Asn |
|---|---|---|---|---|---|---|---|---|---|---|---|---|---|---|---|
| | | | | 85 | | | | | 90 | | | | | 95 | |

| Thr | Arg | Leu | Leu | Thr | Ile | Gln | Ser | His | Val | Gln | Asn | Tyr | Ile | Pro | Leu |
|---|---|---|---|---|---|---|---|---|---|---|---|---|---|---|---|
| | | | 100 | | | | | 105 | | | | | 110 | | |

| Ser | Leu | Thr | Gln | Gln | Met | Ser | Asp | Leu | Arg | Lys | Phe | Ile | Asn | Asp | Leu |
|---|---|---|---|---|---|---|---|---|---|---|---|---|---|---|---|
| | | | 115 | | | | | 120 | | | | | 125 | | |

| Thr | Asn | Lys | Arg | Glu | His | Gln | Glu | Val | Pro | Ile | Gln | Arg | Met | Thr | His |
|---|---|---|---|---|---|---|---|---|---|---|---|---|---|---|---|
| | | 130 | | | | | 135 | | | | | 140 | | | |

| Asp | Arg | Gly | Ile | Glu | Pro | Leu | Asn | Pro | Asp | Lys | Phe | Trp | Arg | Cys | Thr |
|---|---|---|---|---|---|---|---|---|---|---|---|---|---|---|---|
| 145 | | | | | 150 | | | | | 155 | | | | | 160 |

| Ser | Gly | Asn | Pro | Ser | Leu | Thr | Ser | Ser | Pro | Lys | Ile | Arg | Leu | Ile | Pro |
|---|---|---|---|---|---|---|---|---|---|---|---|---|---|---|---|
| | | | | 165 | | | | | 170 | | | | | 175 | |

| Gly | Pro | Gly | Leu | Leu | Ala | Thr | Ser | Thr | Thr | Val | Asn | Gly | Cys | Ile | Arg |
|---|---|---|---|---|---|---|---|---|---|---|---|---|---|---|---|
| | | | | 180 | | | | | 185 | | | | | 190 | |

| Ile | Pro | Ser | Leu | Ala | Ile | Asn | His | Leu | Ile | Tyr | Ala | Tyr | Thr | Ser | Asn |
|---|---|---|---|---|---|---|---|---|---|---|---|---|---|---|---|
| | | 195 | | | | | 200 | | | | | 205 | | | |

| Leu | Ile | Thr | Gln | Gly | Cys | Gln | Asn | Ile | Gly | Lys | Ser | Tyr | Gln | Val | Leu |
|---|---|---|---|---|---|---|---|---|---|---|---|---|---|---|---|
| | 210 | | | | | 215 | | | | | 220 | | | | |

| Gln | Ile | Gly | Ile | Ile | Thr | Ile | Asn | Ser | Asp | Leu | Val | Pro | Asp | Leu | Asn |
|---|---|---|---|---|---|---|---|---|---|---|---|---|---|---|---|
| 225 | | | | | 230 | | | | | 235 | | | | | 240 |

| Pro | Arg | Val | Thr | His | Thr | Phe | Asn | Ile | Asp | Asp | Asn | Arg | Lys | Ser | Cys |
|---|---|---|---|---|---|---|---|---|---|---|---|---|---|---|---|
| | | | | 245 | | | | | 250 | | | | | 255 | |

| Ser | Leu | Ala | Leu | Leu | Asn | Thr | Asp | Val | Tyr | Gln | Leu | Cys | Ser | Thr | Pro |
|---|---|---|---|---|---|---|---|---|---|---|---|---|---|---|---|
| | | | 260 | | | | | 265 | | | | | 270 | | |

| Lys | Val | Asp | Glu | Arg | Ser | Asp | Tyr | Ala | Ser | Thr | Gly | Ile | Glu | Asp | Ile |
|---|---|---|---|---|---|---|---|---|---|---|---|---|---|---|---|
| | | 275 | | | | | 280 | | | | | 285 | | | |

| Val | Leu | Asp | Ile | Val | Thr | Asn | Asn | Gly | Leu | Ile | Ile | Thr | Thr | Arg | Phe |
|---|---|---|---|---|---|---|---|---|---|---|---|---|---|---|---|
| | 290 | | | | | 295 | | | | | 300 | | | | |

| Thr | Asn | Asn | Asn | Ile | Thr | Phe | Asp | Lys | Pro | Tyr | Ala | Ala | Leu | Tyr | Pro |
|---|---|---|---|---|---|---|---|---|---|---|---|---|---|---|---|
| 305 | | | | | 310 | | | | | 315 | | | | | 320 |

| Ser | Val | Gly | Pro | Gly | Ile | Tyr | Tyr | Lys | Gly | Lys | Val | Ile | Phe | Leu | Gly |
|---|---|---|---|---|---|---|---|---|---|---|---|---|---|---|---|
| | | | | 325 | | | | | 330 | | | | | 335 | |

| Tyr | Gly | Gly | Leu | Glu | His | Glu | Glu | Asn | Gly | Asp | Val | Ile | Cys | Asn | Thr |
|---|---|---|---|---|---|---|---|---|---|---|---|---|---|---|---|
| | | | 340 | | | | | 345 | | | | | 350 | | |

| Thr | Gly | Cys | Pro | Gly | Lys | Thr | Gln | Arg | Asp | Cys | Asn | Gln | Ala | Ser | Tyr |
|---|---|---|---|---|---|---|---|---|---|---|---|---|---|---|---|
| | | 355 | | | | | 360 | | | | | 365 | | | |

| Ser | Pro | Trp | Phe | Ser | Asn | Arg | Arg | Met | Val | Asn | Ser | Ile | Ile | Val | Val |
|---|---|---|---|---|---|---|---|---|---|---|---|---|---|---|---|
| | 370 | | | | | 375 | | | | | 380 | | | | |

| Asp | Lys | Gly | Ile | Asp | Ala | Thr | Phe | Ser | Leu | Arg | Val | Trp | Thr | Ile | Pro |
|---|---|---|---|---|---|---|---|---|---|---|---|---|---|---|---|
| 385 | | | | | 390 | | | | | 395 | | | | | 400 |

| Met | Ser | Gln | Asn | Tyr     | Trp | Gly | Ser | Glu | Gly     | Arg | Leu | Leu | Leu     | Leu | Gly |
|     |     |     |     | 405     |     |     |     |     | 410     |     |     |     | 415     |     |     |
| Asp | Arg | Ile | Tyr | Ile     | Tyr | Thr | Arg | Ser | Thr     | Ser | Trp | His | Ser     | Lys | Leu |
|     |     |     | 420 |         |     |     |     | 425 |         |     |     |     | 430     |     |     |
| Gln | Leu | Gly | Val | Ile     | Asp | Ile | Ser | Asp | Tyr     | Asn | Asn | Ile | Arg     | Ile | Asn |
|     |     |     | 435 |         |     |     | 440 |     |         |     |     | 445 |         |     |     |
| Trp | Thr | Trp | His | Asn     | Val | Pro | Ser | Arg | Pro     | Gly | Asn | Asp | Glu     | Cys | Pro |
|     | 450 |     |     |         |     |     | 455 |     |         |     |     | 460 |         |     |     |
| Trp | Gly | His | Ser | Cys     | Pro | Asp | Gly | Cys | Ile     | Thr | Gly | Val | Tyr     | Thr | Asp |
| 465 |     |     |     |         | 470 |     |     |     |         | 475 |     |     |         |     | 480 |
| Ala | Tyr | Pro | Leu | Asn     | Pro | Ser | Gly | Ser | Val     | Val | Ser | Ser | Val     | Ile | Leu |
|     |     |     |     | 485     |     |     |     |     | 490     |     |     |     |         | 495 |     |
| Asp | Ser | Gln | Lys | Ser     | Arg | Glu | Asn | Pro | Ile     | Ile | Thr | Tyr | Ser     | Thr | Ala |
|     |     |     | 500 |         |     |     |     | 505 |         |     |     |     | 510     |     |     |
| Thr | Asn | Arg | Ile | Asn     | Glu | Leu | Ala | Ile | Tyr     | Asn | Arg | Thr | Leu     | Pro | Ala |
|     |     | 515 |     |         |     |     | 520 |     |         |     |     | 525 |         |     |     |
| Ala | Tyr | Thr | Thr | Thr     | Asn | Cys | Ile | Thr | His     | Tyr | Asp | Lys | Gly     | Tyr | Cys |
|     |     | 530 |     |         |     | 535 |     |     |         |     | 540 |     |         |     |     |
| Phe | His | Ile | Val | Glu     | Ile | Asn | His | Arg | Ser     | Leu | Asn | Thr | Phe     | Gln | Pro |
| 545 |     |     |     |         | 550 |     |     |     |         | 555 |     |     |         |     | 560 |
| Met | Leu | Phe | Lys | Thr     | Glu | Val | Pro | Lys | Asn     | Cys | Ser |     |         |     |     |
|     |     |     |     | 565     |     |     |     |     | 570     |     |     |     |         |     |     |

( 2 ) INFORMATION FOR SEQ ID NO:82:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:82:

```
CCTTATGTAT   CATACACATA   CGATTTAGGT   GACACTATAG   AATACAAGCT   TGGGCTGCAG        60

GTCGAC                                                                             66
```

( 2 ) INFORMATION FOR SEQ ID NO:83:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..66

( x i ) SEQUENCE DESCRIPTION: SEQ ID NO:83:

```
GTC   CGC   GCT   GCT   GCG   CCG   CCT   GGG   CCG   GCG   GAA   GAT   CTG   CTC   ATG   CTC      48
Val   Arg   Ala   Ala   Ala   Pro   Pro   Gly   Pro   Ala   Glu   Asp   Leu   Leu   Met   Leu
 1                 5                             10                            15
```

```
GCG GCC GCC ATG CCC CCG                                                              66
Ala Ala Ala Met Pro Pro
             20
```

( 2 ) INFORMATION FOR SEQ ID NO:84:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: protein ( x i ) SEQUENCE DESCRIPTION: SEQ ID NO:84:

```
Val Arg Ala Ala Ala Pro Pro Gly Pro Ala Glu Asp Leu Leu Met Leu
 1               5                  10                  15
Ala Ala Ala Met Pro Pro
             20
```

( 2 ) INFORMATION FOR SEQ ID NO:85:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:85:

```
GGACACCATG TTTTTCCTGC CGCGCGCGGC CGTCGACTCT AGAGGATCCC CGGGCGAGCT    60
CGAATT                                                               66
```

( 2 ) INFORMATION FOR SEQ ID NO:86:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:86:

```
GGATCCCCTC GACGTCTGGG GCGCGGGGGT GGTGCTCTTC GAGACGCTGG CCTACCCCAA    60
GACGAT                                                               66
```

( 2 ) INFORMATION FOR SEQ ID NO:87:

( i ) SEQUENCE CHARACTERISTICS:
        ( A ) LENGTH: 69 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:87:

```
GGATCCCCTC GACGTCGTCT GGGGCGCGGG GGTGGTGCTC TTCGAGACGC TGGCCTACCC    60

CAAGACGAT                                                           69
```

( 2 ) INFORMATION FOR SEQ ID NO:88:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 31..66

( x i ) SEQUENCE DESCRIPTION: SEQ ID NO:88:

```
CACACCTTTG CGCATCTCCA CAGCTACACA ATG AAT TCC ATG TTA CGT CCT GTA    54
                                 Met Asn Ser Met Leu Arg Pro Val
                                  1               5

GAA ACC CCA ACC                                                     66
Glu Thr Pro Thr
 10
```

( 2 ) INFORMATION FOR SEQ ID NO:89:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: protein ( x i ) SEQUENCE DESCRIPTION: SEQ ID NO:89:

```
Met Asn Ser Met Leu Arg Pro Val Glu Thr Pro Thr
 1               5                   10
```

( 2 ) INFORMATION FOR SEQ ID NO:90:

( i ) SEQUENCE CHARACTERISTICS:
        ( A ) LENGTH: 66 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..15

( x i ) SEQUENCE DESCRIPTION: SEQ ID NO:90:

```
CAG GGA GGC AAA CAA TGAATCAACA ACTCTCCCGG GAGATGGGGG AGGCTAACTG    55
Gln Gly Gly Lys Gln
 1               5

AAACACGGAA G                                                       66
```

( 2 ) INFORMATION FOR SEQ ID NO:91:

( i ) SEQUENCE CHARACTERISTICS:

(A) LENGTH: 5 amino acids
(B) TYPE: amino acid
(D) TOPOLOGY: linear (ii) MOLECULE TYPE: protein (xi) SEQUENCE DESCRIPTION: SEQ ID NO:91:

Gln Gly Gly Lys Gln
 1               5

(2) INFORMATION FOR SEQ ID NO:92:

(i) SEQUENCE CHARACTERISTICS:
(A) LENGTH: 66 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:92:

GTCGCCCCCC TTAAGGGTCT CTTGCACAAT CCAGCCGCCT CCGTGTTGCT GCGTTCCGG     60

GGATCC     66

(2) INFORMATION FOR SEQ ID NO:93:

(i) SEQUENCE CHARACTERISTICS:
(A) LENGTH: 39 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:93:

GGGAATTCTG CAGGTCACAT CATACAATTC TAATCTAAG     39

(2) INFORMATION FOR SEQ ID NO:94:

(i) SEQUENCE CHARACTERISTICS:
(A) LENGTH: 43 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:94:

GGGAATTCTG CAGGCTTTAA AAGAGAGAAT TTCCGTTTGG CTA     43

(2) INFORMATION FOR SEQ ID NO:95:

(i) SEQUENCE CHARACTERISTICS:
(A) LENGTH: 31 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:95:

CATAGATCTT GTGGTGCTGT CCGACTTCGC A    31

(2) INFORMATION FOR SEQ ID NO:96:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:96:

CGTGGATCCT CAATTACAAG AGGTATCGTC TAC    33

(2) INFORMATION FOR SEQ ID NO:97:

(i) SEQUENCE CHARACTERISTICS:
        (A) LENGTH: 40 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:97:

AAAAGATCTT AGCAAGGTCA AACTAAATGA CACTTTCAAC    40

(2) INFORMATION FOR SEQ ID NO:98:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:98:

CGTGGATCCA ACTCACAATT CCACATCATT ATCTTTGGGA TT    42

(2) INFORMATION FOR SEQ ID NO:99:

(i) SEQUENCE CHARACTERISTICS:
        (A) LENGTH: 40 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO ( x i ) SEQUENCE DESCRIPTION: SEQ ID NO:99:

TATAGATCTT CATACCCATC ATCTTAAATT CAAGACATTA 40

( 2 ) INFORMATION FOR SEQ ID NO:100:

( i ) SEQUENCE CHARACTERISTICS:
        ( A ) LENGTH: 38 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:100:

CGTGGATCCA TAATTAGATG TTATATGGAG GTGTGTTG 38

( 2 ) INFORMATION FOR SEQ ID NO:101:

( i ) SEQUENCE CHARACTERISTICS:
        ( A ) LENGTH: 40 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:101:

TATAGATCTA ACAGCCATGA GGATGATCAT CAGCATTATC 40

( 2 ) INFORMATION FOR SEQ ID NO:102:

( i ) SEQUENCE CHARACTERISTICS:
        ( A ) LENGTH: 39 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:102:

CGTGGATCCT TCTGAGGTTT AGATTGTAAA CATTATGCA 39

( 2 ) INFORMATION FOR SEQ ID NO:103:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:103:

TATAGATCTT AGACTTACAA CCCTAAAAAA C 31

-continued ( 2 ) INFORMATION FOR SEQ ID NO:104:

( i ) SEQUENCE CHARACTERISTICS:
( A ) LENGTH: 36 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:104:

CGTGGATCCA ACTCTATAAT GTGTGAAACA ATATAG 36

What is claimed is:

1. A live recombinant infectious bovine rhinotracheitis virus comprising a first and a second foreign DNA, each of which encodes a polypeptide of a RNA virus, inserted into an infectious bovine rhinotracheitis virus genome, wherein the first and the second foreign DNA are inserted into a non-essential region of the infectious bovine rhinotracheitis virus genome, which region is the same or different and is selected from the group consisting of the glycoprotein E(gpE) gene, the glycoprotein G(gpG) gene and the US2 gene.

2. The live recombinant infectious bovine rhinotracheitis virus of claim 1, further comprising a deletion within the US2 gene of the infectious bovine rhinotracheitis virus genome.

3. The live recombinant infectious bovine rhinotracheitis virus of claim 1, wherein the first and second foreign DNA sequences are inserted within the glycoprotein E(gE) gene of the infectious bovine rhinotracheitis virus genome.

4. The live recombinant infectious bovine rhinotracheitis virus of claim 1, wherein the foreign DNA encodes a detectable marker.

5. The live recombinant infectious bovine rhinotracheitis virus of claim 4, wherein the detectable marker is *E. coli* β-galactosidase or *E. coli* β-glucoronidase.

6. The live recombinant infectious bovine rhinotracheitis virus of claim 1, wherein the foreign DNA encodes a polypeptide which is antigenic.

7. The live recombinant infectious bovine rhinotracheitis virus of claim 1, wherein the foreign DNA encodes a polypeptide which is selected from a group consisting of Bovine Respiratory Syncytial Virus fusion protein, Bovine Respiratory Syncytial Virus attachment protein, Bovine Respiratory Syncytial Virus nucleocapsid protein, Parainfluenza type 3 fusion protein, Bovine Viral Diarrhea Virus glycoprotein 53, and P Haemolytica Leukotoxin.

* * * * *